(12) United States Patent
Fomsgaard

(10) Patent No.: US 6,649,409 B1
(45) Date of Patent: Nov. 18, 2003

(54) METHOD FOR PRODUCING A NUCLEOTIDE SEQUENCE CONSTRUCT WITH OPTIMIZED CODONS FOR AN HIV GENETIC VACCINE BASED ON A PRIMARY, EARLY HIV ISOLATE AND SYNTHETIC ENVELOPE BX08 CONSTRUCTS

(75) Inventor: Anders Fomsgaard, Frederiksberg (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 09/536,977

(22) Filed: Mar. 29, 2000

Related U.S. Application Data
(60) Provisional application No. 60/128,558, filed on Apr. 9, 1999.

(30) Foreign Application Priority Data

Mar. 29, 1999 (DK) .......................................... 1999 00427

(51) Int. Cl.$^7$ ............................ C12N 5/06; C12N 5/00; C12P 21/06; C07H 21/04; A61K 39/21
(52) U.S. Cl. ................... 435/339.1; 435/69.1; 435/325; 536/23.72; 424/208.1
(58) Field of Search ................................ 435/69.1, 325, 435/339.1; 536/23.72; 424/208.1

(56) References Cited

U.S. PATENT DOCUMENTS

| | | | |
|---|---|---|---|
| 5,786,464 A | 7/1998 | Seed .......................... | 536/23.5 |
| 5,795,737 A | 8/1998 | Seed et al. .................. | 435/69.1 |

FOREIGN PATENT DOCUMENTS

| | | |
|---|---|---|
| WO | 91/05567 | 5/1991 |
| WO | 95/04147 | 2/1995 |
| WO | 96/09378 | 3/1996 |
| WO | 97/11086 | 3/1997 |
| WO | 97/31115 | 8/1997 |
| WO | 97/47358 | 12/1997 |
| WO | 97/48370 | 12/1997 |
| WO | 98/01570 | 1/1998 |
| WO | 98/12207 | 3/1998 |
| WO | 98/34640 | 8/1998 |
| WO | 98/41536 | 9/1998 |

OTHER PUBLICATIONS

Stefanie André et al., "Increased Immune Response Elicited by DNA Vaccination with a Synthetic gp120 Sequence with Optimized Codon Usage.", Journal of Virology, pp. 1497–1503, 1998.

Nicole K. T. Back et al., "An N–Glycan within the Human Immunodeficiency Virus Type 1 gp130 V3 Loop Affects Virus Neutralization.", Virology, vol. 199, pp. 431–438, 1994.

Dhananjay Bhattacharyya et al., "Positioning of Positively Charged Residues in the V3 Loop Correlates with HIV Thpe 1 Syncytium–inducing Phenotype.", Aids Research and Human Retroviruses, vol. 12, No. 2, pp. 83–90, 1996.

(List continued on next page.)

Primary Examiner—Hankyel T. Park
(74) Attorney, Agent, or Firm—Foley & Lardner

(57) ABSTRACT

The present invention relates to a method for producing a nucleotide sequence construct with optimized codons for an HIV genetic vaccine based on a primary, early HIV isolate. Specific such nucleotide sequence construct are the synthetic envelope BX08 constructs. The invention further relates to the medical use of such constructs for the treatment and prophylaxis of HIV through DNA vaccine and for diagnostics.

48 Claims, 33 Drawing Sheets

| Amino acid | One letter amino acid code | Three letter amino acid code | Codon |
|---|---|---|---|
| Alanine | A | Ala | GCC |
| Arginine | R | Arg | CGC |
| Aspargine | N | Asn | AAC |
| Aspartic acid | D | Asp | GAC |
| Cysteine | C | Cys | TGC |
| Glutamine | Q | Gln | CAG |
| Glutamic acid | E | Glu | GAG |
| Glycine | G | Gly | GGC |
| Histidine | H | His | CAC |
| Isoleucine | I | Ile | ATC |
| Leucine | L | Leu | CTG |
| Lysine | K | Lys | AAG |
| Proline | P | Pro | CCC |
| Phenylalanine | F | Phe | TTC |
| Serine | S | Ser | AGC |
| Threonine | T | Thr | ACC |
| Tyrosine | Y | Tyr | TAC |
| Valine | V | Val | GTG |

OTHER PUBLICATIONS

Jean D. Boyer et al., "Protection of chimpanzees from high–dose heterologous HIV–1 challenge by DNA vaccination", Nature Medicine, vol. 3, No. 5, pp. 526–532, 1997.

Karin Bryder et al., "Improved Immunogenicity of HIV–1 Epitopes in HbsAg Chimeric DNA Vaccine Plasmids by Structural Mutations of HbsAg.", DNA and Cell Biology, vol. 18, No. 3, pp. 219–225, 1999.

David C. Chan et al., "Core Structure of gp41 from the HIV Envelope Glycoprotein.", Cell, vol. 89, pp. 263–273, 1997.

Hyeryun Choe et al., "The β–Chemokine Receptors CCR3 and CCR5 Facilitate Infection by Primary HIV–1 Isolates.", Cell, vol. 85, pp. 1135–1148, 1996.

John M. Crawford et al., "Characterization of Primary Isolate–Like Variants of Simian–Human Immunodeficiency Virus.", Journal of Virology, pp. 10199–10207, 1999.

Ludwig Deml et al., "Immunostimulatory CpG Morifs Trigger a T Helper–1 Immune Response to Human Immunodeficiency Virus Type–1 (HIV–1) gp160 Envelope Proteins.", Clinical Chemical Laboratory Medicine, vol. 37, No. 3, pp. 2–12, 1997.

Anders Fomsgaard, "HIV–1 DNA vaccines.", Immunology Letters, vol. 65, pp. 127–131, 1999.

Feng Gao et al., "Molecular Cloning and Analysis of Functional Envelope Genes from Human Immunodeficiency Virus Type 1 Sequence Subtypes A throuth G.", Journal of Virology, vol. 70, No. 3, pp. 1651–1667, 1996.

Jürgen Haas et al., "Codon usage limitation in the expression of HIV–1 envelope glycoprotein.", Current Biology, vol. 6, No. 3, pp. 315–324, 1996.

Shinji Harada et al., "Infection of HTLV–III/LAV in HTLV–I–Carrying Cells MT–2 and MT–4 and Application in a Plaque Assay.", Science, vol. 229, pp. 563–566, 1985.

Annika C. Karisson et al., "Characterization of the viral population during primary HIV–1 infection.", Aids, vol. 12, pp. 839–847, 1998.

M. P. Kieny et al., "Improved antigenicity of the HIV env protein by cleavage site removal.", Protein Engineering, vol. 2, pp. 219–225, 1988.

Peter Kwong et al., "Structure of an HIV gp120 envelope glycoprotein in complex with the CE4 receptor and a neutralizing human antibody.", Nature, vol. 393, No. 18, pp. 648–658, 1998.

Cheryl Lapham et al., "*Brucella abortus* Conjugated with a Peptide Derived from the V3 Loop of Human Immunodeficiency Virus (HIV) Type 1 Induces HIV–Specific Cytotoxic T–Cell Responses in Normal and in $CD4^+$ Cell–Depleted BALB/c Mice.", Journal of Virology, pp. 3084–3092, 1996.

Norman L. Letvin et al., "Potent, protective anti–HIV immune responses generated by bimodal HIV envelope DNA plus protein vaccination.", Proceedings of the National Academy of Sciece, vol. 94, pp. 9378–9383, 1997.

Shan Lu et al., "Immunogenicity of DNA Vaccines Expressing Human Immunodeficiency Virus Type 1 Envelope Glycoprotein with and without Deletions in the V1/2 and V3 Regions.", Aids Research and Human Retroviruses, vol. 14, No. 2, pp. 151–155, 1998.

Ole Marker et al., "Studies on Cell–Mediated Immunity To Lymphocytic Choriomeningitis Virus In Mice.", The Journal of Experimental Medicine, vol. 137, pp. 1511–1524, 1973.

John R. Mascola et al., "Potent and Synergistic Neutralization of Human Immunodeficiency Virus (HIV) Type 1 Primary Isolates by Hyperimmune Anti–HIV Immunoglobulin Combined with Monoclonal Antibodies 2F5 and 2G12.", Journal of Virology, pp. 7198–7206, 1997.

Christine Moog et al., "Neutralization of Primary Human Immunodeficiency Virus Type 1 Isolates: A study of Parameters Implicated in Neutralization in Vitro.", Aids Research and Human Retroviruses, vol. 12, No. 1, pp. 19–27, 1997.

Michael Nelson et al., "Use of DNA Methyltransferase/Endonucleases Enzyme Combinations for Megabase Mapping of Chromosomes.", Methods in Enzymology, vol. 216, pp. 279–303, 1992.

Carsten M. Nielsen et al., "Detection Of HIV Antigens in Eluates From Whole Blood Collected On Filtepaper.", The Lancet, vol. 1, pp. 566–567, 1987.

Nicky M. Peet et al., "The Effect of Low–Profile Serine Substitutions in the V3 Loop of HIV–1 gp120 IIIB/LAI on the immunogenicity of the Envelope Protein.", Virology, vol. 251, pp. 59–70, 1998.

Eric S. Rosenberg et al., "Vigorous HIV–1 Specific $CD4^+$ T Cell Responses Associated with Control of Viremia.", Science, vol. 278, pp. 1447–1450, 1997.

Monica M. Sauter et al., "An Internalization Signal in the Simian Immunodeficiency Virus Transmembrane Protein Cytoplasmic Domain Modulates Expression of Envelope Glycoproteins on the Cell Surface.", The Journal of Cell Biology, vol. 132, No. 5, pp. 795–811, 1996.

Tatsuo Shioda et al., "Small amino acid changes in the V3 hypervariable region of gp120 can affect the T–cell–line and macrophage tropism of human immunodeficiency virus type 1.", Proceedings of the National Academy of Science, vol. 89, pp. 9434–9438, 1992.

Catherine Spenlehauer et al., "Study of the V3 Loop as a Target Epitope for Antibodies Involved in the Neutralization of Primary Isolates versus T–Cell–Line–Adapted Strains of Human Immunodeficiency Virus Type 1.", Journal of Virology, pp. 9855–9864, 1998.

Angelique B. vant Wout et al., "Analysi of the Temporal Relationship between Human Immunodeficiency Virus Type 1 Quasispecies in Sequential Blood Samples and Various Organs Obtained at Autopsy.", Journal of Virology, pp. 488–496, 1998.

Florence C. Verrier et al., "Antibodies to several conformation–dependent epitopes of a gp120/gp41 inhibit CCR–5–dependent cell–to–cell fusion mediated by the native envelope glycoprotein of a primary macrophage–tropic HIV–1 isolate.", Proceedings of the National Academy of Science, vol. 94, pp. 9326–9331, 1997.

Lasse Vinner et al., "Gene gun DNA vaccination with Rev–independetn synthetic HIV–1 gp160 envelope gene using mammalian codons.", Vaccine, vol. 17, pp. 2166–2175, 1999.

Wei–Kung et al., "CCR5 coreceptor utilization involves a highly conserved arginine residue of HIV type 1 gp120.", Proceedings of the National Academy of Sciences, vol. 95, pp. 5740–5745, 1998.

Michael P. Weiner, et al., "Site–directed mutagenesis of double–stranded DNA by the polymerase chain reaction.", Gene, vol. 151, pp. 119–123, 1994.

Richard Wyatt et al., "The antigenic structure of the HIV gp120 envelope glycoprotein.", Nature, vol. 393, No. 18, pp. 705–710, 1998.

Robert G. Webster et al., "DNA Vaccines.", Biopharmaceuticals, BioDrugs, vol. 8, No. 4, pp. 273–292, 1997.

W. J. Wilbur et al., "Rapid similarity searches of nucleic acid and protein data banks." Proceedings of the National Academy of Science, vol. 80, pp. 726–730, 1983.

Susan Zolla–Pazner et al., "Neutralization of Syncytium–Inducing Primary Isolates by Sera from Human Immunodeficiency Virus (HIV)–Uninfected Recipients of Candidate HIV Vaccines.", The Journal of Infectious Diseases, vol. 178, pp. 1502–1506, 1998.

| Amino acid | One letter amino acid code | Three letter amino acid code | Codon |
|---|---|---|---|
| Alanine | A | Ala | GCC |
| Arginine | R | Arg | CGC |
| Aspargine | N | Asn | AAC |
| Aspartic acid | D | Asp | GAC |
| Cysteine | C | Cys | TGC |
| Glutamine | Q | Gln | CAG |
| Glutamic acid | E | Glu | GAG |
| Glycine | G | Gly | GGC |
| Histidine | H | His | CAC |
| Isoleucine | I | Ile | ATC |
| Leucine | L | Leu | CTG |
| Lysine | K | Lys | AAG |
| Proline | P | Pro | CCC |
| Phenylalanine | F | Phe | TTC |
| Serine | S | Ser | AGC |
| Threonine | T | Thr | ACC |
| Tyrosine | Y | Tyr | TAC |
| Valine | V | Val | GTG |

FIG. 1

STARTS: ATG

| aa | | Σ | codons | | | | | |
|---|---|---|---|---|---|---|---|---|
| A | Ala | GCX | GCT | GCC | GCG | GCA | | |
| C | Cys | TGY | TGT | TGC | | | | |
| D | Asp | GAY | GAT | GAC | | | | |
| E | Glu | GAR | GAG | GAA | | | | |
| F | Phe | TTY | TTT | TTC | | | | |
| G | Gly | GGX | GGT | GGC | GGG | GGA | | |
| H | His | CAY | CAT | CAC | | | | |
| I | Ile | ATH | ATT | ATC | ATA | | | |
| K | Lys | AAR | AAG | AAA | | | | |
| L | Leu | YTX | TTG | TTA | CTT | CTC | CTG | CTA |
| M | Met | ATG | ATG | | | | | |
| N | Asn | AAY | AAT | AAC | | | | |
| P | Pro | CCX | CCT | CCC | CCG | CCA | | |
| Q | Gln | CAR | CAG | CAA | | | | |
| R | Arg | MGX | CGT | CGC | CGG | CGA | AGG | AGA |
| S | Ser | WSX | TCT | TCC | TCG | TCA | AGT | AGC |
| T | Thr | ACX | ACT | ACC | ACG | ACA | | |
| V | Val | GTX | GTT | GTC | GTG | GTA | | |
| W | Trp | TGG | TGG | | | | | |
| Y | Tyr | TAY | TAT | TAC | | | | |
| . | * | TRR | TGA | TAG | TAA | | | |
| X | ??? | | | | | | | |

| 5' | 1st | 2nd T | 2nd C | 2nd A | 2nd G | 3rd | 3' |
|---|---|---|---|---|---|---|---|
| | T | Phe | Ser | Tyr | Cys | T | |
| | | Phe | Ser | Tyr | Cys | C | |
| | | Leu | Ser | • | • | A | |
| | | Leu | Ser | • | Trp | G | |
| | C | Leu | Pro | His | Arg | T | |
| | | Leu | Pro | His | Arg | C | |
| | | Leu | Pro | Gln | Arg | A | |
| | | Leu | Pro | Gln | Arg | G | |
| | A | Ile | Thr | Asn | Ser | T | |
| | | Ile | Thr | Asn | Ser | C | |
| | | Ile | Thr | Lys | Arg | A | |
| | | >Met | Thr | Lys | Arg | G | |
| | G | Val | Ala | Asp | Gly | T | |
| | | Val | Ala | Asp | Gly | C | |
| | | Val | Ala | Glu | Gly | A | |
| | | Val | Ala | Glu | Gly | G | |

FIG. 7

PANEL A

PANEL B

PANEL C

| Week | | Percentage of antiserum positive to gp120$_{IIIb}$ and gp41$_{IIIb}$ in western blot assay | | |
|---|---|---|---|---|
| | | 0 | 9 | 18 |
| syn.gp120$_{BX08}$ | gp120 | 0 | 65 | 90 |
| | gp41 | 0 | 0 | 35 |
| syn.gp140$_{BX08}$ | gp120 | 0 | 65 | 100 |
| | gp41 | 0 | 95 | 100 |
| syn.gp150$_{BX08}$ | gp120 | 0 | 30 | 41 |
| | gp41 | 0 | 41 | 53 |
| syn.gp160$_{BX08}$ | gp120 | 0 | 32 | 50 |
| | gp41 | 0 | 44 | 64 |
| wt.gp160$_{BX08}$ | gp120 | 0 | nd | 53 |
| | gp41 | 0 | nd | 48 |
| wt.gp160$_{BX08}$/pRev | gp120 | 0 | nd | 5 |
| | gp41 | 0 | nd | 55 |

SEQUENCE LISTING

```
<160> NUMBER OF SEQ ID NOS: 118

<210> SEQ ID NO 1
<211> LENGTH: 243
<212> TYPE: DNA
<213> ORGANISM: Human immunodeficiency virus
<220> FEATURE:
<221> NAME/KEY: CDS
<222> LOCATION: (1)..(243)

<400> SEQUENCE: 1 gct agc gcg gcc gac cgc ctg tgg gtg acc gtg tac tac ggc gtg ccc      48
Ala Ser Ala Ala Asp Arg Leu Trp Val Thr Val Tyr Tyr Gly Val Pro
 1               5                  10                  15 gtg tgg aag gac gcc acc acc acc ctg ttc tgc gcc agc gac gcc aag      96
Val Trp Lys Asp Ala Thr Thr Thr Leu Phe Cys Ala Ser Asp Ala Lys
            20                  25                  30 gcc tac gac acc gag gtg cac aac gtg tgg gcc acc cac gcg tgc gtg     144
Ala Tyr Asp Thr Glu Val His Asn Val Trp Ala Thr His Ala Cys Val
        35                  40                  45 ccc acc gac ccc aac ccc cag gag gtg gtg ctg ggc aac gtg acc gag     192
Pro Thr Asp Pro Asn Pro Gln Glu Val Val Leu Gly Asn Val Thr Glu
    50                  55                  60 aac ttc aac atg ggc aag aac aac atg gtg gag cag atg cac gag gat     240
Asn Phe Asn Met Gly Lys Asn Asn Met Val Glu Gln Met His Glu Asp
65                  70                  75                  80 atc                                                                 243
Ile

<210> SEQ ID NO 2
<211> LENGTH: 81
<212> TYPE: PRT
<213> ORGANISM: Human immunodeficiency virus

<400> SEQUENCE: 2

Ala Ser Ala Ala Asp Arg Leu Trp Val Thr Val Tyr Tyr Gly Val Pro
 1               5                  10                  15

Val Trp Lys Asp Ala Thr Thr Thr Leu Phe Cys Ala Ser Asp Ala Lys
            20                  25                  30

Ala Tyr Asp Thr Glu Val His Asn Val Trp Ala Thr His Ala Cys Val
        35                  40                  45

Pro Thr Asp Pro Asn Pro Gln Glu Val Val Leu Gly Asn Val Thr Glu
    50                  55                  60
```

```
Asn Phe Asn Met Gly Lys Asn Asn Met Val Glu Gln Met His Glu Asp
 65                  70                  75                  80

Ile
```

<210> SEQ ID NO 3
<211> LENGTH: 143
<212> TYPE: DNA
<213> ORGANISM: Human immunodeficiency virus
<220> FEATURE:
<221> NAME/KEY: CDS
<222> LOCATION: (1)..(141)

<400> SEQUENCE: 3

```
gat atc atc agc ctg tgg gac cag agc ctg aag ccc tgc gtg aag ctg      48
Asp Ile Ile Ser Leu Trp Asp Gln Ser Leu Lys Pro Cys Val Lys Leu
  1               5                  10                  15 acc ccc ctg tgc gtg acc ctg aac tgc acc aag ctg aag aac agc acc      96
Thr Pro Leu Cys Val Thr Leu Asn Cys Thr Lys Leu Lys Asn Ser Thr
             20                  25                  30 gac acc aac aac acc cgc tgg ggc acc cag gag atg aag aac tgc ag      143
Asp Thr Asn Asn Thr Arg Trp Gly Thr Gln Glu Met Lys Asn Cys
         35                  40                  45
```

<210> SEQ ID NO 4
<211> LENGTH: 47
<212> TYPE: PRT
<213> ORGANISM: Human immunodeficiency virus

<400> SEQUENCE: 4

```
Asp Ile Ile Ser Leu Trp Asp Gln Ser Leu Lys Pro Cys Val Lys Leu
  1               5                  10                  15

Thr Pro Leu Cys Val Thr Leu Asn Cys Thr Lys Leu Lys Asn Ser Thr
             20                  25                  30

Asp Thr Asn Asn Thr Arg Trp Gly Thr Gln Glu Met Lys Asn Cys
         35                  40                  45
```

<210> SEQ ID NO 5
<211> LENGTH: 132
<212> TYPE: DNA
<213> ORGANISM: Human immunodeficiency virus
<220> FEATURE:
<221> NAME/KEY: CDS
<222> LOCATION: (2)..(130)

<400> SEQUENCE: 5

```
c tgc agc ttc aac atc agc acc agc gtg cgc aac aag atg aag cgc gag   49
  Cys Ser Phe Asn Ile Ser Thr Ser Val Arg Asn Lys Met Lys Arg Glu
    1               5                  10                  15 tac gcc ctg ttc tac agc ctg gac atc gtg ccc atc gac aac gac aac     97
Tyr Ala Leu Phe Tyr Ser Leu Asp Ile Val Pro Ile Asp Asn Asp Asn
             20                  25                  30 acc agc tac cgc ctg cgc agc tgc aac aca tcg at                     132
Thr Ser Tyr Arg Leu Arg Ser Cys Asn Thr Ser
         35                  40
```

<210> SEQ ID NO 6
<211> LENGTH: 43
<212> TYPE: PRT
<213> ORGANISM: Human immunodeficiency virus

<400> SEQUENCE: 6

```
Cys Ser Phe Asn Ile Ser Thr Ser Val Arg Asn Lys Met Lys Arg Glu
  1               5                  10                  15
```

```
Tyr Ala Leu Phe Tyr Ser Leu Asp Ile Val Pro Ile Asp Asn Asp Asn
            20                  25                  30

Thr Ser Tyr Arg Leu Arg Ser Cys Asn Thr Ser
        35                  40

<210> SEQ ID NO 7
<211> LENGTH: 161
<212> TYPE: DNA
<213> ORGANISM: Human immunodeficiency virus
<220> FEATURE:
<221> NAME/KEY: CDS
<222> LOCATION: (2)..(160)

<400> SEQUENCE: 7 a tcg atc atc acc cag gcc tgc ccc aag gtg agc ttc gag ccc atc ccc          49
  Ser Ile Ile Thr Gln Ala Cys Pro Lys Val Ser Phe Glu Pro Ile Pro
    1               5                  10                  15 atc cac ttc tgc gcc ccc gcc ggc ttc gcc atc ctg aag tgc aac aac            97
Ile His Phe Cys Ala Pro Ala Gly Phe Ala Ile Leu Lys Cys Asn Asn
                20                  25                  30 aag acc ttc aac ggc acc ggc ccc tgc acc aac gtg agc acc gtg cag           145
Lys Thr Phe Asn Gly Thr Gly Pro Cys Thr Asn Val Ser Thr Val Gln
            35                  40                  45 tgc acc cac gga att c                                                     161
Cys Thr His Gly Ile
        50

<210> SEQ ID NO 8
<211> LENGTH: 53
<212> TYPE: PRT
<213> ORGANISM: Human immunodeficiency virus

<400> SEQUENCE: 8

Ser Ile Ile Thr Gln Ala Cys Pro Lys Val Ser Phe Glu Pro Ile Pro
  1               5                  10                  15

Ile His Phe Cys Ala Pro Ala Gly Phe Ala Ile Leu Lys Cys Asn Asn
                20                  25                  30

Lys Thr Phe Asn Gly Thr Gly Pro Cys Thr Asn Val Ser Thr Val Gln
            35                  40                  45

Cys Thr His Gly Ile
        50

<210> SEQ ID NO 9
<211> LENGTH: 254
<212> TYPE: DNA
<213> ORGANISM: Human immunodeficiency virus
<220> FEATURE:
<221> NAME/KEY: CDS
<222> LOCATION: (3)..(254)

<400> SEQUENCE: 9 ga att cgc ccc gtg gtg agc acc cag ctg ctg ctg aac ggc agc ctg            47
   Ile Arg Pro Val Val Ser Thr Gln Leu Leu Leu Asn Gly Ser Leu
     1               5                  10                  15 gcc gag gag gag gtg gtg atc aga tct gag aac ttc acc aac aac gcc           95
Ala Glu Glu Glu Val Val Ile Arg Ser Glu Asn Phe Thr Asn Asn Ala
                20                  25                  30 aag acc atc atc gtg cag ctg aac gag agc gtg gag atc aac tgc acc          143
Lys Thr Ile Ile Val Gln Leu Asn Glu Ser Val Glu Ile Asn Cys Thr
            35                  40                  45 cgc ccc aac aac aac acc cgc aag agc atc cac atc ggc cct ggc cgc          191
Arg Pro Asn Asn Asn Thr Arg Lys Ser Ile His Ile Gly Pro Gly Arg
        50                  55                  60
```

-continued

```
gcc ttc tac acc acc ggc gac atc atc ggc gac atc cgc cag gcc cac    239
Ala Phe Tyr Thr Thr Gly Asp Ile Ile Gly Asp Ile Arg Gln Ala His
 65                  70                  75 tgc aac atc tct aga                                                254
Cys Asn Ile Ser Arg
 80
```

<210> SEQ ID NO 10
<211> LENGTH: 84
<212> TYPE: PRT
<213> ORGANISM: Human immunodeficiency virus

<400> SEQUENCE: 10

```
Ile Arg Pro Val Val Ser Thr Gln Leu Leu Leu Asn Gly Ser Leu Ala
  1               5                  10                  15

Glu Glu Glu Val Val Ile Arg Ser Glu Asn Phe Thr Asn Asn Ala Lys
                 20                  25                  30

Thr Ile Ile Val Gln Leu Asn Glu Ser Val Glu Ile Asn Cys Thr Arg
             35                  40                  45

Pro Asn Asn Asn Thr Arg Lys Ser Ile His Ile Gly Pro Gly Arg Ala
     50                  55                  60

Phe Tyr Thr Thr Gly Asp Ile Ile Gly Asp Ile Arg Gln Ala His Cys
 65                  70                  75                  80

Asn Ile Ser Arg
```

<210> SEQ ID NO 11
<211> LENGTH: 92
<212> TYPE: DNA
<213> ORGANISM: Human immunodeficiency virus
<220> FEATURE:
<221> NAME/KEY: CDS
<222> LOCATION: (1)..(90)

<400> SEQUENCE: 11

```
tct aga acc aac tgg acc aac acc ctg aag cgc gtg gcc gag aag ctg    48
Ser Arg Thr Asn Trp Thr Asn Thr Leu Lys Arg Val Ala Glu Lys Leu
  1               5                  10                  15 cgc gag aag ttc aac aac acc acc atc gtg ttc aac cag agc tc        92
Arg Glu Lys Phe Asn Asn Thr Thr Ile Val Phe Asn Gln Ser
                 20                  25                  30
```

<210> SEQ ID NO 12
<211> LENGTH: 30
<212> TYPE: PRT
<213> ORGANISM: Human immunodeficiency virus

<400> SEQUENCE: 12

```
Ser Arg Thr Asn Trp Thr Asn Thr Leu Lys Arg Val Ala Glu Lys Leu
  1               5                  10                  15

Arg Glu Lys Phe Asn Asn Thr Thr Ile Val Phe Asn Gln Ser
                 20                  25                  30
```

<210> SEQ ID NO 13
<211> LENGTH: 130
<212> TYPE: DNA
<213> ORGANISM: Human immunodeficiency virus
<220> FEATURE:
<221> NAME/KEY: CDS
<222> LOCATION: (2)..(130)

<400> SEQUENCE: 13

```
g agc tcc ggc ggc gac ccc gag atc gtg atg cac agc ttc aac tgc ggc    49
```

-continued

```
Ser Ser Gly Gly Asp Pro Glu Ile Val Met His Ser Phe Asn Cys Gly
 1               5                  10                  15 ggc gag ttc ttc tac tgc aac acc acc cag ctg ttc aac agc acc tgg      97
Gly Glu Phe Phe Tyr Cys Asn Thr Thr Gln Leu Phe Asn Ser Thr Trp
                 20                  25                  30 aac gag acc aac agc gag ggc aac atc act agt                          130
Asn Glu Thr Asn Ser Glu Gly Asn Ile Thr Ser
         35                  40
```

<210> SEQ ID NO 14
<211> LENGTH: 43
<212> TYPE: PRT
<213> ORGANISM: Human immunodeficiency virus

<400> SEQUENCE: 14

```
Ser Ser Gly Gly Asp Pro Glu Ile Val Met His Ser Phe Asn Cys Gly
 1               5                  10                  15

Gly Glu Phe Phe Tyr Cys Asn Thr Thr Gln Leu Phe Asn Ser Thr Trp
                 20                  25                  30

Asn Glu Thr Asn Ser Glu Gly Asn Ile Thr Ser
         35                  40
```

<210> SEQ ID NO 15
<211> LENGTH: 164
<212> TYPE: DNA
<213> ORGANISM: Human immunodeficiency virus
<220> FEATURE:
<221> NAME/KEY: CDS
<222> LOCATION: (1)..(162)

<400> SEQUENCE: 15

```
act agt ggc acc atc acc ctg ccc tgc cgc atc aag cag atc atc aac      48
Thr Ser Gly Thr Ile Thr Leu Pro Cys Arg Ile Lys Gln Ile Ile Asn
 1               5                  10                  15 atg tgg cag gag gtg ggc aag gcc atg tac gcc ccc ccc atc ggc ggc      96
Met Trp Gln Glu Val Gly Lys Ala Met Tyr Ala Pro Pro Ile Gly Gly
                 20                  25                  30 cag atc aag tgc ctg agc aac atc acc ggc ctg ctg ctg acc cgc gac     144
Gln Ile Lys Cys Leu Ser Asn Ile Thr Gly Leu Leu Leu Thr Arg Asp
         35                  40                  45 ggc ggc agc gac aac tcg ag                                           164
Gly Gly Ser Asp Asn Ser
     50
```

<210> SEQ ID NO 16
<211> LENGTH: 54
<212> TYPE: PRT
<213> ORGANISM: Human immunodeficiency virus

<400> SEQUENCE: 16

```
Thr Ser Gly Thr Ile Thr Leu Pro Cys Arg Ile Lys Gln Ile Ile Asn
 1               5                  10                  15

Met Trp Gln Glu Val Gly Lys Ala Met Tyr Ala Pro Pro Ile Gly Gly
                 20                  25                  30

Gln Ile Lys Cys Leu Ser Asn Ile Thr Gly Leu Leu Leu Thr Arg Asp
         35                  40                  45

Gly Gly Ser Asp Asn Ser
     50
```

<210> SEQ ID NO 17
<211> LENGTH: 200
<212> TYPE: DNA

-continued

```
<213> ORGANISM: Human immunodeficiency virus
<220> FEATURE:
<221> NAME/KEY: CDS
<222> LOCATION: (2)..(100)

<400> SEQUENCE: 17 c tcg agc agc ggc aag gag att ttc cgc ccc ggc ggc ggc gac atg cgc      49
  Ser Ser Ser Gly Lys Glu Ile Phe Arg Pro Gly Gly Gly Asp Met Arg
   1               5                  10                  15 gac aac tgg cgc agc gag ctg tac aag tac aag gtg gtg aag atc gag        97
Asp Asn Trp Arg Ser Glu Leu Tyr Lys Tyr Lys Val Val Lys Ile Glu
            20                  25                  30 ccc ctgggcatcg cccccaccaa ggccaagcgc cgcgtggtgc agcgcgagaa            150
Pro gcgcgccgtg ggcatcggcg ctatgttcct cggcttcctg ggcgctgcag                200

<210> SEQ ID NO 18
<211> LENGTH: 33
<212> TYPE: PRT
<213> ORGANISM: Human immunodeficiency virus

<400> SEQUENCE: 18

Ser Ser Ser Gly Lys Glu Ile Phe Arg Pro Gly Gly Gly Asp Met Arg
 1               5                  10                  15

Asp Asn Trp Arg Ser Glu Leu Tyr Lys Tyr Lys Val Val Lys Ile Glu
            20                  25                  30

Pro

<210> SEQ ID NO 19
<211> LENGTH: 212
<212> TYPE: DNA
<213> ORGANISM: Human immunodeficiency virus
<220> FEATURE:
<221> NAME/KEY: CDS
<222> LOCATION: (2)..(157)

<400> SEQUENCE: 19 c tcg agc agc ggc aag gag att ttc cgc ccc ggc ggc ggc gac atg cgc      49
  Ser Ser Ser Gly Lys Glu Ile Phe Arg Pro Gly Gly Gly Asp Met Arg
   1               5                  10                  15 gac aac tgg cgc agc gag ctg tac aag tac aag gtg gtg aag atc gag        97
Asp Asn Trp Arg Ser Glu Leu Tyr Lys Tyr Lys Val Val Lys Ile Glu
            20                  25                  30 ccc ctg ggc atc gcc ccc acc aag gcc aag cgc cgc gtg gtg cag cgc       145
Pro Leu Gly Ile Ala Pro Thr Lys Ala Lys Arg Arg Val Val Gln Arg
        35                  40                  45 gag aag cgc gcc tagggcatcg gcgctatgtt cctcggcttc ctgggcgctg           197
Glu Lys Arg Ala
     50 cagcccgggg gatcc                                                      212

<210> SEQ ID NO 20
<211> LENGTH: 52
<212> TYPE: PRT
<213> ORGANISM: Human immunodeficiency virus

<400> SEQUENCE: 20

Ser Ser Ser Gly Lys Glu Ile Phe Arg Pro Gly Gly Gly Asp Met Arg
 1               5                  10                  15

Asp Asn Trp Arg Ser Glu Leu Tyr Lys Tyr Lys Val Val Lys Ile Glu
            20                  25                  30
```

```
Pro Leu Gly Ile Ala Pro Thr Lys Ala Lys Arg Arg Val Val Gln Arg
        35                  40                  45

Glu Lys Arg Ala
        50

<210> SEQ ID NO 21
<211> LENGTH: 200
<212> TYPE: DNA
<213> ORGANISM: Human immunodeficiency virus
<220> FEATURE:
<221> NAME/KEY: CDS
<222> LOCATION: (2)..(199)

<400> SEQUENCE: 21 c tcg agc agc ggc aag gag att ttc cgc ccc ggc ggc gac atg cgc         49
  Ser Ser Ser Gly Lys Glu Ile Phe Arg Pro Gly Gly Gly Asp Met Arg
   1               5                  10                  15 gac aac tgg cgc agc gag ctg tac aag tac aag gtg gtg aag atc gag      97
Asp Asn Trp Arg Ser Glu Leu Tyr Lys Tyr Lys Val Val Lys Ile Glu
                20                  25                  30 ccc ctg ggc atc gcc ccc acc aag gcc aag cgc cgc gtg gtg cag cgc     145
Pro Leu Gly Ile Ala Pro Thr Lys Ala Lys Arg Arg Val Val Gln Arg
        35                  40                  45 gag aag agc gcc gtg ggc atc ggc gct atg ttc ctc ggc ttc ctg ggc    193
Glu Lys Ser Ala Val Gly Ile Gly Ala Met Phe Leu Gly Phe Leu Gly
    50                   55                  60 gct gca g                                                           200
Ala Ala
 65

<210> SEQ ID NO 22
<211> LENGTH: 66
<212> TYPE: PRT
<213> ORGANISM: Human immunodeficiency virus

<400> SEQUENCE: 22

Ser Ser Ser Gly Lys Glu Ile Phe Arg Pro Gly Gly Gly Asp Met Arg
 1               5                  10                  15

Asp Asn Trp Arg Ser Glu Leu Tyr Lys Tyr Lys Val Val Lys Ile Glu
                20                  25                  30

Pro Leu Gly Ile Ala Pro Thr Lys Ala Lys Arg Arg Val Val Gln Arg
        35                  40                  45

Glu Lys Ser Ala Val Gly Ile Gly Ala Met Phe Leu Gly Phe Leu Gly
    50                   55                  60

Ala Ala
 65

<210> SEQ ID NO 23
<211> LENGTH: 178
<212> TYPE: DNA
<213> ORGANISM: Human immunodeficiency virus
<220> FEATURE:
<221> NAME/KEY: CDS
<222> LOCATION: (2)..(175)

<400> SEQUENCE: 23 c tgc agg cag cac cat ggg cgc cgc cag cct gac cct gac cgt gca ggc    49
  Cys Arg Gln His His Gly Arg Arg Gln Pro Asp Pro Asp Arg Ala Gly
   1               5                  10                  15 ccg cca gct gct gag cgg cat cgt gca gca gca gaa caa cct gct gcg      97
Pro Pro Ala Ala Glu Arg His Arg Ala Ala Ala Glu Gln Pro Ala Ala
                20                  25                  30
```

```
cgc cat cga ggc cca gca gca cct gct cca gct gac cgt gtg ggg cat    145
Arg His Arg Gly Pro Ala Ala Pro Ala Pro Ala Asp Arg Val Gly His
        35                  40                  45 caa gca gct cca ggc ccg cgt gct ggc tct aga                        178
Gln Ala Ala Pro Gly Pro Arg Ala Gly Ser
 50                  55
```

<210> SEQ ID NO 24
<211> LENGTH: 58
<212> TYPE: PRT
<213> ORGANISM: Human immunodeficiency virus

<400> SEQUENCE: 24

```
Cys Arg Gln His His Gly Arg Arg Gln Pro Asp Pro Asp Arg Ala Gly
 1               5                  10                  15

Pro Pro Ala Ala Glu Arg His Arg Ala Ala Ala Glu Gln Pro Ala Ala
                20                  25                  30

Arg His Arg Gly Pro Ala Ala Pro Ala Pro Ala Asp Arg Val Gly His
            35                  40                  45

Gln Ala Ala Pro Gly Pro Arg Ala Gly Ser
 50                  55
```

<210> SEQ ID NO 25
<211> LENGTH: 178
<212> TYPE: DNA
<213> ORGANISM: Human immunodeficiency virus
<220> FEATURE:
<221> NAME/KEY: CDS
<222> LOCATION: (2)..(175)

<400> SEQUENCE: 25

```
c tgc agg cag cac cat ggg cgc cgc cag cct gac cct gac cgt gca ggc   49
  Cys Arg Gln His His Gly Arg Arg Gln Pro Asp Pro Asp Arg Ala Gly
   1               5                  10                  15 ccg cca gct gct gag cgg cat cgt gca gca gca gaa caa cct gct gcg    97
Pro Pro Ala Ala Glu Arg His Arg Ala Ala Ala Glu Gln Pro Ala Ala
                20                  25                  30 cgc cat cga ggc cca gca gca cct gct cca gct gac cgt gtg ggg cat   145
Arg His Arg Gly Pro Ala Ala Pro Ala Pro Ala Asp Arg Val Gly His
            35                  40                  45 caa gca gtg ctg cgg ccg cgt gct ggc tct aga                       178
Gln Ala Val Leu Arg Pro Arg Ala Gly Ser
 50                  55
```

<210> SEQ ID NO 26
<211> LENGTH: 58
<212> TYPE: PRT
<213> ORGANISM: Human immunodeficiency virus

<400> SEQUENCE: 26

```
Cys Arg Gln His His Gly Arg Arg Gln Pro Asp Pro Asp Arg Ala Gly
 1               5                  10                  15

Pro Pro Ala Ala Glu Arg His Arg Ala Ala Ala Glu Gln Pro Ala Ala
                20                  25                  30

Arg His Arg Gly Pro Ala Ala Pro Ala Pro Ala Asp Arg Val Gly His
            35                  40                  45

Gln Ala Val Leu Arg Pro Arg Ala Gly Ser
 50                  55
```

<210> SEQ ID NO 27
<211> LENGTH: 77
<212> TYPE: DNA

<213> ORGANISM: Human immunodeficiency virus
<220> FEATURE:
<221> NAME/KEY: CDS
<222> LOCATION: (1)..(75)

<400> SEQUENCE: 27

```
tct aga gcg cta cct cca gga cca gcg ctt cct ggg cat gtg ggg ctg      48
Ser Arg Ala Leu Pro Pro Gly Pro Ala Leu Pro Gly His Val Gly Leu
 1               5                  10                  15 ctc cgg caa gct gat ctg cac cac ggc cg                               77
Leu Arg Gln Ala Asp Leu His His Gly
            20                  25
```

<210> SEQ ID NO 28
<211> LENGTH: 25
<212> TYPE: PRT
<213> ORGANISM: Human immunodeficiency virus

<400> SEQUENCE: 28

```
Ser Arg Ala Leu Pro Pro Gly Pro Ala Leu Pro Gly His Val Gly Leu
 1               5                  10                  15

Leu Arg Gln Ala Asp Leu His His Gly
            20                  25
```

<210> SEQ ID NO 29
<211> LENGTH: 190
<212> TYPE: DNA
<213> ORGANISM: Human immunodeficiency virus
<220> FEATURE:
<221> NAME/KEY: CDS
<222> LOCATION: (2)..(190)

<400> SEQUENCE: 29

```
c ggc cgt gcc ctg gaa cgc cag ctg gag caa caa gaa cct gag cca gat    49
  Gly Arg Ala Leu Glu Arg Gln Leu Glu Gln Gln Glu Pro Glu Pro Asp
   1               5                  10                  15 ttg gga caa cat gac ctg gat gga gtg gga gcg cga gat cag caa cta      97
Leu Gly Gln His Asp Leu Asp Gly Val Gly Ala Arg Asp Gln Gln Leu
                20                  25                  30 cac cga gat cat cta cag cct gat cga gga gag cca gaa cca gca gga     145
His Arg Asp His Leu Gln Pro Asp Arg Gly Glu Pro Glu Pro Ala Gly
             35                  40                  45 gaa gaa cga gct gga cct gct cca gct gga caa gtg ggc aag ctt         190
Glu Glu Arg Ala Gly Pro Ala Pro Ala Gly Gln Val Gly Lys Leu
     50                  55                  60
```

<210> SEQ ID NO 30
<211> LENGTH: 63
<212> TYPE: PRT
<213> ORGANISM: Human immunodeficiency virus

<400> SEQUENCE: 30

```
Gly Arg Ala Leu Glu Arg Gln Leu Glu Gln Gln Glu Pro Glu Pro Asp
 1               5                  10                  15

Leu Gly Gln His Asp Leu Asp Gly Val Gly Ala Arg Asp Gln Gln Leu
            20                  25                  30

His Arg Asp His Leu Gln Pro Asp Arg Gly Glu Pro Glu Pro Ala Gly
         35                  40                  45

Glu Glu Arg Ala Gly Pro Ala Pro Ala Gly Gln Val Gly Lys Leu
     50                  55                  60
```

<210> SEQ ID NO 31
<211> LENGTH: 177

```
<212> TYPE: DNA
<213> ORGANISM: Human immunodeficiency virus
<220> FEATURE:
<221> NAME/KEY: CDS
<222> LOCATION: (2)..(175)

<400> SEQUENCE: 31 a agc ttg tgg aac tgg ttc aac atc acc aac tgg ctg tgg tac atc aag      49
  Ser Leu Trp Asn Trp Phe Asn Ile Thr Asn Trp Leu Trp Tyr Ile Lys
    1               5                  10                  15 att ttc atc atg atc gtg ggc ggc ctg atc ggc ctg cgc atc gtg ttc        97
Ile Phe Ile Met Ile Val Gly Gly Leu Ile Gly Leu Arg Ile Val Phe
             20                  25                  30 acc gtg ctg agc atc gtg aac cgc gtg cgc cag ggc tac agc ccc ctg       145
Thr Val Leu Ser Ile Val Asn Arg Val Arg Gln Gly Tyr Ser Pro Leu
         35                  40                  45 agc ttc cag acc cgc ctg ccc gtg ccc cgc gg                            177
Ser Phe Gln Thr Arg Leu Pro Val Pro Arg
     50                  55

<210> SEQ ID NO 32
<211> LENGTH: 58
<212> TYPE: PRT
<213> ORGANISM: Human immunodeficiency virus

<400> SEQUENCE: 32

Ser Leu Trp Asn Trp Phe Asn Ile Thr Asn Trp Leu Trp Tyr Ile Lys
  1               5                  10                  15

Ile Phe Ile Met Ile Val Gly Gly Leu Ile Gly Leu Arg Ile Val Phe
             20                  25                  30

Thr Val Leu Ser Ile Val Asn Arg Val Arg Gln Gly Tyr Ser Pro Leu
         35                  40                  45

Ser Phe Gln Thr Arg Leu Pro Val Pro Arg
     50                  55

<210> SEQ ID NO 33
<211> LENGTH: 140
<212> TYPE: DNA
<213> ORGANISM: Human immunodeficiency virus
<220> FEATURE:
<221> NAME/KEY: CDS
<222> LOCATION: (2)..(139)

<400> SEQUENCE: 33 c cgc ggc ccc gac cgc ccc gag ggc atc gag gag gag ggc ggc gag cgc      49
  Arg Gly Pro Asp Arg Pro Glu Gly Ile Glu Glu Glu Gly Gly Glu Arg
    1               5                  10                  15 gac cgc gac cgc agc acc cgc ctg gtg acc ggc ttc ctg ccc ctg atc        97
Asp Arg Asp Arg Ser Thr Arg Leu Val Thr Gly Phe Leu Pro Leu Ile
             20                  25                  30 tgg gac gac ctg cgc agc ctg ttc ctg ttc agc tac cat cga t             140
Trp Asp Asp Leu Arg Ser Leu Phe Leu Phe Ser Tyr His Arg
         35                  40                  45

<210> SEQ ID NO 34
<211> LENGTH: 46
<212> TYPE: PRT
<213> ORGANISM: Human immunodeficiency virus

<400> SEQUENCE: 34

Arg Gly Pro Asp Arg Pro Glu Gly Ile Glu Glu Glu Gly Gly Glu Arg
  1               5                  10                  15

Asp Arg Asp Arg Ser Thr Arg Leu Val Thr Gly Phe Leu Pro Leu Ile
```

```
                    20                  25                  30

Trp Asp Asp Leu Arg Ser Leu Phe Leu Phe Ser Tyr His Arg
        35                  40                  45

<210> SEQ ID NO 35
<211> LENGTH: 129
<212> TYPE: DNA
<213> ORGANISM: Human immunodeficiency virus
<220> FEATURE:
<221> NAME/KEY: CDS
<222> LOCATION: (3)..(128)

<400> SEQUENCE: 35 at cga ttg cgc gac ctg ctg ctg atc gtg gcc cgc atc gtg gag ctg        47
   Arg Leu Arg Asp Leu Leu Leu Ile Val Ala Arg Ile Val Glu Leu
    1               5                  10                  15 ctg ggc cgg cgc ggc tgg gag atc ctg aag tac tgg tgg aac ctg ctc       95
Leu Gly Arg Arg Gly Trp Glu Ile Leu Lys Tyr Trp Trp Asn Leu Leu
                20                  25                  30 cag tac tgg agc cag gag ctg aag aac tct gca g                        129
Gln Tyr Trp Ser Gln Glu Leu Lys Asn Ser Ala
        35                  40

<210> SEQ ID NO 36
<211> LENGTH: 42
<212> TYPE: PRT
<213> ORGANISM: Human immunodeficiency virus

<400> SEQUENCE: 36

Arg Leu Arg Asp Leu Leu Leu Ile Val Ala Arg Ile Val Glu Leu Leu
 1               5                  10                  15

Gly Arg Arg Gly Trp Glu Ile Leu Lys Tyr Trp Trp Asn Leu Leu Gln
            20                  25                  30

Tyr Trp Ser Gln Glu Leu Lys Asn Ser Ala
        35                  40

<210> SEQ ID NO 37
<211> LENGTH: 114
<212> TYPE: DNA
<213> ORGANISM: Human immunodeficiency virus
<220> FEATURE:
<221> NAME/KEY: CDS
<222> LOCATION: (3)..(113)

<400> SEQUENCE: 37 ct gca gtg agc ctg ctg aac gcc acc gcc atc gcc gtg gcc gag ggc        47
   Ala Val Ser Leu Leu Asn Ala Thr Ala Ile Ala Val Ala Glu Gly
    1               5                  10                  15 acc gac cgc gtg atc gag gtg gtg cag cgc atc tgg cgc ggc atc ctg       95
Thr Asp Arg Val Ile Glu Val Val Gln Arg Ile Trp Arg Gly Ile Leu
                20                  25                  30 cac atc ccc acc cga att c                                            114
His Ile Pro Thr Arg Ile
        35

<210> SEQ ID NO 38
<211> LENGTH: 37
<212> TYPE: PRT
<213> ORGANISM: Human immunodeficiency virus

<400> SEQUENCE: 38

Ala Val Ser Leu Leu Asn Ala Thr Ala Ile Ala Val Ala Glu Gly Thr
 1               5                  10                  15
```

```
Asp Arg Val Ile Glu Val Val Gln Arg Ile Trp Arg Gly Ile Leu His
            20                  25                  30
Ile Pro Thr Arg Ile
        35

<210> SEQ ID NO 39
<211> LENGTH: 41
<212> TYPE: DNA
<213> ORGANISM: Human immunodeficiency virus
<220> FEATURE:
<221> NAME/KEY: CDS
<222> LOCATION: (3)..(32)

<400> SEQUENCE: 39 ga att cgc cag ggc ttc gag cgc gcc ctg ctg taaggatcc              41
   Ile Arg Gln Gly Phe Glu Arg Ala Leu Leu
    1               5                  10

<210> SEQ ID NO 40
<211> LENGTH: 10
<212> TYPE: PRT
<213> ORGANISM: Human immunodeficiency virus

<400> SEQUENCE: 40

Ile Arg Gln Gly Phe Glu Arg Ala Leu Leu
 1               5                  10

<210> SEQ ID NO 41
<211> LENGTH: 506
<212> TYPE: DNA
<213> ORGANISM: Human immunodeficiency virus
<220> FEATURE:
<221> NAME/KEY: CDS
<222> LOCATION: (1)..(504)

<400> SEQUENCE: 41 gct agc gcg gcc gac cgc ctg tgg gtg acc gtg tac tac ggc gtg ccc     48
Ala Ser Ala Ala Asp Arg Leu Trp Val Thr Val Tyr Tyr Gly Val Pro
 1               5                  10                  15 gtg tgg aag gac gcc acc acc acc ctg ttc tgc gcc agc gac gcc aag     96
Val Trp Lys Asp Ala Thr Thr Thr Leu Phe Cys Ala Ser Asp Ala Lys
            20                  25                  30 gcc tac gac acc gag gtg cac aac gtg tgg gcc acc cac gcg tgc gtg    144
Ala Tyr Asp Thr Glu Val His Asn Val Trp Ala Thr His Ala Cys Val
        35                  40                  45 ccc acc gac ccc aac ccc cag gag gtg gtg ctg ggc aac gtg acc gag    192
Pro Thr Asp Pro Asn Pro Gln Glu Val Val Leu Gly Asn Val Thr Glu
    50                  55                  60 aac ttc aac atg ggc aag aac aac atg gtg gag cag atg cac gag gat    240
Asn Phe Asn Met Gly Lys Asn Asn Met Val Glu Gln Met His Glu Asp
 65                  70                  75                  80 atc atc agc ctg tgg gac cag agc ctg aag ccc tgc gtg aag ctg acc    288
Ile Ile Ser Leu Trp Asp Gln Ser Leu Lys Pro Cys Val Lys Leu Thr
                85                  90                  95 ccc ctg tgc gtg acc ctg aac tgc acc aag ctg aag aac agc acc gac    336
Pro Leu Cys Val Thr Leu Asn Cys Thr Lys Leu Lys Asn Ser Thr Asp
            100                 105                 110 acc aac aac acc cgc tgg ggc acc cag gag atg aag aac tgc agc ttc    384
Thr Asn Asn Thr Arg Trp Gly Thr Gln Glu Met Lys Asn Cys Ser Phe
        115                 120                 125 aac atc agc acc agc gtg cgc aac aag atg aag cgc gag tac gcc ctg    432
Asn Ile Ser Thr Ser Val Arg Asn Lys Met Lys Arg Glu Tyr Ala Leu
    130                 135                 140
```

```
ttc tac agc ctg gac atc gtg ccc atc gac aac gac aac acc agc tac      480
Phe Tyr Ser Leu Asp Ile Val Pro Ile Asp Asn Asp Asn Thr Ser Tyr
145                 150                 155                 160 cgc ctg cgc agc tgc aac aca tcg at                                   506
Arg Leu Arg Ser Cys Asn Thr Ser
                165

<210> SEQ ID NO 42
<211> LENGTH: 168
<212> TYPE: PRT
<213> ORGANISM: Human immunodeficiency virus

<400> SEQUENCE: 42

Ala Ser Ala Ala Asp Arg Leu Trp Val Thr Val Tyr Tyr Gly Val Pro
1               5                   10                  15

Val Trp Lys Asp Ala Thr Thr Thr Leu Phe Cys Ala Ser Asp Ala Lys
                20                  25                  30

Ala Tyr Asp Thr Glu Val His Asn Val Trp Ala Thr His Ala Cys Val
            35                  40                  45

Pro Thr Asp Pro Asn Pro Gln Glu Val Val Leu Gly Asn Val Thr Glu
        50                  55                  60

Asn Phe Asn Met Gly Lys Asn Asn Met Val Glu Gln Met His Glu Asp
65                  70                  75                  80

Ile Ile Ser Leu Trp Asp Gln Ser Leu Lys Pro Cys Val Lys Leu Thr
                85                  90                  95

Pro Leu Cys Val Thr Leu Asn Cys Thr Lys Leu Lys Asn Ser Thr Asp
                100                 105                 110

Thr Asn Asn Thr Arg Trp Gly Thr Gln Glu Met Lys Asn Cys Ser Phe
            115                 120                 125

Asn Ile Ser Thr Ser Val Arg Asn Lys Met Lys Arg Glu Tyr Ala Leu
        130                 135                 140

Phe Tyr Ser Leu Asp Ile Val Pro Ile Asp Asn Asp Asn Thr Ser Tyr
145                 150                 155                 160

Arg Leu Arg Ser Cys Asn Thr Ser
                165

<210> SEQ ID NO 43
<211> LENGTH: 374
<212> TYPE: DNA
<213> ORGANISM: Human immunodeficiency virus
<220> FEATURE:
<221> NAME/KEY: CDS
<222> LOCATION: (1)..(372)

<400> SEQUENCE: 43 tct aga acc aac tgg acc aac acc ctg aag cgc gtg gcc gag aag ctg      48
Ser Arg Thr Asn Trp Thr Asn Thr Leu Lys Arg Val Ala Glu Lys Leu
1               5                   10                  15 cgc gag aag ttc aac aac acc acc atc gtg ttc aac cag agc tcc ggc      96
Arg Glu Lys Phe Asn Asn Thr Thr Ile Val Phe Asn Gln Ser Ser Gly
                20                  25                  30 ggc gac ccc gag atc gtg atg cac agc ttc aac tgc ggc ggc gag ttc     144
Gly Asp Pro Glu Ile Val Met His Ser Phe Asn Cys Gly Gly Glu Phe
            35                  40                  45 ttc tac tgc aac acc acc cag ctg ttc aac agc acc tgg aac gag acc     192
Phe Tyr Cys Asn Thr Thr Gln Leu Phe Asn Ser Thr Trp Asn Glu Thr
        50                  55                  60 aac agc gag ggc aac atc act agt ggc acc atc acc ctg ccc tgc cgc     240
Asn Ser Glu Gly Asn Ile Thr Ser Gly Thr Ile Thr Leu Pro Cys Arg
65                  70                  75                  80
```

-continued

| | | |
|---|---|---|
| atc aag cag atc atc aac atg tgg cag gag gtg ggc aag gcc atg tac<br>Ile Lys Gln Ile Ile Asn Met Trp Gln Glu Val Gly Lys Ala Met Tyr<br>85                              90                            95 | 288 |
| gcc ccc ccc atc ggc ggc cag atc aag tgc ctg agc aac atc acc ggc<br>Ala Pro Pro Ile Gly Gly Gln Ile Lys Cys Leu Ser Asn Ile Thr Gly<br>100                         105                      110 | 336 |
| ctg ctg ctg acc cgc gac ggc ggc agc gac aac tcg ag<br>Leu Leu Leu Thr Arg Asp Gly Gly Ser Asp Asn Ser<br>115                      120 | 374 |

<210> SEQ ID NO 44
<211> LENGTH: 124
<212> TYPE: PRT
<213> ORGANISM: Human immunodeficiency virus

<400> SEQUENCE: 44

Ser Arg Thr Asn Trp Thr Asn Thr Leu Lys Arg Val Ala Glu Lys Leu
1               5                   10                  15

Arg Glu Lys Phe Asn Asn Thr Thr Ile Val Phe Asn Gln Ser Ser Gly
                20                  25                  30

Gly Asp Pro Glu Ile Val Met His Ser Phe Asn Cys Gly Gly Glu Phe
            35                  40                  45

Phe Tyr Cys Asn Thr Thr Gln Leu Phe Asn Ser Thr Trp Asn Glu Thr
        50                  55                  60

Asn Ser Glu Gly Asn Ile Thr Ser Gly Thr Ile Thr Leu Pro Cys Arg
65                  70                  75                  80

Ile Lys Gln Ile Ile Asn Met Trp Gln Glu Val Gly Lys Ala Met Tyr
                85                  90                  95

Ala Pro Pro Ile Gly Gly Gln Ile Lys Cys Leu Ser Asn Ile Thr Gly
            100                 105                 110

Leu Leu Leu Thr Arg Asp Gly Gly Ser Asp Asn Ser
        115                 120

<210> SEQ ID NO 45
<211> LENGTH: 1277
<212> TYPE: DNA
<213> ORGANISM: Human immunodeficiency virus
<220> FEATURE:
<221> NAME/KEY: CDS
<222> LOCATION: (1)..(1275)

<400> SEQUENCE: 45

| | | |
|---|---|---|
| gct agc gcg gcc gac cgc ctg tgg gtg acc gtg tac tac ggc gtg ccc<br>Ala Ser Ala Ala Asp Arg Leu Trp Val Thr Val Tyr Tyr Gly Val Pro<br>1                  5                      10                      15 | 48 |
| gtg tgg aag gac gcc acc acc acc ctg ttc tgc gcc agc gac gcc aag<br>Val Trp Lys Asp Ala Thr Thr Thr Leu Phe Cys Ala Ser Asp Ala Lys<br>                 20                      25                      30 | 96 |
| gcc tac gac acc gag gtg cac aac gtg tgg gcc acc cac gcg tgc gtg<br>Ala Tyr Asp Thr Glu Val His Asn Val Trp Ala Thr His Ala Cys Val<br>            35                      40                      45 | 144 |
| ccc acc gac ccc aac ccc cag gag gtg gtg ctg ggc aac gtg acc gag<br>Pro Thr Asp Pro Asn Pro Gln Glu Val Val Leu Gly Asn Val Thr Glu<br>       50                      55                      60 | 192 |
| aac ttc aac atg ggc aag aac aac atg gtg gag cag atg cac gag gat<br>Asn Phe Asn Met Gly Lys Asn Asn Met Val Glu Gln Met His Glu Asp<br>65                  70                      75                      80 | 240 |
| atc atc agc ctg tgg gac cag agc ctg aag ccc tgc gtg aag ctg acc<br>Ile Ile Ser Leu Trp Asp Gln Ser Leu Lys Pro Cys Val Lys Leu Thr<br>                 85                      90                      95 | 288 |

-continued

```
ccc ctg tgc gtg acc ctg aac tgc acc aag ctg aag aac agc acc gac    336
Pro Leu Cys Val Thr Leu Asn Cys Thr Lys Leu Lys Asn Ser Thr Asp
            100                 105                 110 acc aac aac acc cgc tgg ggc acc cag gag atg aag aac tgc agc ttc    384
Thr Asn Asn Thr Arg Trp Gly Thr Gln Glu Met Lys Asn Cys Ser Phe
                115                 120                 125 aac atc agc acc agc gtg cgc aac aag atg aag cgc gag tac gcc ctg    432
Asn Ile Ser Thr Ser Val Arg Asn Lys Met Lys Arg Glu Tyr Ala Leu
    130                 135                 140 ttc tac agc ctg gac atc gtg ccc atc gac aac gac aac acc agc tac    480
Phe Tyr Ser Leu Asp Ile Val Pro Ile Asp Asn Asp Asn Thr Ser Tyr
145                 150                 155                 160 cgc ctg cgc agc tgc aac aca tcg atc atc acc cag gcc tgc ccc aag    528
Arg Leu Arg Ser Cys Asn Thr Ser Ile Ile Thr Gln Ala Cys Pro Lys
                165                 170                 175 gtg agc ttc gag ccc atc ccc atc cac ttc tgc gcc ccc gcc ggc ttc    576
Val Ser Phe Glu Pro Ile Pro Ile His Phe Cys Ala Pro Ala Gly Phe
                180                 185                 190 gcc atc ctg aag tgc aac aac aag acc ttc aac ggc acc ggc ccc tgc    624
Ala Ile Leu Lys Cys Asn Asn Lys Thr Phe Asn Gly Thr Gly Pro Cys
    195                 200                 205 acc aac gtg agc acc gtg cag tgc acc cac gga att cgc ccc gtg gtg    672
Thr Asn Val Ser Thr Val Gln Cys Thr His Gly Ile Arg Pro Val Val
210                 215                 220 agc acc cag ctg ctg ctg aac ggc agc ctg gcc gag gag gag gtg gtg    720
Ser Thr Gln Leu Leu Leu Asn Gly Ser Leu Ala Glu Glu Glu Val Val
225                 230                 235                 240 atc aga tct gag aac ttc acc aac aac gcc aag acc atc atc gtg cag    768
Ile Arg Ser Glu Asn Phe Thr Asn Asn Ala Lys Thr Ile Ile Val Gln
                245                 250                 255 ctg aac gag agc gtg gag atc aac tgc acc cgc ccc aac aac aac acc    816
Leu Asn Glu Ser Val Glu Ile Asn Cys Thr Arg Pro Asn Asn Asn Thr
                260                 265                 270 cgc aag agc atc cac atc ggc cct ggc cgc gcc ttc tac acc acc ggc    864
Arg Lys Ser Ile His Ile Gly Pro Gly Arg Ala Phe Tyr Thr Thr Gly
    275                 280                 285 gac atc atc ggc gac atc cgc cag gcc cac tgc aac atc tct aga acc    912
Asp Ile Ile Gly Asp Ile Arg Gln Ala His Cys Asn Ile Ser Arg Thr
290                 295                 300 aac tgg acc aac acc ctg aag cgc gtg gcc gag aag ctg cgc gag aag    960
Asn Trp Thr Asn Thr Leu Lys Arg Val Ala Glu Lys Leu Arg Glu Lys
305                 310                 315                 320 ttc aac aac acc acc atc gtg ttc aac cag agc tcc ggc ggc gac ccc   1008
Phe Asn Asn Thr Thr Ile Val Phe Asn Gln Ser Ser Gly Gly Asp Pro
                325                 330                 335 gag atc gtg atg cac agc ttc aac tgc ggc ggc gag ttc ttc tac tgc   1056
Glu Ile Val Met His Ser Phe Asn Cys Gly Gly Glu Phe Phe Tyr Cys
                340                 345                 350 aac acc acc cag ctg ttc aac agc acc tgg aac gag acc aac agc gag   1104
Asn Thr Thr Gln Leu Phe Asn Ser Thr Trp Asn Glu Thr Asn Ser Glu
    355                 360                 365 ggc aac atc act agt ggc acc atc acc ctg ccc tgc cgc atc aag cag   1152
Gly Asn Ile Thr Ser Gly Thr Ile Thr Leu Pro Cys Arg Ile Lys Gln
370                 375                 380 atc atc aac atg tgg cag gag gtg ggc aag gcc atg tac gcc ccc ccc   1200
Ile Ile Asn Met Trp Gln Glu Val Gly Lys Ala Met Tyr Ala Pro Pro
385                 390                 395                 400 atc ggc ggc cag atc aag tgc ctg agc aac atc acc ggc ctg ctg ctg   1248
Ile Gly Gly Gln Ile Lys Cys Leu Ser Asn Ile Thr Gly Leu Leu Leu
```

-continued

```
           405             410             415
acc cgc gac ggc ggc agc gac aac tcg ag                    1277
Thr Arg Asp Gly Gly Ser Asp Asn Ser
            420             425
```

<210> SEQ ID NO 46
<211> LENGTH: 425
<212> TYPE: PRT
<213> ORGANISM: Human immunodeficiency virus

<400> SEQUENCE: 46

```
Ala Ser Ala Ala Asp Arg Leu Trp Val Thr Val Tyr Tyr Gly Val Pro
 1               5                  10                  15

Val Trp Lys Asp Ala Thr Thr Thr Leu Phe Cys Ala Ser Asp Ala Lys
            20                  25                  30

Ala Tyr Asp Thr Glu Val His Asn Val Trp Ala Thr His Ala Cys Val
        35                  40                  45

Pro Thr Asp Pro Asn Pro Gln Glu Val Val Leu Gly Asn Val Thr Glu
    50                  55                  60

Asn Phe Asn Met Gly Lys Asn Asn Met Val Glu Gln Met His Glu Asp
65                  70                  75                  80

Ile Ile Ser Leu Trp Asp Gln Ser Leu Lys Pro Cys Val Lys Leu Thr
                85                  90                  95

Pro Leu Cys Val Thr Leu Asn Cys Thr Lys Leu Lys Asn Ser Thr Asp
            100                 105                 110

Thr Asn Asn Thr Arg Trp Gly Thr Gln Glu Met Lys Asn Cys Ser Phe
        115                 120                 125

Asn Ile Ser Thr Ser Val Arg Asn Lys Met Lys Arg Glu Tyr Ala Leu
    130                 135                 140

Phe Tyr Ser Leu Asp Ile Val Pro Ile Asp Asn Asp Asn Thr Ser Tyr
145                 150                 155                 160

Arg Leu Arg Ser Cys Asn Thr Ser Ile Ile Thr Gln Ala Cys Pro Lys
                165                 170                 175

Val Ser Phe Glu Pro Ile Pro Ile His Phe Cys Ala Pro Ala Gly Phe
            180                 185                 190

Ala Ile Leu Lys Cys Asn Asn Lys Thr Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asn Ala Lys Thr Ile Ile Val Gln
                245                 250                 255

Leu Asn Glu Ser Val Glu Ile Asn Cys Thr Arg Pro Asn Asn Asn Thr
            260                 265                 270

Arg Lys Ser Ile His Ile Gly Pro Gly Arg Ala Phe Tyr Thr Thr Gly
        275                 280                 285

Asp Ile Ile Gly Asp Ile Arg Gln Ala His Cys Asn Ile Ser Arg Thr
    290                 295                 300

Asn Trp Thr Asn Thr Leu Lys Arg Val Ala Glu Lys Leu Arg Glu Lys
305                 310                 315                 320

Phe Asn Asn Thr Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
            340                 345                 350
```

-continued

```
Asn Thr Thr Gln Leu Phe Asn Ser Thr Trp Asn Glu Thr Asn Ser Glu
            355                 360                 365
Gly Asn Ile Thr Ser Gly Thr Ile Thr Leu Pro Cys Arg Ile Lys Gln
370                 375                 380
Ile Ile Asn Met Trp Gln Glu Val Gly Lys Ala Met Tyr Ala Pro Pro
385                 390                 395                 400
Ile Gly Gly Gln Ile Lys Cys Leu Ser Asn Ile Thr Gly Leu Leu Leu
                405                 410                 415
Thr Arg Asp Gly Gly Ser Asp Asn Ser
            420                 425
```

<210> SEQ ID NO 47
<211> LENGTH: 1277
<212> TYPE: DNA
<213> ORGANISM: Human immunodeficiency virus
<220> FEATURE:
<221> NAME/KEY: CDS
<222> LOCATION: (1)..(1275)

<400> SEQUENCE: 47

```
gct agc gcg gcc gac cgc ctg tgg gtg acc gtg tac tac ggc gtg ccc      48
Ala Ser Ala Ala Asp Arg Leu Trp Val Thr Val Tyr Tyr Gly Val Pro
  1               5                  10                  15 gtg tgg aag gac gcc acc acc acc ctg ttc tgc gcc agc gac gcc aag      96
Val Trp Lys Asp Ala Thr Thr Thr Leu Phe Cys Ala Ser Asp Ala Lys
                 20                  25                  30 gcc tac gac acc gag gtg cac aac gtg tgg gcc acc cac gcg tgc gtg     144
Ala Tyr Asp Thr Glu Val His Asn Val Trp Ala Thr His Ala Cys Val
             35                  40                  45 ccc acc gac ccc aac ccc cag gag gtg gtg ctg ggc aac gtg acc gag     192
Pro Thr Asp Pro Asn Pro Gln Glu Val Val Leu Gly Asn Val Thr Glu
         50                  55                  60 aac ttc aac atg ggc aag aac aac atg gtg gag cag atg cac gag gat     240
Asn Phe Asn Met Gly Lys Asn Asn Met Val Glu Gln Met His Glu Asp
 65                  70                  75                  80 atc atc agc ctg tgg gac cag agc ctg aag ccc tgc gtg aag ctg acc     288
Ile Ile Ser Leu Trp Asp Gln Ser Leu Lys Pro Cys Val Lys Leu Thr
                 85                  90                  95 ccc ctg tgc gtg acc ctg caa tgc acc aag ctg aag cag agc acc gac     336
Pro Leu Cys Val Thr Leu Gln Cys Thr Lys Leu Lys Gln Ser Thr Asp
            100                 105                 110 acc cag aac acc cgc tgg ggc acc cag gag atg aag aac tgc agc ttc     384
Thr Gln Asn Thr Arg Trp Gly Thr Gln Glu Met Lys Asn Cys Ser Phe
            115                 120                 125 aac atc agc acc agc gtg cgc aac aag atg aag cgc gag tac gcc ctg     432
Asn Ile Ser Thr Ser Val Arg Asn Lys Met Lys Arg Glu Tyr Ala Leu
130                 135                 140 ttc tac agc ctg gac atc gtg ccc atc gac aac gac aac acc agc tac     480
Phe Tyr Ser Leu Asp Ile Val Pro Ile Asp Asn Asp Asn Thr Ser Tyr
145                 150                 155                 160 cgc ctg cgc agc tgc aac aca tcg atc atc acc cag gcc tgc ccc aag     528
Arg Leu Arg Ser Cys Asn Thr Ser Ile Ile Thr Gln Ala Cys Pro Lys
                165                 170                 175 gtg agc ttc gag ccc atc ccc atc cac ttc tgc gcc ccc gcc ggc ttc     576
Val Ser Phe Glu Pro Ile Pro Ile His Phe Cys Ala Pro Ala Gly Phe
            180                 185                 190 gcc atc ctg aag tgc aac aac aag acc ttc aac ggc acc ggc ccc tgc     624
Ala Ile Leu Lys Cys Asn Asn Lys Thr Phe Asn Gly Thr Gly Pro Cys
            195                 200                 205
```

```
acc aac gtg agc acc gtg cag tgc acc cac gga att cgc ccc gtg gtg      672
Thr Asn Val Ser Thr Val Gln Cys Thr His Gly Ile Arg Pro Val Val
    210                 215                 220 agc acc cag ctg ctg ctg aac ggc agc ctg gcc gag gag gag gtg gtg      720
Ser Thr Gln Leu Leu Leu Asn Gly Ser Leu Ala Glu Glu Glu Val Val
225                 230                 235                 240 atc aga tct gag aac ttc acc aac aac gcc aag acc atc atc gtg cag      768
Ile Arg Ser Glu Asn Phe Thr Asn Asn Ala Lys Thr Ile Ile Val Gln
                245                 250                 255 ctg aac gag agc gtg gag atc aac tgc acc cgc ccc aac aac aac acc      816
Leu Asn Glu Ser Val Glu Ile Asn Cys Thr Arg Pro Asn Asn Asn Thr
            260                 265                 270 cgc aag agc atc cac atc ggc cct ggc cgc gcc ttc tac acc acc ggc      864
Arg Lys Ser Ile His Ile Gly Pro Gly Arg Ala Phe Tyr Thr Thr Gly
        275                 280                 285 gac atc atc ggc gac atc cgc cag gcc cac tgc aac atc tct aga acc      912
Asp Ile Ile Gly Asp Ile Arg Gln Ala His Cys Asn Ile Ser Arg Thr
    290                 295                 300 aac tgg acc aac acc ctg aag cgc gtg gcc gag aag ctg cgc gag aag      960
Asn Trp Thr Asn Thr Leu Lys Arg Val Ala Glu Lys Leu Arg Glu Lys
305                 310                 315                 320 ttc aac aac acc acc atc gtg ttc aac cag agc tcc ggc ggc gac ccc     1008
Phe Asn Asn Thr Thr Ile Val Phe Asn Gln Ser Ser Gly Gly Asp Pro
                325                 330                 335 gag atc gtg atg cac agc ttc aac tgc ggc ggc gag ttc ttc tac tgc     1056
Glu Ile Val Met His Ser Phe Asn Cys Gly Gly Glu Phe Phe Tyr Cys
            340                 345                 350 aac acc acc cag ctg ttc aac agc acc tgg aac gag acc aac agc gag     1104
Asn Thr Thr Gln Leu Phe Asn Ser Thr Trp Asn Glu Thr Asn Ser Glu
        355                 360                 365 ggc aac atc act agt ggc acc atc acc ctg ccc tgc cgc atc aag cag     1152
Gly Asn Ile Thr Ser Gly Thr Ile Thr Leu Pro Cys Arg Ile Lys Gln
    370                 375                 380 atc atc aac atg tgg cag gag gtg ggc aag gcc atg tac gcc ccc ccc     1200
Ile Ile Asn Met Trp Gln Glu Val Gly Lys Ala Met Tyr Ala Pro Pro
385                 390                 395                 400 atc ggc ggc cag atc aag tgc ctg agc aac atc acc ggc ctg ctg ctg     1248
Ile Gly Gly Gln Ile Lys Cys Leu Ser Asn Ile Thr Gly Leu Leu Leu
                405                 410                 415 acc cgc gac ggc ggc agc gac aac tcg ag                              1277
Thr Arg Asp Gly Gly Ser Asp Asn Ser
            420                 425

<210> SEQ ID NO 48
<211> LENGTH: 425
<212> TYPE: PRT
<213> ORGANISM: Human immunodeficiency virus

<400> SEQUENCE: 48

Ala Ser Ala Ala Asp Arg Leu Trp Val Thr Val Tyr Tyr Gly Val Pro
1               5                   10                  15

Val Trp Lys Asp Ala Thr Thr Thr Leu Phe Cys Ala Ser Asp Ala Lys
            20                  25                  30

Ala Tyr Asp Thr Glu Val His Asn Val Trp Ala Thr His Ala Cys Val
        35                  40                  45

Pro Thr Asp Pro Asn Pro Gln Glu Val Val Leu Gly Asn Val Thr Glu
    50                  55                  60

Asn Phe Asn Met Gly Lys Asn Asn Met Val Glu Gln Met His Glu Asp
65                  70                  75                  80
```

```
Ile Ile Ser Leu Trp Asp Gln Ser Leu Lys Pro Cys Val Lys Leu Thr
             85                  90                  95
Pro Leu Cys Val Thr Leu Gln Cys Thr Lys Leu Lys Gln Ser Thr Asp
            100                 105                 110
Thr Gln Asn Thr Arg Trp Gly Thr Gln Glu Met Lys Asn Cys Ser Phe
            115                 120                 125
Asn Ile Ser Thr Ser Val Arg Asn Lys Met Lys Arg Glu Tyr Ala Leu
            130                 135                 140
Phe Tyr Ser Leu Asp Ile Val Pro Ile Asp Asn Asp Asn Thr Ser Tyr
145                 150                 155                 160
Arg Leu Arg Ser Cys Asn Thr Ser Ile Ile Thr Gln Ala Cys Pro Lys
                165                 170                 175
Val Ser Phe Glu Pro Ile Pro Ile His Phe Cys Ala Pro Ala Gly Phe
                180                 185                 190
Ala Ile Leu Lys Cys Asn Asn Lys Thr Phe Asn Gly Thr Gly Pro Cys
                195                 200                 205
Thr Asn Val Ser Thr Val Gln Cys Thr His Gly Ile Arg Pro Val Val
            210                 215                 220
Ser Thr Gln Leu Leu Leu Asn Gly Ser Leu Ala Glu Glu Val Val
225                 230                 235                 240
Ile Arg Ser Glu Asn Phe Thr Asn Asn Ala Lys Thr Ile Ile Val Gln
                245                 250                 255
Leu Asn Glu Ser Val Glu Ile Asn Cys Thr Arg Pro Asn Asn Asn Thr
            260                 265                 270
Arg Lys Ser Ile His Ile Gly Pro Gly Arg Ala Phe Tyr Thr Thr Gly
            275                 280                 285
Asp Ile Ile Gly Asp Ile Arg Gln Ala His Cys Asn Ile Ser Arg Thr
290                 295                 300
Asn Trp Thr Asn Thr Leu Lys Arg Val Ala Glu Lys Leu Arg Glu Lys
305                 310                 315                 320
Phe Asn Asn Thr Thr Ile Val Phe Asn Gln Ser Ser Gly Gly Asp Pro
            325                 330                 335
Glu Ile Val Met His Ser Phe Asn Cys Gly Gly Glu Phe Phe Tyr Cys
            340                 345                 350
Asn Thr Thr Gln Leu Phe Asn Ser Thr Trp Asn Glu Thr Asn Ser Glu
            355                 360                 365
Gly Asn Ile Thr Ser Gly Thr Ile Thr Leu Pro Cys Arg Ile Lys Gln
370                 375                 380
Ile Ile Asn Met Trp Gln Glu Val Gly Lys Ala Met Tyr Ala Pro Pro
385                 390                 395                 400
Ile Gly Gly Gln Ile Lys Cys Leu Ser Asn Ile Thr Gly Leu Leu Leu
                405                 410                 415
Thr Arg Asp Gly Gly Ser Asp Asn Ser
            420                 425

<210> SEQ ID NO 49
<211> LENGTH: 1277
<212> TYPE: DNA
<213> ORGANISM: Human immunodeficiency virus

<400> SEQUENCE: 49
gctagcgcgg ccgaccgcct gtgggtgacc gtgtactacg gcgtgcccgt gtggaaggac    60
gccaccacca ccctgttctg cgccagcgac gccaaggcct acgacaccga ggtgcacaac   120
gtgtgggcca cccacgcgtg cgtgcccacc gaccccaacc ccaggaggt ggtgctgggc   180
```

-continued

```
aacgtgaccg agaacttcaa catgggcaag aacaacatgg tggagcagat gcacgaggat    240
atcatcagcc tgtgggacca gagcctgaag ccctgcgtga agctgacccc cctgtgcgtg    300
accctgcaat gcaccaagct gaagcagagc accgacaccc agaacacccg ctggggcacc    360
caggagatga agaactgcag cttccagatc agcaccagcg tgcgcaacaa gatgaagcgc    420
gagtacgccc tgttctacag cctggacatc gtgcccatca caacgacca gaccagctac    480
cgcctgcgca gctgcaacac atcgatcatc acccaggcct gccccaaggt gagcttcgag    540
cccatcccca tccacttctg cgcccccgcc ggcttcgcca tcctgaagtg caacaacaag    600
accttcaacg gcaccggccc ctgcaccaac gtgagcaccg tgcagtgcac ccacggaatt    660
cgccccgtgg tgagcaccca gctgctgctg aacggcagcc tggccgagga ggaggtggtg    720
atcagatctg agaacttcac caacaacgcc aagaccatca tcgtgcagct gaacgagagc    780
gtggagatca actgcacccg ccccaacaac aacacccgca agagcatcca catcggccct    840
ggccgcgcct tctacaccac cggcgacatc atcggcgaca tccgccaggc ccactgcaac    900
atctctagaa ccaactggac caacaccctg aagcgcgtgg ccgagaagct cgcgagaag    960
ttcaacaaca ccaccatcgt gttcaaccag agctccggcg gcgacccga tcgtgatg    1020
cacagcttca actgcggcgg cgagttcttc tactgcaaca ccacccagct gttcaacagc    1080
acctggaacg agaccaacag cgagggcaac atcactagtg gcaccatcac cctgccctgc    1140
cgcatcaagc agatcatcaa catgtggcag gaggtgggca aggccatgta cgccccccc    1200
atcggcggcc agatcaagtg cctgagcaac atcaccggcc tgctgctgac ccgcgacggc    1260
ggcagcgaca actcgag                                                   1277
```

<210> SEQ ID NO 50
<211> LENGTH: 425
<212> TYPE: PRT
<213> ORGANISM: Human immunodeficiency virus

<400> SEQUENCE: 50

```
Ala Ser Ala Ala Asp Arg Leu Trp Val Thr Val Tyr Tyr Gly Val Pro
  1               5                  10                  15

Val Trp Lys Asp Ala Thr Thr Thr Leu Phe Cys Ala Ser Asp Ala Lys
             20                  25                  30

Ala Tyr Asp Thr Glu Val His Asn Val Trp Ala Thr His Ala Cys Val
         35                  40                  45

Pro Thr Asp Pro Asn Pro Gln Glu Val Val Leu Gly Asn Val Thr Glu
     50                  55                  60

Asn Phe Asn Met Gly Lys Asn Asn Met Val Glu Gln Met His Glu Asp
 65                  70                  75                  80

Ile Ile Ser Leu Trp Asp Gln Ser Leu Lys Pro Cys Val Lys Leu Thr
                 85                  90                  95

Pro Leu Cys Val Thr Leu Gln Cys Thr Lys Leu Lys Gln Ser Thr Asp
            100                 105                 110

Thr Gln Asn Thr Arg Trp Gly Thr Gln Glu Met Lys Asn Cys Ser Phe
        115                 120                 125

Gln Ile Ser Thr Ser Val Arg Asn Lys Met Lys Arg Glu Tyr Ala Leu
    130                 135                 140

Phe Tyr Ser Leu Asp Ile Val Pro Ile Asp Asn Asp Gln Thr Ser Tyr
145                 150                 155                 160

Arg Leu Arg Ser Cys Asn Thr Ser Ile Ile Thr Gln Ala Cys Pro Lys
                165                 170                 175
```

```
Val Ser Phe Glu Pro Ile Pro Ile His Phe Cys Ala Pro Ala Gly Phe
            180                 185                 190
Ala Ile Leu Lys Cys Asn Asn Lys Thr Phe Asn Gly Thr Gly Pro Cys
            195                 200                 205
Thr Asn Val Ser Thr Val Gln Cys Thr His Gly Ile Arg Pro Val Val
            210                 215                 220
Ser Thr Gln Leu Leu Leu Asn Gly Ser Leu Ala Glu Glu Val Val
225                 230                 235                 240
Ile Arg Ser Glu Asn Phe Thr Asn Asn Ala Lys Thr Ile Ile Val Gln
                245                 250                 255
Leu Asn Glu Ser Val Glu Ile Asn Cys Thr Arg Pro Asn Asn Asn Thr
            260                 265                 270
Arg Lys Ser Ile His Ile Gly Pro Gly Arg Ala Phe Tyr Thr Thr Gly
            275                 280                 285
Asp Ile Ile Gly Asp Ile Arg Gln Ala His Cys Asn Ile Ser Arg Thr
            290                 295                 300
Asn Trp Thr Asn Thr Leu Lys Arg Val Ala Glu Lys Leu Arg Glu Lys
305                 310                 315                 320
Phe Asn Asn Thr Thr Ile Val Phe Asn Gln Ser Ser Gly Gly Asp Pro
                325                 330                 335
Glu Ile Val Met His Ser Phe Asn Cys Gly Gly Glu Phe Phe Tyr Cys
            340                 345                 350
Asn Thr Thr Gln Leu Phe Asn Ser Thr Trp Asn Glu Thr Asn Ser Glu
            355                 360                 365
Gly Asn Ile Thr Ser Gly Thr Ile Thr Leu Pro Cys Arg Ile Lys Gln
            370                 375                 380
Ile Ile Asn Met Trp Gln Glu Val Gly Lys Ala Met Tyr Ala Pro Pro
385                 390                 395                 400
Ile Gly Gly Gln Ile Lys Cys Leu Ser Asn Ile Thr Gly Leu Leu Leu
                405                 410                 415
Thr Arg Asp Gly Gly Ser Asp Asn Ser
            420                 425

<210> SEQ ID NO 51
<211> LENGTH: 1277
<212> TYPE: DNA
<213> ORGANISM: Human immunodeficiency virus

<400> SEQUENCE: 51
gctagcgcgg ccgaccgcct gtgggtgacc gtgtactacg gcgtgcccgt gtggaaggac      60
gccaccacca ccctgttctg cgccagcgac gccaaggcct acgacaccga ggtgcacaac     120
gtgtgggcca cccacgcgtg cgtgcccacc gaccccaacc cccaggaggt ggtgctgggc     180
aacgtgaccg agaacttcaa catgggcaag aacaacatgg tggagcagat gcacgaggat     240
atcatcagcc tgtgggacca gagcctgaag ccctgcgtga agctgacccc cctgtgcgtg     300
accctgaact gcaccaagct gaagaacagc accgacacca caacacccg ctggggcacc      360
caggagatga agaactgcag cttccagatc agcaccagcg tgcgcaacaa gatgaagcgc     420
gagtacgccc tgttctacag cctggacatc gtgcccatcg acaacgacca gaccagctac     480
cgcctgcgca gctgcaacac atcgatcatc acccaggcct gccccaaggt gagcttcgag     540
cccatcccca tccacttctg cgcccccgcc ggcttcgcca tcctgaagtg caacaacaag     600
accttcaacg gcaccggccc ctgcaccaac gtgagcaccg tgcagtgcac ccacggaatt     660
```

-continued

```
cgccccgtgg tgagcaccca gctgctgctg aacggcagcc tggccgagga ggaggtggtg    720
atcagatctg agaacttcac caacaacgcc aagaccatca tcgtgcagct gaacgagagc    780
gtggagatca actgcacccg ccccaacaac aacacccgca agagcatcca catcggccct    840
ggccgcgcct tctacaccac cggcgacatc atcggcgaca tccgccaggc ccactgcaac    900
atctctagaa ccaactggac caacaccctg aagcgcgtgg ccgagaagct gcgcgagaag    960
ttcaacaaca ccaccatcgt gttcaaccag agctccggcg gcgaccccga tcgtgatg     1020 cacagcttca actgcggcgg cgagttcttc tactgcaaca ccacccagct gttcaacagc    1080
acctggaacg agaccaacag cgagggcaac atcactagtg gcaccatcac cctgccctgc    1140
cgcatcaagc agatcatcaa catgtggcag gaggtgggca aggccatgta cgcccccccc    1200
atcggcggcc agatcaagtg cctgagcaac atcaccggcc tgctgctgac ccgcgacggc    1260
ggcagcgaca actcgag                                                   1277
```

<210> SEQ ID NO 52
<211> LENGTH: 425
<212> TYPE: PRT
<213> ORGANISM: Human immunodeficiency virus

<400> SEQUENCE: 52

```
Ala Ser Ala Ala Asp Arg Leu Trp Val Thr Val Tyr Tyr Gly Val Pro
  1               5                  10                  15

Val Trp Lys Asp Ala Thr Thr Thr Leu Phe Cys Ala Ser Asp Ala Lys
             20                  25                  30

Ala Tyr Asp Thr Glu Val His Asn Val Trp Ala Thr His Ala Cys Val
         35                  40                  45

Pro Thr Asp Pro Asn Pro Gln Glu Val Val Leu Gly Asn Val Thr Glu
     50                  55                  60

Asn Phe Asn Met Gly Lys Asn Asn Met Val Glu Gln Met His Glu Asp
 65                  70                  75                  80

Ile Ile Ser Leu Trp Asp Gln Ser Leu Lys Pro Cys Val Lys Leu Thr
                 85                  90                  95

Pro Leu Cys Val Thr Leu Asn Cys Thr Lys Leu Lys Asn Ser Thr Asp
            100                 105                 110

Thr Asn Asn Thr Arg Trp Gly Thr Gln Glu Met Lys Asn Cys Ser Phe
        115                 120                 125

Gln Ile Ser Thr Ser Val Arg Asn Lys Met Lys Arg Glu Tyr Ala Leu
    130                 135                 140

Phe Tyr Ser Leu Asp Ile Val Pro Ile Asp Asn Asp Gln Thr Ser Tyr
145                 150                 155                 160

Arg Leu Arg Ser Cys Asn Thr Ser Ile Thr Gln Ala Cys Pro Lys
                165                 170                 175

Val Ser Phe Glu Pro Ile Pro Ile His Phe Cys Ala Pro Ala Gly Phe
            180                 185                 190

Ala Ile Leu Lys Cys Asn Asn Lys Thr Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asn Ala Lys Thr Ile Ile Val Gln
                245                 250                 255

Leu Asn Glu Ser Val Glu Ile Asn Cys Thr Arg Pro Asn Asn Asn Thr
```

-continued

```
                        260                 265                 270
Arg Lys Ser Ile His Ile Gly Pro Gly Arg Ala Phe Tyr Thr Thr Gly
            275                 280                 285

Asp Ile Ile Gly Asp Ile Arg Gln Ala His Cys Asn Ile Ser Arg Thr
    290                 295                 300

Asn Trp Thr Asn Thr Leu Lys Arg Val Ala Glu Lys Leu Arg Glu Lys
305                 310                 315                 320

Phe Asn Asn Thr Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
                340                 345                 350

Asn Thr Thr Gln Leu Phe Asn Ser Thr Trp Asn Glu Thr Asn Ser Glu
            355                 360                 365

Gly Asn Ile Thr Ser Gly Thr Ile Thr Leu Pro Cys Arg Ile Lys Gln
    370                 375                 380

Ile Ile Asn Met Trp Gln Glu Val Gly Lys Ala Met Tyr Ala Pro Pro
385                 390                 395                 400

Ile Gly Gly Gln Ile Lys Cys Leu Ser Asn Ile Thr Gly Leu Leu Leu
                405                 410                 415

Thr Arg Asp Gly Gly Ser Asp Asn Ser
                420                 425
```

<210> SEQ ID NO 53
<211> LENGTH: 432
<212> TYPE: DNA
<213> ORGANISM: Human immunodeficiency virus
<220> FEATURE:
<221> NAME/KEY: CDS
<222> LOCATION: (2)..(430)

<400> SEQUENCE: 53

```
t cta gag cgc tac ctc cag gac cag cgc ttc ctg ggc atg tgg ggc tgc        49
  Leu Glu Arg Tyr Leu Gln Asp Gln Arg Phe Leu Gly Met Trp Gly Cys
    1               5                  10                  15 tcc ggc aag ctg atc tgc acc acg gcc gtg ccc tgg aac gcc agc tgg          97
Ser Gly Lys Leu Ile Cys Thr Thr Ala Val Pro Trp Asn Ala Ser Trp
            20                  25                  30 agc aac aag aac ctg agc cag att tgg gac aac atg acc tgg atg gag         145
Ser Asn Lys Asn Leu Ser Gln Ile Trp Asp Asn Met Thr Trp Met Glu
        35                  40                  45 tgg gag cgc gag atc agc aac tac acc gag atc atc tac agc ctg atc        193
Trp Glu Arg Glu Ile Ser Asn Tyr Thr Glu Ile Ile Tyr Ser Leu Ile
    50                  55                  60 gag gag agc cag aac cag cag gag aag aac gag ctg gac ctg ctc cag        241
Glu Glu Ser Gln Asn Gln Gln Glu Lys Asn Glu Leu Asp Leu Leu Gln
65                  70                  75                  80 ctg gac aag tgg gca agc ttg tgg aac tgg ttc aac atc acc aac tgg        289
Leu Asp Lys Trp Ala Ser Leu Trp Asn Trp Phe Asn Ile Thr Asn Trp
                85                  90                  95 ctg tgg tac atc aag att ttc atc atg atc gtg ggc ggc ctg atc ggc        337
Leu Trp Tyr Ile Lys Ile Phe Ile Met Ile Val Gly Gly Leu Ile Gly
            100                 105                 110 ctg cgc atc gtg ttc acc gtg ctg agc atc gtg aac cgc gtg cgc cag        385
Leu Arg Ile Val Phe Thr Val Leu Ser Ile Val Asn Arg Val Arg Gln
        115                 120                 125 ggc tac agc ccc ctg agc ttc cag acc cgc ctg ccc gtg ccc cgc gg         432
Gly Tyr Ser Pro Leu Ser Phe Gln Thr Arg Leu Pro Val Pro Arg
    130                 135                 140
```

-continued

<210> SEQ ID NO 54
<211> LENGTH: 143
<212> TYPE: PRT
<213> ORGANISM: Human immunodeficiency virus

<400> SEQUENCE: 54

```
Leu Glu Arg Tyr Leu Gln Asp Gln Arg Phe Leu Gly Met Trp Gly Cys
  1               5                  10                  15

Ser Gly Lys Leu Ile Cys Thr Thr Ala Val Pro Trp Asn Ala Ser Trp
             20                  25                  30

Ser Asn Lys Asn Leu Ser Gln Ile Trp Asp Asn Met Thr Trp Met Glu
         35                  40                  45

Trp Glu Arg Glu Ile Ser Asn Tyr Thr Glu Ile Ile Tyr Ser Leu Ile
     50                  55                  60

Glu Glu Ser Gln Asn Gln Gln Glu Lys Asn Glu Leu Asp Leu Leu Gln
 65                  70                  75                  80

Leu Asp Lys Trp Ala Ser Leu Trp Asn Trp Phe Asn Ile Thr Asn Trp
                 85                  90                  95

Leu Trp Tyr Ile Lys Ile Phe Ile Met Ile Val Gly Gly Leu Ile Gly
            100                 105                 110

Leu Arg Ile Val Phe Thr Val Leu Ser Ile Val Asn Arg Val Arg Gln
        115                 120                 125

Gly Tyr Ser Pro Leu Ser Phe Gln Thr Arg Leu Pro Val Pro Arg
    130                 135                 140
```

<210> SEQ ID NO 55
<211> LENGTH: 434
<212> TYPE: DNA
<213> ORGANISM: Human immunodeficiency virus
<220> FEATURE:
<221> NAME/KEY: CDS
<222> LOCATION: (2)..(424)

<400> SEQUENCE: 55

```
t cta gag cgc tac ctc cag gac cag cgc ttc ctg ggc atg tgg ggc tgc      49
  Leu Glu Arg Tyr Leu Gln Asp Gln Arg Phe Leu Gly Met Trp Gly Cys
    1               5                  10                  15 tcc ggc aag ctg atc tgc acc acg gcc gtg ccc tgg aac gcc agc tgg        97
Ser Gly Lys Leu Ile Cys Thr Thr Ala Val Pro Trp Asn Ala Ser Trp
             20                  25                  30 agc aac aag aac ctg agc cag att tgg gac aac atg acc tgg atg gag       145
Ser Asn Lys Asn Leu Ser Gln Ile Trp Asp Asn Met Thr Trp Met Glu
         35                  40                  45 tgg gag cgc gag atc agc aac tac acc gag atc atc tac agc ctg atc      193
Trp Glu Arg Glu Ile Ser Asn Tyr Thr Glu Ile Ile Tyr Ser Leu Ile
     50                  55                  60 gag gag agc cag aac cag cag gag aag aac gag ctg gac ctg ctc cag      241
Glu Glu Ser Gln Asn Gln Gln Glu Lys Asn Glu Leu Asp Leu Leu Gln
 65                  70                  75                  80 ctg gac aag tgg gca agc ttg tgg aac tgg ttc aac atc acc aac tgg      289
Leu Asp Lys Trp Ala Ser Leu Trp Asn Trp Phe Asn Ile Thr Asn Trp
                 85                  90                  95 ctg tgg tac atc aag att ttc atc atg atc gtg ggc ggc ctg atc ggc      337
Leu Trp Tyr Ile Lys Ile Phe Ile Met Ile Val Gly Gly Leu Ile Gly
            100                 105                 110 ctg cgc atc gtg ttc acc gtg ctg agc atc gtg aac cgc gtg cgc cag      385
Leu Arg Ile Val Phe Thr Val Leu Ser Ile Val Asn Arg Val Arg Gln
        115                 120                 125 gga tgc agc ccc ctg agc ttc cag acc cgc ctg ccc gtg tgacggatcc       434
```

```
Gly Cys Ser Pro Leu Ser Phe Gln Thr Arg Leu Pro Val
    130                 135                 140

<210> SEQ ID NO 56
<211> LENGTH: 141
<212> TYPE: PRT
<213> ORGANISM: Human immunodeficiency virus

<400> SEQUENCE: 56

Leu Glu Arg Tyr Leu Gln Asp Gln Arg Phe Leu Gly Met Trp Gly Cys
  1               5                  10                  15

Ser Gly Lys Leu Ile Cys Thr Thr Ala Val Pro Trp Asn Ala Ser Trp
             20                  25                  30

Ser Asn Lys Asn Leu Ser Gln Ile Trp Asp Asn Met Thr Trp Met Glu
         35                  40                  45

Trp Glu Arg Glu Ile Ser Asn Tyr Thr Glu Ile Ile Tyr Ser Leu Ile
 50                  55                  60

Glu Glu Ser Gln Asn Gln Gln Glu Lys Asn Glu Leu Asp Leu Leu Gln
 65                  70                  75                  80

Leu Asp Lys Trp Ala Ser Leu Trp Asn Trp Phe Asn Ile Thr Asn Trp
                 85                  90                  95

Leu Trp Tyr Ile Lys Ile Phe Ile Met Ile Val Gly Gly Leu Ile Gly
            100                 105                 110

Leu Arg Ile Val Phe Thr Val Leu Ser Ile Val Asn Arg Val Arg Gln
        115                 120                 125

Gly Cys Ser Pro Leu Ser Phe Gln Thr Arg Leu Pro Val
    130                 135                 140

<210> SEQ ID NO 57
<211> LENGTH: 281
<212> TYPE: DNA
<213> ORGANISM: Human immunodeficiency virus
<220> FEATURE:
<221> NAME/KEY: CDS
<222> LOCATION: (2)..(268)

<400> SEQUENCE: 57 t cta gag cgc tac ctc cag gac cag cgc ttc ctg ggc atg tgg ggc tgc      49
  Leu Glu Arg Tyr Leu Gln Asp Gln Arg Phe Leu Gly Met Trp Gly Cys
    1               5                  10                  15 tcc ggc aag ctg atc tgc acc acg gcc gtg ccc tgg aac gcc agc tgg       97
Ser Gly Lys Leu Ile Cys Thr Thr Ala Val Pro Trp Asn Ala Ser Trp
             20                  25                  30 agc aac aag aac ctg agc cag att tgg gac aac atg acc tgg atg gag      145
Ser Asn Lys Asn Leu Ser Gln Ile Trp Asp Asn Met Thr Trp Met Glu
         35                  40                  45 tgg gag cgc gag atc agc aac tac acc gag atc atc tac agc ctg atc      193
Trp Glu Arg Glu Ile Ser Asn Tyr Thr Glu Ile Ile Tyr Ser Leu Ile
 50                  55                  60 gag gag agc cag aac cag cag gag aag aac gag ctg gac ctg ctc cag      241
Glu Glu Ser Gln Asn Gln Gln Glu Lys Asn Glu Leu Asp Leu Leu Gln
 65                  70                  75                  80 ctg gac aag tgg gca agc ttg tgt gac tgattgagga tcc                    281
Leu Asp Lys Trp Ala Ser Leu Cys Asp
                 85

<210> SEQ ID NO 58
<211> LENGTH: 89
<212> TYPE: PRT
<213> ORGANISM: Human immunodeficiency virus
```

-continued

```
<400> SEQUENCE: 58

Leu Glu Arg Tyr Leu Gln Asp Gln Arg Phe Leu Gly Met Trp Gly Cys
  1               5                  10                  15

Ser Gly Lys Leu Ile Cys Thr Thr Ala Val Pro Trp Asn Ala Ser Trp
             20                  25                  30

Ser Asn Lys Asn Leu Ser Gln Ile Trp Asp Asn Met Thr Trp Met Glu
         35                  40                  45

Trp Glu Arg Glu Ile Ser Asn Tyr Thr Glu Ile Ile Tyr Ser Leu Ile
     50                  55                  60

Glu Glu Ser Gln Asn Gln Gln Glu Lys Asn Glu Leu Asp Leu Leu Gln
 65                  70                  75                  80

Leu Asp Lys Trp Ala Ser Leu Cys Asp
                 85

<210> SEQ ID NO 59
<211> LENGTH: 272
<212> TYPE: DNA
<213> ORGANISM: Human immunodeficiency virus
<220> FEATURE:
<221> NAME/KEY: CDS
<222> LOCATION: (3)..(263)

<400> SEQUENCE: 59 at cga ttg cgc gac ctg ctg ctg atc gtg gcc cgc atc gtg gag ctg        47
   Arg Leu Arg Asp Leu Leu Leu Ile Val Ala Arg Ile Val Glu Leu
     1               5                  10                  15 ctg ggc cgg cgc ggc tgg gag atc ctg aag tac tgg tgg aac ctg ctc        95
Leu Gly Arg Arg Gly Trp Glu Ile Leu Lys Tyr Trp Trp Asn Leu Leu
                 20                  25                  30 cag tac tgg agc cag gag ctg aag aac tct gca gtg agc ctg ctg aac       143
Gln Tyr Trp Ser Gln Glu Leu Lys Asn Ser Ala Val Ser Leu Leu Asn
             35                  40                  45 gcc acc gcc atc gcc gtg gcc gag ggc acc gac cgc gtg atc gag gtg       191
Ala Thr Ala Ile Ala Val Ala Glu Gly Thr Asp Arg Val Ile Glu Val
         50                  55                  60 gtg cag cgc atc tgg cgc ggc atc ctg cac atc ccc acc cga att cgc       239
Val Gln Arg Ile Trp Arg Gly Ile Leu His Ile Pro Thr Arg Ile Arg
     65                  70                  75 cag ggc ttc gag cgc gcc ctg ctg taaggatcc                             272
Gln Gly Phe Glu Arg Ala Leu Leu
 80                  85

<210> SEQ ID NO 60
<211> LENGTH: 87
<212> TYPE: PRT
<213> ORGANISM: Human immunodeficiency virus

<400> SEQUENCE: 60

Arg Leu Arg Asp Leu Leu Leu Ile Val Ala Arg Ile Val Glu Leu Leu
  1               5                  10                  15

Gly Arg Arg Gly Trp Glu Ile Leu Lys Tyr Trp Trp Asn Leu Leu Gln
             20                  25                  30

Tyr Trp Ser Gln Glu Leu Lys Asn Ser Ala Val Ser Leu Leu Asn Ala
         35                  40                  45

Thr Ala Ile Ala Val Ala Glu Gly Thr Asp Arg Val Ile Glu Val Val
     50                  55                  60

Gln Arg Ile Trp Arg Gly Ile Leu His Ile Pro Thr Arg Ile Arg Gln
 65                  70                  75                  80

Gly Phe Glu Arg Ala Leu Leu
```

-continued

```
<210> SEQ ID NO 61
<211> LENGTH: 798
<212> TYPE: DNA
<213> ORGANISM: Human immunodeficiency virus
<220> FEATURE:
<221> NAME/KEY: CDS
<222> LOCATION: (2)..(796)

<400> SEQUENCE: 61 c tcg agc agc ggc aag gag att ttc cgc ccc ggc ggc gac atg cgc       49
  Ser Ser Ser Gly Lys Glu Ile Phe Arg Pro Gly Gly Gly Asp Met Arg
  1               5                   10                  15 gac aac tgg cgc agc gag ctg tac aag tac aag gtg gtg aag atc gag     97
Asp Asn Trp Arg Ser Glu Leu Tyr Lys Tyr Lys Val Val Lys Ile Glu
            20                  25                  30 ccc ctg ggc atc gcc ccc acc aag gcc aag cgc cgc gtg gtg cag cgc    145
Pro Leu Gly Ile Ala Pro Thr Lys Ala Lys Arg Arg Val Val Gln Arg
        35                  40                  45 gag aag cgc gcc gtg ggc atc ggc gct atg ttc ctc ggc ttc ctg ggc    193
Glu Lys Arg Ala Val Gly Ile Gly Ala Met Phe Leu Gly Phe Leu Gly
    50                  55                  60 gct gca ggc agc acc atg ggc gcc gcc agc ctg acc ctg acc gtg cag    241
Ala Ala Gly Ser Thr Met Gly Ala Ala Ser Leu Thr Leu Thr Val Gln
65                  70                  75                  80 gcc cgc cag ctg ctg agc ggc atc gtg cag cag cag aac aac ctg ctg    289
Ala Arg Gln Leu Leu Ser Gly Ile Val Gln Gln Gln Asn Asn Leu Leu
                85                  90                  95 cgc gcc atc gag gcc cag cag cac ctc ctc cag ctg acc gtg tgg ggc    337
Arg Ala Ile Glu Ala Gln Gln His Leu Leu Gln Leu Thr Val Trp Gly
            100                 105                 110 atc aag cag ctc cag gcc cgc gtg ctg gct cta gag cgc tac ctc cag    385
Ile Lys Gln Leu Gln Ala Arg Val Leu Ala Leu Glu Arg Tyr Leu Gln
        115                 120                 125 gac cag cgc ttc ctg ggc atg tgg ggc tgc tcc ggc aag ctg atc tgc    433
Asp Gln Arg Phe Leu Gly Met Trp Gly Cys Ser Gly Lys Leu Ile Cys
    130                 135                 140 acc acg gcc gtg ccc tgg aac gcc agc tgg agc aac aag aac ctg agc    481
Thr Thr Ala Val Pro Trp Asn Ala Ser Trp Ser Asn Lys Asn Leu Ser
145                 150                 155                 160 cag att tgg gac aac atg acc tgg atg gag tgg gag cgc gag atc agc    529
Gln Ile Trp Asp Asn Met Thr Trp Met Glu Trp Glu Arg Glu Ile Ser
                165                 170                 175 aac tac acc gag atc atc tac agc ctg atc gag gag agc cag aac cag    577
Asn Tyr Thr Glu Ile Ile Tyr Ser Leu Ile Glu Glu Ser Gln Asn Gln
            180                 185                 190 cag gag aag aac gag ctg gac ctg ctc cag ctg gac aag tgg gca agc    625
Gln Glu Lys Asn Glu Leu Asp Leu Leu Gln Leu Asp Lys Trp Ala Ser
        195                 200                 205 ttg tgg aac tgg ttc aac atc acc aac tgg ctg tgg tac atc aag att    673
Leu Trp Asn Trp Phe Asn Ile Thr Asn Trp Leu Trp Tyr Ile Lys Ile
    210                 215                 220 ttc atc atg atc gtg ggc ggc ctg atc ggc ctg cgc atc gtg ttc acc    721
Phe Ile Met Ile Val Gly Gly Leu Ile Gly Leu Arg Ile Val Phe Thr
225                 230                 235                 240 gtg ctg agc atc gtg aac cgc gtg cgc cag ggc tac agc ccc ctg agc    769
Val Leu Ser Ile Val Asn Arg Val Arg Gln Gly Tyr Ser Pro Leu Ser
                245                 250                 255 ttc cag acc cgc ctg ccc gtg ccc cgc gg                             798
Phe Gln Thr Arg Leu Pro Val Pro Arg
```

-continued

```
                    260                 265

<210> SEQ ID NO 62
<211> LENGTH: 265
<212> TYPE: PRT
<213> ORGANISM: Human immunodeficiency virus

<400> SEQUENCE: 62

Ser Ser Ser Gly Lys Glu Ile Phe Arg Pro Gly Gly Gly Asp Met Arg
  1               5                  10                  15

Asp Asn Trp Arg Ser Glu Leu Tyr Lys Tyr Lys Val Val Lys Ile Glu
             20                  25                  30

Pro Leu Gly Ile Ala Pro Thr Lys Ala Lys Arg Arg Val Val Gln Arg
         35                  40                  45

Glu Lys Arg Ala Val Gly Ile Gly Ala Met Phe Leu Gly Phe Leu Gly
     50                  55                  60

Ala Ala Gly Ser Thr Met Gly Ala Ala Ser Leu Thr Leu Thr Val Gln
 65                  70                  75                  80

Ala Arg Gln Leu Leu Ser Gly Ile Val Gln Gln Gln Asn Asn Leu Leu
                 85                  90                  95

Arg Ala Ile Glu Ala Gln Gln His Leu Leu Gln Leu Thr Val Trp Gly
            100                 105                 110

Ile Lys Gln Leu Gln Ala Arg Val Leu Ala Leu Glu Arg Tyr Leu Gln
        115                 120                 125

Asp Gln Arg Phe Leu Gly Met Trp Gly Cys Ser Gly Lys Leu Ile Cys
    130                 135                 140

Thr Thr Ala Val Pro Trp Asn Ala Ser Trp Ser Asn Lys Asn Leu Ser
145                 150                 155                 160

Gln Ile Trp Asp Asn Met Thr Trp Met Glu Trp Glu Arg Glu Ile Ser
                165                 170                 175

Asn Tyr Thr Glu Ile Ile Tyr Ser Leu Ile Glu Ser Gln Asn Gln
            180                 185                 190

Gln Glu Lys Asn Glu Leu Asp Leu Leu Gln Leu Asp Lys Trp Ala Ser
        195                 200                 205

Leu Trp Asn Trp Phe Asn Ile Thr Asn Trp Leu Trp Tyr Ile Lys Ile
    210                 215                 220

Phe Ile Met Ile Val Gly Gly Leu Ile Gly Leu Arg Ile Val Phe Thr
225                 230                 235                 240

Val Leu Ser Ile Val Asn Arg Val Arg Gln Gly Tyr Ser Pro Leu Ser
                245                 250                 255

Phe Gln Thr Arg Leu Pro Val Pro Arg
            260                 265

<210> SEQ ID NO 63
<211> LENGTH: 800
<212> TYPE: DNA
<213> ORGANISM: Human immunodeficiency virus
<220> FEATURE:
<221> NAME/KEY: CDS
<222> LOCATION: (2)..(790)

<400> SEQUENCE: 63 c tcg agc agc ggc aag gag att ttc cgc ccc ggc ggc ggc gac atg cgc     49
  Ser Ser Ser Gly Lys Glu Ile Phe Arg Pro Gly Gly Gly Asp Met Arg
    1               5                  10                  15 gac aac tgg cgc agc gag ctg tac aag tac aag gtg gtg aag atc gag     97
Asp Asn Trp Arg Ser Glu Leu Tyr Lys Tyr Lys Val Val Lys Ile Glu
             20                  25                  30
```

```
ccc ctg ggc atc gcc ccc acc aag gcc aag cgc cgc gtg gtg cag cgc      145
Pro Leu Gly Ile Ala Pro Thr Lys Ala Lys Arg Arg Val Val Gln Arg
            35                  40                  45 gag aag cgc gcc gtg ggc atc ggc gct atg ttc ctc ggc ttc ctg ggc      193
Glu Lys Arg Ala Val Gly Ile Gly Ala Met Phe Leu Gly Phe Leu Gly
 50                  55                  60 gct gca ggc agc acc atg ggc gcc gcc agc ctg acc ctg acc gtg cag      241
Ala Ala Gly Ser Thr Met Gly Ala Ala Ser Leu Thr Leu Thr Val Gln
 65                  70                  75                  80 gcc cgc cag ctg ctg agc ggc atc gtg cag cag cag aac aac ctg ctg      289
Ala Arg Gln Leu Leu Ser Gly Ile Val Gln Gln Gln Asn Asn Leu Leu
                 85                  90                  95 cgc gcc atc gag gcc cag cag cac ctg ctc cag ctg acc gtg tgg ggc      337
Arg Ala Ile Glu Ala Gln Gln His Leu Leu Gln Leu Thr Val Trp Gly
            100                 105                 110 atc aag cag ctc cag gcc cgc gtg ctg gct cta gag cgc tac ctc cag      385
Ile Lys Gln Leu Gln Ala Arg Val Leu Ala Leu Glu Arg Tyr Leu Gln
        115                 120                 125 gac cag cgc ttc ctg ggc atg tgg ggc tgc tcc ggc aag ctg atc tgc      433
Asp Gln Arg Phe Leu Gly Met Trp Gly Cys Ser Gly Lys Leu Ile Cys
130                 135                 140 acc acg gcc gtg ccc tgg aac gcc agc tgg agc aac aag aac ctg agc      481
Thr Thr Ala Val Pro Trp Asn Ala Ser Trp Ser Asn Lys Asn Leu Ser
145                 150                 155                 160 cag att tgg gac aac atg acc tgg atg gag tgg gag cgc gag atc agc      529
Gln Ile Trp Asp Asn Met Thr Trp Met Glu Trp Glu Arg Glu Ile Ser
                165                 170                 175 aac tac acc gag atc atc tac agc ctg atc gag gag agc cag aac cag      577
Asn Tyr Thr Glu Ile Ile Tyr Ser Leu Ile Glu Glu Ser Gln Asn Gln
            180                 185                 190 cag gag aag aac gag ctg gac ctg ctc cag ctg gac aag tgg gca agc      625
Gln Glu Lys Asn Glu Leu Asp Leu Leu Gln Leu Asp Lys Trp Ala Ser
        195                 200                 205 ttg tgg aac tgg ttc aac atc acc aac tgg ctg tgg tac atc aag att      673
Leu Trp Asn Trp Phe Asn Ile Thr Asn Trp Leu Trp Tyr Ile Lys Ile
    210                 215                 220 ttc atc atg atc gtg ggc ggc ctg atc ggc ctg cgc atc gtg ttc acc      721
Phe Ile Met Ile Val Gly Gly Leu Ile Gly Leu Arg Ile Val Phe Thr
225                 230                 235                 240 gtg ctg agc atc gtg aac cgc gtg cgc cag gga tgc agc ccc ctg agc      769
Val Leu Ser Ile Val Asn Arg Val Arg Gln Gly Cys Ser Pro Leu Ser
                245                 250                 255 ttc cag acc cgc ctg ccc gtg tgacggatcc                               800
Phe Gln Thr Arg Leu Pro Val
            260
```

<210> SEQ ID NO 64
<211> LENGTH: 263
<212> TYPE: PRT
<213> ORGANISM: Human immunodeficiency virus

<400> SEQUENCE: 64

```
Ser Ser Ser Gly Lys Glu Ile Phe Arg Pro Gly Gly Gly Asp Met Arg
  1               5                  10                  15

Asp Asn Trp Arg Ser Glu Leu Tyr Lys Tyr Lys Val Val Lys Ile Glu
             20                  25                  30

Pro Leu Gly Ile Ala Pro Thr Lys Ala Lys Arg Arg Val Val Gln Arg
        35                  40                  45

Glu Lys Arg Ala Val Gly Ile Gly Ala Met Phe Leu Gly Phe Leu Gly
 50                  55                  60
```

-continued

```
                        50                  55                  60
Ala Ala Gly Ser Thr Met Gly Ala Ala Ser Leu Thr Leu Thr Val Gln
 65                  70                  75                  80

Ala Arg Gln Leu Leu Ser Gly Ile Val Gln Gln Asn Asn Leu Leu
                 85                  90                  95

Arg Ala Ile Glu Ala Gln Gln His Leu Leu Gln Leu Thr Val Trp Gly
            100                 105                 110

Ile Lys Gln Leu Gln Ala Arg Val Leu Ala Leu Glu Arg Tyr Leu Gln
        115                 120                 125

Asp Gln Arg Phe Leu Gly Met Trp Gly Cys Ser Gly Lys Leu Ile Cys
    130                 135                 140

Thr Thr Ala Val Pro Trp Asn Ala Ser Trp Ser Asn Lys Asn Leu Ser
145                 150                 155                 160

Gln Ile Trp Asp Asn Met Thr Trp Met Glu Trp Glu Arg Glu Ile Ser
                165                 170                 175

Asn Tyr Thr Glu Ile Ile Tyr Ser Leu Ile Glu Glu Ser Gln Asn Gln
            180                 185                 190

Gln Glu Lys Asn Glu Leu Asp Leu Leu Gln Leu Asp Lys Trp Ala Ser
        195                 200                 205

Leu Trp Asn Trp Phe Asn Ile Thr Asn Trp Leu Trp Tyr Ile Lys Ile
    210                 215                 220

Phe Ile Met Ile Val Gly Gly Leu Ile Gly Leu Arg Ile Val Phe Thr
225                 230                 235                 240

Val Leu Ser Ile Val Asn Arg Val Arg Gln Gly Cys Ser Pro Leu Ser
                245                 250                 255

Phe Gln Thr Arg Leu Pro Val
            260
```

<210> SEQ ID NO 65
<211> LENGTH: 647
<212> TYPE: DNA
<213> ORGANISM: Human immunodeficiency virus
<220> FEATURE:
<221> NAME/KEY: CDS
<222> LOCATION: (2)..(634)

<400> SEQUENCE: 65

```
c tcg agc agc ggc aag gag att ttc cgc ccc ggc ggc ggc gac atg cgc      49
  Ser Ser Ser Gly Lys Glu Ile Phe Arg Pro Gly Gly Gly Asp Met Arg
   1               5                  10                  15 gac aac tgg cgc agc gag ctg tac aag tac aag gtg gtg aag atc gag       97
Asp Asn Trp Arg Ser Glu Leu Tyr Lys Tyr Lys Val Val Lys Ile Glu
             20                  25                  30 ccc ctg ggc atc gcc ccc acc aag gcc aag cgc cgc gtg gtg cag cgc     145
Pro Leu Gly Ile Ala Pro Thr Lys Ala Lys Arg Arg Val Val Gln Arg
         35                  40                  45 gag aag cgc gcc gtg ggc atc ggc gct atg ttc ctc ggc ttc ctg ggc     193
Glu Lys Arg Ala Val Gly Ile Gly Ala Met Phe Leu Gly Phe Leu Gly
     50                  55                  60 gct gca ggc agc acc atg ggc gcc gcc agc ctg acc ctg acc gtg cag     241
Ala Ala Gly Ser Thr Met Gly Ala Ala Ser Leu Thr Leu Thr Val Gln
 65                  70                  75                  80 gcc cgc cag ctg ctg agc ggc atc gtg cag cag cag aac aac ctg ctg     289
Ala Arg Gln Leu Leu Ser Gly Ile Val Gln Gln Gln Asn Asn Leu Leu
                 85                  90                  95 cgc gcc atc gag gcc cag cag cac ctg ctc cag ctg acc gtg tgg ggc     337
Arg Ala Ile Glu Ala Gln Gln His Leu Leu Gln Leu Thr Val Trp Gly
            100                 105                 110
```

```
atc aag cag ctc cag gcc cgc gtg ctg gct cta gag cgc tac ctc cag        385
Ile Lys Gln Leu Gln Ala Arg Val Leu Ala Leu Glu Arg Tyr Leu Gln
        115                 120                 125 gac cag cgc ttc ctg ggc atg tgg ggc tgc tcc ggc aag ctg atc tgc        433
Asp Gln Arg Phe Leu Gly Met Trp Gly Cys Ser Gly Lys Leu Ile Cys
130                 135                 140 acc acg gcc gtg ccc tgg aac gcc agc tgg agc aac aag aac ctg agc        481
Thr Thr Ala Val Pro Trp Asn Ala Ser Trp Ser Asn Lys Asn Leu Ser
145                 150                 155                 160 cag att tgg gac aac atg acc tgg atg gag tgg gag cgc gag atc agc        529
Gln Ile Trp Asp Asn Met Thr Trp Met Glu Trp Glu Arg Glu Ile Ser
            165                 170                 175 aac tac acc gag atc atc tac agc ctg atc gag gag agc cag aac cag        577
Asn Tyr Thr Glu Ile Ile Tyr Ser Leu Ile Glu Glu Ser Gln Asn Gln
                180                 185                 190 cag gag aag aac gag ctg gac ctg ctc cag ctg gac aag tgg gca agc        625
Gln Glu Lys Asn Glu Leu Asp Leu Leu Gln Leu Asp Lys Trp Ala Ser
            195                 200                 205 ttg tgt gac tgattgagga tcc                                              647
Leu Cys Asp
    210
```

<210> SEQ ID NO 66
<211> LENGTH: 211
<212> TYPE: PRT
<213> ORGANISM: Human immunodeficiency virus

<400> SEQUENCE: 66

```
Ser Ser Ser Gly Lys Glu Ile Phe Arg Pro Gly Gly Gly Asp Met Arg
1               5                   10                  15

Asp Asn Trp Arg Ser Glu Leu Tyr Lys Tyr Lys Val Val Lys Ile Glu
            20                  25                  30

Pro Leu Gly Ile Ala Pro Thr Lys Ala Lys Arg Arg Val Val Gln Arg
        35                  40                  45

Glu Lys Arg Ala Val Gly Ile Gly Ala Met Phe Leu Gly Phe Leu Gly
    50                  55                  60

Ala Ala Gly Ser Thr Met Gly Ala Ala Ser Leu Thr Leu Thr Val Gln
65                  70                  75                  80

Ala Arg Gln Leu Leu Ser Gly Ile Val Gln Gln Gln Asn Asn Leu Leu
                85                  90                  95

Arg Ala Ile Glu Ala Gln Gln His Leu Leu Gln Leu Thr Val Trp Gly
            100                 105                 110

Ile Lys Gln Leu Gln Ala Arg Val Leu Ala Leu Glu Arg Tyr Leu Gln
        115                 120                 125

Asp Gln Arg Phe Leu Gly Met Trp Gly Cys Ser Gly Lys Leu Ile Cys
130                 135                 140

Thr Thr Ala Val Pro Trp Asn Ala Ser Trp Ser Asn Lys Asn Leu Ser
145                 150                 155                 160

Gln Ile Trp Asp Asn Met Thr Trp Met Glu Trp Glu Arg Glu Ile Ser
            165                 170                 175

Asn Tyr Thr Glu Ile Ile Tyr Ser Leu Ile Glu Glu Ser Gln Asn Gln
                180                 185                 190

Gln Glu Lys Asn Glu Leu Asp Leu Leu Gln Leu Asp Lys Trp Ala Ser
            195                 200                 205

Leu Cys Asp
    210
```

<210> SEQ ID NO 67
<211> LENGTH: 1918
<212> TYPE: DNA
<213> ORGANISM: Human immunodeficiency virus
<220> FEATURE:
<221> NAME/KEY: CDS
<222> LOCATION: (1)..(1905)

<400> SEQUENCE: 67

```
gct agc gcg gcc gac cgc ctg tgg gtg acc gtg tac tac ggc gtg ccc      48
Ala Ser Ala Ala Asp Arg Leu Trp Val Thr Val Tyr Tyr Gly Val Pro
1               5                   10                  15 gtg tgg aag gac gcc acc acc acc ctg ttc tgc gcc agc gac gcc aag      96
Val Trp Lys Asp Ala Thr Thr Thr Leu Phe Cys Ala Ser Asp Ala Lys
            20                  25                  30 gcc tac gac acc gag gtg cac aac gtg tgg gcc acc cac gcg tgc gtg     144
Ala Tyr Asp Thr Glu Val His Asn Val Trp Ala Thr His Ala Cys Val
        35                  40                  45 ccc acc gac ccc aac ccc cag gag gtg gtg ctg ggc aac gtg acc gag     192
Pro Thr Asp Pro Asn Pro Gln Glu Val Val Leu Gly Asn Val Thr Glu
    50                  55                  60 aac ttc aac atg ggc aag aac aac atg gtg gag cag atg cac gag gat     240
Asn Phe Asn Met Gly Lys Asn Asn Met Val Glu Gln Met His Glu Asp
65                  70                  75                  80 atc atc agc ctg tgg gac cag agc ctg aag ccc tgc gtg aag ctg acc     288
Ile Ile Ser Leu Trp Asp Gln Ser Leu Lys Pro Cys Val Lys Leu Thr
                85                  90                  95 ccc ctg tgc gtg acc ctg aac tgc acc aag ctg aag aac agc acc gac     336
Pro Leu Cys Val Thr Leu Asn Cys Thr Lys Leu Lys Asn Ser Thr Asp
            100                 105                 110 acc aac aac acc cgc tgg ggc acc cag gag atg aag aac tgc agc ttc     384
Thr Asn Asn Thr Arg Trp Gly Thr Gln Glu Met Lys Asn Cys Ser Phe
        115                 120                 125 aac atc agc acc agc gtg cgc aac aag atg aag cgc gag tac gcc ctg     432
Asn Ile Ser Thr Ser Val Arg Asn Lys Met Lys Arg Glu Tyr Ala Leu
    130                 135                 140 ttc tac agc ctg gac atc gtg ccc atc gac aac gac aac acc agc tac     480
Phe Tyr Ser Leu Asp Ile Val Pro Ile Asp Asn Asp Asn Thr Ser Tyr
145                 150                 155                 160 cgc ctg cgc agc tgc aac aca tcg atc atc acc cag gcc tgc ccc aag     528
Arg Leu Arg Ser Cys Asn Thr Ser Ile Ile Thr Gln Ala Cys Pro Lys
                165                 170                 175 gtg agc ttc gag ccc atc ccc atc cac ttc tgc gcc ccc gcc ggc ttc     576
Val Ser Phe Glu Pro Ile Pro Ile His Phe Cys Ala Pro Ala Gly Phe
            180                 185                 190 gcc atc ctg aag tgc aac aac aag acc ttc aac ggc acc ggc ccc tgc     624
Ala Ile Leu Lys Cys Asn Asn Lys Thr Phe Asn Gly Thr Gly Pro Cys
        195                 200                 205 acc aac gtg agc acc gtg cag tgc acc cac gga att cgc ccc gtg gtg     672
Thr Asn Val Ser Thr Val Gln Cys Thr His Gly Ile Arg Pro Val Val
    210                 215                 220 agc acc cag ctg ctg ctg aac ggc agc ctg gcc gag gag gag gtg gtg     720
Ser Thr Gln Leu Leu Leu Asn Gly Ser Leu Ala Glu Glu Glu Val Val
225                 230                 235                 240 atc aga tct gag aac ttc acc aac aac gcc aag acc atc atc gtg cag     768
Ile Arg Ser Glu Asn Phe Thr Asn Asn Ala Lys Thr Ile Ile Val Gln
                245                 250                 255 ctg aac gag agc gtg gag atc aac tgc acc cgc ccc aac aac aac acc     816
Leu Asn Glu Ser Val Glu Ile Asn Cys Thr Arg Pro Asn Asn Asn Thr
            260                 265                 270
```

```
                                                               -continued cgc aag agc atc cac atc ggc cct ggc cgc gcc ttc tac acc acc ggc      864
Arg Lys Ser Ile His Ile Gly Pro Gly Arg Ala Phe Tyr Thr Thr Gly
        275                 280                 285 gac atc atc ggc gac atc cgc cag gcc cac tgc aac atc tct aga acc      912
Asp Ile Ile Gly Asp Ile Arg Gln Ala His Cys Asn Ile Ser Arg Thr
290                 295                 300 aac tgg acc aac acc ctg aag cgc gtg gcc gag aag ctg cgc gag aag      960
Asn Trp Thr Asn Thr Leu Lys Arg Val Ala Glu Lys Leu Arg Glu Lys
305                 310                 315                 320 ttc aac aac acc acc atc gtg ttc aac cag agc tcc ggc ggc gac ccc     1008
Phe Asn Asn Thr Thr Ile Val Phe Asn Gln Ser Ser Gly Gly Asp Pro
                325                 330                 335 gag atc gtg atg cac agc ttc aac tgc ggc ggc gag ttc ttc tac tgc     1056
Glu Ile Val Met His Ser Phe Asn Cys Gly Gly Glu Phe Phe Tyr Cys
                340                 345                 350 aac acc acc cag ctg ttc aac agc acc tgg aac gag acc aac agc gag     1104
Asn Thr Thr Gln Leu Phe Asn Ser Thr Trp Asn Glu Thr Asn Ser Glu
            355                 360                 365 ggc aac atc act agt ggc acc atc acc ctg ccc tgc cgc atc aag cag     1152
Gly Asn Ile Thr Ser Gly Thr Ile Thr Leu Pro Cys Arg Ile Lys Gln
370                 375                 380 atc atc aac atg tgg cag gag gtg ggc aag gcc atg tac gcc ccc ccc     1200
Ile Ile Asn Met Trp Gln Glu Val Gly Lys Ala Met Tyr Ala Pro Pro
385                 390                 395                 400 atc ggc ggc cag atc aag tgc ctg agc aac atc acc ggc ctg ctg ctg     1248
Ile Gly Gly Gln Ile Lys Cys Leu Ser Asn Ile Thr Gly Leu Leu Leu
                405                 410                 415 acc cgc gac ggc ggc agc gac aac tcg agc agc ggc aag gag att ttc     1296
Thr Arg Asp Gly Gly Ser Asp Asn Ser Ser Ser Gly Lys Glu Ile Phe
                420                 425                 430 cgc ccc ggc ggc ggc gac atg cgc gac aac tgg cgc agc gag ctg tac     1344
Arg Pro Gly Gly Gly Asp Met Arg Asp Asn Trp Arg Ser Glu Leu Tyr
            435                 440                 445 aag tac aag gtg gtg aag atc gag ccc ctg ggc atc gcc ccc acc aag     1392
Lys Tyr Lys Val Val Lys Ile Glu Pro Leu Gly Ile Ala Pro Thr Lys
    450                 455                 460 gcc aag cgc cgc gtg gtg cag cgc gag aag cgc gcc gtg ggc atc ggc     1440
Ala Lys Arg Arg Val Val Gln Arg Glu Lys Arg Ala Val Gly Ile Gly
465                 470                 475                 480 gct atg ttc ctc ggc ttc ctg ggc gct gca ggc agc acc atg ggc gcc     1488
Ala Met Phe Leu Gly Phe Leu Gly Ala Ala Gly Ser Thr Met Gly Ala
                485                 490                 495 gcc agc ctg acc ctg acc gtg cag gcc cgc cag ctg ctg agc ggc atc     1536
Ala Ser Leu Thr Leu Thr Val Gln Ala Arg Gln Leu Leu Ser Gly Ile
                500                 505                 510 gtg cag cag cag aac aac ctg ctg cgc gcc atc gag gcc cag cag cac     1584
Val Gln Gln Gln Asn Asn Leu Leu Arg Ala Ile Glu Ala Gln Gln His
            515                 520                 525 ctg ctc cag ctg acc gtg tgg ggc atc aag cag ctc cag gcc cgc gtg     1632
Leu Leu Gln Leu Thr Val Trp Gly Ile Lys Gln Leu Gln Ala Arg Val
        530                 535                 540 ctg gct cta gag cgc tac ctc cag gac cag cgc ttc ctg ggc atg tgg     1680
Leu Ala Leu Glu Arg Tyr Leu Gln Asp Gln Arg Phe Leu Gly Met Trp
545                 550                 555                 560 ggc tgc tcc ggc aag ctg atc tgc acc acg gcc gtg ccc tgg aac gcc     1728
Gly Cys Ser Gly Lys Leu Ile Cys Thr Thr Ala Val Pro Trp Asn Ala
                565                 570                 575 agc tgg agc aac aag aac ctg agc cag att tgg gac aac atg acc tgg     1776
Ser Trp Ser Asn Lys Asn Leu Ser Gln Ile Trp Asp Asn Met Thr Trp
                580                 585                 590
```

-continued

```
atg gag tgg gag cgc gag atc agc aac tac acc gag atc atc tac agc      1824
Met Glu Trp Glu Arg Glu Ile Ser Asn Tyr Thr Glu Ile Ile Tyr Ser
    595                 600                 605 ctg atc gag gag agc cag aac cag cag gag aag aac gag ctg gac ctg      1872
Leu Ile Glu Glu Ser Gln Asn Gln Gln Glu Lys Asn Glu Leu Asp Leu
610                 615                 620 ctc cag ctg gac aag tgg gca agc ttg tgt gac tgattgagga tcc           1918
Leu Gln Leu Asp Lys Trp Ala Ser Leu Cys Asp
625                 630                 635
```

<210> SEQ ID NO 68
<211> LENGTH: 635
<212> TYPE: PRT
<213> ORGANISM: Human immunodeficiency virus

<400> SEQUENCE: 68

```
Ala Ser Ala Ala Asp Arg Leu Trp Val Thr Val Tyr Tyr Gly Val Pro
  1               5                  10                  15

Val Trp Lys Asp Ala Thr Thr Thr Leu Phe Cys Ala Ser Asp Ala Lys
             20                  25                  30

Ala Tyr Asp Thr Glu Val His Asn Val Trp Ala Thr His Ala Cys Val
         35                  40                  45

Pro Thr Asp Pro Asn Pro Gln Glu Val Val Leu Gly Asn Val Thr Glu
     50                  55                  60

Asn Phe Asn Met Gly Lys Asn Asn Met Val Glu Gln Met His Glu Asp
 65                  70                  75                  80

Ile Ile Ser Leu Trp Asp Gln Ser Leu Lys Pro Cys Val Lys Leu Thr
                 85                  90                  95

Pro Leu Cys Val Thr Leu Asn Cys Thr Lys Leu Lys Asn Ser Thr Asp
            100                 105                 110

Thr Asn Asn Thr Arg Trp Gly Thr Gln Glu Met Lys Asn Cys Ser Phe
        115                 120                 125

Asn Ile Ser Thr Ser Val Arg Asn Lys Met Lys Arg Glu Tyr Ala Leu
130                 135                 140

Phe Tyr Ser Leu Asp Ile Val Pro Ile Asp Asn Asp Asn Thr Ser Tyr
145                 150                 155                 160

Arg Leu Arg Ser Cys Asn Thr Ser Ile Ile Thr Gln Ala Cys Pro Lys
                165                 170                 175

Val Ser Phe Glu Pro Ile Pro Ile His Phe Cys Ala Pro Ala Gly Phe
            180                 185                 190

Ala Ile Leu Lys Cys Asn Asn Lys Thr Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Asn Gly Ser Leu Ala Glu Glu Val Val
225                 230                 235                 240

Ile Arg Ser Glu Asn Phe Thr Asn Ala Lys Thr Ile Ile Val Gln
                245                 250                 255

Leu Asn Glu Ser Val Glu Ile Asn Cys Thr Arg Pro Asn Asn Asn Thr
            260                 265                 270

Arg Lys Ser Ile His Ile Gly Pro Gly Arg Ala Phe Tyr Thr Thr Gly
        275                 280                 285

Asp Ile Ile Gly Asp Ile Arg Gln Ala His Cys Asn Ile Ser Arg Thr
    290                 295                 300

Asn Trp Thr Asn Thr Leu Lys Arg Val Ala Glu Lys Leu Arg Glu Lys
```

-continued

```
305                 310                 315                 320
Phe Asn Asn Thr Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
                340                 345                 350

Asn Thr Thr Gln Leu Phe Asn Ser Thr Trp Asn Glu Thr Asn Ser Glu
                355                 360                 365

Gly Asn Ile Thr Ser Gly Thr Ile Thr Leu Pro Cys Arg Ile Lys Gln
                370                 375                 380

Ile Ile Asn Met Trp Gln Glu Val Gly Lys Ala Met Tyr Ala Pro Pro
385                 390                 395                 400

Ile Gly Gly Gln Ile Lys Cys Leu Ser Asn Ile Thr Gly Leu Leu Leu
                405                 410                 415

Thr Arg Asp Gly Gly Ser Asp Asn Ser Ser Gly Lys Glu Ile Phe
                420                 425                 430

Arg Pro Gly Gly Gly Asp Met Arg Asp Asn Trp Arg Ser Glu Leu Tyr
                435                 440                 445

Lys Tyr Lys Val Val Lys Ile Glu Pro Leu Gly Ile Ala Pro Thr Lys
                450                 455                 460

Ala Lys Arg Arg Val Val Gln Arg Glu Lys Arg Ala Val Gly Ile Gly
465                 470                 475                 480

Ala Met Phe Leu Gly Phe Leu Gly Ala Ala Gly Ser Thr Met Gly Ala
                485                 490                 495

Ala Ser Leu Thr Leu Thr Val Gln Ala Arg Gln Leu Leu Ser Gly Ile
                500                 505                 510

Val Gln Gln Gln Asn Asn Leu Leu Arg Ala Ile Glu Ala Gln Gln His
                515                 520                 525

Leu Leu Gln Leu Thr Val Trp Gly Ile Lys Gln Leu Gln Ala Arg Val
                530                 535                 540

Leu Ala Leu Glu Arg Tyr Leu Gln Asp Gln Arg Phe Leu Gly Met Trp
545                 550                 555                 560

Gly Cys Ser Gly Lys Leu Ile Cys Thr Thr Ala Val Pro Trp Asn Ala
                565                 570                 575

Ser Trp Ser Asn Lys Asn Leu Ser Gln Ile Trp Asp Asn Met Thr Trp
                580                 585                 590

Met Glu Trp Glu Arg Glu Ile Ser Asn Tyr Thr Glu Ile Ile Tyr Ser
                595                 600                 605

Leu Ile Glu Glu Ser Gln Asn Gln Gln Glu Lys Asn Glu Leu Asp Leu
                610                 615                 620

Leu Gln Leu Asp Lys Trp Ala Ser Leu Cys Asp
625                 630                 635
```

```
<210> SEQ ID NO 69
<211> LENGTH: 2071
<212> TYPE: DNA
<213> ORGANISM: Human immunodeficiency virus
<220> FEATURE:
<221> NAME/KEY: CDS
<222> LOCATION: (1)..(2061)

<400> SEQUENCE: 69 gct agc gcg gcc gac cgc ctg tgg gtg acc gtg tac tac ggc gtg ccc        48
Ala Ser Ala Ala Asp Arg Leu Trp Val Thr Val Tyr Tyr Gly Val Pro
  1               5                  10                  15 gtg tgg aag gac gcc acc acc acc ctg ttc tgc gcc agc gac gcc aag        96
Val Trp Lys Asp Ala Thr Thr Thr Leu Phe Cys Ala Ser Asp Ala Lys
```

-continued

```
                    20                    25                        30
gcc tac gac acc gag gtg cac aac gtg tgg gcc acc cac gcg tgc gtg     144
Ala Tyr Asp Thr Glu Val His Asn Val Trp Ala Thr His Ala Cys Val
             35                    40                    45 ccc acc gac ccc aac ccc cag gag gtg gtg ctg ggc aac gtg acc gag     192
Pro Thr Asp Pro Asn Pro Gln Glu Val Val Leu Gly Asn Val Thr Glu
         50                    55                    60 aac ttc aac atg ggc aag aac aac atg gtg gag cag atg cac gag gat     240
Asn Phe Asn Met Gly Lys Asn Asn Met Val Glu Gln Met His Glu Asp
 65                    70                    75                    80 atc atc agc ctg tgg gac cag agc ctg aag ccc tgc gtg aag ctg acc     288
Ile Ile Ser Leu Trp Asp Gln Ser Leu Lys Pro Cys Val Lys Leu Thr
                 85                    90                    95 ccc ctg tgc gtg acc ctg aac tgc acc aag ctg aag aac agc acc gac     336
Pro Leu Cys Val Thr Leu Asn Cys Thr Lys Leu Lys Asn Ser Thr Asp
             100                   105                   110 acc aac aac acc cgc tgg ggc acc cag gag atg aag aac tgc agc ttc     384
Thr Asn Asn Thr Arg Trp Gly Thr Gln Glu Met Lys Asn Cys Ser Phe
         115                   120                   125 aac atc agc acc agc gtg cgc aac aag atg aag cgc gag tac gcc ctg     432
Asn Ile Ser Thr Ser Val Arg Asn Lys Met Lys Arg Glu Tyr Ala Leu
130                   135                   140 ttc tac agc ctg gac atc gtg ccc atc gac aac gac aac acc agc tac     480
Phe Tyr Ser Leu Asp Ile Val Pro Ile Asp Asn Asp Asn Thr Ser Tyr
145                   150                   155                   160 cgc ctg cgc agc tgc aac aca tcg atc atc acc cag gcc tgc ccc aag     528
Arg Leu Arg Ser Cys Asn Thr Ser Ile Ile Thr Gln Ala Cys Pro Lys
                 165                   170                   175 gtg agc ttc gag ccc atc ccc atc cac ttc tgc gcc ccc gcc ggc ttc     576
Val Ser Phe Glu Pro Ile Pro Ile His Phe Cys Ala Pro Ala Gly Phe
             180                   185                   190 gcc atc ctg aag tgc aac aac aag acc ttc aac ggc acc ggc ccc tgc     624
Ala Ile Leu Lys Cys Asn Asn Lys Thr Phe Asn Gly Thr Gly Pro Cys
         195                   200                   205 acc aac gtg agc acc gtg cag tgc acc cac gga att cgc ccc gtg gtg     672
Thr Asn Val Ser Thr Val Gln Cys Thr His Gly Ile Arg Pro Val Val
     210                   215                   220 agc acc cag ctg ctg ctg aac ggc agc ctg gcc gag gag gag gtg gtg     720
Ser Thr Gln Leu Leu Leu Asn Gly Ser Leu Ala Glu Glu Glu Val Val
225                   230                   235                   240 atc aga tct gag aac ttc acc aac aac gcc aag acc atc atc gtg cag     768
Ile Arg Ser Glu Asn Phe Thr Asn Asn Ala Lys Thr Ile Ile Val Gln
                 245                   250                   255 ctg aac gag agc gtg gag atc aac tgc acc cgc ccc aac aac aac acc     816
Leu Asn Glu Ser Val Glu Ile Asn Cys Thr Arg Pro Asn Asn Asn Thr
             260                   265                   270 cgc aag agc atc cac atc ggc cct ggc cgc gcc ttc tac acc acc ggc     864
Arg Lys Ser Ile His Ile Gly Pro Gly Arg Ala Phe Tyr Thr Thr Gly
         275                   280                   285 gac atc atc ggc gac atc cgc cag gcc cac tgc aac atc tct aga acc     912
Asp Ile Ile Gly Asp Ile Arg Gln Ala His Cys Asn Ile Ser Arg Thr
     290                   295                   300 aac tgg acc aac acc ctg aag cgc gtg gcc gag aag ctg cgc gag aag     960
Asn Trp Thr Asn Thr Leu Lys Arg Val Ala Glu Lys Leu Arg Glu Lys
305                   310                   315                   320 ttc aac aac acc acc atc gtg ttc aac cag agc tcc ggc ggc gac ccc    1008
Phe Asn Asn Thr Thr Ile Val Phe Asn Gln Ser Ser Gly Gly Asp Pro
                 325                   330                   335 gag atc gtg atg cac agc ttc aac tgc ggc ggc gag ttc ttc tac tgc    1056
```

-continued

```
                Glu Ile Val Met His Ser Phe Asn Cys Gly Glu Phe Phe Tyr Cys
                            340                 345                 350 aac acc acc cag ctg ttc aac agc acc tgg aac gag acc aac agc gag      1104
Asn Thr Thr Gln Leu Phe Asn Ser Thr Trp Asn Glu Thr Asn Ser Glu
                355                 360                 365 ggc aac atc act agt ggc acc atc acc ctg ccc tgc cgc atc aag cag      1152
Gly Asn Ile Thr Ser Gly Thr Ile Thr Leu Pro Cys Arg Ile Lys Gln
        370                 375                 380 atc atc aac atg tgg cag gag gtg ggc aag gcc atg tac gcc ccc ccc      1200
Ile Ile Asn Met Trp Gln Glu Val Gly Lys Ala Met Tyr Ala Pro Pro
385                 390                 395                 400 atc ggc ggc cag atc aag tgc ctg agc aac atc acc ggc ctg ctg ctg      1248
Ile Gly Gly Gln Ile Lys Cys Leu Ser Asn Ile Thr Gly Leu Leu Leu
                405                 410                 415 acc cgc gac ggc ggc agc gac aac tcg agc agc ggc aag gag att ttc      1296
Thr Arg Asp Gly Gly Ser Asp Asn Ser Ser Ser Gly Lys Glu Ile Phe
                420                 425                 430 cgc ccc ggc ggc ggc gac atg cgc gac aac tgg cgc agc gag ctg tac      1344
Arg Pro Gly Gly Gly Asp Met Arg Asp Asn Trp Arg Ser Glu Leu Tyr
        435                 440                 445 aag tac aag gtg gtg aag atc gag ccc ctg ggc atc gcc ccc acc aag      1392
Lys Tyr Lys Val Val Lys Ile Glu Pro Leu Gly Ile Ala Pro Thr Lys
        450                 455                 460 gcc aag cgc cgc gtg gtg cag cgc gag aag cgc gcc gtg ggc atc ggc      1440
Ala Lys Arg Arg Val Val Gln Arg Glu Lys Arg Ala Val Gly Ile Gly
465                 470                 475                 480 gct atg ttc ctc ggc ttc ctg ggc gct gca ggc agc acc atg ggc gcc      1488
Ala Met Phe Leu Gly Phe Leu Gly Ala Ala Gly Ser Thr Met Gly Ala
                485                 490                 495 gcc agc ctg acc ctg acc gtg cag gcc cgc cag ctg ctg agc ggc atc      1536
Ala Ser Leu Thr Leu Thr Val Gln Ala Arg Gln Leu Leu Ser Gly Ile
                500                 505                 510 gtg cag cag cag aac aac ctg ctg cgc gcc atc gag gcc cag cag cac      1584
Val Gln Gln Gln Asn Asn Leu Leu Arg Ala Ile Glu Ala Gln Gln His
        515                 520                 525 ctg ctc cag ctg acc gtg tgg ggc atc aag cag ctc cag gcc cgc gtg      1632
Leu Leu Gln Leu Thr Val Trp Gly Ile Lys Gln Leu Gln Ala Arg Val
        530                 535                 540 ctg gct cta gag cgc tac ctc cag gac cag cgc ttc ctg ggc atg tgg      1680
Leu Ala Leu Glu Arg Tyr Leu Gln Asp Gln Arg Phe Leu Gly Met Trp
545                 550                 555                 560 ggc tgc tcc ggc aag ctg atc tgc acc acg gcc gtg ccc tgg aac gcc      1728
Gly Cys Ser Gly Lys Leu Ile Cys Thr Thr Ala Val Pro Trp Asn Ala
                565                 570                 575 agc tgg agc aac aag aac ctg agc cag att tgg gac aac atg acc tgg      1776
Ser Trp Ser Asn Lys Asn Leu Ser Gln Ile Trp Asp Asn Met Thr Trp
                580                 585                 590 atg gag tgg gag cgc gag atc agc aac tac acc gag atc atc tac agc      1824
Met Glu Trp Glu Arg Glu Ile Ser Asn Tyr Thr Glu Ile Ile Tyr Ser
        595                 600                 605 ctg atc gag gag agc cag aac cag cag gag aag aac gag ctg gac ctg      1872
Leu Ile Glu Glu Ser Gln Asn Gln Gln Glu Lys Asn Glu Leu Asp Leu
        610                 615                 620 ctc cag ctg gac aag tgg gca agc ttg tgg aac tgg ttc aac atc acc      1920
Leu Gln Leu Asp Lys Trp Ala Ser Leu Trp Asn Trp Phe Asn Ile Thr
625                 630                 635                 640 aac tgg ctg tgg tac atc aag att ttc atc atg atc gtg ggc ggc ctg      1968
Asn Trp Leu Trp Tyr Ile Lys Ile Phe Ile Met Ile Val Gly Gly Leu
                645                 650                 655
```

-continued

```
atc ggc ctg cgc atc gtg ttc acc gtg ctg agc atc gtg aac cgc gtg      2016
Ile Gly Leu Arg Ile Val Phe Thr Val Leu Ser Ile Val Asn Arg Val
        660                 665                 670 cgc cag gga tgc agc ccc ctg agc ttc cag acc cgc ctg ccc gtg          2061
Arg Gln Gly Cys Ser Pro Leu Ser Phe Gln Thr Arg Leu Pro Val
        675                 680                 685 tgacggatcc                                                            2071
```

<210> SEQ ID NO 70
<211> LENGTH: 687
<212> TYPE: PRT
<213> ORGANISM: Human immunodeficiency virus

<400> SEQUENCE: 70

```
Ala Ser Ala Ala Asp Arg Leu Trp Val Thr Val Tyr Tyr Gly Val Pro
 1               5                  10                  15

Val Trp Lys Asp Ala Thr Thr Thr Leu Phe Cys Ala Ser Asp Ala Lys
                20                  25                  30

Ala Tyr Asp Thr Glu Val His Asn Val Trp Ala Thr His Ala Cys Val
            35                  40                  45

Pro Thr Asp Pro Asn Pro Gln Glu Val Val Leu Gly Asn Val Thr Glu
        50                  55                  60

Asn Phe Asn Met Gly Lys Asn Asn Met Val Glu Gln Met His Glu Asp
 65                 70                  75                  80

Ile Ile Ser Leu Trp Asp Gln Ser Leu Lys Pro Cys Val Lys Leu Thr
                85                  90                  95

Pro Leu Cys Val Thr Leu Asn Cys Thr Lys Leu Lys Asn Ser Thr Asp
            100                 105                 110

Thr Asn Asn Thr Arg Trp Gly Thr Gln Glu Met Lys Asn Cys Ser Phe
        115                 120                 125

Asn Ile Ser Thr Ser Val Arg Asn Lys Met Lys Arg Glu Tyr Ala Leu
130                 135                 140

Phe Tyr Ser Leu Asp Ile Val Pro Ile Asp Asn Asp Asn Thr Ser Tyr
145                 150                 155                 160

Arg Leu Arg Ser Cys Asn Thr Ser Ile Ile Thr Gln Ala Cys Pro Lys
                165                 170                 175

Val Ser Phe Glu Pro Ile Pro Ile His Phe Cys Ala Pro Ala Gly Phe
            180                 185                 190

Ala Ile Leu Lys Cys Asn Asn Lys Thr Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asn Asn Ala Lys Thr Ile Ile Val Gln
                245                 250                 255

Leu Asn Glu Ser Val Glu Ile Asn Cys Thr Arg Pro Asn Asn Asn Thr
            260                 265                 270

Arg Lys Ser Ile His Ile Gly Pro Gly Arg Ala Phe Tyr Thr Thr Gly
        275                 280                 285

Asp Ile Ile Gly Asp Ile Arg Gln Ala His Cys Asn Ile Ser Arg Thr
    290                 295                 300

Asn Trp Thr Asn Thr Leu Lys Arg Val Ala Glu Lys Leu Arg Glu Lys
305                 310                 315                 320

Phe Asn Asn Thr Thr Ile Val Phe Asn Gln Ser Ser Gly Gly Asp Pro
```

-continued

```
                    325                 330                 335
Glu Ile Val Met His Ser Phe Asn Cys Gly Gly Glu Phe Phe Tyr Cys
                340                 345                 350
Asn Thr Thr Gln Leu Phe Asn Ser Thr Trp Asn Glu Thr Asn Ser Glu
            355                 360                 365
Gly Asn Ile Thr Ser Gly Thr Ile Thr Leu Pro Cys Arg Ile Lys Gln
        370                 375                 380
Ile Ile Asn Met Trp Gln Glu Val Gly Lys Ala Met Tyr Ala Pro Pro
385                 390                 395                 400
Ile Gly Gly Gln Ile Lys Cys Leu Ser Asn Ile Thr Gly Leu Leu Leu
                405                 410                 415
Thr Arg Asp Gly Gly Ser Asp Asn Ser Ser Gly Lys Glu Ile Phe
            420                 425                 430
Arg Pro Gly Gly Gly Asp Met Arg Asp Asn Trp Arg Ser Glu Leu Tyr
        435                 440                 445
Lys Tyr Lys Val Val Lys Ile Glu Pro Leu Gly Ile Ala Pro Thr Lys
        450                 455                 460
Ala Lys Arg Arg Val Val Gln Arg Glu Lys Arg Ala Val Gly Ile Gly
465                 470                 475                 480
Ala Met Phe Leu Gly Phe Leu Gly Ala Ala Gly Ser Thr Met Gly Ala
                485                 490                 495
Ala Ser Leu Thr Leu Thr Val Gln Ala Arg Gln Leu Leu Ser Gly Ile
            500                 505                 510
Val Gln Gln Gln Asn Asn Leu Leu Arg Ala Ile Glu Ala Gln Gln His
        515                 520                 525
Leu Leu Gln Leu Thr Val Trp Gly Ile Lys Gln Leu Gln Ala Arg Val
        530                 535                 540
Leu Ala Leu Glu Arg Tyr Leu Gln Asp Gln Arg Phe Leu Gly Met Trp
545                 550                 555                 560
Gly Cys Ser Gly Lys Leu Ile Cys Thr Thr Ala Val Pro Trp Asn Ala
                565                 570                 575
Ser Trp Ser Asn Lys Asn Leu Ser Gln Ile Trp Asp Asn Met Thr Trp
            580                 585                 590
Met Glu Trp Glu Arg Glu Ile Ser Asn Tyr Thr Glu Ile Ile Tyr Ser
        595                 600                 605
Leu Ile Glu Glu Ser Gln Asn Gln Gln Glu Lys Asn Glu Leu Asp Leu
        610                 615                 620
Leu Gln Leu Asp Lys Trp Ala Ser Leu Trp Asn Trp Phe Asn Ile Thr
625                 630                 635                 640
Asn Trp Leu Trp Tyr Ile Lys Ile Phe Ile Met Ile Val Gly Gly Leu
                645                 650                 655
Ile Gly Leu Arg Ile Val Phe Thr Val Leu Ser Ile Val Asn Arg Val
            660                 665                 670
Arg Gln Gly Cys Ser Pro Leu Ser Phe Gln Thr Arg Leu Pro Val
        675                 680                 685

<210> SEQ ID NO 71
<211> LENGTH: 2469
<212> TYPE: DNA
<213> ORGANISM: Human immunodeficiency virus
<220> FEATURE:
<221> NAME/KEY: CDS
<222> LOCATION: (1)..(2460)

<400> SEQUENCE: 71
```

```
-continued gct agc gcg gcc gac cgc ctg tgg gtg acc gtg tac tac ggc gtg ccc        48
Ala Ser Ala Ala Asp Arg Leu Trp Val Thr Val Tyr Tyr Gly Val Pro
 1               5                  10                  15 gtg tgg aag gac gcc acc acc acc ctg ttc tgc gcc agc gac gcc aag        96
Val Trp Lys Asp Ala Thr Thr Thr Leu Phe Cys Ala Ser Asp Ala Lys
             20                  25                  30 gcc tac gac acc gag gtg cac aac gtg tgg gcc acc cac gcg tgc gtg       144
Ala Tyr Asp Thr Glu Val His Asn Val Trp Ala Thr His Ala Cys Val
         35                  40                  45 ccc acc gac ccc aac ccc cag gag gtg gtg ctg ggc aac gtg acc gag       192
Pro Thr Asp Pro Asn Pro Gln Glu Val Val Leu Gly Asn Val Thr Glu
     50                  55                  60 aac ttc aac atg ggc aag aac aac atg gtg gag cag atg cac gag gat       240
Asn Phe Asn Met Gly Lys Asn Asn Met Val Glu Gln Met His Glu Asp
 65                  70                  75                  80 atc atc agc ctg tgg gac cag agc ctg aag ccc tgc gtg aag ctg acc       288
Ile Ile Ser Leu Trp Asp Gln Ser Leu Lys Pro Cys Val Lys Leu Thr
                 85                  90                  95 ccc ctg tgc gtg acc ctg aac tgc acc aag ctg aag aac agc acc gac       336
Pro Leu Cys Val Thr Leu Asn Cys Thr Lys Leu Lys Asn Ser Thr Asp
            100                 105                 110 acc aac aac acc cgc tgg ggc acc cag gag atg aag aac tgc agc ttc       384
Thr Asn Asn Thr Arg Trp Gly Thr Gln Glu Met Lys Asn Cys Ser Phe
        115                 120                 125 aac atc agc acc agc gtg cgc aac aag atg aag cgc gag tac gcc ctg       432
Asn Ile Ser Thr Ser Val Arg Asn Lys Met Lys Arg Glu Tyr Ala Leu
130                 135                 140 ttc tac agc ctg gac atc gtg ccc atc gac aac gac aac acc agc tac       480
Phe Tyr Ser Leu Asp Ile Val Pro Ile Asp Asn Asp Asn Thr Ser Tyr
145                 150                 155                 160 cgc ctg cgc agc tgc aac aca tcg atc atc acc cag gcc tgc ccc aag       528
Arg Leu Arg Ser Cys Asn Thr Ser Ile Ile Thr Gln Ala Cys Pro Lys
                165                 170                 175 gtg agc ttc gag ccc atc ccc atc cac ttc tgc gcc ccc gcc ggc ttc       576
Val Ser Phe Glu Pro Ile Pro Ile His Phe Cys Ala Pro Ala Gly Phe
            180                 185                 190 gcc atc ctg aag tgc aac aac aag acc ttc aac ggc acc ggc ccc tgc       624
Ala Ile Leu Lys Cys Asn Asn Lys Thr Phe Asn Gly Thr Gly Pro Cys
        195                 200                 205 acc aac gtg agc acc gtg cag tgc acc cac gga att cgc ccc gtg gtg       672
Thr Asn Val Ser Thr Val Gln Cys Thr His Gly Ile Arg Pro Val Val
    210                 215                 220 agc acc cag ctg ctg ctg aac ggc agc ctg gcc gag gag gag gtg gtg       720
Ser Thr Gln Leu Leu Leu Asn Gly Ser Leu Ala Glu Glu Glu Val Val
225                 230                 235                 240 atc aga tct gag aac ttc acc aac aac gcc aag acc atc atc gtg cag       768
Ile Arg Ser Glu Asn Phe Thr Asn Asn Ala Lys Thr Ile Ile Val Gln
                245                 250                 255 ctg aac gag agc gtg gag atc aac tgc acc cgc ccc aac aac aac acc       816
Leu Asn Glu Ser Val Glu Ile Asn Cys Thr Arg Pro Asn Asn Asn Thr
            260                 265                 270 cgc aag agc atc cac atc ggc cct ggc cgc gcc ttc tac acc acc ggc       864
Arg Lys Ser Ile His Ile Gly Pro Gly Arg Ala Phe Tyr Thr Thr Gly
        275                 280                 285 gac atc atc ggc gac atc cgc cag gcc cac tgc aac atc tct aga acc       912
Asp Ile Ile Gly Asp Ile Arg Gln Ala His Cys Asn Ile Ser Arg Thr
    290                 295                 300 aac tgg acc aac acc ctg aag cgc gtg gcc gag aag ctg cgc gag aag       960
Asn Trp Thr Asn Thr Leu Lys Arg Val Ala Glu Lys Leu Arg Glu Lys
305                 310                 315                 320
```

```
ttc aac aac acc acc atc gtg ttc aac cag agc tcc ggc ggc gac ccc    1008
Phe Asn Asn Thr Thr Ile Val Phe Asn Gln Ser Ser Gly Gly Asp Pro
            325                 330                 335 gag atc gtg atg cac agc ttc aac tgc ggc ggc gag ttc ttc tac tgc    1056
Glu Ile Val Met His Ser Phe Asn Cys Gly Gly Glu Phe Phe Tyr Cys
            340                 345                 350 aac acc acc cag ctg ttc aac agc acc tgg aac gag acc aac agc gag    1104
Asn Thr Thr Gln Leu Phe Asn Ser Thr Trp Asn Glu Thr Asn Ser Glu
            355                 360                 365 ggc aac atc act agt ggc acc atc acc ctg ccc tgc cgc atc aag cag    1152
Gly Asn Ile Thr Ser Gly Thr Ile Thr Leu Pro Cys Arg Ile Lys Gln
370                 375                 380 atc atc aac atg tgg cag gag gtg ggc aag gcc atg tac gcc ccc ccc    1200
Ile Ile Asn Met Trp Gln Glu Val Gly Lys Ala Met Tyr Ala Pro Pro
385                 390                 395                 400 atc ggc ggc cag atc aag tgc ctg agc aac atc acc ggc ctg ctg ctg    1248
Ile Gly Gly Gln Ile Lys Cys Leu Ser Asn Ile Thr Gly Leu Leu Leu
            405                 410                 415 acc cgc gac ggc ggc agc gac aac tcg agc agc ggc aag gag att ttc    1296
Thr Arg Asp Gly Gly Ser Asp Asn Ser Ser Ser Gly Lys Glu Ile Phe
            420                 425                 430 cgc ccc ggc ggc ggc gac atg cgc gac aac tgg cgc agc gag ctg tac    1344
Arg Pro Gly Gly Gly Asp Met Arg Asp Asn Trp Arg Ser Glu Leu Tyr
            435                 440                 445 aag tac aag gtg gtg aag atc gag ccc ctg ggc atc gcc ccc acc aag    1392
Lys Tyr Lys Val Val Lys Ile Glu Pro Leu Gly Ile Ala Pro Thr Lys
450                 455                 460 gcc aag cgc cgc gtg gtg cag cgc gag aag cgc gcc gtg ggc atc ggc    1440
Ala Lys Arg Arg Val Val Gln Arg Glu Lys Arg Ala Val Gly Ile Gly
465                 470                 475                 480 gct atg ttc ctc ggc ttc ctg ggc gct gca ggc agc acc atg ggc gcc    1488
Ala Met Phe Leu Gly Phe Leu Gly Ala Ala Gly Ser Thr Met Gly Ala
            485                 490                 495 gcc agc ctg acc ctg acc gtg cag gcc cgc cag ctg ctg agc ggc atc    1536
Ala Ser Leu Thr Leu Thr Val Gln Ala Arg Gln Leu Leu Ser Gly Ile
            500                 505                 510 gtg cag cag cag aac aac ctg ctg cgc gcc atc gag gcc cag cag cac    1584
Val Gln Gln Gln Asn Asn Leu Leu Arg Ala Ile Glu Ala Gln Gln His
            515                 520                 525 ctg ctc cag ctg acc gtg tgg ggc atc aag cag ctc cag gcc cgc gtg    1632
Leu Leu Gln Leu Thr Val Trp Gly Ile Lys Gln Leu Gln Ala Arg Val
530                 535                 540 ctg gct cta gag cgc tac ctc cag gac cag cgc ttc ctg ggc atg tgg    1680
Leu Ala Leu Glu Arg Tyr Leu Gln Asp Gln Arg Phe Leu Gly Met Trp
545                 550                 555                 560 ggc tgc tcc ggc aag ctg atc tgc acc acg gcc gtg ccc tgg aac gcc    1728
Gly Cys Ser Gly Lys Leu Ile Cys Thr Thr Ala Val Pro Trp Asn Ala
            565                 570                 575 agc tgg agc aac aag aac ctg agc cag att tgg gac aac atg acc tgg    1776
Ser Trp Ser Asn Lys Asn Leu Ser Gln Ile Trp Asp Asn Met Thr Trp
            580                 585                 590 atg gag tgg gag cgc gag atc agc aac tac acc gag atc atc tac agc    1824
Met Glu Trp Glu Arg Glu Ile Ser Asn Tyr Thr Glu Ile Ile Tyr Ser
            595                 600                 605 ctg atc gag gag agc cag aac cag cag gag aag aac gag ctg gac ctg    1872
Leu Ile Glu Glu Ser Gln Asn Gln Gln Glu Lys Asn Glu Leu Asp Leu
610                 615                 620 ctc cag ctg gac aag tgg gca agc ttg tgg aac tgg ttc aac atc acc    1920
Leu Gln Leu Asp Lys Trp Ala Ser Leu Trp Asn Trp Phe Asn Ile Thr
```

```
                625              630              635              640
aac tgg ctg tgg tac atc aag att ttc atc atg atc gtg ggc ggc ctg    1968
Asn Trp Leu Trp Tyr Ile Lys Ile Phe Ile Met Ile Val Gly Gly Leu
                    645              650              655 atc ggc ctg cgc atc gtg ttc acc gtg ctg agc atc gtg aac cgc gtg    2016
Ile Gly Leu Arg Ile Val Phe Thr Val Leu Ser Ile Val Asn Arg Val
            660              665              670 cgc cag ggc tac agc ccc ctg agc ttc cag acc cgc ctg ccc gtg ccc    2064
Arg Gln Gly Tyr Ser Pro Leu Ser Phe Gln Thr Arg Leu Pro Val Pro
        675              680              685 cgc ggc ccc gac cgc ccc gag ggc atc gag gag gag ggc ggc gag cgc    2112
Arg Gly Pro Asp Arg Pro Glu Gly Ile Glu Glu Glu Gly Gly Glu Arg
    690              695              700 gac cgc gac cgc agc acc cgc ctg gtg acc ggc ttc ctg ccc ctg atc    2160
Asp Arg Asp Arg Ser Thr Arg Leu Val Thr Gly Phe Leu Pro Leu Ile
705              710              715              720 tgg gac gac ctg cgc agc ctg ttc ctg ttc agc tac cat cga ttg cgc    2208
Trp Asp Asp Leu Arg Ser Leu Phe Leu Phe Ser Tyr His Arg Leu Arg
                725              730              735 gac ctg ctg ctg atc gtg gcc cgc atc gtg gag ctg ctg ggc cgg cgc    2256
Asp Leu Leu Leu Ile Val Ala Arg Ile Val Glu Leu Leu Gly Arg Arg
            740              745              750 ggc tgg gag atc ctg aag tac tgg tgg aac ctg ctc cag tac tgg agc    2304
Gly Trp Glu Ile Leu Lys Tyr Trp Trp Asn Leu Leu Gln Tyr Trp Ser
        755              760              765 cag gag ctg aag aac tct gca gtg agc ctg ctg aac gcc acc gcc atc    2352
Gln Glu Leu Lys Asn Ser Ala Val Ser Leu Leu Asn Ala Thr Ala Ile
    770              775              780 gcc gtg gcc gag ggc acc gac cgc gtg atc gag gtg gtg cag cgc atc    2400
Ala Val Ala Glu Gly Thr Asp Arg Val Ile Glu Val Val Gln Arg Ile
785              790              795              800 tgg cgc ggc atc ctg cac atc ccc acc cga att cgc cag ggc ttc gag    2448
Trp Arg Gly Ile Leu His Ile Pro Thr Arg Ile Arg Gln Gly Phe Glu
                805              810              815 cgc gcc ctg ctg taaggatcc                                          2469
Arg Ala Leu Leu
            820

<210> SEQ ID NO 72
<211> LENGTH: 820
<212> TYPE: PRT
<213> ORGANISM: Human immunodeficiency virus

<400> SEQUENCE: 72

Ala Ser Ala Ala Asp Arg Leu Trp Val Thr Val Tyr Tyr Gly Val Pro
 1               5                  10                  15

Val Trp Lys Asp Ala Thr Thr Thr Leu Phe Cys Ala Ser Asp Ala Lys
                20                  25                  30

Ala Tyr Asp Thr Glu Val His Asn Val Trp Ala Thr His Ala Cys Val
            35                  40                  45

Pro Thr Asp Pro Asn Pro Gln Glu Val Val Leu Gly Asn Val Thr Glu
        50                  55                  60

Asn Phe Asn Met Gly Lys Asn Asn Met Val Glu Gln Met His Glu Asp
65                  70                  75                  80

Ile Ile Ser Leu Trp Asp Gln Ser Leu Lys Pro Cys Val Lys Leu Thr
                85                  90                  95

Pro Leu Cys Val Thr Leu Asn Cys Thr Lys Leu Lys Asn Ser Thr Asp
            100                 105                 110
```

```
Thr Asn Asn Thr Arg Trp Gly Thr Gln Glu Met Lys Asn Cys Ser Phe
        115                 120                 125

Asn Ile Ser Thr Ser Val Arg Asn Lys Met Lys Arg Glu Tyr Ala Leu
130                 135                 140

Phe Tyr Ser Leu Asp Ile Val Pro Ile Asp Asn Asp Asn Thr Ser Tyr
145                 150                 155                 160

Arg Leu Arg Ser Cys Asn Thr Ser Ile Ile Thr Gln Ala Cys Pro Lys
                165                 170                 175

Val Ser Phe Glu Pro Ile Pro Ile His Phe Cys Ala Pro Ala Gly Phe
            180                 185                 190

Ala Ile Leu Lys Cys Asn Asn Lys Thr Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asn Asn Ala Lys Thr Ile Ile Val Gln
                245                 250                 255

Leu Asn Glu Ser Val Glu Ile Asn Cys Thr Arg Pro Asn Asn Asn Thr
            260                 265                 270

Arg Lys Ser Ile His Ile Gly Pro Gly Arg Ala Phe Tyr Thr Thr Gly
        275                 280                 285

Asp Ile Ile Gly Asp Ile Arg Gln Ala His Cys Asn Ile Ser Arg Thr
    290                 295                 300

Asn Trp Thr Asn Thr Leu Lys Arg Val Ala Glu Lys Leu Arg Glu Lys
305                 310                 315                 320

Phe Asn Thr Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
            340                 345                 350

Asn Thr Thr Gln Leu Phe Asn Ser Thr Trp Asn Glu Thr Asn Ser Glu
        355                 360                 365

Gly Asn Ile Thr Ser Gly Thr Ile Thr Leu Pro Cys Arg Ile Lys Gln
    370                 375                 380

Ile Ile Asn Met Trp Gln Glu Val Gly Lys Ala Met Tyr Ala Pro Pro
385                 390                 395                 400

Ile Gly Gly Gln Ile Lys Cys Leu Ser Asn Ile Thr Gly Leu Leu Leu
                405                 410                 415

Thr Arg Asp Gly Gly Ser Asp Asn Ser Ser Ser Gly Lys Glu Ile Phe
            420                 425                 430

Arg Pro Gly Gly Gly Asp Met Arg Asp Asn Trp Arg Ser Glu Leu Tyr
        435                 440                 445

Lys Tyr Lys Val Val Lys Ile Glu Pro Leu Gly Ile Ala Pro Thr Lys
    450                 455                 460

Ala Lys Arg Arg Val Val Gln Arg Glu Lys Arg Ala Val Gly Ile Gly
465                 470                 475                 480

Ala Met Phe Leu Gly Phe Leu Gly Ala Ala Gly Ser Thr Met Gly Ala
                485                 490                 495

Ala Ser Leu Thr Leu Thr Val Gln Ala Arg Gln Leu Leu Ser Gly Ile
            500                 505                 510

Val Gln Gln Gln Asn Asn Leu Leu Arg Ala Ile Glu Ala Gln Gln His
        515                 520                 525

Leu Leu Gln Leu Thr Val Trp Gly Ile Lys Gln Leu Gln Ala Arg Val
```

-continued

```
                  530                 535                 540
Leu Ala Leu Glu Arg Tyr Leu Gln Asp Gln Arg Phe Leu Gly Met Trp
545                 550                 555                 560

Gly Cys Ser Gly Lys Leu Ile Cys Thr Thr Ala Val Pro Trp Asn Ala
                565                 570                 575

Ser Trp Ser Asn Lys Asn Leu Ser Gln Ile Trp Asp Asn Met Thr Trp
                580                 585                 590

Met Glu Trp Glu Arg Glu Ile Ser Asn Tyr Thr Glu Ile Ile Tyr Ser
                595                 600                 605

Leu Ile Glu Glu Ser Gln Asn Gln Gln Glu Lys Asn Glu Leu Asp Leu
                610                 615                 620

Leu Gln Leu Asp Lys Trp Ala Ser Leu Trp Asn Trp Phe Asn Ile Thr
625                 630                 635                 640

Asn Trp Leu Trp Tyr Ile Lys Ile Phe Ile Met Ile Val Gly Gly Leu
                645                 650                 655

Ile Gly Leu Arg Ile Val Phe Thr Val Leu Ser Ile Val Asn Arg Val
                660                 665                 670

Arg Gln Gly Tyr Ser Pro Leu Ser Phe Gln Thr Arg Leu Pro Val Pro
                675                 680                 685

Arg Gly Pro Asp Arg Pro Glu Gly Ile Glu Glu Gly Gly Glu Arg
690                 695                 700

Asp Arg Asp Arg Ser Thr Arg Leu Val Thr Gly Phe Leu Pro Leu Ile
705                 710                 715                 720

Trp Asp Asp Leu Arg Ser Leu Phe Leu Phe Ser Tyr His Arg Leu Arg
                725                 730                 735

Asp Leu Leu Leu Ile Val Ala Arg Ile Val Glu Leu Leu Gly Arg Arg
                740                 745                 750

Gly Trp Glu Ile Leu Lys Tyr Trp Trp Asn Leu Leu Gln Tyr Trp Ser
                755                 760                 765

Gln Glu Leu Lys Asn Ser Ala Val Ser Leu Leu Asn Ala Thr Ala Ile
                770                 775                 780

Ala Val Ala Glu Gly Thr Asp Arg Val Ile Glu Val Val Gln Arg Ile
785                 790                 795                 800

Trp Arg Gly Ile Leu His Ile Pro Thr Arg Ile Arg Gln Gly Phe Glu
                805                 810                 815

Arg Ala Leu Leu
                820

<210> SEQ ID NO 73
<211> LENGTH: 1431
<212> TYPE: DNA
<213> ORGANISM: Human immunodeficiency virus
<220> FEATURE:
<221> NAME/KEY: CDS
<222> LOCATION: (1)..(1428)

<400> SEQUENCE: 73 gct agc gcg gcc gac cgc ctg tgg gtg acc gtg tac tac ggc gtg ccc     48
Ala Ser Ala Ala Asp Arg Leu Trp Val Thr Val Tyr Tyr Gly Val Pro
 1               5                  10                  15 gtg tgg aag gac gcc acc acc acc ctg ttc tgc gcc agc gac gcc aag     96
Val Trp Lys Asp Ala Thr Thr Thr Leu Phe Cys Ala Ser Asp Ala Lys
            20                  25                  30 gcc tac gac acc gag gtg cac aac gtg tgg gcc acc cac gcg tgc gtg    144
Ala Tyr Asp Thr Glu Val His Asn Val Trp Ala Thr His Ala Cys Val
        35                  40                  45
```

-continued

| | |
|---|---|
| ccc acc gac ccc aac ccc cag gag gtg gtg ctg ggc aac gtg acc gag<br>Pro Thr Asp Pro Asn Pro Gln Glu Val Val Leu Gly Asn Val Thr Glu<br>50            55                  60 | 192 |
| aac ttc aac atg ggc aag aac aac atg gtg gag cag atg cac gag gat<br>Asn Phe Asn Met Gly Lys Asn Asn Met Val Glu Gln Met His Glu Asp<br>65              70                  75              80 | 240 |
| atc atc agc ctg tgg gac cag agc ctg aag ccc tgc gtg aag ctg acc<br>Ile Ile Ser Leu Trp Asp Gln Ser Leu Lys Pro Cys Val Lys Leu Thr<br>            85                  90                  95 | 288 |
| ccc ctg tgc gtg acc ctg aac tgc acc aag ctg aag aac agc acc gac<br>Pro Leu Cys Val Thr Leu Asn Cys Thr Lys Leu Lys Asn Ser Thr Asp<br>        100                 105                 110 | 336 |
| acc aac aac acc cgc tgg ggc acc cag gag atg aag aac tgc agc ttc<br>Thr Asn Asn Thr Arg Trp Gly Thr Gln Glu Met Lys Asn Cys Ser Phe<br>        115                 120                 125 | 384 |
| aac atc agc acc agc gtg cgc aac aag atg aag cgc gag tac gcc ctg<br>Asn Ile Ser Thr Ser Val Arg Asn Lys Met Lys Arg Glu Tyr Ala Leu<br>        130                 135                 140 | 432 |
| ttc tac agc ctg gac atc gtg ccc atc gac aac gac aac acc agc tac<br>Phe Tyr Ser Leu Asp Ile Val Pro Ile Asp Asn Asp Asn Thr Ser Tyr<br>145                 150                 155                 160 | 480 |
| cgc ctg cgc agc tgc aac aca tcg atc atc acc cag gcc tgc ccc aag<br>Arg Leu Arg Ser Cys Asn Thr Ser Ile Ile Thr Gln Ala Cys Pro Lys<br>        165                 170                 175 | 528 |
| gtg agc ttc gag ccc atc ccc atc cac ttc tgc gcc ccc gcc ggc ttc<br>Val Ser Phe Glu Pro Ile Pro Ile His Phe Cys Ala Pro Ala Gly Phe<br>        180                 185                 190 | 576 |
| gcc atc ctg aag tgc aac aac aag acc ttc aac ggc acc ggc ccc tgc<br>Ala Ile Leu Lys Cys Asn Asn Lys Thr Phe Asn Gly Thr Gly Pro Cys<br>        195                 200                 205 | 624 |
| acc aac gtg agc acc gtg cag tgc acc cac gga att cgc ccc gtg gtg<br>Thr Asn Val Ser Thr Val Gln Cys Thr His Gly Ile Arg Pro Val Val<br>        210                 215                 220 | 672 |
| agc acc cag ctg ctg ctg aac ggc agc ctg gcc gag gag gag gtg gtg<br>Ser Thr Gln Leu Leu Leu Asn Gly Ser Leu Ala Glu Glu Glu Val Val<br>225                 230                 235                 240 | 720 |
| atc aga tct gag aac ttc acc aac aac gcc aag acc atc atc gtg cag<br>Ile Arg Ser Glu Asn Phe Thr Asn Asn Ala Lys Thr Ile Ile Val Gln<br>        245                 250                 255 | 768 |
| ctg aac gag agc gtg gag atc aac tgc acc cgc ccc aac aac aac acc<br>Leu Asn Glu Ser Val Glu Ile Asn Cys Thr Arg Pro Asn Asn Asn Thr<br>        260                 265                 270 | 816 |
| cgc aag agc atc cac atc ggc cct ggc cgc gcc ttc tac acc acc ggc<br>Arg Lys Ser Ile His Ile Gly Pro Gly Arg Ala Phe Tyr Thr Thr Gly<br>        275                 280                 285 | 864 |
| gac atc atc ggc gac atc cgc cag gcc cac tgc aac atc tct aga acc<br>Asp Ile Ile Gly Asp Ile Arg Gln Ala His Cys Asn Ile Ser Arg Thr<br>        290                 295                 300 | 912 |
| aac tgg acc aac acc ctg aag cgc gtg gcc gag aag ctg cgc gag aag<br>Asn Trp Thr Asn Thr Leu Lys Arg Val Ala Glu Lys Leu Arg Glu Lys<br>305                 310                 315                 320 | 960 |
| ttc aac aac acc acc atc gtg ttc aac cag agc tcc ggc ggc gac ccc<br>Phe Asn Asn Thr Thr Ile Val Phe Asn Gln Ser Ser Gly Gly Asp Pro<br>        325                 330                 335 | 1008 |
| gag atc gtg atg cac agc ttc aac tgc ggc ggc gag ttc ttc tac tgc<br>Glu Ile Val Met His Ser Phe Asn Cys Gly Gly Glu Phe Phe Tyr Cys<br>        340                 345                 350 | 1056 |
| aac acc acc cag ctg ttc aac agc acc tgg aac gag acc aac agc gag<br>Asn Thr Thr Gln Leu Phe Asn Ser Thr Trp Asn Glu Thr Asn Ser Glu<br>        355                 360                 365 | 1104 |

-continued

```
ggc aac atc act agt ggc acc atc acc ctg ccc tgc cgc atc aag cag       1152
Gly Asn Ile Thr Ser Gly Thr Ile Thr Leu Pro Cys Arg Ile Lys Gln
        370                 375                 380 atc atc aac atg tgg cag gag gtg ggc aag gcc atg tac gcc ccc ccc       1200
Ile Ile Asn Met Trp Gln Glu Val Gly Lys Ala Met Tyr Ala Pro Pro
385                 390                 395                 400 atc ggc ggc cag atc aag tgc ctg agc aac atc acc ggc ctg ctg ctg       1248
Ile Gly Gly Gln Ile Lys Cys Leu Ser Asn Ile Thr Gly Leu Leu Leu
                405                 410                 415 acc cgc gac ggc ggc agc gac aac tcg agc agc ggc aag gag att ttc       1296
Thr Arg Asp Gly Gly Ser Asp Asn Ser Ser Ser Gly Lys Glu Ile Phe
            420                 425                 430 cgc ccc ggc ggc ggc gac atg cgc gac aac tgg cgc agc gag ctg tac       1344
Arg Pro Gly Gly Gly Asp Met Arg Asp Asn Trp Arg Ser Glu Leu Tyr
        435                 440                 445 aag tac aag gtg gtg aag atc gag ccc ctg ggc atc gcc ccc acc aag       1392
Lys Tyr Lys Val Val Lys Ile Glu Pro Leu Gly Ile Ala Pro Thr Lys
450                 455                 460 gcc aag cgc cgc gtg gtg cag cgc gag aag cgc gcc tag                   1431
Ala Lys Arg Arg Val Val Gln Arg Glu Lys Arg Ala
465                 470                 475
```

<210> SEQ ID NO 74
<211> LENGTH: 476
<212> TYPE: PRT
<213> ORGANISM: Human immunodeficiency virus

<400> SEQUENCE: 74

```
Ala Ser Ala Ala Asp Arg Leu Trp Val Thr Val Tyr Tyr Gly Val Pro
1               5                   10                  15

Val Trp Lys Asp Ala Thr Thr Thr Leu Phe Cys Ala Ser Asp Ala Lys
            20                  25                  30

Ala Tyr Asp Thr Glu Val His Asn Val Trp Ala Thr His Ala Cys Val
        35                  40                  45

Pro Thr Asp Pro Asn Pro Gln Glu Val Val Leu Gly Asn Val Thr Glu
    50                  55                  60

Asn Phe Asn Met Gly Lys Asn Asn Met Val Glu Gln Met His Glu Asp
65                  70                  75                  80

Ile Ile Ser Leu Trp Asp Gln Ser Leu Lys Pro Cys Val Lys Leu Thr
                85                  90                  95

Pro Leu Cys Val Thr Leu Asn Cys Thr Lys Leu Lys Asn Ser Thr Asp
            100                 105                 110

Thr Asn Asn Thr Arg Trp Gly Thr Gln Glu Met Lys Asn Cys Ser Phe
        115                 120                 125

Asn Ile Ser Thr Ser Val Arg Asn Lys Met Lys Arg Glu Tyr Ala Leu
    130                 135                 140

Phe Tyr Ser Leu Asp Ile Val Pro Ile Asp Asn Asp Asn Thr Ser Tyr
145                 150                 155                 160

Arg Leu Arg Ser Cys Asn Thr Ser Ile Ile Thr Gln Ala Cys Pro Lys
                165                 170                 175

Val Ser Phe Glu Pro Ile Pro Ile His Phe Cys Ala Pro Ala Gly Phe
            180                 185                 190

Ala Ile Leu Lys Cys Asn Asn Lys Thr Phe Asn Gly Thr Gly Pro Cys
        195                 200                 205

Thr Asn Val Ser Thr Val Gln Cys Thr His Gly Ile Arg Pro Val Val
    210                 215                 220
```

-continued

```
Ser Thr Gln Leu Leu Leu Asn Gly Ser Leu Ala Glu Glu Val Val
225                 230                 235                 240

Ile Arg Ser Glu Asn Phe Thr Asn Asn Ala Lys Thr Ile Ile Val Gln
                245                 250                 255

Leu Asn Glu Ser Val Glu Ile Asn Cys Thr Arg Pro Asn Asn Asn Thr
                260                 265                 270

Arg Lys Ser Ile His Ile Gly Pro Gly Arg Ala Phe Tyr Thr Thr Gly
            275                 280                 285

Asp Ile Ile Gly Asp Ile Arg Gln Ala His Cys Asn Ile Ser Arg Thr
            290                 295                 300

Asn Trp Thr Asn Thr Leu Lys Arg Val Ala Glu Lys Leu Arg Glu Lys
305                 310                 315                 320

Phe Asn Asn Thr Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
                340                 345                 350

Asn Thr Thr Gln Leu Phe Asn Ser Thr Trp Asn Glu Thr Asn Ser Glu
                355                 360                 365

Gly Asn Ile Thr Ser Gly Thr Ile Thr Leu Pro Cys Arg Ile Lys Gln
            370                 375                 380

Ile Ile Asn Met Trp Gln Glu Val Gly Lys Ala Met Tyr Ala Pro Pro
385                 390                 395                 400

Ile Gly Gly Gln Ile Lys Cys Leu Ser Asn Ile Thr Gly Leu Leu Leu
                405                 410                 415

Thr Arg Asp Gly Gly Ser Asp Asn Ser Ser Ser Gly Lys Glu Ile Phe
                420                 425                 430

Arg Pro Gly Gly Gly Asp Met Arg Asp Asn Trp Arg Ser Glu Leu Tyr
            435                 440                 445

Lys Tyr Lys Val Val Lys Ile Glu Pro Leu Gly Ile Ala Pro Thr Lys
            450                 455                 460

Ala Lys Arg Arg Val Val Gln Arg Glu Lys Arg Ala
465                 470                 475
```

```
<210> SEQ ID NO 75
<211> LENGTH: 1038
<212> TYPE: DNA
<213> ORGANISM: Human immunodeficiency virus
<220> FEATURE:
<221> NAME/KEY: CDS
<222> LOCATION: (1)..(1035)

<400> SEQUENCE: 75 gcc gtg ggc atc ggc gct atg ttc ctc ggc ttc ctg ggc gct gca ggc      48
Ala Val Gly Ile Gly Ala Met Phe Leu Gly Phe Leu Gly Ala Ala Gly
 1               5                  10                  15 agc acc atg ggc gcc gcc agc ctg acc ctg acc gtg cag gcc cgc cag      96
Ser Thr Met Gly Ala Ala Ser Leu Thr Leu Thr Val Gln Ala Arg Gln
                20                  25                  30 ctg ctg agc ggc atc gtg cag cag cag aac aac ctg ctg cgc gcc atc     144
Leu Leu Ser Gly Ile Val Gln Gln Gln Asn Asn Leu Leu Arg Ala Ile
            35                  40                  45 gag gcc cag cag cac ctg ctc cag ctg acc gtg tgg ggc atc aag cag     192
Glu Ala Gln Gln His Leu Leu Gln Leu Thr Val Trp Gly Ile Lys Gln
        50                  55                  60 ctc cag gcc cgc gtg ctg gct cta gag cgc tac ctc cag gac cag cgc     240
Leu Gln Ala Arg Val Leu Ala Leu Glu Arg Tyr Leu Gln Asp Gln Arg
 65                  70                  75                  80
```

```
ttc ctg ggc atg tgg ggc tgc tcc ggc aag ctg atc tgc acc acg gcc        288
Phe Leu Gly Met Trp Gly Cys Ser Gly Lys Leu Ile Cys Thr Thr Ala
                 85                  90                  95 gtg ccc tgg aac gcc agc tgg agc aac aag aac ctg agc cag att tgg        336
Val Pro Trp Asn Ala Ser Trp Ser Asn Lys Asn Leu Ser Gln Ile Trp
            100                 105                 110 gac aac atg acc tgg atg gag tgg gag cgc gag atc agc aac tac acc        384
Asp Asn Met Thr Trp Met Glu Trp Glu Arg Glu Ile Ser Asn Tyr Thr
            115                 120                 125 gag atc atc tac agc ctg atc gag gag agc cag aac cag cag gag aag        432
Glu Ile Ile Tyr Ser Leu Ile Glu Glu Ser Gln Asn Gln Gln Glu Lys
        130                 135                 140 aac gag ctg gac ctg ctc cag ctg gac aag tgg gca agc ttg tgg aac        480
Asn Glu Leu Asp Leu Leu Gln Leu Asp Lys Trp Ala Ser Leu Trp Asn
145                 150                 155                 160 tgg ttc aac atc acc aac tgg ctg tgg tac atc aag att ttc atc atg        528
Trp Phe Asn Ile Thr Asn Trp Leu Trp Tyr Ile Lys Ile Phe Ile Met
                165                 170                 175 atc gtg ggc ggc ctg atc ggc ctg cgc atc gtg ttc acc gtg ctg agc        576
Ile Val Gly Gly Leu Ile Gly Leu Arg Ile Val Phe Thr Val Leu Ser
            180                 185                 190 atc gtg aac cgc gtg cgc cag ggc tac agc ccc ctg agc ttc cag acc        624
Ile Val Asn Arg Val Arg Gln Gly Tyr Ser Pro Leu Ser Phe Gln Thr
            195                 200                 205 cgc ctg ccc gtg ccc cgc ggc ccc gac cgc ccc gag ggc atc gag gag        672
Arg Leu Pro Val Pro Arg Gly Pro Asp Arg Pro Glu Gly Ile Glu Glu
        210                 215                 220 gag ggc ggc gag cgc gac cgc gac cgc agc acc cgc ctg gtg acc ggc        720
Glu Gly Gly Glu Arg Asp Arg Asp Arg Ser Thr Arg Leu Val Thr Gly
225                 230                 235                 240 ttc ctg ccc ctg atc tgg gac gac ctg cgc agc ctg ttc ctg ttc agc        768
Phe Leu Pro Leu Ile Trp Asp Asp Leu Arg Ser Leu Phe Leu Phe Ser
                245                 250                 255 tac cat cga ttg cgc gac ctg ctg ctg atc gtg gcc cgc atc gtg gag        816
Tyr His Arg Leu Arg Asp Leu Leu Leu Ile Val Ala Arg Ile Val Glu
            260                 265                 270 ctg ctg ggc cgg cgc ggc tgg gag atc ctg aag tac tgg tgg aac ctg        864
Leu Leu Gly Arg Arg Gly Trp Glu Ile Leu Lys Tyr Trp Trp Asn Leu
        275                 280                 285 ctc cag tac tgg agc cag gag ctg aag aac tct gca gtg agc ctg ctg        912
Leu Gln Tyr Trp Ser Gln Glu Leu Lys Asn Ser Ala Val Ser Leu Leu
    290                 295                 300 aac gcc acc gcc atc gcc gtg gcc gag ggc acc gac cgc gtg atc gag        960
Asn Ala Thr Ala Ile Ala Val Ala Glu Gly Thr Asp Arg Val Ile Glu
305                 310                 315                 320 gtg gtg cag cgc atc tgg cgc ggc atc ctg cac atc ccc acc cga att       1008
Val Val Gln Arg Ile Trp Arg Gly Ile Leu His Ile Pro Thr Arg Ile
                325                 330                 335 cgc cag ggc ttc gag cgc gcc ctg ctg taa                               1038
Arg Gln Gly Phe Glu Arg Ala Leu Leu
            340                 345

<210> SEQ ID NO 76
<211> LENGTH: 345
<212> TYPE: PRT
<213> ORGANISM: Human immunodeficiency virus

<400> SEQUENCE: 76

Ala Val Gly Ile Gly Ala Met Phe Leu Gly Phe Leu Gly Ala Ala Gly
 1               5                  10                  15
```

```
Ser Thr Met Gly Ala Ala Ser Leu Thr Leu Thr Val Gln Ala Arg Gln
            20                  25                  30

Leu Leu Ser Gly Ile Val Gln Gln Asn Asn Leu Leu Arg Ala Ile
        35                  40                  45

Glu Ala Gln Gln His Leu Leu Gln Leu Thr Val Trp Gly Ile Lys Gln
 50                  55                  60

Leu Gln Ala Arg Val Leu Ala Leu Glu Arg Tyr Leu Gln Asp Gln Arg
 65                  70                  75                  80

Phe Leu Gly Met Trp Gly Cys Ser Gly Lys Leu Ile Cys Thr Thr Ala
                85                  90                  95

Val Pro Trp Asn Ala Ser Trp Ser Asn Lys Asn Leu Ser Gln Ile Trp
                    100                 105                 110

Asp Asn Met Thr Trp Met Glu Trp Glu Arg Glu Ile Ser Asn Tyr Thr
                115                 120                 125

Glu Ile Ile Tyr Ser Leu Ile Glu Glu Ser Gln Asn Gln Gln Glu Lys
            130                 135                 140

Asn Glu Leu Asp Leu Leu Gln Leu Asp Lys Trp Ala Ser Leu Trp Asn
145                 150                 155                 160

Trp Phe Asn Ile Thr Asn Trp Leu Trp Tyr Ile Lys Ile Phe Ile Met
                    165                 170                 175

Ile Val Gly Gly Leu Ile Gly Leu Arg Ile Val Phe Thr Val Leu Ser
                180                 185                 190

Ile Val Asn Arg Val Arg Gln Gly Tyr Ser Pro Leu Ser Phe Gln Thr
                195                 200                 205

Arg Leu Pro Val Pro Arg Gly Pro Asp Arg Pro Glu Gly Ile Glu Glu
210                 215                 220

Glu Gly Gly Glu Arg Asp Arg Asp Arg Ser Thr Arg Leu Val Thr Gly
225                 230                 235                 240

Phe Leu Pro Leu Ile Trp Asp Asp Leu Arg Ser Leu Phe Leu Phe Ser
                245                 250                 255

Tyr His Arg Leu Arg Asp Leu Leu Leu Ile Val Ala Arg Ile Val Glu
                260                 265                 270

Leu Leu Gly Arg Arg Gly Trp Glu Ile Leu Lys Tyr Trp Trp Asn Leu
            275                 280                 285

Leu Gln Tyr Trp Ser Gln Glu Leu Lys Asn Ser Ala Val Ser Leu Leu
        290                 295                 300

Asn Ala Thr Ala Ile Ala Val Ala Glu Gly Thr Asp Arg Val Ile Glu
305                 310                 315                 320

Val Val Gln Arg Ile Trp Arg Gly Ile Leu His Ile Pro Thr Arg Ile
                325                 330                 335

Arg Gln Gly Phe Glu Arg Ala Leu Leu
                340                 345

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      epitope

<400> SEQUENCE: 77

Ile Gly Pro Gly Gly Arg Ala Phe Tyr Thr Thr
 1               5                  10

<210> SEQ ID NO 78
```

<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 78
ctagctagcg cggccgaccg cct                                              23

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 79
ctcgatatcc tcgtgcatct gctc                                             24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 80
ccggaattcg ccccgtggtg agca                                             24

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 81
ctgctctaga gatgttgcag tgggcct                                          27

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 82
agcggataac aatttcacac agga                                             24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 83
cgccagggtt ttcccagtca cgac                                             24

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 84
gaatcgatca tcacccag                                               18

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 85
gacgaattcc gtgggtgcac t                                           21

<210> SEQ ID NO 86
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aattcgccag ggcttcgagc gcgccctgct gtaag                            35

<210> SEQ ID NO 87
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gatccttaca gcagggcgcg ctcgaagccc tggcg                            35

<210> SEQ ID NO 88
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tcgagcagcg gcaaggagat tttccgcccc ggcggcggcg acatgcgcga caactggcgc     60
agcgagct                                                              68

<210> SEQ ID NO 89
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtacagctcg ctgcgccagt tgtcgcgcat gtcgccgccg ccggggcgga aaatctcctt     60
gccgctgc                                                              68

<210> SEQ ID NO 90
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 90
gtacaagtac aaggtggtga agatcgagcc cctgggcatc gcccccacca aggccaagcg      60
c                                                                     61

<210> SEQ ID NO 91
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cacgcggcgc ttggccttgg tgggggcgat gcccaggggc tcgatcttca ccaccttgta      60
ctt                                                                   63

<210> SEQ ID NO 92
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cgcgtggtgc agcgcgagaa gcgcgccgtg ggcatcggcg ctatgttcct cggcttcctg      60
ggcgctgca                                                             69

<210> SEQ ID NO 93
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gcgcccagga agccgaggaa catagcgccg atgcccacgg cgcgcttctc gcgctgcac       59

<210> SEQ ID NO 94
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggcagcacca tgggcgccgc cagcctgacc ctgaccgtgc aggcccgcca gctgctgagc      60
ggcatcgtgc agcagcagaa caacctgctg                                      90

<210> SEQ ID NO 95
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cgcgcagcag gttgttctgc tgctgcacga tgccgctcag cagctggcgg gcctgcacgg      60
tcagggtcag gctggcggcg cccatggtgc tgcctgca                             98
```

<210> SEQ ID NO 96
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
cgcgccatcg aggcccagca gcacctgctc cagctgaccg tgtggggcat caagcagctc    60
caggcccgcg tgctggct                                                 78

<210> SEQ ID NO 97
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
ctagagccag cacgcgggcc tggagctgct tgatgcccca cacggtcagc tggagcaggt    60
gctgctgggc ctcgatgg                                                 78

<210> SEQ ID NO 98
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 98
caggaaacag ctatgac                                                  17

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 99
taatacgact cactataggg                                               20

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 100
gttgtaaaac gacggccag                                                19

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 101
tctggaagct caggggctg catccctggc                                     30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 102
cccgcctgcc cgtgtgacgg atccagctcc                                         30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 103
tgtgtgactg attgaggatc cccaactggc                                         30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 104
agcttgccca cttgtccagc tggagcaggt                                         30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 105
cttctcgcgc tgcaccacgc ggcgcttggc                                         30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 106
cgcgcctagg gcatcggcgc tatgttcctc                                         30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 107
cttctcgcgc tgcaccacgc ggcgcttggc                                         30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 108
agcgccgtgg gcatcggcgc tatgttcctc                30

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 109
ctgcttgatg ccccacacgg tcagctg                27

<210> SEQ ID NO 110
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 110
tgctgcggcc gcgtgctggc tctaga                26

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 111
attaaccctc actaaag                17

<210> SEQ ID NO 112
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tcgaggctag cgccgtgggc atcggcgcta tgttcctcgg cttcctgggc gctgca                56

<210> SEQ ID NO 113
<211> LENGTH: 48
<212> TYPE: DNA
<213> ORGANISM: Artificial Sequence
<220> FEATURE:
<223> OTHER INFORMATION: Description of Artificial Sequence: Linker

<400> SEQUENCE: 113
gcgcccagga agccgaggaa catagcgccg atgcccacgg cgctagcc                48

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 114
agacataata gctgacagac                20

-continued

```
<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 115
gattgtattt ctgtccctca c                                              21

<210> SEQ ID NO 116
<211> LENGTH: 12
<212> TYPE: PRT
<213> ORGANISM: Mus sp.

<400> SEQUENCE: 116

Met Arg Asp Asn Trp Arg Ser Glu Leu Tyr Lys Tyr
  1               5                  10

<210> SEQ ID NO 117
<211> LENGTH: 15
<212> TYPE: PRT
<213> ORGANISM: Mus sp.

<400> SEQUENCE: 117

Ser Ile His Ile Gly Pro Gly Arg Ala Phe Tyr Thr Thr Gly Asp
  1               5                  10                  15

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      epitope

<400> SEQUENCE: 118

Ile Gly Pro Gly Arg Ala Phe Tyr Thr Thr
  1               5                  10
```

METHOD FOR PRODUCING A NUCLEOTIDE SEQUENCE CONSTRUCT WITH OPTIMIZED CODONS FOR AN HIV GENETIC VACCINE BASED ON A PRIMARY, EARLY HIV ISOLATE AND SYNTHETIC ENVELOPE BX08 CONSTRUCTS

This application is based on Provisional Application Ser. No. 60/128,558, filed Apr. 9, 1999.

FIELD OF THE INVENTION

The invention relates to a DNA vaccine against HIV, which is designed from a clinical primary isolate. One aspect of the invention relates to a method of producing a nucleotide sequence construct, in a prefered aspect based on a cassette system, the nucleotide sequence construct being used as a DNA vaccine. The method can, for example, lead to the disclosed synthetic BX08 HIV-1 envelope vaccine nucleotide sequence construct, designed to generate suitable DNA vaccines against HIV, specifically HIV-1. Furthermore, the invention can be used for the production of recombinant protein antigens.

BACKGROUND OF THE INVENTION

There is an urgent need for new vaccine strategies against HIV. One such new promising strategy is called genetic immunization or DNA vaccine (Webster et al 1997). Some of the advantages of a DNA vaccine against HIV is the induction of Th cell activation, induction of antibodies also against conformational dependent epitopes, and the induction of cellular immunity. So far, most DNA vaccine envelope genes tried, have been from tissue culture adapted virus strains (Boyer et al 1997) that often differs in several aspects from primary clinical isolates (such as early isolates) e.g. in co-receptor usage (Choe et al 1996, Dragic et al 1997).

One disadvantage in HIV envelope based DNA vaccines may be the intrinsic relatively low expression which is regulated by the Rev expression. This may prevent an optimal investigation of the vaccines in small animal models like mice where Rev is functioning suboptimally. Recently it has been shown using the tissue culture adapted HIV-1 MN strain, that an exchange of the HIV codon usage to that of highly expressed mammalian genes greatly improves the expression in mammalian cell lines and renders the HIV expression Rev independent (Haas et al 1996). Additionally, it is known that rare codons cause pausing of the ribosome, which leads to a failure in completing the nascent polypeptide chain and a uncoupling of transcription and translation. Pausing of the ribosome is thought to lead to exposure of the 3' end of the mRNA to cellular ribonucleases. The worldwide spread of HIV-1 has presently resulted in 8,500 new infections daily and AIDS is now the number 1 cause of death among US males (and number 3 among US females) aged 25–40 years. The epidemic hot-spots now include Eastern Europe, India and South East Asia and southern Africa. The attempts to solve this world-wide problem involve education, prevention, treatment and vaccine development. Affordable protective vaccines represent the best solution to the world-wide problem of infection with HIV-1. Induction of virus neutralizing antibodies is one of the key components in vaccine development. Several recombinant envelope vaccines have been tested in humans and animals, but they seem unable to induce sufficient protection. In this respect DNA vaccination may provide a different and more natural mode of antigen presentation. It is hoped that the immune responses induced by such DNA vaccines could aid in limiting virus replication, slowing disease progression or preventing occurrence of disease. Unfortunately many HIV envelope vaccines induce only moderate levels of antibodies. This could in part be due to limitations in expression, influenced by regulation by the Rev protein and by a species-specific and biased HIV codon usage. Also the virus variability is considered a barrier for development of antibody based vaccines and thus a tool for more easy producing of closely related vaccine variants is needed.

It has been suggested to improve the immunogenicity and antigenicity of epitopes by certain mutations in the envelope gene. An elimination of certain immune dominant epitopes (like V3) could render less immune dominant but more relevant, conserved, or hidden epitopes more immunogenic (Bryder et al 1999). Also elimination of certain N-linked glycosylation sites could improve the exposure of relevant epitopes and increase the immunogenicity of those epitopes. Thus, it is possible that elimination of the glycosylation sites in V1 and V2 may in a more favourable way expose neutralising epitopes (Kwong et al 1998, Wyatt et al 1998). The HIV envelope contains putative internalization sequences in the intracellular part of gp41 (Sauter et al 1996). Thus it would be relevant to eliminate and/or mutate the internalization signals in a membrane bound HIV envelope vaccine gene to increase the amount of surface exposed vaccine derived HIV glycoproteins as gp150. Since the antibody response, that is measured and calculated in titers, is improved by adding the secreted gp120 as opposed to adding the membrane bound form (Vinner et al 1999), it could be advantageous to express the vaccine as a secreted gp120 or a secreted gp140. This would include important parts of gp41, such as the 2F5 neutralising linear epitope (Mascola et al 1997).

SUMMARY OF THE INVENTION

Our suggested solution to the problems described above is to design DNA envelope vaccines from a clinical primary isolate with Rev-independent high expression in mammals, that is-built as a cassette for easy variant vaccine production.

A method of producing a nucleotide sequence construct with codons from highly expressed mammalian proteins based on a cassette system coding for an early, primary HIV envelope is described. The method comprises the steps of direct cloning of an HIV gene, derived from a patient within the first 12 months of infection, thereby obtaining a first nucleotide sequence; designing a second nucleotide sequence utilising the most frequent codons from mammalian highly expressed proteins to encode the same amino acid sequence as the first nucleotide sequence; redesigning the second nucleotide sequence so that restriction enzyme sites surround the regions of the nucleotide sequence encoding functional regions of the amino acid sequence and so that selected restriction enzyme sites are removed, thereby obtaining a third nucleotide sequence encoding the same amino acid sequence as the first and the second nucleotide sequence; redesigning the third nucleotide sequence so that the terminals contain convenient restriction enzyme sites for cloning into an expression vehicle; producing snuts between restriction enzyme sites as well as terminal snuts and introducing snuts into an expression vehicle by ligation. The nucleotide sequence construct obtained by this method uses the mammalian highly expressed codons (FIG. 1) and renders the envelope gene expression Rev independent and allows easy cassette exchange of regions surrounded by restriction enzyme sites that are important for immunogenicity, function, and expression.

The method can, for example, lead to the disclosed synthetic, Rev-independent, clinical (such as early), primary HIV-1 envelope vaccine gene, built as a multi cassette. From the sequence of the envelope of the HIV-1 BX08 isolate (personal communication from Marc Girard, Institute Pasteur, Paris), the present inventors have designed a synthetic BX08 HIV-1 envelope vaccine nucleotide sequence construct.

With the great diversity of envelopes in HIV among different patients and within one patient, it would be of advantage to vaccinate with several envelope variants, all being highly expressed. To avoid synthesising several full length envelopes, it is much easier to exchange relevant parts of an envelope cassette to various strains in a multivalent vaccine.

Whether it is the disclosed synthetic BX08 nucleotide sequence construct, or any of the nucleotide sequence constructs obtained by the method, they are designed to generate suitable DNA vaccines against HIV, specifically HIV-1. In this case the mammal, preferably a human being, is inoculated with the nucleotide sequence construct in an expression vehicle and constitutes a host for the transcription and translation of the nucleotide sequence construct. The nucleotide sequence constructs of the present invention can furthermore be used for the production of recombinant protein antigens. In this case the nucleotide sequence construct is placed in an expression vehicle and introduced into a system (e.g. a cell-line), allowing production of a recombinant protein with the same amino acid sequence. The recombinant protein is then isolated and administered to the mammal, preferably a human being. The immune system of the mammal will then direct antibodies against epitopes on the recombinant protein. The mammal, preferably a human being, can thus be primed or boosted with DNA and/or recombinant protein obtained by the method of the invention.

A relevant HIV DNA vaccine can potentially be used not only as a prophylactic vaccine, but also as a therapeutic vaccine in HIV infected patients, e.g. during antiviral therapy. An HIV specific DNA vaccine will have the possibility to induce or re-induce the wanted specific immunity and help the antiviral therapy in limiting or even eliminating the HIV infection. The immunogenicity and antigenicity of epitopes in the envelope can be improved by certain mutations in the envelope gene. The cassette system allows for easy access to the relevant parts of the envelope gene, and thereby eased efforts in the process of genetic manipulation. Some suggested mutations are: an elimination of certain immune dominant epitopes (like V3); elimination of certain N-linked glycosylation sites (like glycosylation sites around V2); elimination and/or mutation of the nucleotide sequence encoding the internalization signals in the cytoplasmic part of a membrane bound HIV envelope to increase the amount of surface exposed vaccine derived HIV glycoproteins; elimination or mutation of the cleavage site between gp120 and gp41; with introduced mutations in gp41 for preserving conformational epitopes.

Table 1 below, lists the nucleotide sequence constructs of the invention by the names used herein, as well as by reference to relevant SEQ ID NOs of DNA sequences, and the amino acid sequence encoded by the DNA sequence in the preferred reading frame. It should be noted, that the snut name consist of the number of the approximate position for the end of the snut and the restriction enzyme used to cleave and/or ligate that end of the snut.

TABLE 1

List of names of nucleotide sequence constructs (Snuts (S) and Pieces (P)) with reference to SEQ ID NO for the nucleotide sequence and protein sequence.

| Name | Nucleotide SEQ ID NO: | Protein SEQ ID NO: |
|---|---|---|
| $S_{0-N-Lang}$ | 1 | 2 |
| $S_{235EcoRV}$ | 3 | 4 |
| $S_{375PstI}$ | 5 | 6 |
| $S_{495ClaI}$ | 7 | 8 |
| $S_{650-720EcoRI}$ | 9 | 10 |
| $S_{900XbaI}$ | 11 | 12 |
| $S_{990SacI}$ | 13 | 14 |
| $S_{1110SpeI}$ | 15 | 16 |
| $S_{1265XhoI}$ | 17 | 18 |
| $S_{1265gp120}$ | 19 | 20 |
| $S_{1265gp160}$ | 21 | 22 |
| $S_{1465PstI}$ | 23 | 24 |
| $S_{1465PstI\,cys}$ | 25 | 26 |
| $S_{1630XbaI}$ | 27 | 28 |
| $S_{1700EagI}$ | 29 | 30 |
| $S_{1890HindIII}$ | 31 | 32 |
| $S_{2060SacII}$ | 33 | 34 |
| $S_{2190ClaI}$ | 35 | 36 |
| $S_{2330PstI}$ | 37 | 38 |
| $S_{2425ES}$ | 39 | 40 |
| $P_1$ | 41 | 42 |
| $P_2$ | 43 | 44 |
| $P_3$ | 45 | 46 |
| $P_{3GV1}$ | 47 | 48 |
| $P_{3GV1V2}$ | 49 | 50 |
| $P_{3GV2}$ | 51 | 52 |
| $P_{4gp160}$ | 53 | 54 |
| $P_{4gp150}$ | 55 | 56 |
| $P_{4gp140}$ | 57 | 58 |
| $P_5$ | 59 | 60 |
| $P_{8gp160}$ | 61 | 62 |
| $P_{8gp150}$ | 63 | 64 |
| $P_{8gp140}$ | 65 | 66 |
| synBX08-140 | 67 | 68 |
| synBX08-150 | 69 | 70 |
| synBX08-160 | 71 | 72 |
| synBX08-120 | 73 | 74 |
| synBX08-41 | 75 | 76 |

DETAILED DISCLOSURE OF THE INVENTION

One aspect of the present invention relates to a method for producing a nucleotide sequence construct coding for an HIV gene. The nucleotide sequence construct is produced as a cassette system consisting of snuts. A snut (S) is a nucleotide sequences construct between restriction enzyme cleavage sites comprising the minimal entity of the cassette system. First an HIV gene is obtained from a patient within the first 12 months of infection. The term HIV should be understood in the broadest sense and include HIV 1 and HIV 2. It is possible to determine the period in which the infection has taken place with an accuracy depending on the frequency of the blood tests taken from the patient. For example, patients suffering from various diseases such as lack of certain factors in their blood or hepatitis have their blood tested on a regular basis making it possible to determine the period in which the infection has taken place. Apart from patients with diseases wherein blood tests are used to monitor the course of the disease, other groups of patients have blood tests taken, e.g. blood donors. Unfortunately, humans are still infected due to transfer of virus in blood samples, medical equipment, etc., making it possible to determine the date where the infection has taken place within the time frame of a few days. The importance of obtaining the virus early in the course of the infection is due to the known fact that many early isolates share the common feature of staying relatively constant in their envelope sequences (Karlsson et al., 1998). As these early isolates may share cross-reactive antibody- and/or T-cell epitopes a vaccine based on such early isolates would have a better chance of inducing immune response to shared epitopes of the virus. It is believed that an early, directly cloned virus isolate will share immunogenic sites with other early virus isolates seen during an HIV infection, so that if a mammal generates antibodies and/or T-cells directed against these epitopes, the transferred virus will be eliminated prior to the extensive mutations that may occur after approximately 12 months of infection. Thus, the virus should be isolated as early as possible, that is within the first 12 months of infection, such as 11, 10, 9, 8, 7, 6, 5, 4, 3, 2, 1, or 0.5 month after infection.

The HIV gene for genetic vaccine is preferably cloned directly from viral RNA or from proviral DNA. Direct cloning in this application stands for the virus not being multiplied in stable cell lines in vitro. It is presently expected that passing the virus through a stable cell line will promote mutation in the virus gene. It is particularly preferred not to pass the virus through cells lines selecting for viruses with CXCR4 receptor usage. Direct cloning also includes multiplication of virus in e.g. PBMC (peripheral blood mononuclear cells) since all virus can multiply in PBMC, and this type of multiplication generally does not select for CXCR4 receptor usage. Multiplication of virus is often necessary prior to cloning. Preferably cloning is performed directly on samples from the patient. In one embodiment of the invention, cloning is performed from patient serum. The cloning is then performed directly on the HIV virus, that is on RNA. In another embodiment of the invention cloning, is performed from infected cells. The cloning is then performed on HIV virus incorporated in the genes in an infected cell (e.g. a lymphocyte), that is on DNA. In the latter case the virus might be a silent virus, that is a non-replicating virus. To evaluate if the virus is silent, capability of multiplication in e.g. PBMC is tested.

Cloning is a technique well known to a person skilled in the art. A first nucleotide sequence is hereby obtained. In another aspect of the invention, the first nucleotide sequence, sharing the properties mentioned with direct cloning, is obtained by other means. This could be from a database of primary isolates or the like.

Based on the first nucleotide sequence, the amino acid sequence encoded by said nucleotide sequence is determined. A second nucleotide sequence encoding the same amino acid sequence is then designed utilizing the most frequent codons from highly expressed proteins in mammalians (see FIG. 1, for example, presenting the most frequent codons from highly expressed proteins in humans).

Presently, it appears that the usage of the most frequent codons from mammalian highly expressed proteins has two advantages: 1) the expression is Rev independent; 2) the level of expression is high. The Rev independence is especially advantageous when performing experiments in mice where the Rev systems is functioning sub-optimally. For the use in human vaccine, Rev independence and high expression are important to increase the amount of antigen produced. The determination of the codons for high expression is in this context based on the statistics from human highly expressed proteins (Haas, Park and Seed, 1996, hereby incorporated by reference). It is contemplated that the expression of a protein can be even higher, when current research in binding between codon (on the mRNA) and anticodon (on the tRNA) reveals codons with optimal binding capabilities, and when interactions in-between codons and/or in-between anticodons are known.

The second nucleotide sequence designed utilizing optimized codons is then redesigned to obtain a third nucleotide sequence. The purpose of the redesigning is to create unique restriction enzyme sites around the nucleotide sequence encoding functional regions of the amino acid sequence. By having unique restriction enzyme sites around the nucleotide sequence encoding functional regions of the amino acid sequence, the nucleotide sequence encoding functional regions of the amino acid sequence can easily be isolated, changed, and re-inserted. Examples of functional regions of the amino acid sequence are transmembrane spanning regions, immunodominant regions, regions with antibody cross reacting domains, fusion domains and other regions important for immunogenicity and expression such as variable region 1 (V1), variable region 2 (V2), variable region 3 (V3), variable region 4 (V4) and variable region 5 (V5).

It is important to select the restriction enzymes sites with care. By changing the second nucleotide sequence to insert restriction enzyme sites around the nucleotide sequence encoding functional regions of the amino acid sequence, the third nucleotide sequence must still code for the same amino acid sequence as the second and first nucleotide sequence do. Thus, if necessary, the second nucleotide sequence is redesigned by changing from optimized codons to less optimal codons. It is understood, that the restriction enzyme sites around the nucleotide sequence encoding functional regions of the amino acid sequence should preferably be placed in the terminal region of the nucleotide sequence encoding functional regions of the amino acid sequence. That is preferably outside the nucleotide sequence encoding functional regions of the amino acid sequence, such as 90 nucleotides away, e.g. 81, 72, 63, 54, 45, 36, 27, 21, 18, 15, 12, 9, 6, 3 nucleotides away, but could also be inside the nucleotide sequence encoding functional regions of the amino acid sequence, such as 54, 45, 36, 27, 21, 18, 15, 12, 9, 6, 3 nucleotides inside the nucleotide sequence encoding the functional region of the amino acid sequence.

The type of restriction enzyme sites allowed is determined by the choice of expression vector. In certain cases, the number of restriction enzyme sites is limited and it is hard, if not impossible, to place unique restriction enzyme sites around all the nucleotide sequences coding for functional regions of the amino acid sequence. This problem can be solved by dividing the entire nucleotide sequence into pieces, so that each piece comprises only unique restriction enzyme sites. Modifications to each of the piece is performed separately prior to assembly of the pieces. It is preferred that the nucleotide sequence is divided into 9 pieces. In another aspect, the nucleotide sequence is divided into 8 pieces, or 7, or 6, or 5, or 4, or 3, or 2 pieces. It is especially preferred that the nucleotide sequence is divided into 3 pieces.

Thus, the redesign of the second nucleotide sequence is an interaction between the choice of cloning vector, expression vector, selection of restriction enzyme sites, dividing into pieces, and exchange of codons to insert restriction enzyme sites. In a preferred embodiment of the present invention the cloning vector is Bluescript allowing the restriction enzyme sites chosen from the group consisting of: EagI, MluI, EcoRV, PstI, ClaI, EcoRI, XbaI, SacI, SpeI, XhoI, HindIII, SacII, NotI, BamHI, SmaI, SalI, DraI, KpnI. If other cloning vectors are chosen, other restriction enzyme sites will be available as known by the person skilled in the art.

As a part of the redesigning of the second nucleotide sequence, selected restriction enzyme sites may be removed. The selected restriction enzyme sites to be removed are those sites that are sites of the same type as the ones already chosen above and that are placed within the same piece. The removal of these restriction enzyme sites is performed by changing from optimized codons to less optimal codons, maintaining codons for the same amino acid sequence.

The third nucleotide sequence is redesigned so that the terminal snuts contain convenient restriction enzyme sites for cloning into an expression vehicle. The expression "vehicle" means any nucleotide molecule e.g. a DNA molecule, derived e.g. from a plasmid, bacteriophage, or mammalian or insect virus, into which fragments of nucleic acid may be inserted or cloned. An expression vehicle will contain one or more unique restriction enzyme sites and may be capable of autonomous replication in a defined host or vehicle organism such that the cloned sequence is produced. The expression vehicle is an autonomous element capable of directing the synthesis of a protein. Examples of expression vehicles are mammalian plasmids and viruses, tag containing vectors and viral vectors such as adenovirus, vaccinia ankara, adenoassociated virus, cannarypox virus, simliki forest virus (sfv), Modified Vaccinia Virus Ankara (MVA), and simbis virus. In one embodiment of the invention, the expression vector contains tag sequences. In another embodiment of the invention a bacteria is transformed with an expression plasmid vector and the bacteria is then delivered to the patient. Preferred expression vehicles are simliki forest virus (sfv), adenovirus and Modified Vaccinia Virus Ankara (MVA).

The snuts are produced by techniques well known by the person skilled in the art. The preferred method for synthesizing snuts, is herein referred to as "the minigene approach" wherein complementary nucleotide strands are synthesized with specific overhanging sequences for annealing and subsequent ligation into a vector. This can be performed with two sets of complementary nucleotide strands, or with three sets of complementary nucleotide strands. The minigene approach minimises the known PCR errors of mismatches and/or deletions, which may occur due to hairpins in a GC rich gene with mammalian highly expressed codons. In FIGS. 10–21, the production of a representative selection of snuts is illustrated.

For the production of long snuts, that is snuts of more than about 240 nucleotides, the technique of overlapping PCR is preferred as illustrated in FIG. 8. Herein two nucleotide strands about 130 nucleotides long with an overlap are filled to obtain a double strand, which is subsequently amplified by PCR.

For the production of multiple snuts with a length of less than about 210 nucleotides, one preferred technique is normal PCR. In a preferred production technique the snuts are synthesized with the same 5' flanking sequences and with the same 3' flanking sequences, as illustrated in FIG. 9. The advantages of this approach is, that the same PCR primer set can be used for amplification of several different snuts.

As known by the person skilled in the art, special conditions have to be used for each individual PCR reaction and it should be optimized to avoid inherent problems like deletions mismatches when amplifying GC rich genes from synthetic ssDNA material. Whichever of the above-mentioned techniques are used, it is well known by the person skilled in the art, that it will be necessary to correct unavoidable mismatches produced either due to the nucleotide strand synthesis material and/or the PCR reaction. This can be performed by site directed mutagenesis techniques.

After the various snuts have been produced, they are assembled into pieces and subsequently into the complete gene. Methods for assembly (such as ligation) are well known by the person skilled in the art.

In a preferred embodiment of the present invention the HIV gene encodes the entire HIV envelope. It is understood that the HIV envelope can be the full length envelope gp160 as well as shorter versions such as gp150, gp140, and gp120 with or without parts of gp41.

As will be known by the person skilled in the art, the HIV is divided into several groups. These groups presently include group M, group O, and group N. Further, the HIV is divided into subtypes A, B, C, D, E, F, G, H, I, and J. In the present invention subtype B is preferred due to the high prevalence of this subtype in the Western countries.

The determination of groups and subtypes is based on the degree of nucleotide sequence identity in the envelope gene is presently defined as follows: If the sequence identity is more than 90% the viruses belong to the same subtype; If the sequence identity is between 80% and 90% the viruses belong to the same group. If the sequence identity is less than 80% the viruses are considered as belonging to different groups.

One aspect of the invention relates to a nucleotide sequence construct in isolated form which has a nucleotide sequence with the general formula (I), (II), (III), or (IV)

$$P_1\text{-}S_{495ClaI}\text{-}S_{650\text{-}720EcoRI}\text{-}P_2\text{-}S_{1265gp120} \quad (I)$$

$$P_1\text{-}S_{495ClaI}\text{-}S_{650\text{-}720EcoRI}\text{-}P_2\text{-}S_{1265XhoI}\text{-}S_{1465PstI}\text{-}P_{4gp140} \quad (II)$$

$$P_1\text{-}S_{495ClaI}\text{-}S_{650\text{-}720EcoRI}\text{-}P_2\text{-}S_{1265XhoI}\text{-}S_{1465PstI}\text{-}P_{4gp150} \quad (III)$$

$$P_1\text{-}S_{495ClaI}\text{-}S_{650\text{-}720EcoRI}\text{-}P_2\text{-}S_{1265XhoI}\text{-}S_{1465PstI}\text{-}P_{4gp160}\text{-}S_{2060SacII}\text{-}P_5 \quad (IV)$$

wherein $P_1$ designates the nucleotide sequence SEQ ID NO:41, a nucleotide sequence complementary thereto, or a nucleotide sequence with a sequence identity of at least 90% thereto;

wherein $S_{495Cial}$ designates the nucleotide sequence SEQ ID NO: 7, a nucleotide sequence complementary thereto, or a nucleotide sequence with a sequence identity of at least 95% thereto;

wherein $S_{650\text{-}720EcoRI}$ designates the nucleotide sequence SEQ ID NO: 9, a nucleotide sequence complementary thereto, or a nucleotide sequence with a sequence identity of at least 95% thereto;

wherein $P_2$ designates the nucleotide sequence SEQ ID NO: 43, a nucleotide sequence complementary thereto, or a nucleotide sequence with a sequence identity of at least 85% thereto;

wherein $S_{1265gp120}$ designates the nucleotide sequence SEQ ID NO: 19, a nucleotide sequence complementary thereto, or a nucleotide sequence with a sequence identity of at least 70% thereto;

wherein $S_{1265XhoI}$ designates the nuclebtide sequence SEQ ID NO: 17, a nucleotide sequence complementary thereto, or a nucleotide sequence with a sequence identity of at least 80% thereto;

wherein $S_{1465PstI}$ designates the nucleotide sequence SEQ ID NO: 23, a nucleotide sequence complementary thereto, or a nucleotide sequence with a sequence identity of at least 90% thereto;

wherein $P_{4gp140}$ designates the nucleotide sequence SEQ ID NO: 57, a nucleotide sequence complementary thereto, or a nucleotide sequence with a sequence identity of at least 85% thereto;

wherein $P_{4gp150}$ designates the nucleotide sequence SEQ ID NO: 55, a nucleotide sequence complementary thereto, or a nucleotide sequence with a sequence identity of at least 85% thereto;

wherein $P_{4gp160}$ designates the nucleotide sequence SEQ ID NO: 53, a nucleotide sequence complementary thereto, or a nucleotide sequence with a sequence identity of at least 85% thereto;

wherein $S_{2060SacII}$ designates the nucleotide sequence SEQ ID NO: 33, a nucleotide sequence complementary thereto, or a nucleotide sequence with a sequence identity of at least 98% thereto; and wherein $P_5$ designates the nucleotide sequence SEQ ID NO: 59, a nucleotide sequence complementary thereto, or a nucleotide sequence with a sequence identity of at least 85% thereto.

The design of the parent synthetic BX08 gp160 envelope cassette gene with its variant length genes gp150, gp140, gp120 is outlined in FIG. 2.

The nucleotide sequence construct with the formula (I)

$$P_1\text{-}S_{495ClaI}\text{-}S_{650\text{-}720EcoRI}\text{-}P_2\text{-}S_{1265gp120} \quad (I)$$

(visualized in FIG. 3) (SEQ ID NO: 73) codes for the amino acid sequence of gp120 (SEQ ID NO: 74). This amino acid sequence is the part of the HIV envelope that is secreted. Thus, it contains the immunogenic epitopes without being bound to the cell membrane. This is of particular advantage if the nucleotide sequence construct is used for production of recombinant antigens or for a DNA vaccine as the antibody immune response may be higher to secreted versus membrane bound HIV antigens.

The nucleotide sequence construct with the formula (II)

$$P_1\text{-}S_{495ClaI}\text{-}S_{650\text{-}720EcoRI}\text{-}P_2\text{-}S_{1265XhoI}\text{-}S_{1465PstI}\text{-}P_{4gp140} \quad (II)$$

(visualized in FIG. 4) (SEQ ID NO: 67) codes for the amino acid sequence of gp140 (SEQ ID NO: 68). This amino acid sequence encodes the gp120 and the extracellular part of the gp41 protein. The amino acid sequence is secreted due to the lack of the transmembrane spanning region. This is of particular advantage if the nucleotide sequence construct is used for production of recombinant antigens as the immunogenic and/or antigenic epitopes in the extracellular part of gp41 are included and is of particular advantage for a DNA vaccine as the antibody immune response may be higher to secreted gp120 versus membrane bound HIV antigens.

The nucleotide sequence construct with the formula (III)

$$P_1\text{-}S_{495ClaI}\text{-}S_{650\text{-}720EcoRI}\text{-}P_2\text{-}S_{1265XhoI}\text{-}S_{1465PstI}\text{-}P_{4gp150} \quad (III)$$

(visualized in FIG. 5) (SEQ ID NO: 69) codes for the amino acid sequence of gp150 (SEQ ID NO: 70). This amino acid sequence contains all of the envelope protein gp160 except the c-terminal tyrosin containing internalization signals in the intracellular part of gp41. The membrane bound surface expression of the amino acid sequence is thereby maintained and enhanced. Mimicking the organization of the native epitope conformation may by expected, making this nucleotide sequence construct of particular advantage if the nucleotide sequence construct is used as a vaccine.

The nucleotide sequence construct with the formula (IV)

$$P_1\text{-}S_{495ClaI}\text{-}S_{650\text{-}720EcoRI}\text{-}P_2\text{-}S_{1265XhoI}\text{-}S_{1465PstI}\text{-}P_{4gp160}\text{-}S_{2060SacII}\text{-}P_5 \quad (IV)$$

(visualized in FIG. 6) (SEQ ID NO: 71) codes for the amino acid sequence of gp160 (SEQ ID NO: 72) i.e. the entire envelope.

The nucleotide sequence construct designated $P_1$ comprises the nucleotide sequence encoding the amino acid sequence in the first variable region (V1) and the amino acid sequence in the second variable region (V2). In one embodiment of the invention the first variable region is surrounded by EcoRV and PstI restriction enzyme sites, and the second variable region is surrounded by PstI and ClaI restriction enzyme sites but as stated above, the choice of restriction enzyme sites can alter.

The nucleotide sequence construct designated $S_{650\text{-}720EcoRI}$ comprises the nucleotide sequence encoding the amino acid sequence in the third variable region (V3). In one embodiment of the present invention $S_{650\text{-}720EcoRI}$ is characterized by the restriction enzyme sites EcoRI and XbaI in the terminals.

The nucleotide sequence construct designated $P_2$ comprises the nucleotide sequence encoding the amino acid sequence of the fourth variable and constant region (V4 and C4). In one embodiment of the present invention the forth variable region is surrounded by SacI and XhoI restriction enzyme sites.

The nucleotide sequence construct designated $S_{1265gp120}$ comprises the nucleotide sequence encoding amino acid sequence of the fifth variable and constant region (V5 and C5). $S_{1265gp120}$ further comprises a nucleotide sequence encoding a C-terminal stop codon.

The nucleotide sequence construct designated $P_{4gp140}$ comprises the nucleotide sequence encoding amino acid sequence of the transmembrane spanning region. $P_{4gp140}$ further comprises a nucleotide sequence encoding a C-terminal stop codon prior to the transmembrane spanning region.

The nucleotide sequence construct designated $P_{4gp160}$ comprises the nucleotide sequence encoding amino acid sequence of the transmembrane spanning region (trans membrane spanning domain: TMD). In a preferred embodiment of the present invention the transmembrane spanning region is surrounded by HindIII and SacII restriction enzyme sites.

The term "sequence identity" indicates the degree of identity between two amino acid sequences or between two nucleotide sequences calculated by the Wilbur-Lipman alignment method (Wilbur et al, 1983).

The nucleotide sequence constructs with the formula (I), (II), (III), or (IV) illustrates the flexibility in the present invention. By producing a gene with the'described method enables the production of a plethora of antigens with various immunogenic epitopes and various advantages for production and vaccine purposes. To further illustrate the flexibility of the invention, other changes and mutations are suggested below.

In order to improve the immunogenicity of the nucleotide sequence constructs of the invention it is suggested to change the nucleotide sequence such that one or more glycosylation sites are removed in the amino acid sequence. By removal of shielding glycosylations, epitopes are revealed to the immunesystem of the mammal rendering the construct more immunogenic. The increased immunogenicity can be determined by an improved virus neutralization. Changes in the nucleotide sequence such that one or more N-linked glycosylation sites are removed in the amino acid sequence is well known by the person skilled in the art. Potential glycosylation sites are N in the amino acid sequences N-X-T or N-X-S (wherein X is any amino acid besides P). The glycosylation site can be removed by changing N to any amino acid, changing X to a P, or changing T to any amino acid. It is preferred that N is changed to Q by an A to C mutation at the first nucleotide in the codon, and a C to G mutation at the third nucleotide in the codon. This is preferred to increase the GC content in the nucleotide sequence construct. As an alternative N is changed to Q by an A to C mutation at the first nucleotide in the codon, and a C to A mutation at the third nucleotide in the codon. Preferred mutations in the synthetic BX08 envelope gene to remove potential N-linked glycosylation sites in V1 and/or V2 are A307C+C309A and/or A325C+C327G and/or A340C+C342A and/or A385C+C387A and/or A469C+C471A. Examples of such changes is illustrated in SEQ ID NOs: 47, 49, and 51.

For historical reasons the HIVs have been divided into syncytia inducing strains and non syncytia inducing strains. The assay to determine whether a strain is syncytia inducing is described in Verrier et al 1997, hereby incorporated by reference: It is presently known, that viruses utilising the CXCR4 co-receptor are syncytia inducing strains. It is also, at the present, known that the binding site for the CXCR4 involves the third variable region (V3). In a preferred embodiment the nucleotide sequence construct is changed to create a binding site for the CXCR4 co-receptor. It is presently performed in the third variable regions, preferably by the mutation G865C+A866G.

It is well-established that the HIV envelope comprises immunodominant epitopes. An immunodominant epitope is an epitope that most antibodies from the mammal are directed against. The antibodies directed against these immunodominant epitopes may have little effect in elimination of the virus. It is therefore anticipated that modification of the immunodominant epitopes will induce antibodies directed against other parts of the envelope leading to a better elimination and neutralization of the virus. By modification is understood any change in the nucleotide sequence encoding an immunodominant epitope in the amino acid sequence such that said amino acid sequence no longer contains an immunodominant epitope. Thus, modification includes removal of the immunodominant epitope and decrease of immunogenicity performed by mutagenesis. In a preferred embodiment of the present invention an immunodominant epitope in the third variable region (V3) is modified, such as deleted or altered. In a much preferred embodiment the nucleotides 793–897 are deleted. In yet another preferred embodiment of the present invention an immunodominant epitope has been removed from gp41, such as deleted. This is performed in $P_7$ or $P_8$ by elimination of the nucleotides 1654–1710.

It is anticipated that when gp120 is dissociated from gp41 in a vaccine or antigen, two immunodominant epitopes, one on each protein, are exposed and antibodies are directed against these in the mammal. In the infectious virus, gp120 is coiled on top of gp41 and the gp120/gp41 is most likely organized in a trimer, so that these immunodominant epitopes are hidden and therefore less elimination of virus is observed. By removing the cleavage site between gp41 and gp120 a full length gp160, gp150, or gp140 can be obtained with a covalent binding between gp41 and gp120. Removal of the cleavage site between gp41 and gp120 is preferably performed by a mutation at position C1423A. An example of such a mutation is illustrated in the mutation of $S_{1265XhoI}$ (SEQ ID NO: 17) to $S_{1265gp160}$ (SEQ ID NO: 21).

In order to stabilize the full length gp160, gp150, and gp140 for example when the cleavage site between gp41 and gp120 has been removed as described above, cysteines can be inserted, preferably inside the gp41 helix creating disulphide bounds to stabilise a trimer of gp41s. In a preferred embodiment of the present invention the cysteines are inserted by the mutation 1618:CTCCAGGC:1625 to 1618:TGCTGCGG:1625. An example of such a change is illustrated in SEQ ID NO: 25.

The above mentioned decrease in immunodominant epitopes combined with the increase in immunogenicity of the other epitopes is expected to greatly enhance the efficacy of the nucleotide sequence construct as a vaccine.

During the production of the nucleotide sequence construct, it is convenient to ligate the snuts into pieces. The pieces, as described above, are characterized by their reversible assembly as there are no duplicate restriction enzyme sites. In a preferred embodiment one piece (herein designated $P_3$) contains $P_1$, $S_{495ClaI}$, $S_{650-720EcoRI}$, and $P_2$. Another piece (herein designated $P_8$) contains $S_{1265XhoI}$, $S_{1465PstI}$, and $P_{4gp160}$. Yet another piece (herein designated $P_7$) contains $S_{1265XhoI}$, $S_{1465PstI}$, $P_{4gp160}$, $S_{2060SacII, and P5}$.

One advantage of the present nucleotide sequence construct is the easy access to exchange and alterations in the content and function of the nucleotide sequence and the encoded amino acid sequence. In one embodiment the nucleotide sequence coding for a functional region or parts thereof of the amino acid sequence is repeated. The repeat could be back-to-back or a functional region or parts thereof could be repeated somewhere else in the sequence. Repeated could mean two (one repetition) but could also be three, six, or nine repeats. In a much preferred embodiment the repetition nucleotide sequence codes for amino acids in the third variable region.

In order to improve the protective capabilities of the invention against infections with HIV, one embodiment of the invention relates to the combination of epitopes. The present nucleotide sequence construct allows insertion of one or more new nucleotide sequences isolated from another group and/or subtype of HIV and/or isolated from another patient. Hereby a vaccine or antigen with two or more epitopes from two or more HIVs is obtained. In a preferred embodiment, the V3 is replaced by the new nucleotide sequence. In a much preferred embodiment, the new nucleotide sequence codes for amino acids in the third variable region of a different HIV isolate.

In order to improve the efficacy of the vaccine, aiming at raising cellular immunity, a nucleotide sequence coding for a T-helper cell epitope is included in the nucleotide sequence construct. The nucleotide sequence coding for a T-helper cell epitope or a T-helper cell epitope containing amino acid sequence can be put in anywhere in the nucleotide sequence construct as long as it does not interact with the function of the envelope molecule. However, it is preferably placed in the tail of the nucleotide sequence construct or between the leader sequence and the envelope gene. The T-helper epitopes are preferably selected from core proteins such as P24gag or from a non-HIV pathogen such as virus, bacteria, e.g. BCG antigen 85. For a therapeutic vaccine an HIV helper epitope is preferred since the patient is already primed by the HIV infection. For a prophylactic vaccine, a T-helper cell epitope from a frequently occurring non HIV pathogen such as Hepatitis B, BCG, CMV, EBV is preferred. Also, since the synthetic BX08 envelope genes may contain T-helper cell epitopes in addition to important antibody epitopes, the synthetic BX08 vaccine genes can be mixed with other DNA vaccines to improve the efficacy of the other DNA vaccine.

One aspect of the present invention relates to individualized immunotherapy, wherein the virus from a newly diagnosed patient is directly cloned, the envelope or subunits corresponding to snuts or pieces is produced with highly expressed codons, inserted into any of the nucleotide sequence constructs described above and administered to the patient as a vaccine. Hereby a therapeutic DNA vaccine is obtained, that will help the patient to break immune-tolerance or induce/reinduce an appropriate immune response. In one embodiment the variable regions of the virus are produced with highly expressed codons and exchanged into any of the nucleotide sequence constructs described above.

In one embodiment of the invention, the nucleotide sequence construct as described above satisfies at least one of the following criteria:

a) serum extracted from a Macaque primate which has been immunized by administration of an expression vector containing the nucleotide sequence construct is capable of eliminating SHIV as determined by quantitative PCR and/or virus culturing.

b) serum extracted from a primate which has been immunized by administration of an expression vector containing the nucleotide sequence construct is capable of neutralising HIV-1 BX08 and /or other HIV-1 strains in vitro.

c) serum, extracted from a mouse which has been immunized by administration of an expression vector containing the nucleotide sequence construct four times in intervals of three weeks and boosted after 15 weeks, is capable of decreasing the concentration of HIV-antigen in a culture of HIV, serum or PBMCs by at least 50%.

An example of such procudure is shown in example 9.

In one embodiment of the invention, the nucleotide sequence construct of the invention, is used in medicine. That is, it is used as a vaccine, for the production of a recombinant protein, such that the recombinant protein is used as a vaccine, or the nucleotide sequence construct or the recombinant protein is used in a diagnostic composition. Thus, the nucleotide sequence construct of the invention can be used for the manufacture of a vaccine for the prophylactics of infection with HIV in humans.

Intramuscular inoculation of nucleotide constructs, i.e. DNA plasmids encoding proteins have been shown to result in the generation of the encoded protein in situ in muscle cells and dendritic cells. By using cDNA plasmids encoding viral proteins, both antibody and CTL responses were generated, providing homologous and heterologous protection against subsequent challenge with either the homologous or cross-strain reaction, respectively. The standard techniques of molecular biology for preparing and purifying DNA constructs enable the preparation of the DNA therapeutics of this invention. While standard techniques of molecular biology are therefore sufficient for the production of the products of this invention, the specific constructs disclosed hereinprovide novel therapeutics which can produce cross-strain protection, a result heretofore unattainable with standard inactivated whole virus or subunit protein vaccines.

The amount of expressible DNA to be introduced to a vaccine recipient will depend on the strength of the transcription and translation promoters used in the DNA construct, and on the immunogenicity of the expressed gene product. In general, an immunologically or prophylactically effective dose of about 10 μg to 300 μg is administered directly into muscle tissue. Subcutaneous injection, intradermal introduction, impression through the skin, inoculation by gene gun preferably DNA coated gold particles, and other modes of administration such as intraperitoneal, intravenous, peroral, topic, vaginal, rectal, intranasal or by inhalation delivery are also contemplated. It is also contemplated that booster vaccinations are to be provided. It is further contemplated that booster vaccinations with recombinant antigens are to be provided, administered as described above.

The DNA may be naked, that is, unassociated with any proteins, adjuvants or other agents which impact on the recipients immune system. In this case, it is desirable for the DNA to be in a physiologically acceptable solution, such as, but not limited to, sterile saline or sterile buffered saline. Alternatively, the DNA may be associated with surfactants, liposomes, such as lecithin liposomes or other liposomes, such as ISCOMs, known in the art, as a DNA-liposome mixture, (see for example WO93/24640) or the DNA may be associated with and adjuvant known in the art to boost immune responses, such as a protein or other carrier. Agents which assist in the cellular uptake of DNA, such as, but not limited to, calcium ions, detergents, viral proteins and other transfection facilitating agents may also be used to advantage. These agents are generally referred to as transfection facilitating agents and as pharmaceutically acceptable carriers.

Those skilled in the field of molecular biology will understand that any of a wide variety of expression systems may be used. A wide range of suitable mammalian cells are available from a wide range of sources (e.g. the American Type Culture Collection, Rockland, Md.; also, see Ausubel et al. 1992). The method of transformation or transfection and the choice of expression vehicle will depend on the host system selected. Transformation and transfection methods are described, for example, in Ausubel et al 1992; expression vehicles may be chosen from those provided, for example, in P. H. Pouwels et al. 1985.

In one embodiment of the present invention the protein encoded by the nucleotide sequence construct is produced by introduction into a suitable mammalian cell to create a stably-transfected mammalian cell line capable of producing the recombinant protein. A number of vectors suitable for stable transfection of mammalian cells are available to the public, for exmaple, in *Cloning Vectors: a Laboratory Manual* (P. H. Pouwels et al. 1985); methods for constructing such cell lines are also publicly available, e.g., in Ausubel et al. 1992.

Standard reference works describing the general principles of recombinant DNA technology include Watson, J. D. et al 1987; Darnell, J. E. et al 1986; Old, R. W. et al, 1981; Maniatis,T. et al 1989; and Ausubel et al. 1992.

FIGURE LEGEENDS

The invention is further illustrated in the following non-limiting examples and the drawing wherein FIG. 1 provides the codon preference of highly expressed proteins in human cells.

FIG. 2 illustrates the outline of gp120, gp140, gp150, and gp160 encoding synthetic genes derived from the wild type sequence at the top. Variable (V) and constant (C) regions are shown together with the leader peptide (LP) and the transmembrane spanning domain (TMD). The approximate nucleotide positions of the restriction enzyme sites are shown. The approximate position of the three restriction enzyme sites dividing the full-length gp160 gene into the three pieces each containing only unique restriction enzyme sites are shown in bold.

FIG. 3 building of the synthetic gp120 gene. Variable (V) and constant (C) regions are shown together with the leader peptide (LP) and the transmembrane spanning domain (TMD). The approximate nucleotide positions of the restriction enzyme sites are shown.

FIG. 4 building of the synthetic gp140 gene. Variable (V) and constant (C) regions are shown together with the leader peptide (LP) and the transmembrane spanning domain (TMD). The approximate nucleotide positions of the restriction enzyme sites are shown, FIG. 5 building of the synthetic gp140 gene. Variable (V) and constant (C) regions are shown together with the leader peptide (LP) and the transmembrane spanning domain (TMD). The approximate nucleotide positions of the restriction enzyme sites are shown.

FIG. 6 building of the synthetic gp160 gene. Variable (V) and constant (C) regions are shown together with the leader peptide (LP) and the transmembrane spanning domain (TMD). The approximate nucleotide positions of the restriction enzyme sites are shown.

FIG. 7 illustrates the codons coding amino acids in general

Figure 22A:
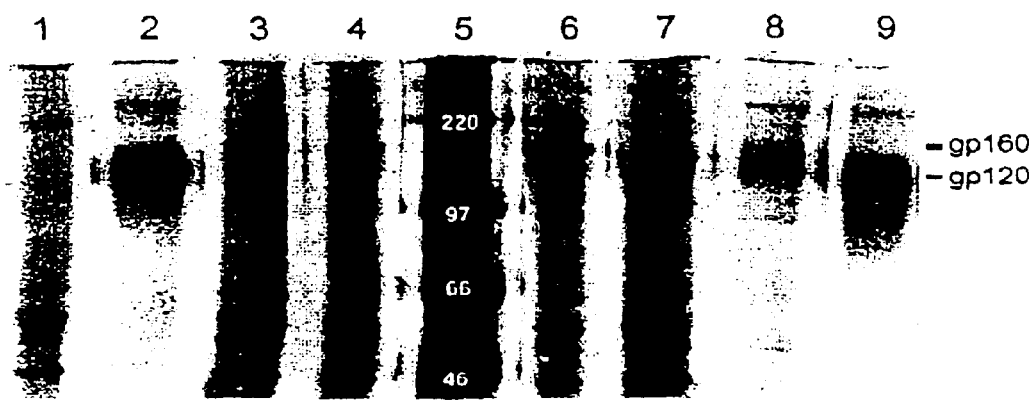

FIG. 22a SDS PAGE of $^{35}$S-labelled HIV-1 BX08 envelope glycoproteins radio-immuno precipitated from transiently transfected 293 cells using the indicated plasmids. Cell pellet (membrane bound antigens) or cell supernatant (secreted antigens) were precipitated by a polyclonal anti-HIV-1 antibody pool. Lane 1: untransfected cells. Lane 2: supernatant from syn.gp120$_{MN}$ transfected cells. Lane 3: cell pellet from wt.gp160$_{BX08}$ transfected cells. Lane 4: cell pellet from cells co-transfected by wt.gp160$_{BX08}$ and pRev. Lane 5: Mwt. marker. Lane 6: cell pellet from syn.gp160$_{BX08}$ transfected 293 cells. Lane 7: cell pellet from syn.gp150$_{BX08}$ transfected 293 cells. Lane 8: supernatant from syn.gp140$_{BX08}$ transfected cells. Lane 9: supernatant from syn.gp120$_{BX08}$ transfected cells.

Figure 22B:
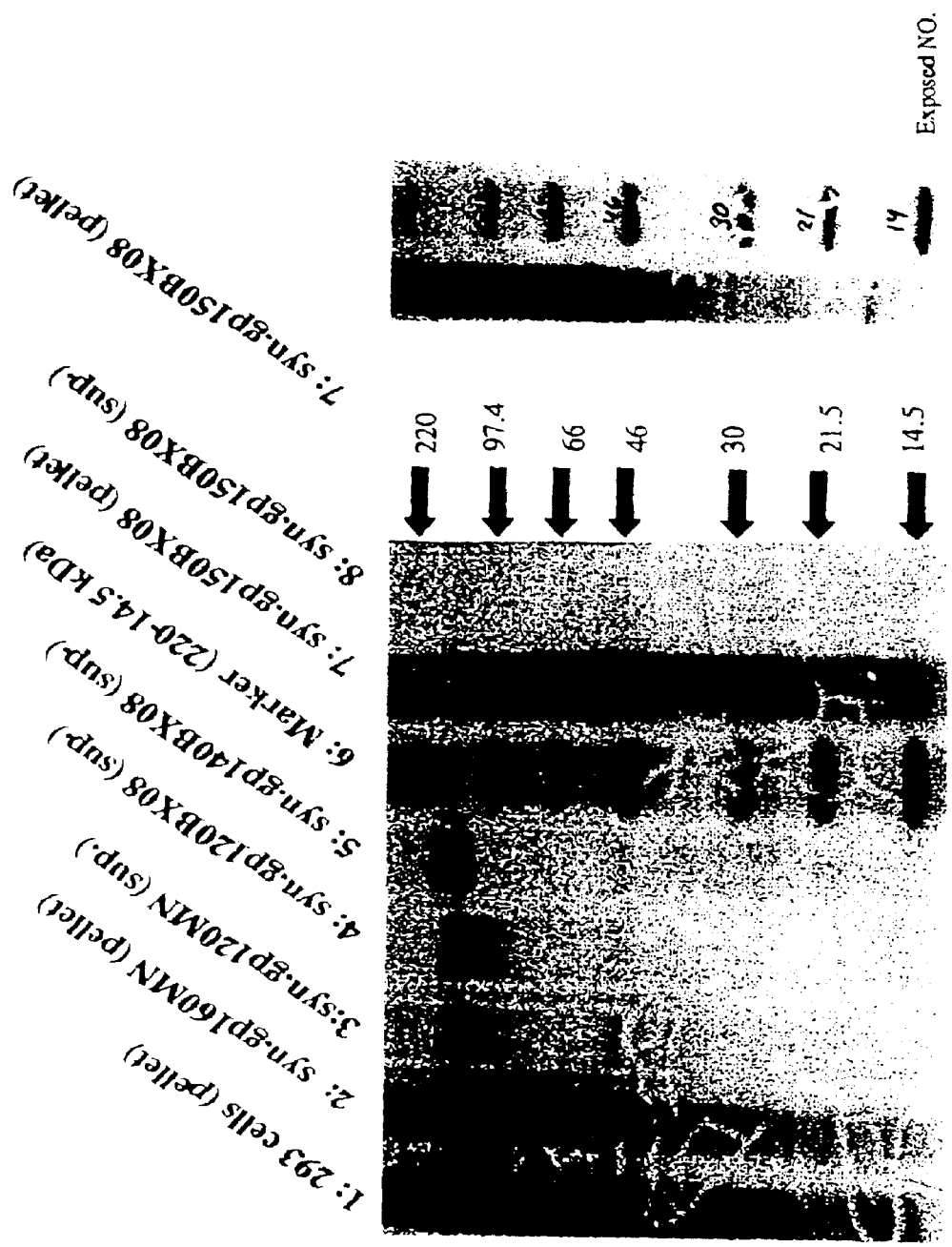

FIG. 22b is an SDS-PAGE of $^{35}$S-labeled HIV-1 BX08 envelope glycoproteins radio-immune precipitated from transiently transfected 293 cells as cell pellet (membrane bound) or cell supernatant (secreted antigens) by anti-HIV-1 antibody pool using the indicated plasmids. Lane 1: untransfected 293 cells. Lane 2: cell pellet from syn.gp160MN transfected 293 cells as positive control (Vinner et al 1999). Lane 3: Cell supernatant from syn.gp120MN transfected 293 cells as positive control (Vinner et al 1999). Lane 4: Cell supernatant from syn.gp120BX08 transfected 293 cells demonstrating a glycoprotein band of 120 kDa. Lane 5: Cell supernatant from syn.gp140BX08 transfected 293 cells demonstrating a glycoprotein band of 120 kDa. Lane 6: Mwt. marker. Lane7 at two different exposure times: Cell pellet from syn.gp150BX08 transfected 293 cells demonstrating a glycoprotein band of 120 kDa (lower gp30 band is not well seen in this exposure). Lane 8: Cell supernatant from syn.gp150BX08 transfected 293 cells showing no secreted proteins (all protein is membrane bound, see lane 7).

Figure 22C:
Figure 22C:
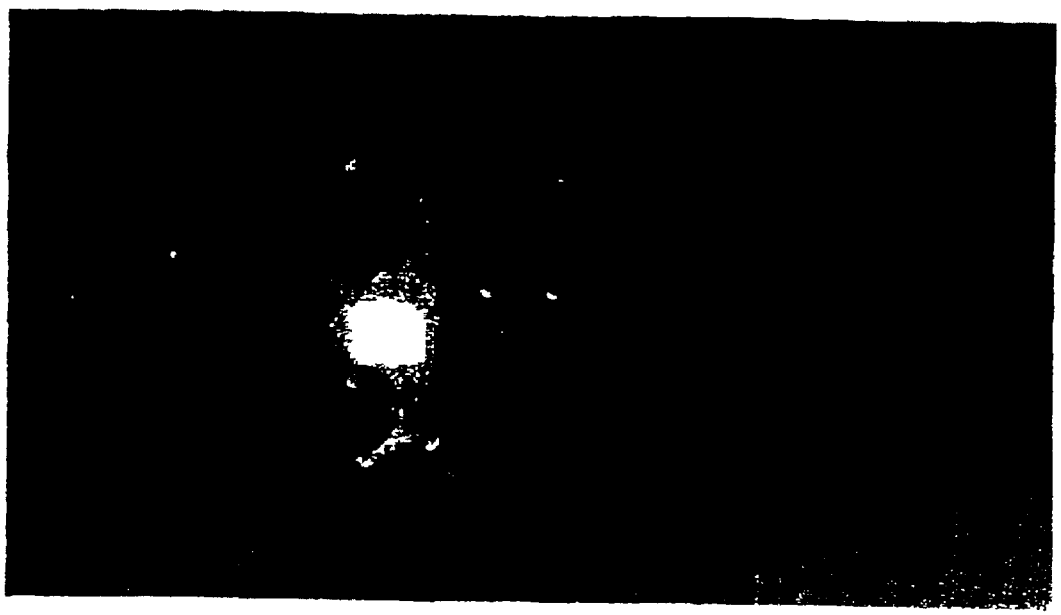
Figure 22C:
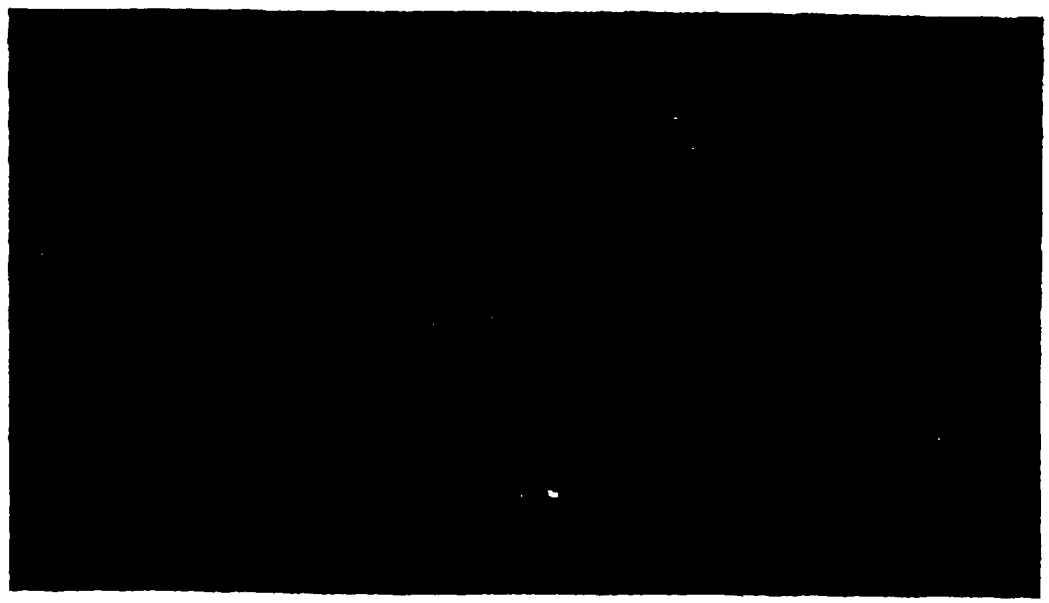

FIG. 22c show fluorescent microscopy of U87.CD4.CCR5 cells transfected with BX08 gp160 genes plus pGFP. Panel A: cells transfected with empty WRG7079 vector plus pGFP showing no syncytia. Panel B: cells transfected with wild type BX08gp160 gene plus pGFP showing some syncytia. Panel C: cells transfected with synBX08gp160 plus pGFP showing extreeme degree of syncytia formation. This demonstrates expression, functionality, and tropism of the expressed BX08 glycoprotein with much more expressed functionally active gp160 from the synthetic BX08 gene.

Figure 23:
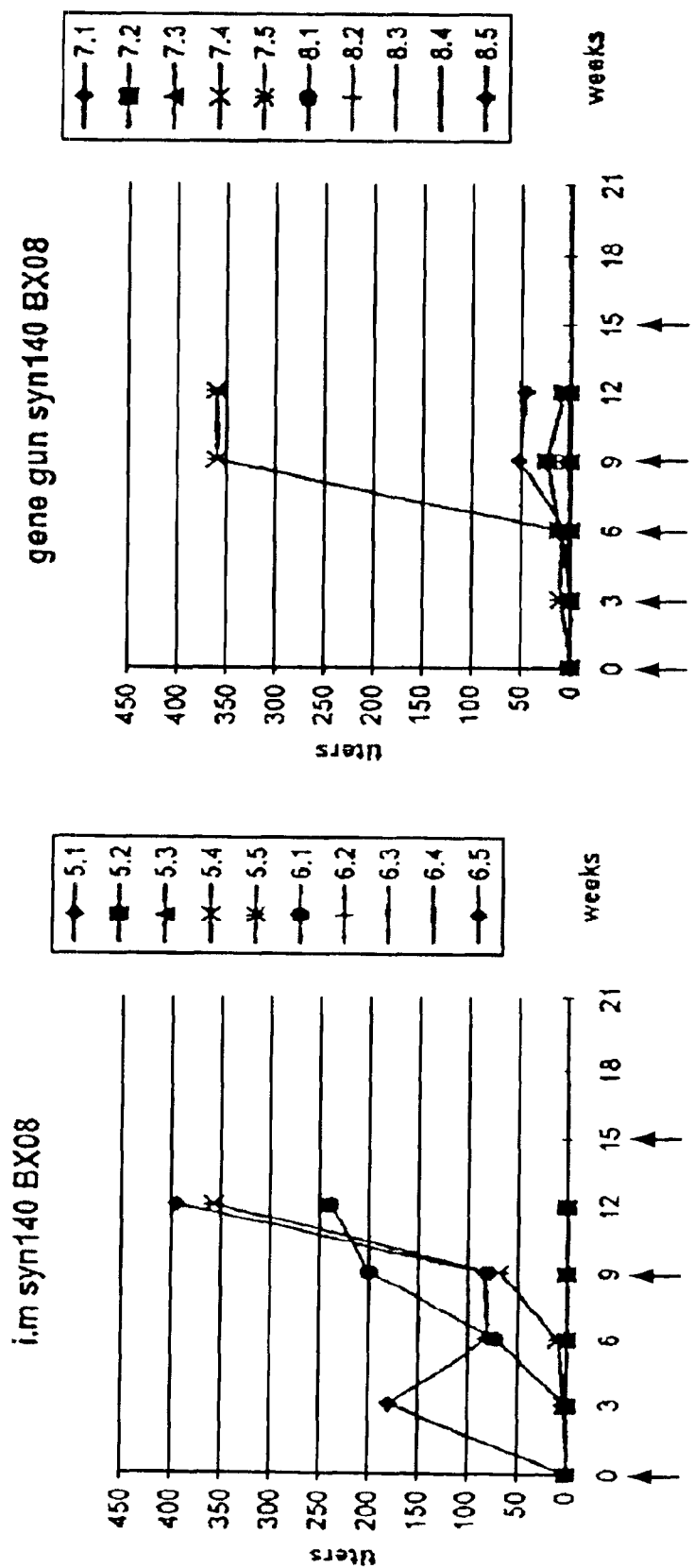

FIG. 23 shows the anti-Env-V3 BX08 antibody titers (IgG1). Panels show individual mice DNA immunized with syn.gp140BX08 plasmid either i.m. (left panel) or by gene gun (right panel), respectively. Immunization time points are indicated by arrows.

Figure 24:
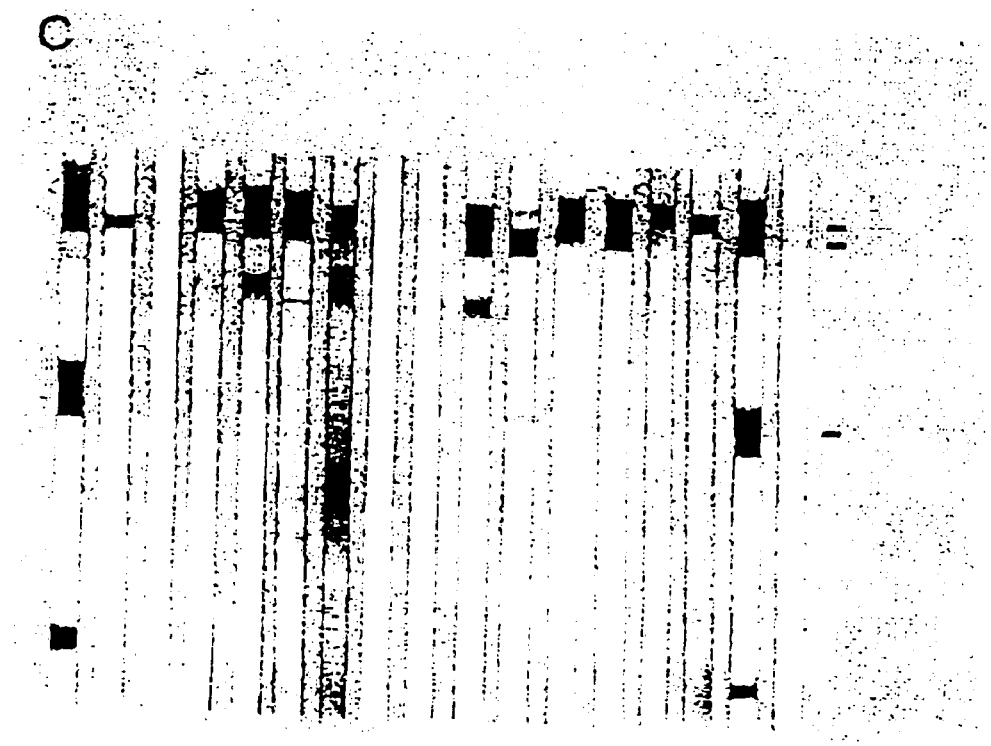

FIG. 24 shows a Western Blotting of (from left to right) one control strip, followed by sere (1:50) from 2 mice i.m. immunized with synBX08gp120, 2 mice i.m. immunized with synBX08gp140, 2 mice i.m. immunized with synBX08gp150, and 2 mice immunized with synBX08gp160, followed by 2 mice gene gun immunized with synBX08gp120, 2 mice gene gun immunized with synBX08gp140, 2 mice gene gun immunized with syn BX08gp150, and 2 mice gene gun immunized with synBX08gp160 respectively. Strip 5 is a mouse 5.1 DNA immunized i.m. with synBX08gp140 plasmid (same mouse as in FIG. 23). Plasma was examined at week 18. The positing of gp160 (spiked with four coupled gp51), gp120 and gp41 is indicated at the right. A positive reaction to HIV glycoproteins futher demonstrates the mouse anti-HIV immunoglobulin reacting to HIV of a strain (IIIB) different from BX08 to illustrate cross-strain reactivity.

Figure 25:
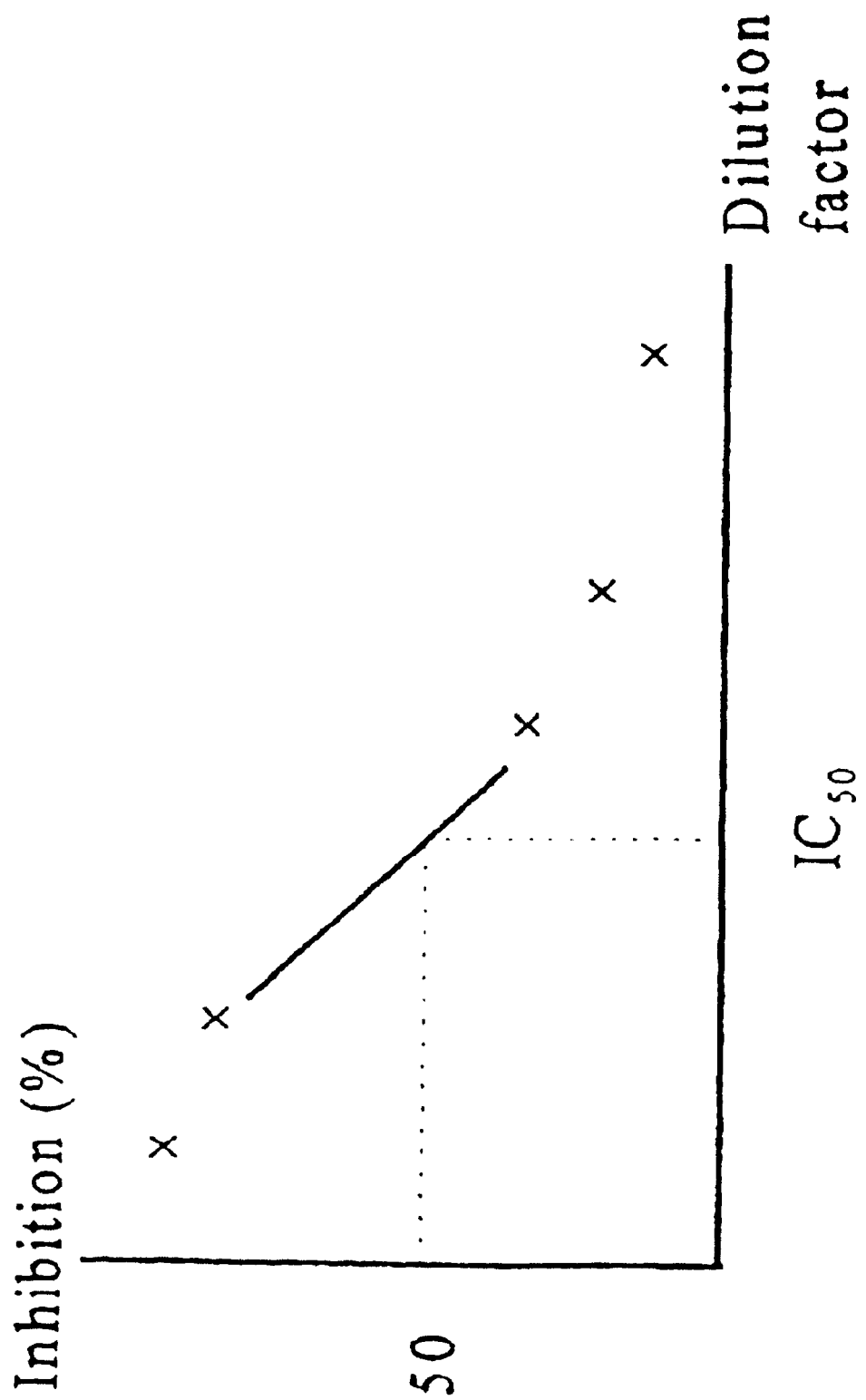

FIG. 25 Theoretical example of calculation of the 50% inhibitory concentration (IC$_{50}$) values. IC$_{50}$ for each mouse serum is determined by interpolation from the plots of percent inhibition versus the dilution of serum.

Figure 26A:
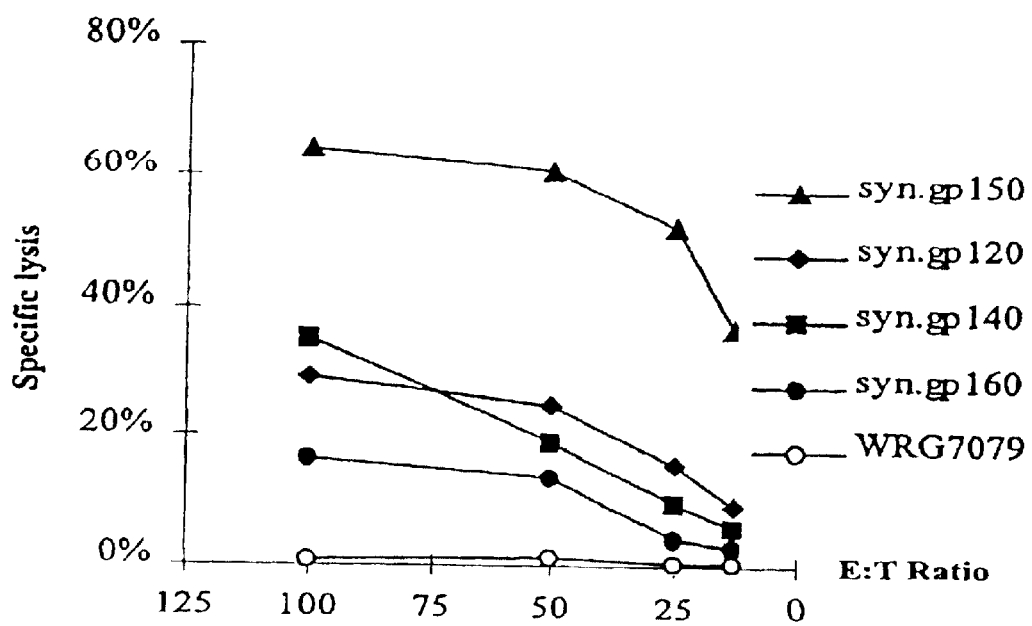
Figure 26B:
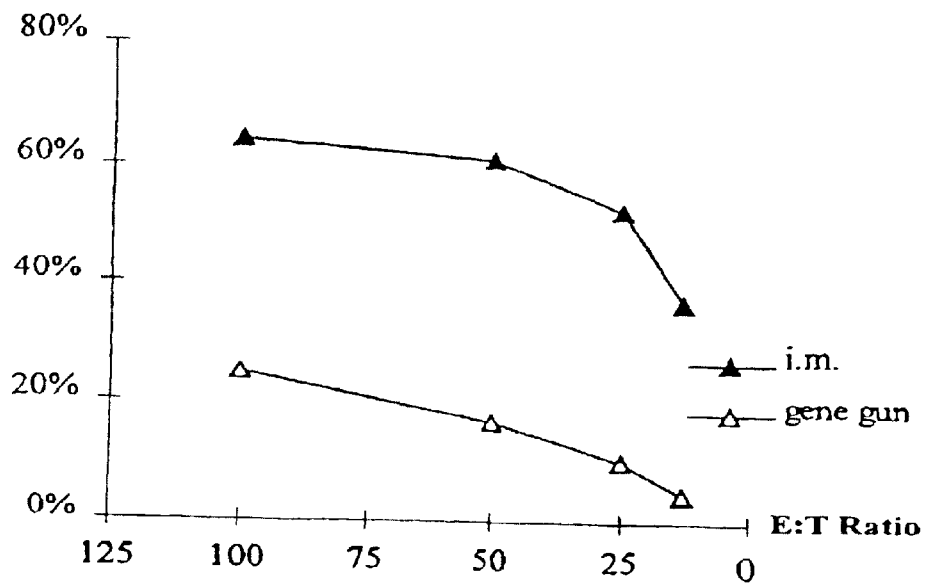

FIG. 26 CTL responses were measured at week 18 to the mouse H-2D$^d$ restricted BX08 V3 CTL epitope (IGPGGRAFYTT) (SEQ ID NO: 77) for BALB/c mice (H-2D$^d$) i.m. immunized at week 0, 9, and 15 with the synthetic vaccine genes: syn.gp120$_{BX08}$, syn.gp140$_{BX08}$, syn.gp150$_{BX08}$, and syn.gp160$_{BX08}$, respectively, and median values of different E:T ratios for groups of mice are shown (26A). Intramuscular DNA immunization with syn.gp150$_{BX08}$ induced a higher CTL reponse when injected i.m. in high amounts versus gene gun inoculation of skin (26B).

FIG. 27 Summary of western immuno blotting assay of mice sera (1:40) collected at week 0, 9, and 18 from mice genetically immunized with syn.gp120$_{BX08}$, syn.gp140$_{BX08}$, syn.gp150$_{BX08}$, syn.gp160$_{BX08}$, wt.gp160$_{BX08}$, and wt.gp160$_{BX08}$ plus pRev, respectively. Percent responders in groups of 17–25 mice against gp120 and gp41 are shown.

Figure 28A:
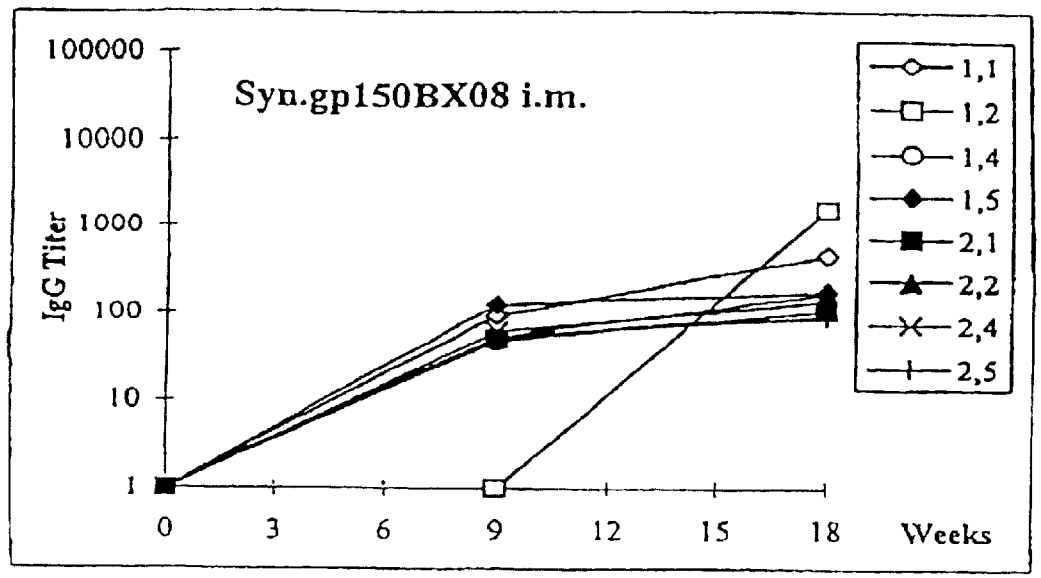
Figure 28B:
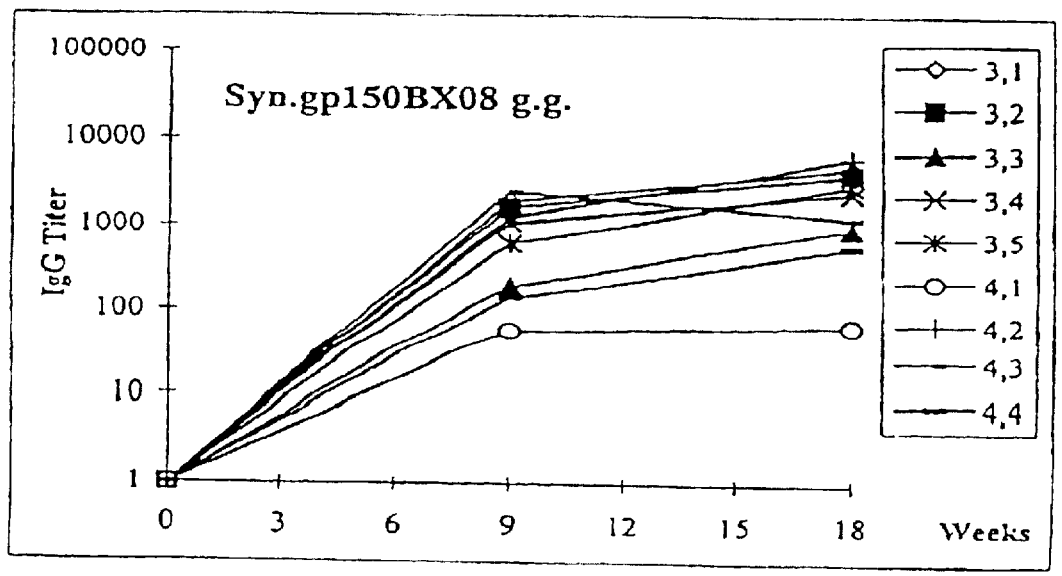

FIG. 28 IgG anti-rgp120 (IIIB) antibody titers of individual mice inoculated at week 0, 9, 15 (28A), or gene gun immunized at week 3, 6, 9, and 15 (28B) with the syn.gp150$_{BX08}$ DNA vaccine.

Figure 29A:
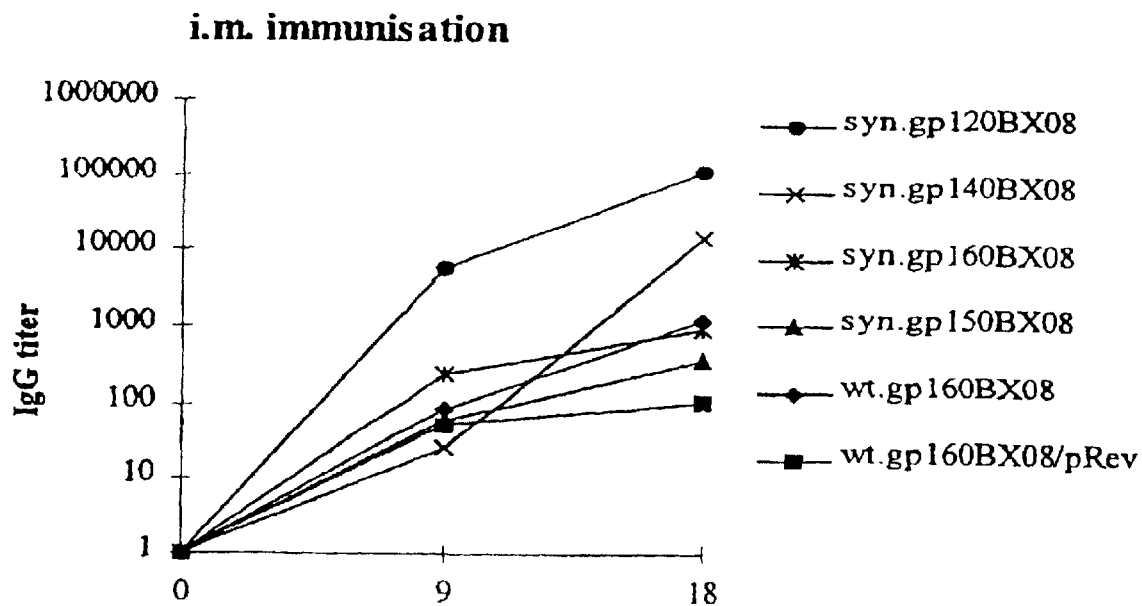
Figure 29B:
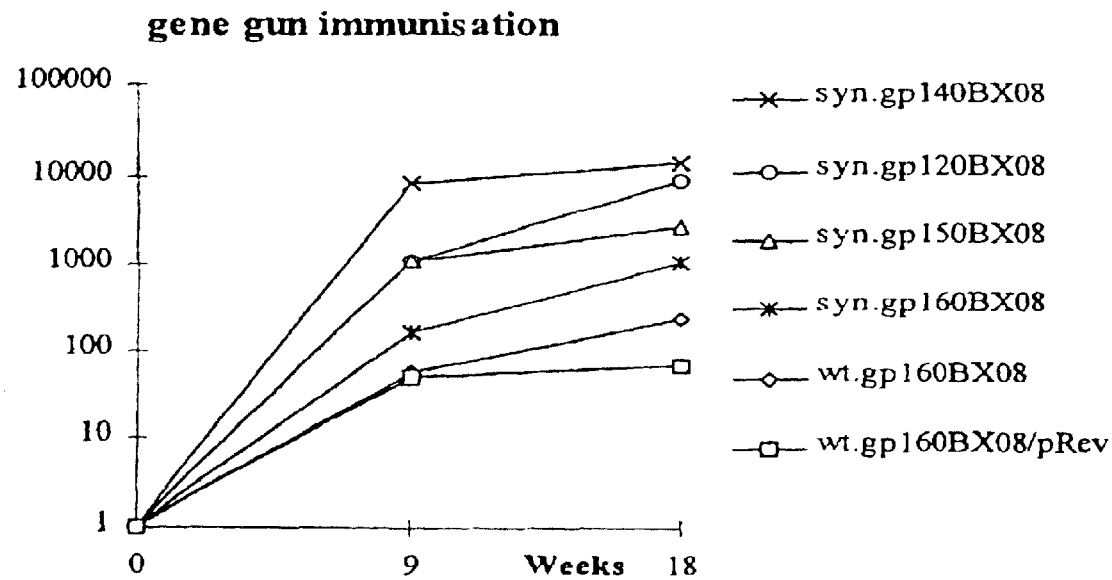

FIG. 29 IgG antibody titers to HIV-1 rgp120$_{IIIB}$. Median titers are shown from groups of mice i.m. inoculated at week 0, 9, and 15 (29A), or gene gun immunized at week 0, 3, 6, 9, and 15 (29B) with the synthetic genes syn.gp120$_{BX08}$, syn gp140$_{BX08}$, syn gp150$_{BX08}$, and syn.gp160$_{BX08}$, respectively.

EXAMPLES

Example 1

Designing the Nucleotide Sequence Construct

Initially the overall layout of the nucleotide sequence construct is decided. The overall layout comprises the various derivatives the gene will be expressed as. For BX08 these include, but are not restricted to gp160, gp150, gp140, gp120, and gp41.

Next, the vehicle of expression (plasmid or virus) is to be determined: Preparation for a suitable vector determines both need for leader sequence, terminal restriction enzyme sites and whether or not an N- or C-terminal protein tag is to be considered (Poly-his, Myc-antibody-epitop, etc.). For BX08 a plasmid expression vehicle was chosen. All native wild type HIV codons are systematically exchanged with the codons most frequently represented in a pool of highly expressed human genes (FIG. 1). By this exchange the amino acid sequence is conserved while the nucleotide sequence is dramatically altered. Thus, gene structures like overlapping reading frames (e.g. vpu, rev, and tat) or secondary structures (e.g. RRE) are most likely destroyed whereas protein cleavage sites, and glycosylation sites are maintained. The 100% amino acid identity between wtBX08 and synthetic BX08 in the present examples should be calculated after the initial Ala-Ser amino acid sequence, as that sequence is a part of the 6 amino acid sequence long NheI restriction enzyme site.

Depending on the restriction enzyme sites located in the expression vector it is decided which restriction enzyme sites can be present (tolerated) throughout the finished gene construct. The terminal restriction enzyme sites of the synthetic gene must remain unique to enable cloning into the vector chosen for expression. General requirements for restriction enzyme sites of choice: Preferably creating cohesive ends facilitating ligation, creating no compatible ends with adjacent restriction enzyme sites (e.g. BamHI/Bg/II), and being efficient cutters. For BX08 the restriction enzyme sites accepted were the ones present in the polylinker of the pBluescript cloning vectors (EagI, MluI, EcoRV, PstI, ClaI, EcoRI, XbaI, SacI, SpeI, XhoI, HindII, SacII, NotI, BamHI, SmaI, SalI, DraI, KpnI with the exception of BglII and NheI). This was decided to satisfy the original cloning strategy using individual cloning of snuts in pBluescript with restriction enzyme cleaved (trimmed) ends after PCR amplification, which is not necessary when blunt-end cloning and assembling of complementary oligonucleotides are employed. All locations at which the selected restriction enzyme sites can be introduced by silent mutations (keeping 100% loyal to the amino acid sequence) are identified using the SILMUT software or equivalent.

From these possible restriction enzyme sites, a selection of restriction enzyme sites are introduced by silent nucleotide substitutions around functional regions of choice of the corresponding gene (e.g. RRE) or gene products (e.g. variable region 1 (V1), V2, V3, CD4 binding area, transmembrane domain, and regions of immunological significance, etc.). Restriction enzyme sites are located at terminal positions of subcloned snuts (building entities) but additional restriction enzyme sites may, be present within subunits. For BX08 the construct was initially to be cloned in the WRG7079 vector containing a tPA-leader sequence. Cloning sites were 5'-NheI→BamHI-3'. The entire humanized BX08 sequence was divided into thirds: 5'-NheI→XhoI→SacII→BamHI-3'. These sites were chosen in this particular order because it resembles the polylinker of pBluescript (KS$^-$) enabling successive ligations of the assembled thirds in this cloning vector. Within these thirds restriction enzyme sites were kept unique. Next, restriction enzyme sites were placed to flank the functional regions chosen as follows:

A. (5'-V1): EcoRV-235: Between C1 and V1. Alternatives: 3×HindIII (already excluded because exclusive use at position 1890) or EcoRV.
B. (V1-3'): Only alternative PstI 375.
C. (5'-V2): as B.
D. (V2–3'): Alternatives: SpeI, ClaI 495. ClaI chosen because it is closer to V2.
E. EcoRI 650 placed because next possible site was too far away.
F. (5'-V3): BglII 720 was the alternative closest to the V3 region and further more unique.
G. (V3–3'): Alternatives XhoI (excluded) and XbaI 900 located very close to the V3 loop.
H. (5'-V4) SacI 990: alternatively EcoRI or BamHI (both excluded)
I. (V4–3'): Alternatives SpeI 1110, KpnI 1145, PstI 1135. PstI already used, SpeI chosen because of distance to previous site (SacI 990).
J. (5'-V5): XhoI initially determined.
K. (Fusion peptide-3') PstI 1465 was the closest alternative to XhoI 1265.
L. (5'-lmmunodominant region): XbaI 1630 chosen among EcoRV (blunt end), PstI and XhoI (both already used).
M. (Immunodominant region-3'): EagI 1700 perfect location.
N. (C34 and C43–3' (Chan, Fass, et al. 1997), and 5'-trans membrane domain): SacII. No alternatives.
O. (Trans membrane domain-3'): SacII 2060 already present.
P. ClaI 2190 perfect position in relation to previous RE-site.
Q: PstI perfect position in relation to previous RE-site.
R. EcoRI 2400 introduced to facilitate later substitution of terminal snut.
S. BamHI 2454 determined by the WRG7079 vector.

Remove undesired restriction enzyme sites by nucleotide substitutions (keeping loyal to the amino acid sequence). Nucleotide substitution should preferably create codon frequently used in highly expressed human genes (FIG. 1). If that is not possible, the codons should be the selected from the regular codons (FIG. 7). The substitutions made to the second nucleotide sequence to obtain desired restriction enzyme sites are shown in Table 2.

TABLE 2 lists silent nucleotide substitutions in the humanized BX08 envelope sequence. Substitutions were made to create or delete restriction enzyme sites.

Figure 8:
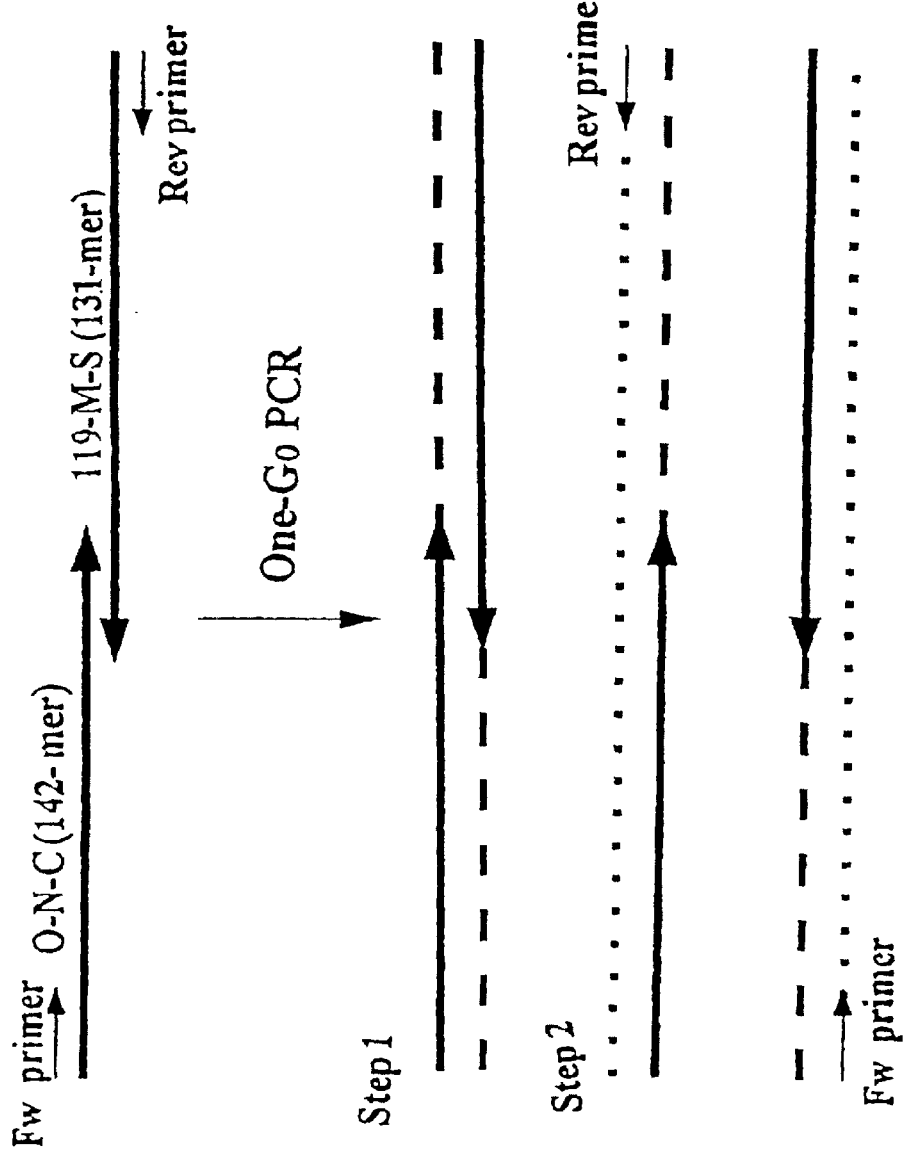
FIG. 8 illustrates how overlapping PCR is performed.

| Position: | substitution | Remarks: |
|---|---|---|
| 138 | c → g | creates Mlu I site on pos. 134–139 |
| 240 | c → t | creates EcoRV site on pos. 238–243 |
| 501 | c → a | creates Cla I site on pos. 501–506 |
| 502 | a → t | " |
| 503 | g → c | " |
| 504 | c → g | " |
| 657 | c → a | creates EcoRI site on pos. 656–661 |
| 660 | c → t | " |
| 724 | c → a | creates Bgl II site on pos. 724–729 |
| 726 | c → g | " |
| 727 | a → t | " |
| 728 | g → c | " |
| 729 | c → t | " |
| 840 | c → t | EagI site is eliminated |
| 904 | a → t | creates Xba I site on pos. 904–909 |
| 905 | g → c | " |
| 906 | c → t | " |
| 907 | c → a | " |
| 909 | c → a | " |
| 994 | a → t | creates Sac I site on pos. 990–995 |
| 995 | g → c | " |
| 1116 | c → t | creates SpeI site on pos. 1114–1119 |
| 1119 | c → t | " |
| 1273 | a → t | creates XhoI site on pos. 1272–1277 |
| 1274 | g → c | " |
| 1275 | c → g | " |
| 1293 | c → t | Bgl II site is eliminated |
| 1443 | c → t | BstXI site is eliminated |
| 1452 | g → c | " |
| 1467 | c → t | PstI site on pos. 1466–1471 |
| 1470 | c → a | " |
| 1590 | g → c | PstI site on pos. 1588–1593 is eliminated |
| 1620 | g → c | PstI site on pos. 1618–1623 is eliminated |
| 1638 | c → t | creates XbaI site on pos. 1638–1643 |
| 1641 | g → a | " |
| 1653 | g → c | PstI site is eliminated |
| 1687 | a → t | PstI site is eliminated |
| 1688 | g → c | PstI site is eliminated |
| 1710 | c → g | creates EagI site on pos. 1709–1714 |
| 1758 | c → t | Bgl II site is eliminated |
| 1875 | g → c | PstI site is eliminated |
| 1893 | c → a | Hind III pos. 1893–1898 |
| 1897 | c → t | " |
| 1944 | c → t | Bgl II site is eliminated |
| 2199 | c → t | Cla I site on pos. 2198–2203 |
| 2202 | c → t | " |
| 2203 | c → t | " |
| 2253 | c → g | SacII site is eliminated |
| 2292 | g → c | PstI site is eliminated |
| 2320 | a → t | PstI site on pos. 2321–2326 is eliminated |
| 2321 | a → t | " |
| 2322 | g → t | " |
| 2325 | c → a | " |
| 2430 | c → a | creates EcoRI site on pos. 2429–2434 |
| 2433 | c → t | " |

Example 2

Synthesis of Oligos

In order to clone the individual snuts, nucleotide strands were synthesized or purchased. In total 28 synthetic nucleotide strands were synthesized. Nucleotide strands were synthesized by standard 0.2 μmol β-cyanoethyl-phosphoramidite chemistry on an Applied Biosystems DNA synthesiser model 392, employing 2000 Å CPG columns (Cruachem, Glasgow, Scotland), acetonitrile containing less than 0.001% water (Labscan, Dublin, Ireland) and standard DNA-synthesis chemicals from Cruachem, including phosphoramidites at 0.1 M and Tetrahydrofuran/N-methylimidazole as cap B solution. The nucleotide strands O-N-C and 119MS-RC (for cloning of snut O-N-Lang), 650-E-BG and 720-XBAC-31 (for cloning of snut 650-720-EcoRI), 2425esup and 2425ESdo (for cloning of snut 2425-E-S) were synthesized with 5' end "trityl on" and purified on "Oligonucleotide Purification Cartridges" (Perkin Elmer, Calif., USA) as described by the manufacturer. Other nucleotide strands (235-ECO5, 375-pst1.seq, 495-CIa1.seq,900-XbaI, 990-sac1, 1110-SPE, 1630-Xba.seq, 1700-Eag.seq, 17-Eag.seq, 1890-Hind.MPD, 2060-sac, 2190-cla, 2330-pst) were synthesized with 5' end "trityl off" and purified by standard ethanol precipitation. Oligoes 1265-1 UP, 1265-1DO, 1265-2UP, 1265-2DO, 1265-3UP, 1265-3DO, 1465-1UP, 1465-1DO, 1465-2DO were purchased from Pharmacia.

Example 3

Cloning of Snuts

The nucleotide sequence construct was designed in 17 DNA small pieces called snuts (Table 3) encompassing important structures like variable and constant regions each flanked with restriction enzyme (RE) sites to facilitate cassette exchange within each third of the gene: NheI-XhoI, XhoI-SacII, SacII-BamHI.

Each snut was cloned individually in a commercial vector (pBluescriptKS or pMOSblue) and kept as individual DNA plasmids, named after the snut which gives the nucleotide position of the RE in the BX08.

TABLE 3 list the snuts by their name and cloning vector.

| Name | Cloning vector: |
|---|---|
| $S_{O\text{-}N\text{-}Lang}$ | pMOSblue |
| $S_{235EcoRV}$ | pMOSblue |
| $S_{375PstI}$ | pBluescriptSK |
| $S_{495ClaI}$ | pMOSblue |
| $S_{650\text{–}720EcoRI}$ | pMOSblue |
| $S_{900XbaI}$ | pMOSblue |
| $S_{990SacI}$ | pMOSblue |
| $S_{1110SpeI}$ | pMOSblue |
| $S_{1265XhoI}$ | pBluescriptSK |
| $S_{1465PstI}$ | pBluescriptSK |
| $S_{1630XbaI}$ | pBluescriptSK |
| $S_{1700EagI}$ | pBluescriptSK |
| $S_{1890HindIII}$ | pBluescriptSK |
| $S_{2060SacII}$ | pMOSblue |
| $S_{2190ClaI}$ | pMOSblue |
| $S_{2330PstI}$ | pMOSblue |
| $S_{2425ES}$ | pBluescriptSK |

Three principally different methods were used to obtain the dsDNA corresponding to each of the 17 snuts needed to build the synthetic BX08 genes.

1) "Overlapping" PCR: is based on the use of two ssDNA template nucleotide strands (forward and reverse) that complement each other in their 3'-end (FIG. 8). During the first PCR cycle, both templates annealed to each other at the 3'-ends allowing the full-length polymerization of each complementary strand during the elongation step. The newly polymerized dsDNA strand are then amplified during the following cycles using an adequate forward and reverse primers set (FIG. 8).

Snut O-N-LANG: ($S_{O-N-Lang}$) two ng of the forward template nucleotide strands O-N-C and 2 ng of the reward template-nucleotide strand 119MS-RC were mixed together with 50 pmoles of the forward primer O-N-LANG-5 (5'-CTAGCTAGCGCGGCCGACCGCCT -3') (SEQ ID NO: 78) and 50pmoles of the reverse primer O-N-LANG-3 (5'-CTCGATATCCTCGTGCATCTGCTC-3') (SEQ ID NO: 79) in a 100 µl PCR reaction volume containing 0.2 mM dNTP's, 1×ExpandHF buffer with $MgCl_2$ (1.5 mM) and 2.6 units of enzyme mix (Expand™ High fidelity PCR system from Boehringer Mannheim). The PCR was performed with the PE Amp 9600 thermocycler (Perkin Elmer) using the following cycle conditions: initial denaturation at 94° C. for 30 sec., followed by 30 cycles of 94° C. for 15 sec., 65° C. for 30 sec., 72° C. for 45 sec., with a final elongation at 72° C. for 5 min., and cooling to 4° C.

Snut 650–720-EcoRI: ($S_{650-720EcoAI}$) PCR amplification was performed as described for snut O-N-LANG. One µg of the forward ssDNA template-oligonucleotide 650-E-BG and 1 µg of the reverse ssDNA template-oligonucleotide 720-XBAC were mixed with 40 pmoles of the forward primer 650-E-5 (5'-CCGGAATT-CGCCCCGTGGTGAGCA-3') (SEQ ID NO: 80) and 40 pmoles of the reverse primer 720-X-3 (5'-CTGCTCTAGAGATGTTGCAGTGGGCCT-3') (SEQ ID NO: 81).

Figure 9:
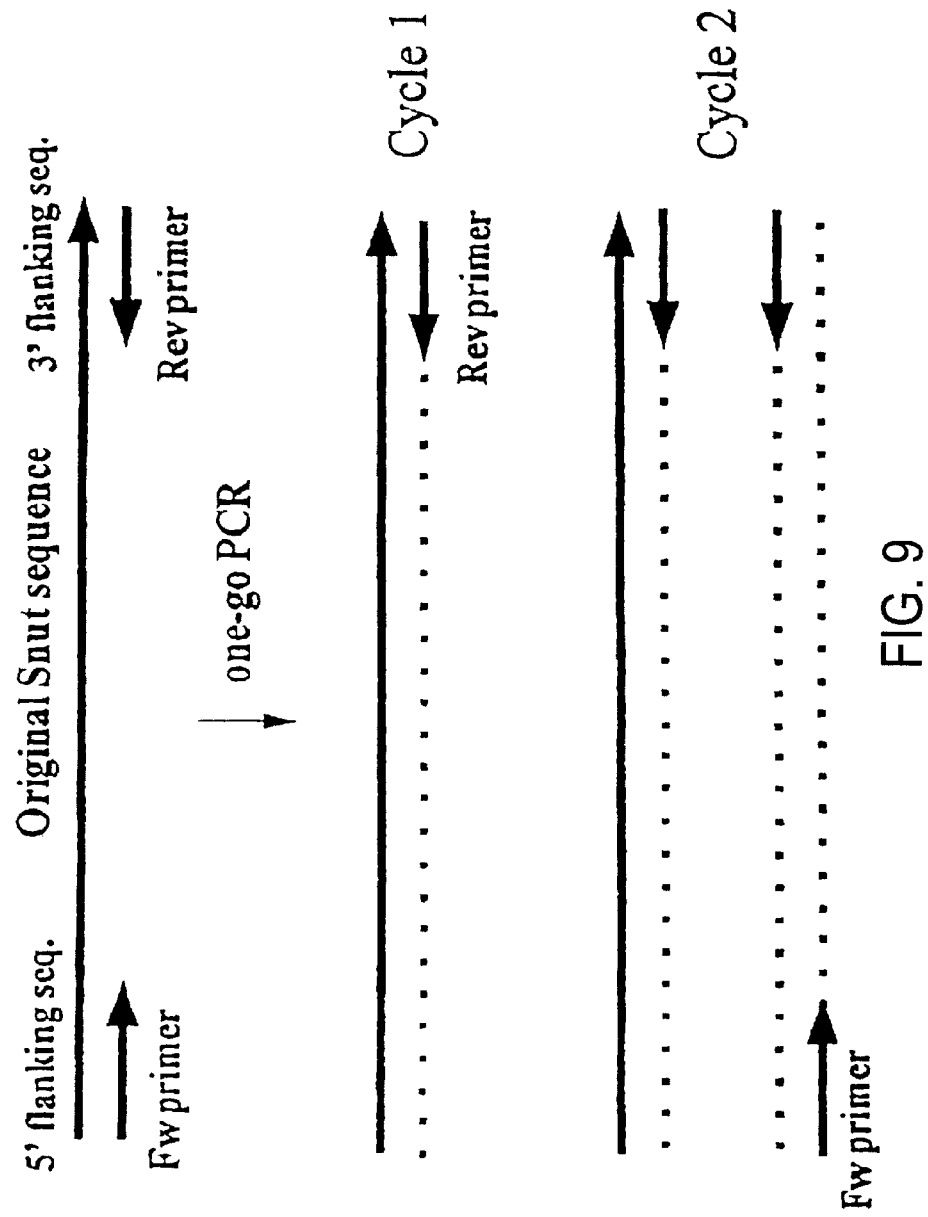
FIG. 9 illustrates how PCR using conserved flanking ends is performed.

2) "Normal" PCR amplification: Eleven nucleotide strands: 235-ECO5, 375-pst1, 900-xba1, 990-sac1, 1110-SPE, 1630-XBA, 1700-EAG, 1890-HIN, 2060-sac, 2190-cla, and 2330-pst, were designed with common 5' and 3' flanking sequences which allowed PCR amplification with the same primer set (Forward primer: BX08-5 (5'-AGCGGATAACAATTTCACACAGGA-3') (SEQ ID NO: 82) and revers primer: BX08-3 (5'-CGCCAGGGTTTT CCCAGTCACGAC-3') (SEQ ID NO: 83) (FIG. 9). The 495-Cla1 oligonucleotide was designed without a common flanking sequence and was therefore amplified with a specific set of primers 495-5N/495-3N (5'-GAATCGATCATCACCCAG-3') (SEQ ID NO: 84) and 5'-GACGAATTCCGTGGGTGCACT-3') (SEQ ID NO: 85). Each oligonucleotide was resuspended in 1 ml of water and kept as a stock solution (approximately 0.2 mM). PCR amplification was performed with the Expand™ High Fidelity PCR System from Boehringer Mannheim (Cat. No. 1759078). Four concentrations of template nucleotide strand were systematically used: undiluted stock solution, stock solution $10^{-1}$, stock solution $10^{-2}$, stock solution $10^{-3}$. One to 5 µl of synthetic ssDNA template was amplified using the following conditions: BX08-5 (0.5 µM), BX08-3 (0.5 µM), 4 dNTP's (0.2 mM), 1×ExpandHF buffer with $MgCl_2$ (1.5 mM) and 2.6 units of enzyme mix. The PCR was performed using the PE Amp 9600 thermocycler (Perkin Elmer) using the following cycle conditions: initial denaturation at 94° C. for 15 sec., followed by 30 cycles of 94° C. for 15 sec., 65° C. for 30 sec. and 72° C. for 45 sec., with a final elongation at 72° C. for 7 min., and cooling to 4° C.

3) Minigene approach: This method was used to synthesise $S_{1265XhoI}$, $S_{1465XbaI}$ and $S_{2425ES}$.

Snut 2425-E-S ($S_{2425ES}$): 100 picomoles of each oligonucleotide 2425ES-up (35-mer; 5'-AATTCGCCAGGGC TTCGAGCGCGCCCTGCTGTAAG-3') (SEQ ID NO: 86) and 2425ES-do (35-mer; GATCCTTACAGCAGGGCG CGCTCGAAGC-CCTGGCG-3') (SEQ ID NO: 87) were mixed together in a 100 µl final volume of annealing buffer containing NaCl 25 mM, Tris 10 mM and 1 mM EDTA. After denaturation at 94° C. for 15 min., the mixed oligonucleotides were allowed to anneal at 65° C. during 15 min. The annealing temperature was allowed to slowly decrease from the 65° C. to room temperature (22° C.) during overnight incubation. The resulting double-strand dsDNA fragments harbored EcoRI- and BamHI-restriction sites overhangs that allowed direct cloning in pBluescript KS(+) vector using standard cloning techniques (Maniatis 1996).

Figure 10:
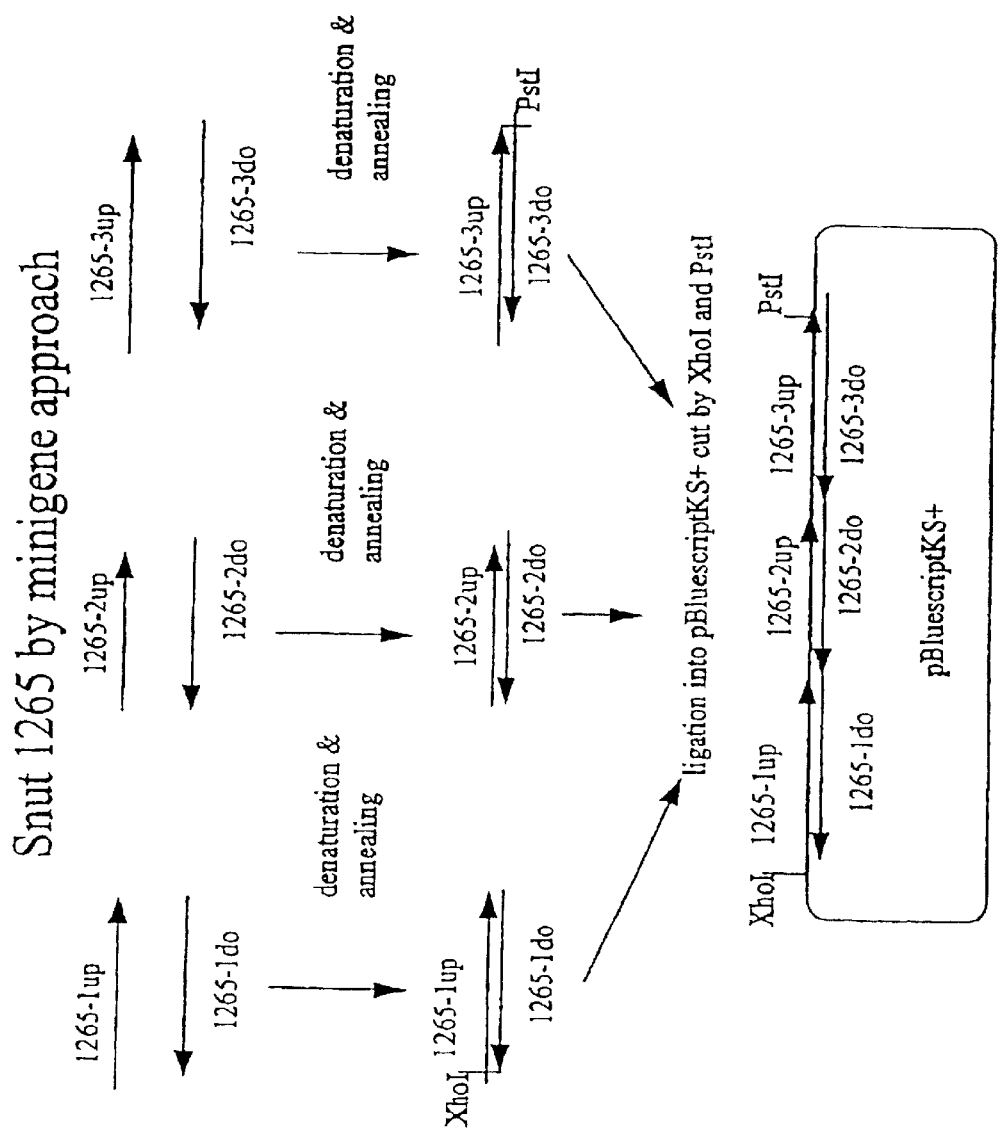
FIG. 10 illustrates how $S_{1265XhoI}$ is produced using complementary strands (minigene-approach) technology. The $S_{1265XhoI}$ is ligated from three sets of complementary strands into the vector pBluescript KS$^+$ between restriction enzyme sites XhoI and PstI.

Snut 1265-XhoI ($S_{1265XhoI}$): This snut was built according to the strategy depicted in FIG. 10. Three minigenes were constructed following the same method described for snut 2425-E-S. These minigenes are named 1265-1, 1265-2 and 1265-3. The minigene 1265-1 results from the annealing of the oligonucleotides 1265-1up (68-mer ; 5'-TCG AGC AGC GGC AAG GAG ATT TTC CGC CCC GGC GGC GGC GAC ATGC GCG ACA ACT GGC GCA GCG AGC T-3') (SEQ ID NO: 88) and 1265-1do (68-mer; 5'-GTA CAG CTC GCT GCG CCA GTT GTC GCG CAT GTC GCC GCC GCC GGG GCG G AAA ATC TCC TTG CCG CTG C-3') (SEQ ID NO: 89). 1265-2 results from the annealing of 1265-2up (61-mer ; 5'-GTA CAA GTA CAA GGT GGT GAA GAT CGA GCC CCT GGG CAT CGC CCC CAC CAA GGC CAA GCG C-3') (SEQ ID NO: 90) and 1265-2do (63-mer; 5'-CAC GCG GCG CTT GGC CTT GGT GGG GGC GAT GCC CAG GGG CTC GAT CTT CAC CAC CTT GTA CTT-3') (SEQ ID NO: 91). Finally, 1265-3 results from the annealing of 1265-3up (69-mer; 5'-CGC GTG GTG CAG CGC GAG AAG CGC GCC GTG GGC ATC GGC GCT ATG TTC CTC GGC TTC CTG GGC GCT GCA-3') (SEQ ID NO: 92) and 1265-3do (59-mer; 5'-GCG CCC AGG AAG CCG AGG AAC ATA GCG CCG ATG CCC ACG GCG CGC TTC TCG CGC TGC AC-3') (SEQ ID NO: 93). Each minigene were designed in order to present single strand overhangs at their 5' and 3'- ends that allow easy ligation and XhoI-PstI direct cloning into pBlueScript KS+vector.

Figure 11:
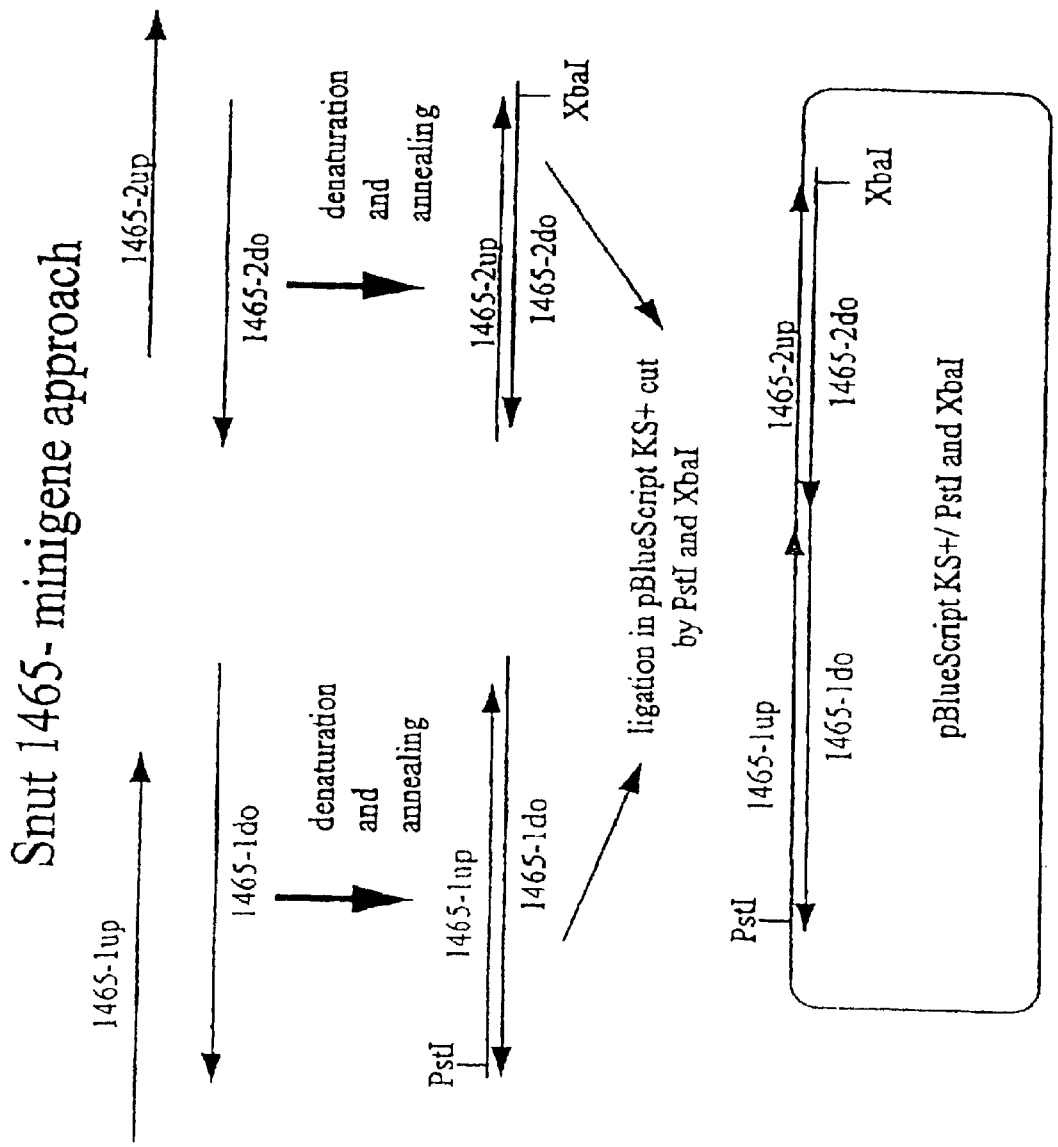
FIG. 11 illustrates how $S_{1465PstI}$ is produced. The same approach, as the approach used for the production of $S_{1265XhoI}$, was used except that only two sets of complementary strands were used.

Snut 1465-PstI ($S_{1465PstI}$): Two minigenes were constructed following the same methode described for snut 2425-E-S. These minigenes are named 1465-1 and 1465-2. The minigene 1465-1 was obtained after annealing of 1465-1up (90-mer: 5'-GGC AGC ACC ATG GGC GCC GCC AGC CTG ACC CTG ACC GTG CAG GCC CGC CAG CTG CTG AGC GGC ATC GTG CAG CAG CAG AAC AAC CTG CTG-3') (SEQ ID NO: 94) and 1465–1do (98-mer: 5'-CGC GCA GCA GGT TGT TCT GCT GCT GCA CGA TGC CGC TCA GCA GCT GGC GGG CCT GCA CGG TCA GGG TCA GGC TGG CGG CGC CCA TGG TGC TGC CTG CA-3') (SEQ ID NO: 95), whereas minigene 1465-2 results from the annealing of 1465-2up (78-mer; 5'-CGC GCC ATC GAG GCC CAG CAG CAC CTG CTC CAG CTGA CCG TGT GGG GCA TCA AGC AGC TCC AGG CCC GCG TGC TGG CT-3')(SEQ ID NO: 96) and 1465-2do (78-mer; 5'-CTA GAG CCA GCA CGC GGG CCT GGA GCT GCT TGA TGC CCC ACA CGG TCA GCT GGA GCA GGT GCT GCT GGG CCT CGA TGG-3') (SEQ ID NO: 97). Each minigene were designed in order to present single strand overhangs at their 5' and 3'-ends that allow easy ligation and PstI-XbaI direct cloning into pBlueScript KS+vector using standard cloning techniques (Maniatis) (see FIG. 11).

Example 4

Assembly of Snuts to Pieces

The snut genes were then assembled into pieces (Table 4) so that unique restriction enzyme sites or mutagenesis can be used within each of these. This strategy will require fewer assemblings for optimal use of the cassette system. The following piece clones were made and kept individually for construction of the synBX08 gp160 gene (FIG. 6):

TABLE 4 lists pieces by their name and their snut composition.

| Piece name | snut composition | vector |
|---|---|---|
| $P_1$ | $S_{O-N-LANG}$-$S_{235EcoRV}$-$S_{375PstI}$ | pBluescriptSK |
| $P_2$ | $S_{900XbaI}$-$S_{990SacI}$-$S_{1110SpeI}$ | pMOSblue |
| $P_3$ | $P_1$-$S_{495ClaI}$-$S_{650-720EcoRI}$-$P_2$ | pBluescriptSK |
| $P_{4gp160}$ | $S_{1630XbaI}$-$S_{1700EagI}$-$S_{1890HinIII}$ | pBluescriptSK |
| $P_5$ | $S_{2190ClaI}$-$S_{2330PstI}$-$S_{2425ES}$ | pBluescriptKS |
| $P_7$ | $P_{8gp160}$-$S_{2060SacII}$-$P_5$ | pBluescriptKS |
| $P_{8gp160}$ | $S_{1265XhoI}$-$S_{1465PstI}$-$P_{4gp160}$ | pBluescriptKS |

Figure 12:
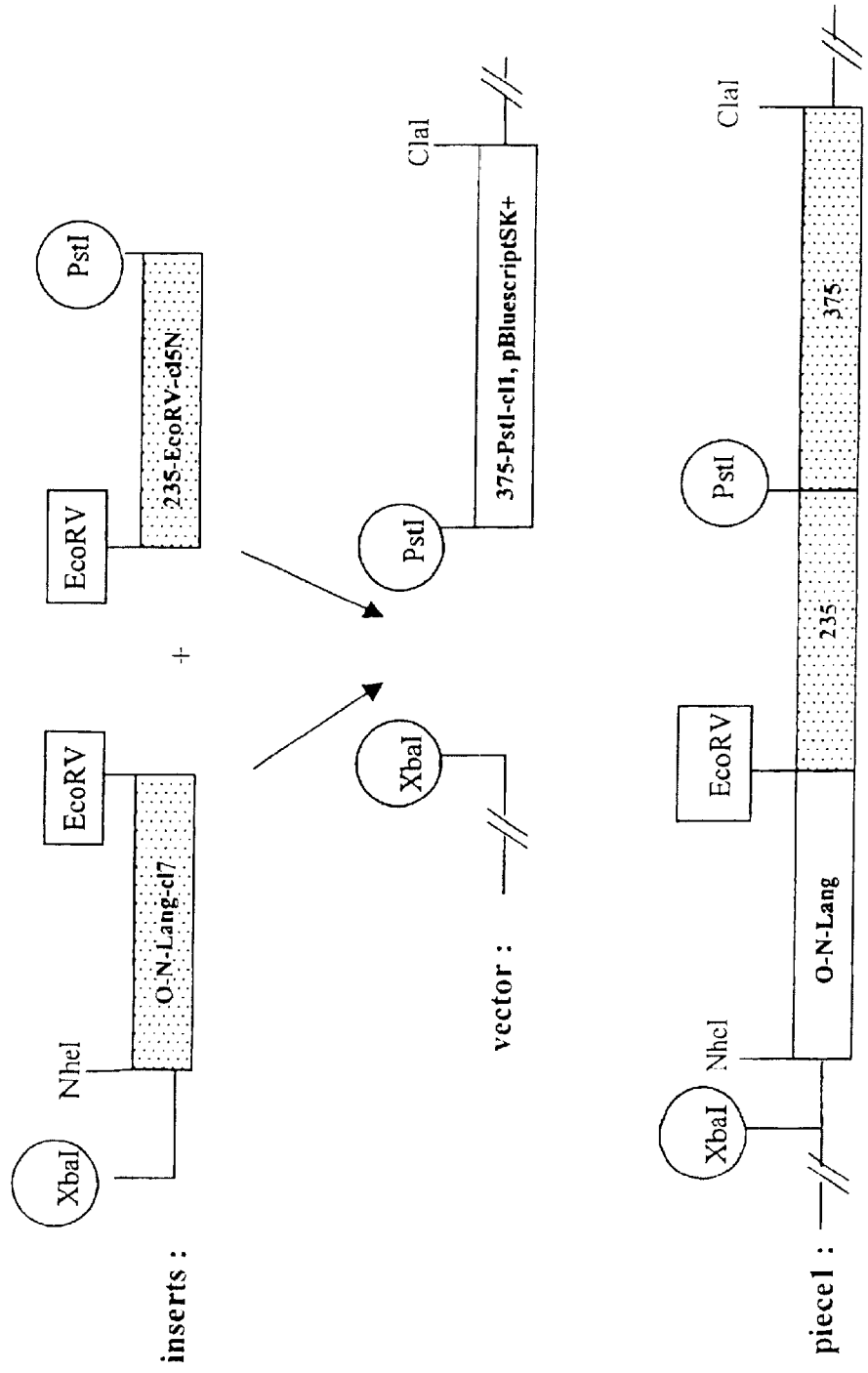
FIG. 12 illustrates the assembly of $P_1$. The $S_{O-N-Lang}$ and $S_{235EcoRV}$ are ligated into the XbaI and PstI site of the $S_{375}$PstI containing plasmid.

Piece 1: The building strategy is shown in FIG. 12.

Preoaration of the insert DNA: Five to 15 µg of each plasmid O-N-LANG-cl7 and 235-EcoRV-cl5N, respectively, were double-digested by XbaI/EcoRV, and PstI/EcoRV, according to classical RE digestion procedure (Maniatis). The RE digestion products, were agarose gel purified according classical method (Maniatis). All RE digests were loaded on a 3% Nusieve 3:1 (FMC), TBE 0.5×agarose gel and submitted to electrophoresis (7 Volts/mm during 2–3 hours) until optimal fragment separation. The agarose-band containing the DNA fragments that correspond to the snut's sequence sizes (243-bp for O-N-LANG and 143-bp for 235-EcoRV) were excized from the gel. The DNA was extracted from agarose by centrifugation 20 min at 5000 g using a spin-X column (Costar cat#8160). Preoaration of the vector: The snut 375-Pst1 klon1 was used as plasmid vector. Five µg were digested with XbaI and Pst1. Removal of the polylinker XbaI/PstI fragment was performed by classical agarose gel purification, using a 0.9% Seakem-GTG agarose, TBE 0.5X gel. The linearized plasmid DNA was extracted from the agarose by filtration through spin-X column. All purified DNA fragments were quantified by spectrophotometry. Ligation: All three DNA fragments O-N-LANG (XbaI/EcoRV), 235-EcoRV (PstI/EcoRV) and 375-PstI(XbaI/PstI), were ligated together by classical ligation procedure, using an equimolar (vector:insert1:insert2) ratio of 1:1:1. Thus for, 200 ng (0.1 pmole) of XbaI/PstI-linearized 375-PstI-cl1 were mixed with 16 ng of O-N-LANG (XbaI/EcoRV) and 10 ng of 235-EcoRV (PstI/EcoRV) in a final reaction volume of 20 µl of 1×ligation buffer containing 10U of T4 DNA ligase (Biolabs, cat#202S). The ligation was allowed overnight at 16° C. Transformation: Competent XL1-Blue bacteria (Stratagene cat#200130, transformation efficiency >5·10⁶ col/µg) were transformed by classical heat-chock procedure: ¹⁄₁₀th of the pre-chilled ligation reaction was mixed with 50 µl of competent bacteria. The mixture was allowed to stand in ice during 30 min. Bacteria were heat-shocked at 42° C. during 45 sec. and then left 2 min. on ice before being resuspended in 450 µl of SOC medium. Transformed bacteria were incubated 1 hour at 37° C. under shaking (250 rpm) and plated on LB-ampicilin agar plates. The recombinant clones were allowed to grow 16 hours at 37° C. Colony screening: 10 to 50 recombinant colonies were screened by direct PCR screening according to the protocole described into the pMOSBlue blunt-ended cloning kit booklet (RPN 5110, Amersham). Each colony was picked and resuspended in 50 µl of water. DNA was freed by a boilling procedure (100° C., 5 min).Ten µl of bacterial lysate were mixed to 1 µl of a 10 mM solution of premixed 4 dNTP's , 1 µl of M13reverse primer (5 pmoles/µl, 5'-CAGGAAACAGCTA TGAC-3') (SEQ ID NO: 98), 1 µl of T7 primer (5 pmoles/µl, 5'-TAATACGACTCACTATAGGG-3') (SEQ ID NO: 99), 5 µl of 10×Expand HF buffer 2 (Boehringer Mannheim, cat#1759078), 0.5 µl of Enzyme mix (Boehringer Mannheim, 5U/µl) in a final volume of 50 µl. DNA amplification was performed with a thermo-cycler PE9600 (Perkin-Elmer) using the following cycling parameters: 94° C., 2 min, 35 cycles(94° C., 30 sec; 50° C., 15 sec; 72° C., 30 sec); 72° C., 5 min; 4' C. hold. Five µl of the PCR products were analysed after electrophoresis on a 0.9% SeakemGTG, 0.5×TBE agarose gel. Nucleotide sequence confirmation: ds-DNA was purified from minicultures of the selected clones with the JETstar mini plasmid purification system Genomed Inc.). Sequencing was performed using M13reverse and T7 primers and with the Big DyeTM Terminator Cycle Sequencing Ready reaction kit (Perkin-Elmer, Norwalk, Conn., P/N43031 52) and the ABI-377 automated DNA sequenator (Applied Biosystems, Perkin-Elmer, Norwalk, Conn.). Data were processed with the Sequence Navigator and Autoassembler softwares (Applied Biosystems, Perkin-Elmer, Norwalk, Conn.).

Figure 13:
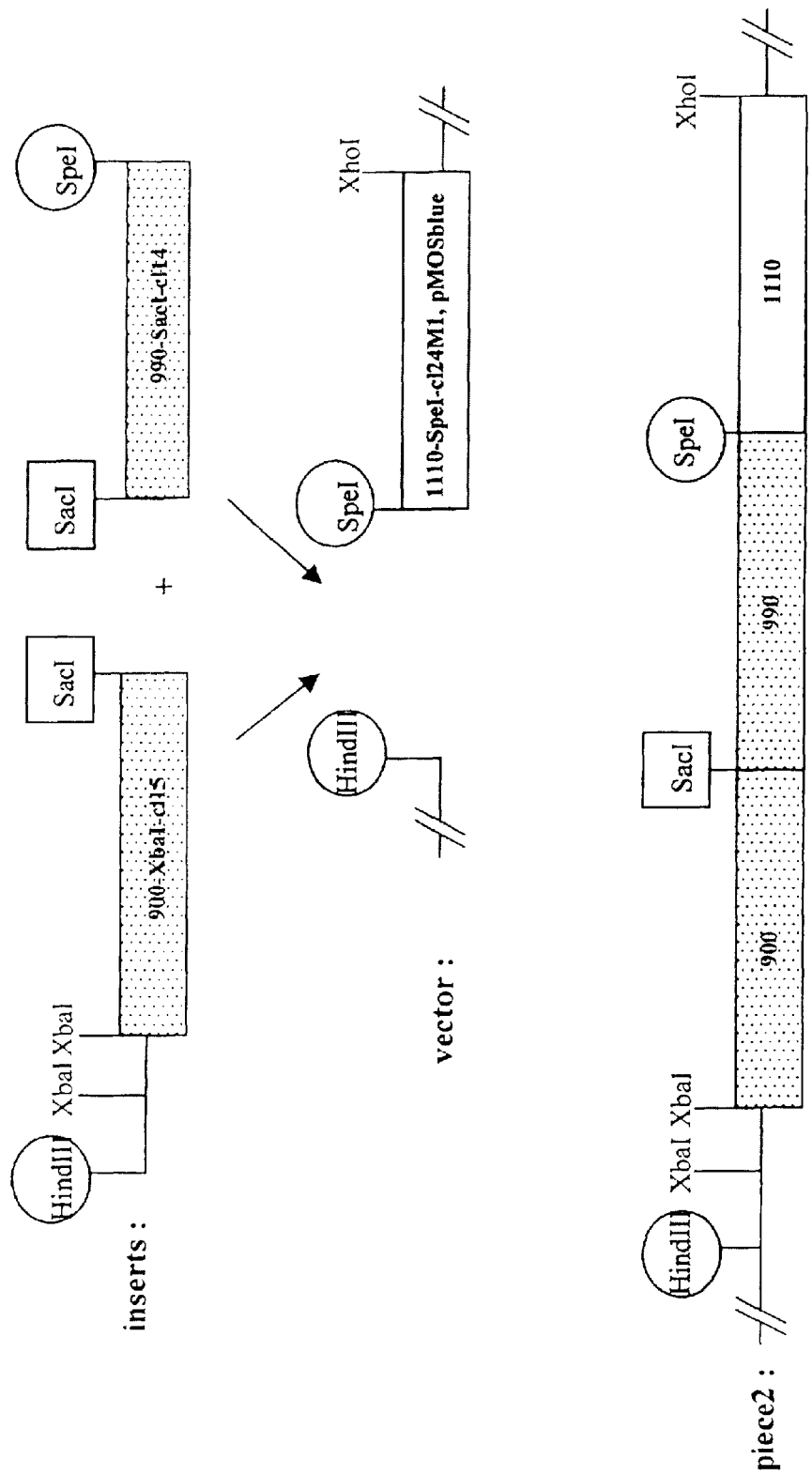
FIG. 13 illustrates the assembly of $P_2$. The $S_{900XbaI}$ was excerted by HindIII and SacI from its plasmid and ligated with $S_{990SacI}$ (SacI-SpeI) into the $S_{110SpaI}$ plasmid that was opened at the HindIII and SpeI sites.

Piece 2: The strategy for building that piece is depicted in FIG. 13. RE digestion, DNA fragments purification, ligation as well as direct PCR screening of recombinant colonies were performed according the same procedures described above for piece 1, except the following:

The linearized plasmid 1110-SpeI-cl24M1 was used as vector after being digested by HindIII and SpeI, and agarose gel purified.

A 166-bp HindIII/SacI, obtained from snut 900-XbaI-cl15, as well as a 130-bp SacI/SpeI fragment, obtained from snut 990-SacI-cl14, were agarose gel purified.

Equimolar amount (0.1 pmoles) of the three DNA fragments described above were ligated in an one step ligation.

100 µl of competent SCS110 bacteria (Stratagene cat# 200247) were transformed with ¹⁄₁₀th of the ligation products according to the manufacturer's instruction.

Direct colony PCR screening was performed using T7 primer and pMOS-R (5'-GTTGTAAAACGACGGC CAG-3') (SEQ ID NO: 100).

Figure 14:
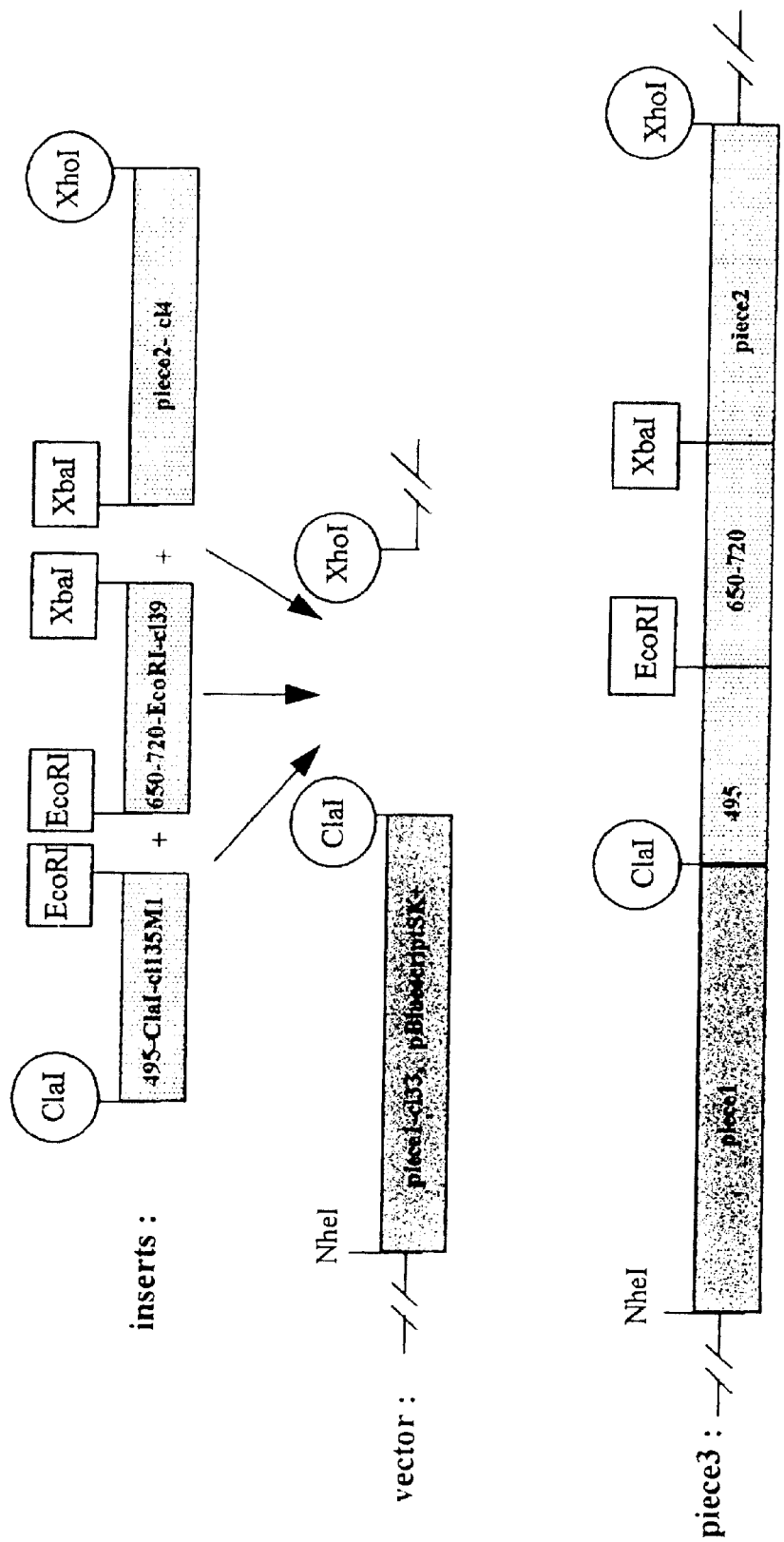
FIG. 14 illustrates the assembly of $P_3$. $S_{495ClaI}$ (ClaI-EcoRI) and $S_{650-720}$EcoRI (EcoRI-XbaI) and $P_2$ (XbaI-XhoI) were ligated simultaneously into the $P_1$ plasmid opened at the ClaI and XhoI sites to obtain the $P_3$ plasmid.

Piece 3: The strategy for building that piece is depicted in FIG. 14. RE digestion, DNA fragments purification, ligation as well as direct PCR screening of recombinant colonies were performed according the same procedures described above for piece 1, except the following:

The plasmid piece 1-cl33 was linearized by ClaI and XhoI, in order to be used as vector, and agarose gel purified.

A 161-bp ClaI/EcoRI fragment, obtained from 495-ClaI-cl135M1 as well as a 254-bp EcoRI/XbaI fragment, obtained from 650-720-EcoRI-cl39, and a 374-bp XbaI/XhoI fragment, obtained from piece2-cl4, were agarose gel purified.

Equimolar amount (0.1 pmole) of each of these 4 DNA fragments were mixed and ligated together.

50 µl of competent XL1 Blue bacteria were transformed with ¹⁄₁₀th of the ligation products according to the protocole described for piece 1.

Direct colony PCR screening was performed using M13Reverse and T7 primers.

Figure 15:
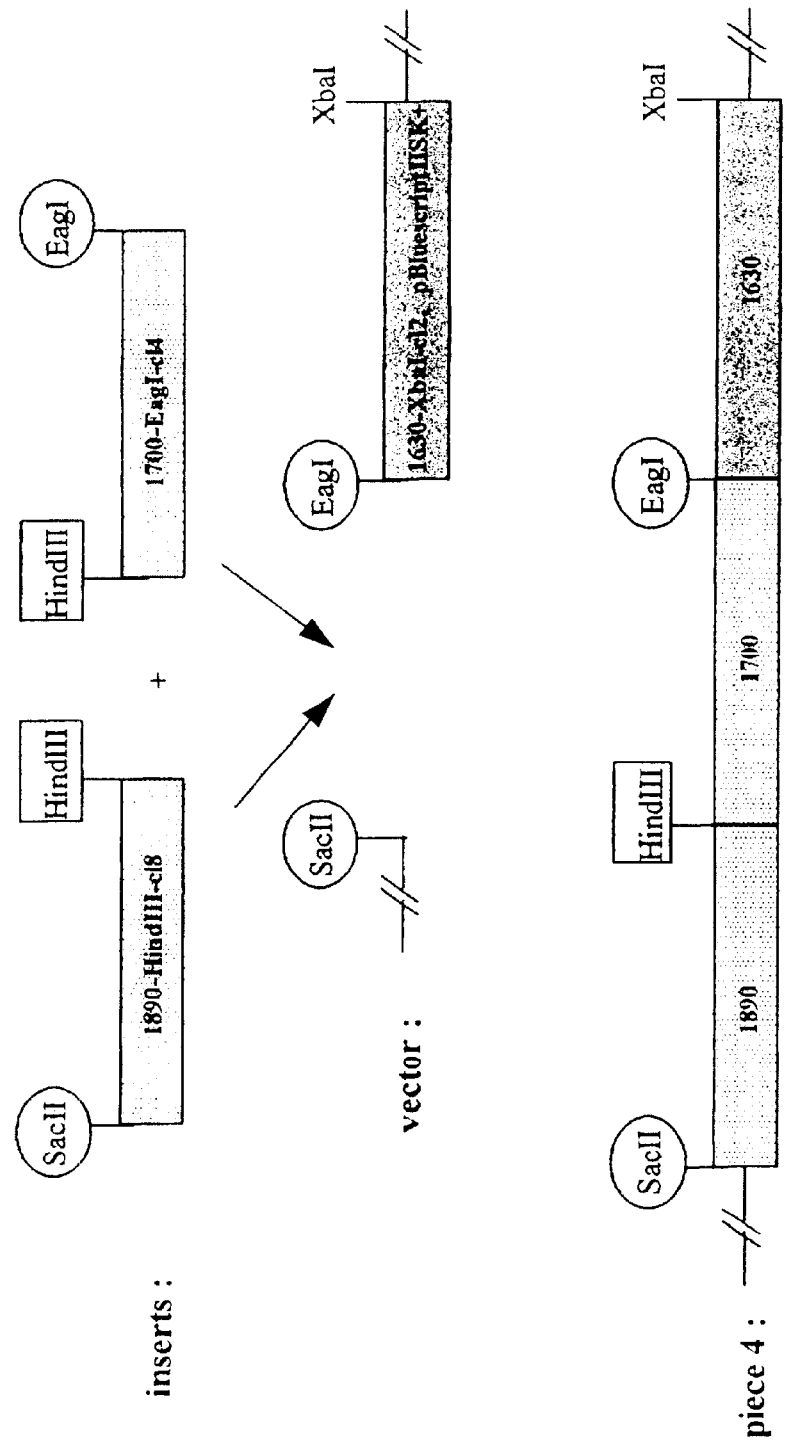
FIG. 15 illustrates the assembly of $P_{4gp160}$. $S_{1890HindIII}$ (SacI-HindIII) and $S_{1700eagI}$ (HindIII-EagI) were ligated simultaneously into the $S_{1630XhaI}$ plasmid opened by SacII and EagI.

Piece 4 gp160: The strategy for building that piece is depicted in FIG. 15. RE digestion, DNA fragments purification, ligation as well as direct PCR screening of recombinant colonies were performed according the same procedures described above for piece 1, except the following:

The plasmid 1630-XbaI-cl2 was linearized by SacII/EagI digestion and agarose gel purified, in order to be used as vector.

A 190-bp EagI/HindIII fragment, obtained from snut 1700-EagI-cl4, as well as a 177-bp SacII/HindIII fragment, obtained from snut 1890-HindIII-cl8, were agarose gel purified.

Equimolar amount (0.1 pmoles) of the three DNA fragments described above were ligated in an one step ligation.

50 µl of competent XL1 Blue bacteria were transformed with 1/10th of the ligation products according to the protocole described for piece 1.

Direct colony PCR screening was performed using M13Reverse and T7 primers.

Piece 4-gp150: PCR-based site-directed mutagenesis was performed on double-stranded plasmid-DNA from piece4-cl4 according an adaptation of the ExSiteTM PCR-Based Site-Directed Mutagenesis Kit procedure (Stratagene cat#200502)(Weiner, M. P., Costa, G. L., Schoettlin, W., Cline, J., Marthur, E., and Bauer, J. C. (1994) Gene 151:119–123). The mutations introduced are shown in bold letters in the primer sequences below. PCR amplification was performed with the Expand™ High Fidelity PCR System (Boehringer Mannheim, cat#1759078). Briefly, 1.5 µg, 0.5 µg or 0.1 µg of circular dsDNA was mixed with 1.5 pmoles of P$_4$M2S (5'-TCTGGAAGCTCAGG GGGCTGCATCCCTGGC-3') (SEQ ID NO: 101) and 1.5 pmoles of P4M2AS (5'-CCCGCCTGCCCGTGTGACG GATCCAGCTCC-3') (SEQ ID NO: 102) in a final volume of 50 µl containing 4 dNTPs (250 µM each), 1×Expand HF buffer 2 (Boehringer Mannheim, cat#1759078), 0.7561A of Enzyme mix (Boehringer Mannheim, 5 U/µl). The PCR was performed with a PE9600 thermo-cycler (Perkin-Elmer Corporation) under the following cycling parameters: 94° C., 2 min ; 15 cycles (94° C., 45 sec; 68° C., 4 min); 72° C, 7 min and 4° C., hold. PCR products were phenol:chloroform extracted and precipitated (Maniatis). Plasmid template was removed from PCR products by DpnI treatment (Biolabs)(Nelson, M., and McClelland, M., 1992) followed by ethanol-precipitation. Amplicons were resuspended in 50 µl sterile water, and phosphorylated according the following procedure: 7.5 µl of amplicons were mixed with 0.5 µl of 100 mM DTT, 1 µl of 10×pk buffer and 1 µl of pk mix enzyme (pMOSBlue blunt-ended cloning kit, Amersham cat#RPN 5110). DNA kinasing was allowed 5 min at 22° C. After heat-inactivation (10 min, 75° C.) of the pk enzyme, 1 µl of ligase (4 units, Amersham , cat#RPN 5110) was directly added to the pk reaction. The ligation was allowed overnight at 22° C. 50 µl of competent XL1 Blue bacteria were transformed with 1/10th of the ligation reaction according to the classical protocol (Maniatis). Insertion of mutations was checked by sequencing.

Piece 4-gp140: PCR-based site-directed mutagenesis was performed on piece 4-cl4, according to the procedure described for piece4-gp150 except that the primers P4M1AS (5'-TGTGTGACTGATTGAGGATCCCCAACTGGC-3') (SEQ ID NO: 103) and P4S (5'-AGCTTGCCCACTTGT CCAGCTGGAGCAGGT-3') (SEQ ID NO: 104) were used.

Snut 1265-XhoI-gp120: PCR-based site-directed mutagenesis was performed on plasmid 1265-XhoI-cl2M1 according to the procedure described for piece4-gp150 except that the primers 1265MAS (5'-CTTCTCGC GCTGCACCACGCGGCGCTTGGC-3') (SEQ ID NO: 105) and 1265M2S (5'-CGCGCCTAGGGCATCG GCGCTATGTTCCTC-3') (SEQ ID NO: 106) were used.

Snut 1265-XhoI-gp160/uncleaved: PCR-based site-directed mutagenesis was performed on plasmid 1265-XhoI-cl2M1 according to the procedure described for piece4-gp150 except that the primers 1265MAS (5'-CTTCTCGCGCTGCACCACGCGGCGCTTGGC-3') (SEQ ID NO: 107) and 1265M2S (5'-AGCGCCGTGG GCATCGGCGCTATGTTCCTC-3') (SEQ ID NO: 108) were used.

Snut 1465-PstI-CCG: PCR-based site-directed mutagenesis was performed on plasmid 1465-PstI-cl25 according to the procedure described for piece4-gp150 except that the primers 1465MAS (5'-CTGCTTGATGCCCCA CACGGTCAGCTG-3') (SEQ ID NO: 109) nd 1465MS (5'-TGCTGCGGCCGCGTGCTGGCTCTAGA-3') (SEQ ID NO: 110) were used.

Figure 16:
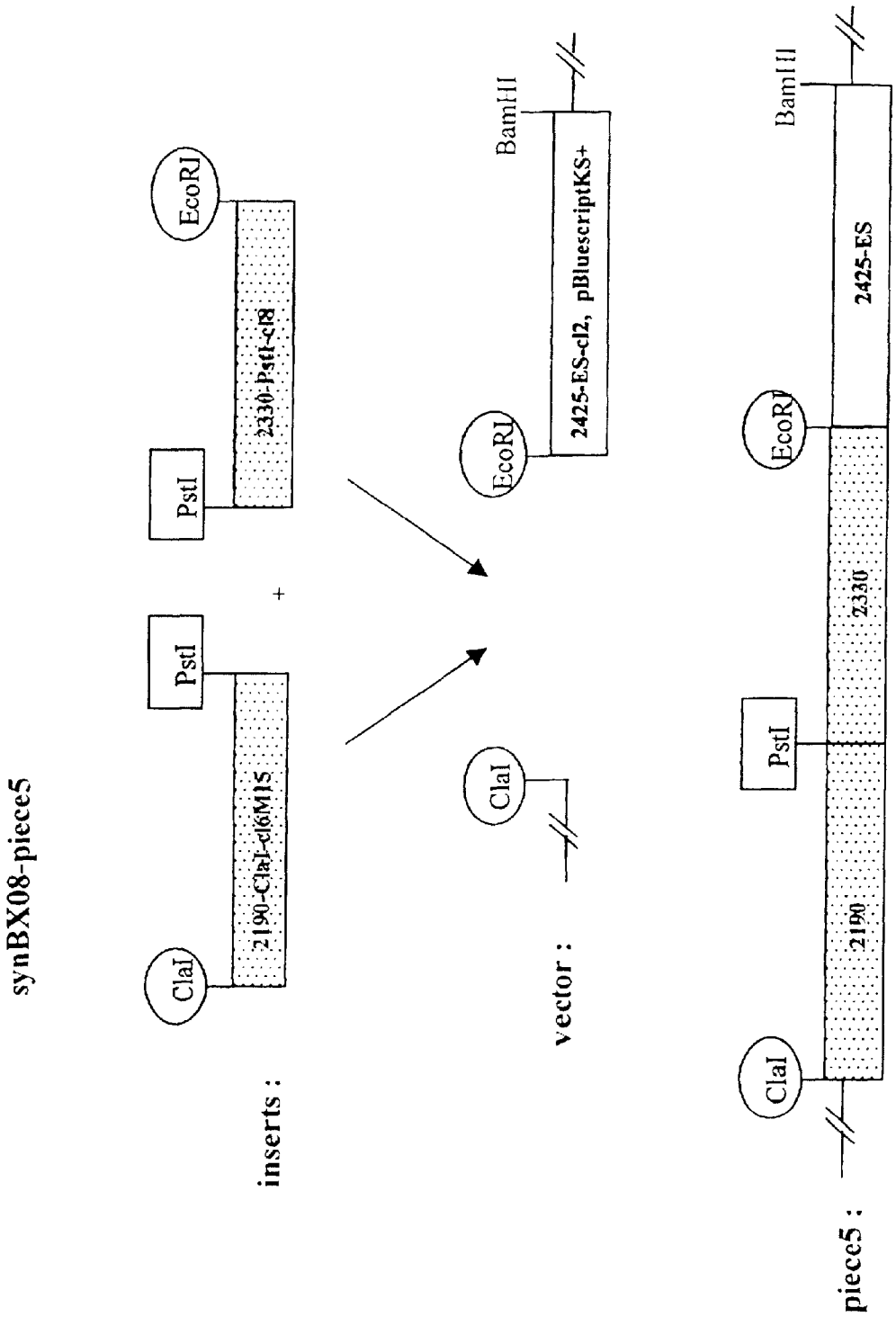
FIG. 16 illustrates the assembly of $P_5$. $S_{2190ClaI}$ (ClaI-PstI) and $S_{2330}$PstI (PstI-EcoRI) were ligated into the $S_{2425Es}$ plasmid opened by ClaI and EcoRI.

Piece 5: The strategy for building that piece is depicted in FIG. 16. RE digestion, DNA fragments purification, ligation as well as direct PCR screening of recombinant colonies were performed according the same procedures described above for piece 1, except the following:

The plasmid 2425-ES-cl2 was linearized by ClaI/EcoRI digestion and agarose gel purified, in order to be used as vector.

A 129-bp PstI/ClaI fragment, obtained 2190-ClaI-cl6M15, as well as a 114-bp PstI/EcorI fragment, obtained from 2330-PstI-cl8, were agarose gel purified.

Equimolar amount (0.1 pmoles) of the three DNA fragments described above were ligated in an one step ligation.

50 µl of competent XL1 Blue bacteria were transformed with 1/10th of the ligation products according to the protocole described for piece 1.

Figure 17:
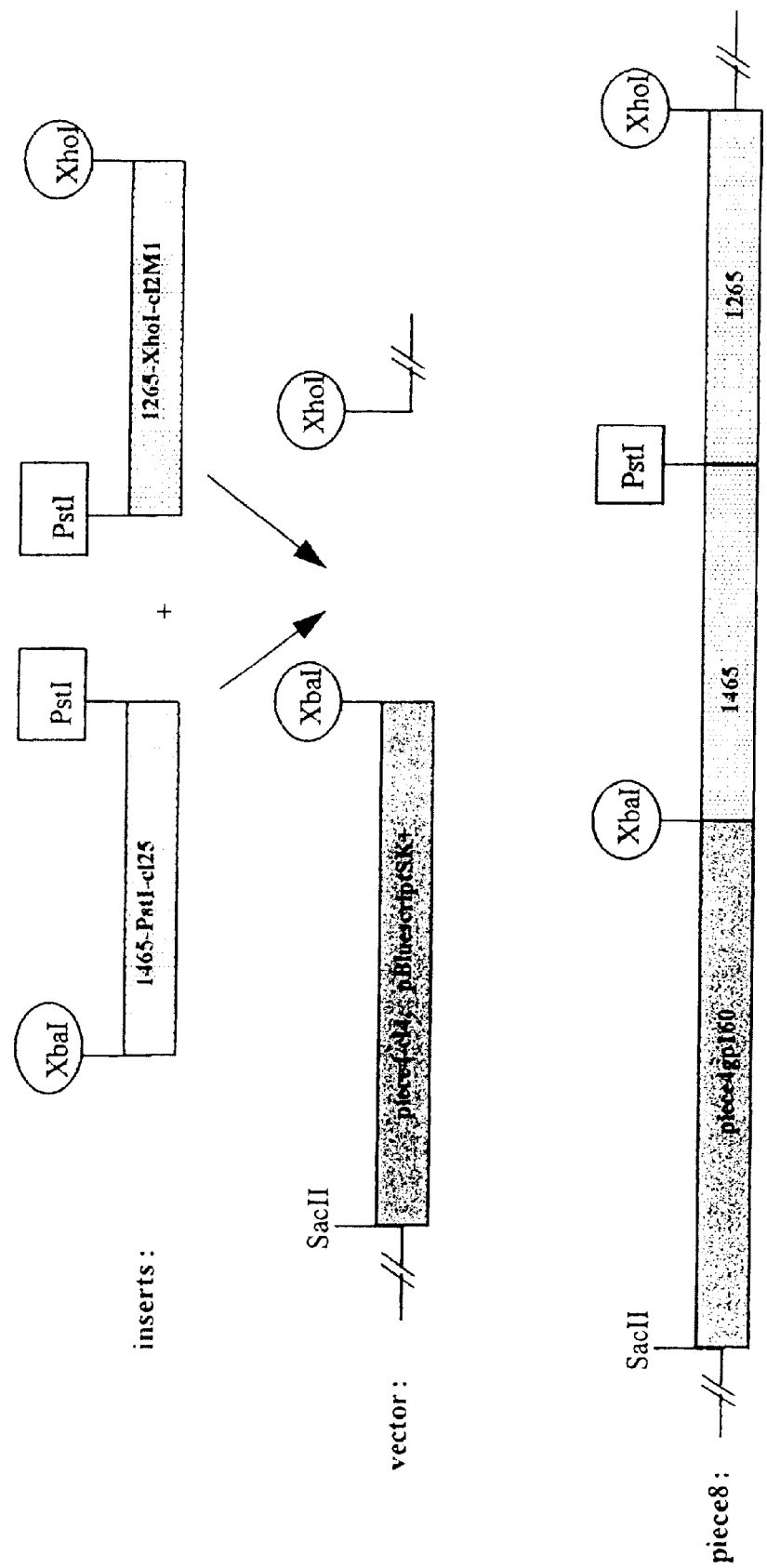
FIG. 17 illustrates the assembly of $P_{8gp160}$. $S_{1465PstI}$ (XbaI-PstI) and $S_{1265XhoI}$ (PstI-XhoI) were ligated into the $P_{4gp160}$ plasmid opened by XbaI and XhoI.

Direct colony PCR screening was performed using T3 (5'-ATTAACCCTCACTAAAG-3') (SEQ ID NO: 111) and T7 primers.

piece 8: The strategy for building that piece is depicted in FIG. 17. RE digestion, DNA fragments purification, ligation as well as direct PCR screening of recombinant colonies were performed according the same procedures described above for piece 1, except the following:

The plasmid piece4-cl4 was linearized by XbaI/XhoI and agarose gel purified, in order to be used as vector.

A 200-bp XhoI/PstI fragment, obtained from 1265-XhoI-cl2M1 as well as a 178-bp PstI/XbaI fragment, obtained from 1465-PstI-cl25 were agarose gel purified.

Equimolar amount (0.1 pmole) of these 3 DNA fragments were mixed and ligated together.

50 µl of competent XL1 Blue bacteria were transformed with 1/10th of the ligation products according to the protocole described for piece 1.

Figure 18:
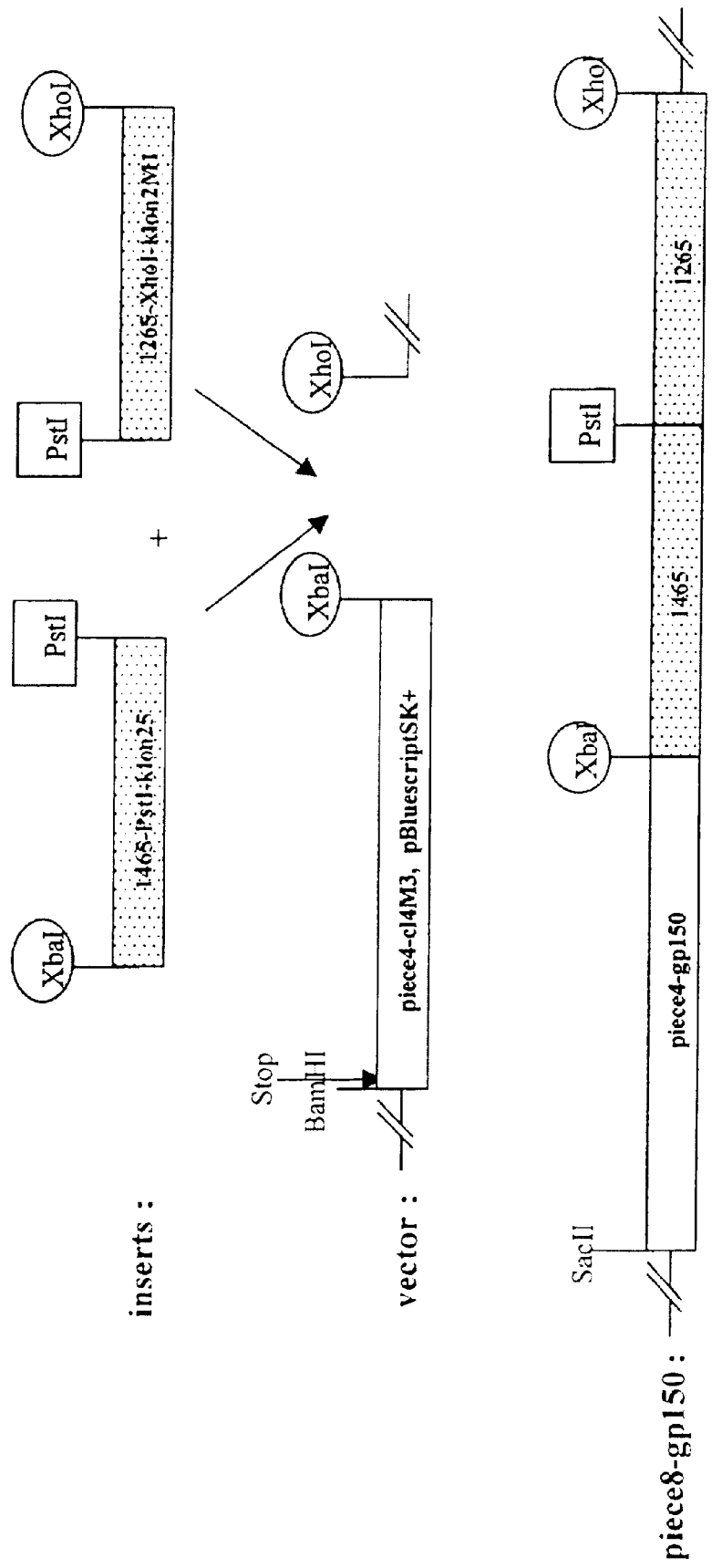
FIG. 18 illustrates the assembly of $P_{8gp150}$. $S_{1465PstI}$ (XbaI-PstI) and $S_{1265XhoI}$ (PstI-XhoI) were ligated into the plasmid containing $P_{4gp150}$ with the stop codon. $P_{4gp150}$ plasmid was opened at the XbaI and XhoI sites for the ligation.
Figure 19:
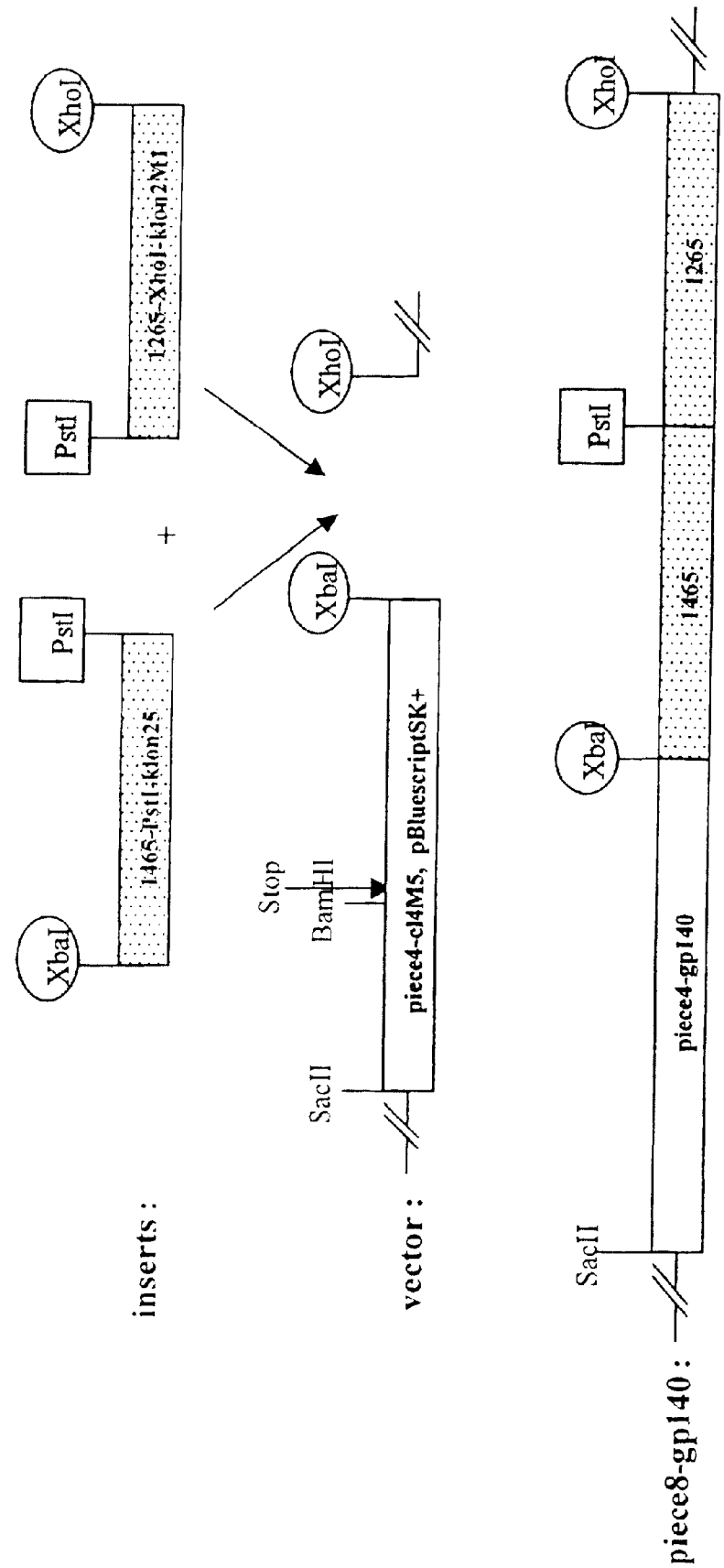
FIG. 19 illustrates the assembly of $P_{8gp140}$. $S_{1465PstI}$ (XbaI-PstI) and $S_{1265XhoI}$ (PstI-XhoI) were ligated into the plasmid containing $P_{4gp140}$ with a stop codon. $P_{4gp140}$ plasmid was opened at the XbaI and XhoI sites for the ligation.

Direct colony PCR screening was performed using T3 and T7 primers.

piece 8-gp150: The strategy for building that piece was identical to that of piece 8, except hat piece4-cl4M3 was used as vector (FIG. 18).

piece8-gp150/uncleaved: The strategy for building that piece is identical to that of piece 8, except that piece4 gp160-cl4M3 is used as vector and a 200-bp XhoI/PstI fragment, obtained from snut 1265-XhoI-gp160/uncleaved as well as a 178-bp PstI/XbaI fragment, obtained from snut 1465-PstI-CCG are used like inserts.

piece 8-gp140: The strategy for building that piece was identical to that of piece 8, except that piece4-cl4M5 was used as vector (figure19).

piece8-gp140/uncleaved: The strategy for building that piece is identical to that of piece 8, except that piece4-cl4M5 is used as vector and a 200-bp XhoI/PstI fragment, obtained from snut 1265-XhoI-gp160/uncleaved as well as a 178-bp PstI/XbaI fragment, obtained from snut 1465-PstI-CCG are used like inserts.

Figure 20:
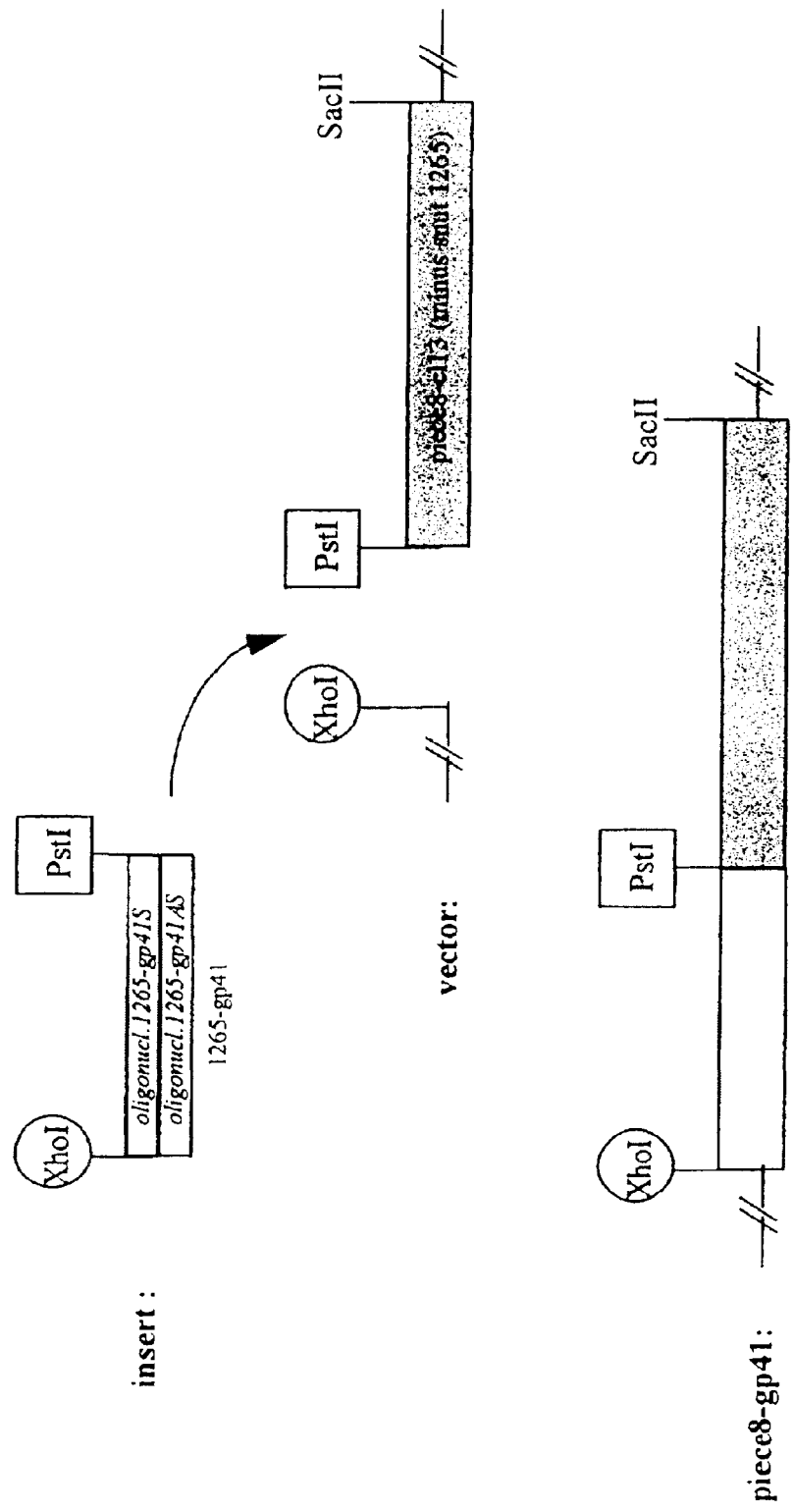
FIG. 20 illustrates the assembly of $P_{8gp41}$. Two complementary nucleotide strands 1265gp41S and 1265gp41AS designed with overhang creating a 5' XhoI and a 3' PstI restriction enzyme site were anealed and ligated into the piece 8 which is already opened at the XhoI and PstI sites whereby $S_{1265}$ is deleted.
Figure 21:
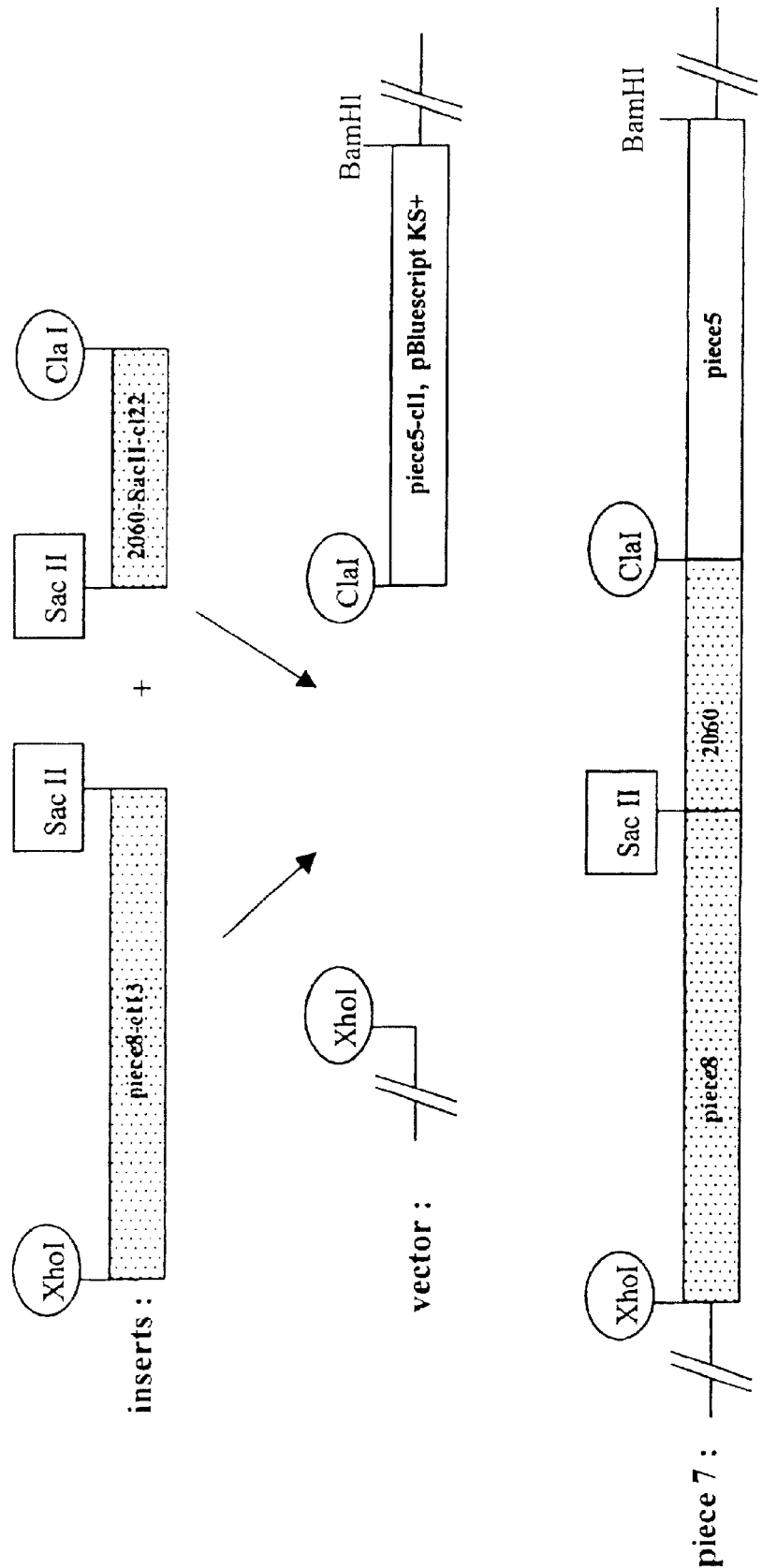
FIG. 21 illustrates the assembly of $P_7$. $P_8$ (XhoI-SacII) and $S_{2060SacII}$ (SacII-ClaI) were ligated into $P_5$ plasmid opened at XhoI and ClaI.

Piece8-gp41: The strategy for building that piece is depicted in FIG. 20. RE digestion, DNA fragments purification, ligation as well as direct PCR screening of recombinant colonies were performed according the same procedures described for synBX08 gp160 gene. A 63 bp linker is to be made according to the method described for snut 2425-ES, the minigene appraoch. Thus for 2 complementary oligonucleotides: 1265-gp41 S(5'-TCGAGgctagcGCCGTGGGCATCGGCGCTATGTTCCT CGGCTTCCTGGGCGctgca-3') (SEQ ID NO: 112) and 1265-gp41 AS (5'-gCGCCCAGGAAGCCGAGGAAC-ATAGCGCCGATGCCCACGGCgctagcC-3') (SEQ ID NO: 113) should be annealed together. This synthetic linker will be directly ligated into the XhoI/PstI sites of piece8-klon13 from which the snut 1265-XhoI-cl 2M1 would have been removed.

piece7: The strategy for building that piece is depicted in FIG. 21. RE digestion, DNA fragments purification, ligation as well as direct PCR screening of recombinant colonies were performed according the same procedures described above for piece 1, except the following:

The plasmid piece5-cl1 was linearized by ClaI/XhoI and agarose gel purified, in order to be used as vector.

A 798-bp XhoI/SacII fragment, obtained from piece8-cl3 as well as a 140-bp SacI/ClaI fragment, obtained from 2060-SacII-cl21 were agarose gel purified.

The ligation of the 3 fragments was performed using a vector:insert ratio of 1:1, 1:2 or 1:5.

50 µl of competent XL1 Blue bacteria were transformed with 1/10th of the ligation products according to the protocole described for piece 1.

Direct colony PCR screening was performed using M13Reverse and T7 primers.

Example 5

Figure 5:
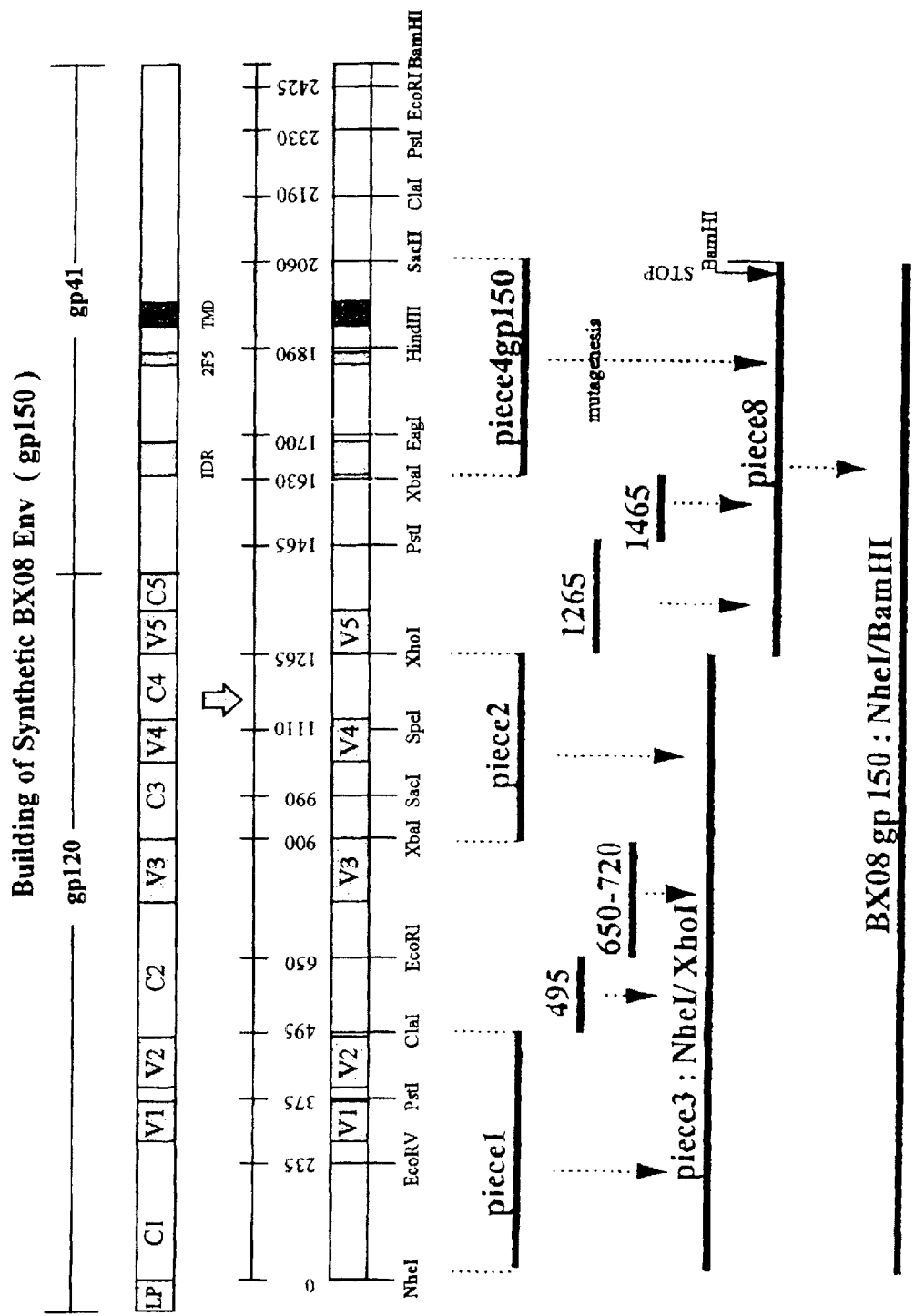
Figure 6:
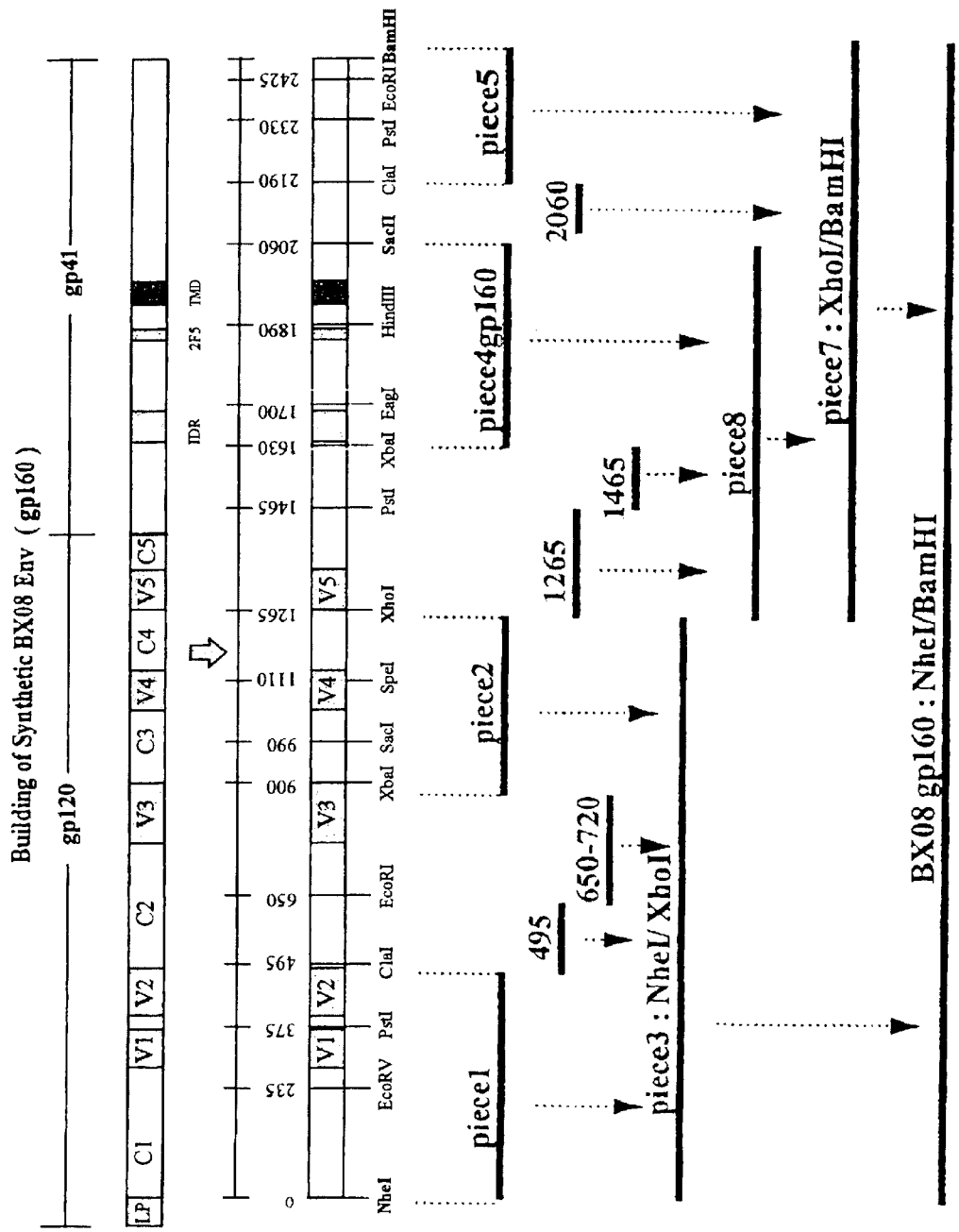

Assembly of Genes synBX08 gp160 gene: The strategy for building that gene is depicted in FIG. 6. RE digestion, DNA fragments purification, ligation as well as direct PCR screening of recombinant colonies were performed according the same procedures described for piece 1. 20 µg of the expression plasmid WRG7079 were digested by NheI/BamHI. Plasmid DNA-ends were dephosphorylated by Calf Intestin Phosphatase treatment (CIP, Biolabs) (Maniatis) to avoid auto-ligation of any partially digested vector. CIP enzyme was heat-inactivated and removed by classical phenol-chloroforme extraction. A 1277-bp NheI/XhoI fragment, obtained from piece3-cl27, as well as a 1194-bp XhoI/BamHI fragment, obtained from piece7-cl1, were agarose gel purified. The ligation was performed using a vector:insert ratio of 1:1 or 1:2. Fifty µl of competent XL1 Blue bacteria were transformed with 1/10th of the ligation product according to the protocole described for piece 1. After transformation bacteria were plated on LB-kanamycin agar plates. Direct PCR colony screening was performed using the primer set WRG-F (5'-AGACATAATAGCTGAC AGAC-3') (SEQ ID NO: 114) and WRG-R (5'-GATTGTAT TTCTGTCCCTCAC-3') (SEQ ID NO: 115). The nucleotide sequence was determined according the methods described above for piece 1.

synBX08 gp150 gene: The strategy for building that gene is depicted in FIG. 5. RE digestion, DNA fragments purification, ligation as well as direct PCR screening of recombinant colonies were performed according the same procedures described for synBX08 gp160 gene. A 1277-bp NheI/XhoI fragment, obtained from piece3-cl27, as well as a 800-bp XhoI/BamHI fragment, obtained from piece 8-gp150-cl26, were agarose gel purified and then ligated into the NheI/BamHI WRG7079 sites. The ligation was performed using a vector:insert ratio of 1:1 or 1:2.

Figure 2:
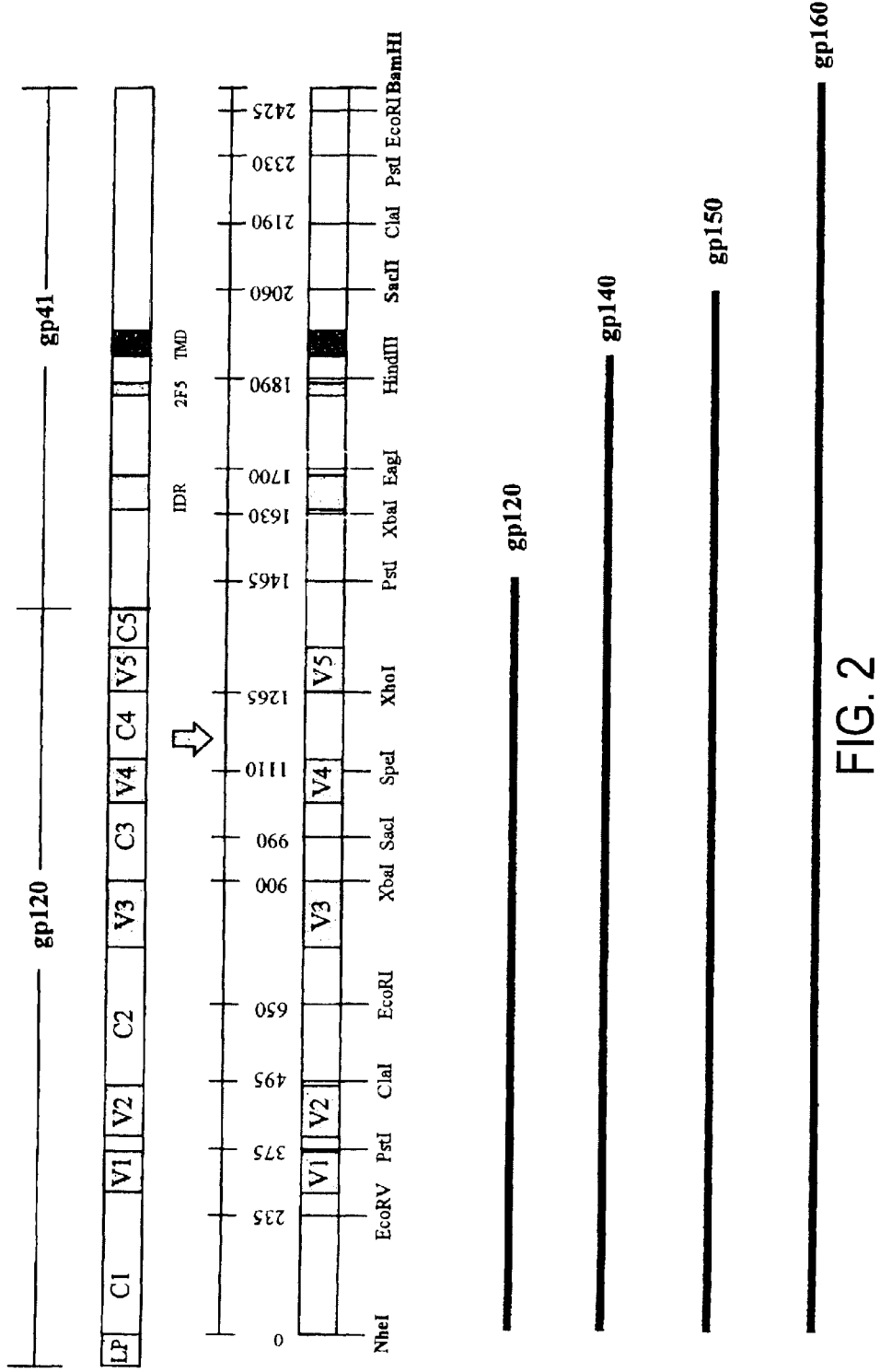
Figure 3:
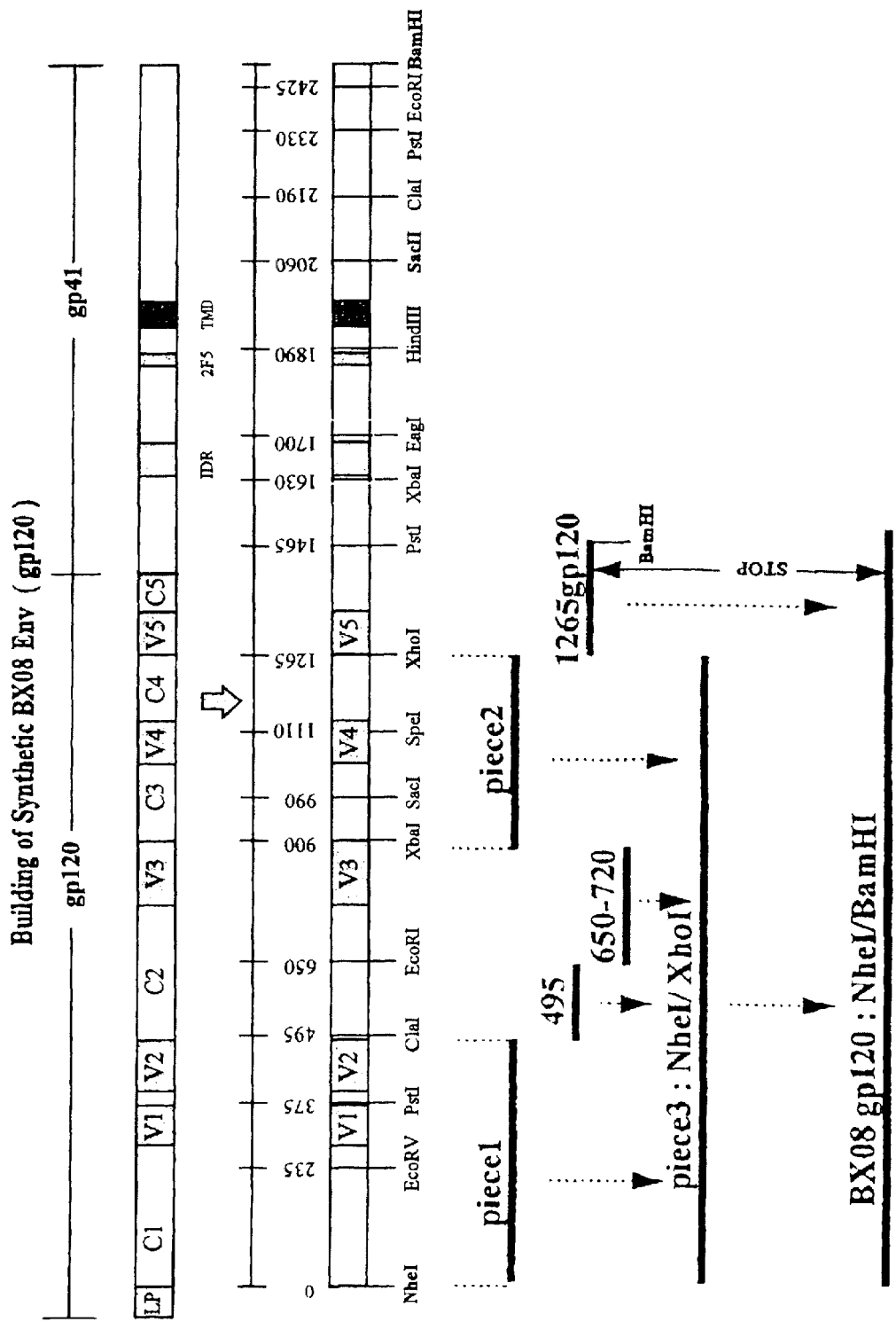
Figure 4:
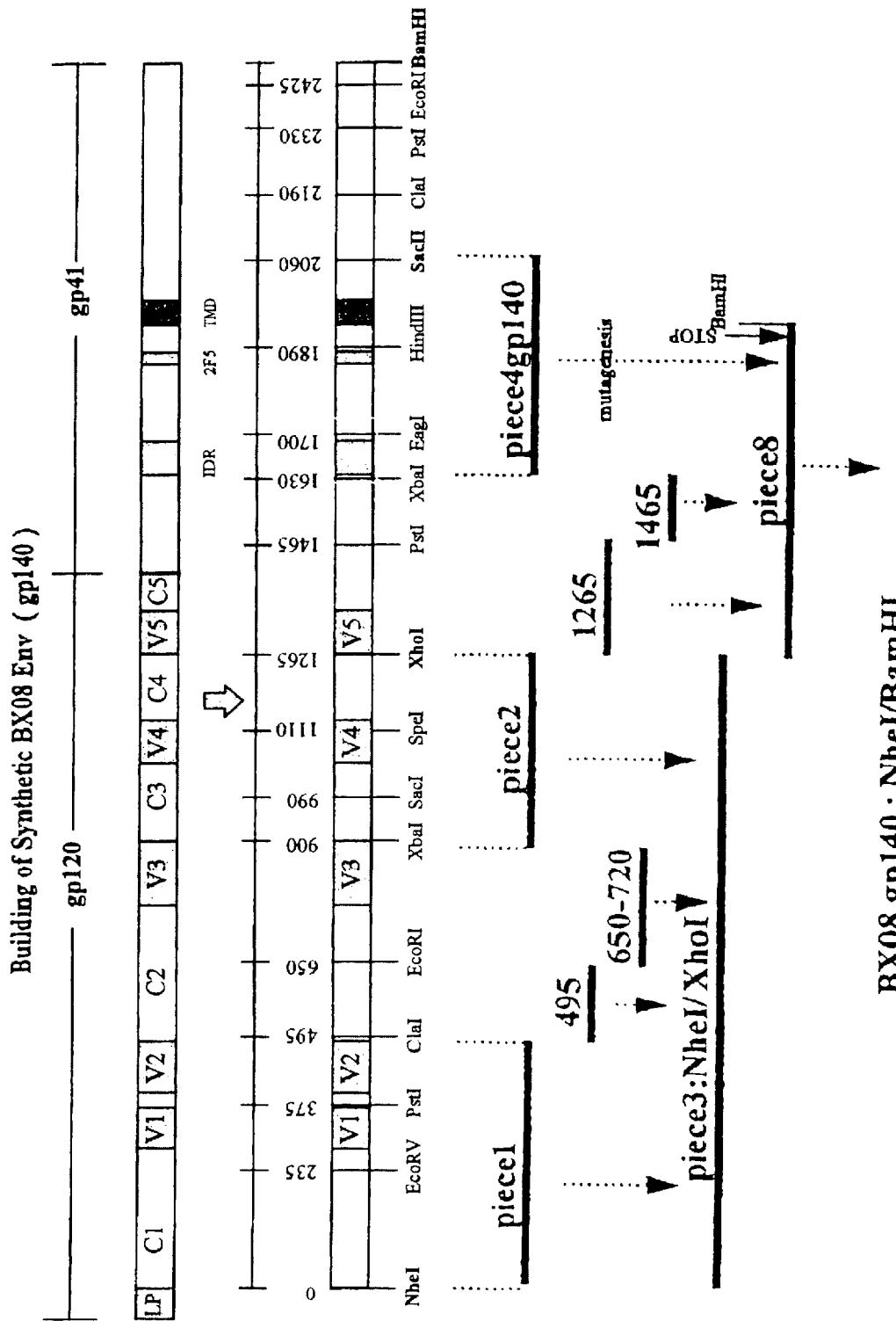

For construction of the synthetic BX08 gp150, piece4 was mutated to Piece4gp150 whereby a tyrosine→cysteine was changed and a stop codon was introduced after the transmembrane spanning domaine (TMD), followed by a BamHI cloning site. A new piece8gp150 was constructed composed of snut1265/snut1465/piece4gp150.

synBX08 gp150/uncleaved gene: RE digestion, DNA fragments purification, ligation as well as direct PCR screening of recombinant colonies are performed according the same procedures described for synBX08gp160 gene. A 1277-bp NheI/XhoI fragment, obtained from piece3-cl27, as well as a 800-bp XhoI/BamHI fragment, obtained from piece 8-gp150/uncleaved, are agarose gel purified and then are ligated into the NheI/BamHI WRG7079 sites. The ligation was performed using a vector:insert ratio of 1:1 or 1:2.

synBX08 gp 140 gene: The strategy for building that gene is depicted in FIG. 4. RE digestion, DNA fragments purification, ligation as well as direct PCR screening of recombinant colonies were performed according the same procedures described for synBX08 gp160 gene. A 1277-bp NheI/XhoI fragment, obtained from piece3-cl27, as well as a 647-bp XhoI/BamHI fragment, obtained from piece 8-gp140-cl2, were agarose gel purified and then ligated into the NheI/BamHI sites of WRG7079. The ligation was performed using a vector:insert ratio of 1:1 or 1:2. For construction of the synthetic BX08 gp140, piece4 was mutated to Piece4gp140 whereby a stop codon was introduced just before the TMD followed by a BamHI cloning site. A new piece8gp140 was constructed composed of snutl265/1465/piece4gp140.

synBX08 gp140/uncleaved gene: RE digestion, DNA fragments purification, ligation as well as direct PCR screening of recombinant colonies are performed according the same procedures described for synBX08 gp160 gene. A 1277-bp NheI/XhoI fragment, obtained from piece3-cl27, as well as a 800-bp XhoI/BamHI fragment, obtained from piece 8-gp140/uncleaved, are agarose gel purified and then ligated into the NheI/BamHI WRG7079 sites. The ligation was performed using a vector:insert ratio of 1:1 or 1:2.

synBX08 gp 120 gene: The strategy for building that piece is depicted in FIG. 3. RE digestion, DNA fragments purification, ligation as well as direct PCR screening of recombinant colonies were performed according the same procedures described for synBX08 gp160 gene. A 1277-bp NheII/XhoI fragment, obtained from piece3-cl27, as well as a 206-bp XhoI/BamHI fragment, obtained from 1265-XhoI-gp120-clM5, were agarose gel purified and then ligated into the NheI/BamHI sites of WRG7079. The ligation was performed using a vector:insert ratio of 1:1 or 1:2. For construction of the synthetic BX08 gp120, snut 1265 was mutated to $S_{1265gp120}$ to introduce a stop codon at the gp120/gp41 cleavage site followed by a BamH1 cloning site.

The gp160, gp150, gp140, and gp120 genes are cloned (NheI-BamHI) and maintained in an eucaryotic expression vectors containing a CMV promotor and a tPA leader, but other expression vectors may be chosen based on other criteria e.g. antibiotic resistance selection, other leader sequences like CD5 etc, presence or not of immune stimulatory sequences etc.

SynBX08 gp41 gene: The strategy for building that gene is depicted in FIG. 20. RE digestion, DNA fragments purification, ligation as well as direct PCR screening of recombinant colonies were performed according the same procedures described for synBX08 gp160 gene. Piece 8-gp41 is ligated with snut 2060-SacII-klon21 and piece 5 as already decribed for the construction of piece 7, creating piece 7-gp41 ($P_{7gp41}$). Subsequently the piece 7-gp41 containing the entire gp41 gene will be cloned in WRG7079 using the NheI and BamHI sites.

Example 6a

High Expression by Codon Optimization

To analyze the expression of glycoproteins from the wild type and synthetic BX08 envelope genes RIPA was performed on transfected mammalian cell lines. Both cell membrane associated and secreted HIV-1 glycoproteins from the cell supernatants were assayed. The envelope plasmids were transfected into the human embryonic kidney cell line 293 (ATCC, Rockville, Md.) or the mouse $P_{815}$ (H-2$D^d$) cell line using calcium phosphate (CellPhect Transfection kit, Pharmacia). For radio immune precipitation assay (RIPA), transfected cells were incubated overnight, washed twice and incubated for 1 hour with DMEM lacking cysteine and methionine (Gibco). Then the medium was replaced with medium containing 50 μCi per ml of [$^{35}$S] cysteine and 50 μCi/ml of [$^{35}$S] methionine (Amersham Int., Amersham, UK) and incubation continued overnight. Cells were centrifuged, washed twice with HBSS and lysed in 1 ml ice-cold RIPA buffer (10 mM Tris, pH 7.4, 150 mM NaCl, 50 mM EDTA, 1% Nonidet P-40, 0.5% sodiumdeoxycholate) to detect membrane bound Env glycoproteins. The cell lysates were centrifuged for 15 min. at 100,000×g to remove any undissolved particles and 100 μl immune precipitated with protein A-sepharose coupled human polyclonal IgG anti-HIV antibodies (Nielsen et al., 1987). For analysis of secreted Env glycoproteins 500 μl of the 5 ml supernatants from transfected cells were incubated with protein A-sepharose coupled human polyclonal IgG anti-HIV antibodies. After washing three times in cold RIPA buffer and once in PBS, the immuno precipitates were boiled for 4 min. in 0.05 M Tris-HCl, pH 6.8, 2% SDS, 10% 2-mercaptoethanol, 10% sucrose, 0.01% bromophenol blue and subjected to SDS PAGE (Vinner et al., 1999). Electrophoresis was carried out at 80 mV for 1 hour in the stacking gel containing 10% acrylamide, and at 30 mV for 18 hours in the separating gradient gel containing 5–15% acrylamide. Gels were fixed in 30% ethanol-10% acetic acid for 1 hour, soaked for 30 min. in En3Hance (Dupont #NEF 981), washed 2×15 min. in distilled water, dried and autoradiography performed on Kodak XAR-5 film. Transfection of human 293 cells with the syn.gp$120_{BX08}$ and syn.gp$140_{BX08}$ genes, respectively, resulted in high amounts of only secreted HIV-1 glycoproteins (FIG. 22*a*, lane 9 and 8). Thus, the synthetic gene in the absence of rev expresses the HIV-1 surface glycoprotein of the expected size which is recognized by human anti-HIV-1 antisera. The expression of BX08 gp120 was Rev independent and with roughly the same high amount of gp120 from the syn.gp120MN gene (FIG. 22*a*, lane 2). FIG. 22*a*, lane 6 and lane 7 shows the expression of only membrane bound gp160 and gp150 from 293 cells transfected with syn.gp$160_{BX08}$ and syn.gp$150_{BX08}$ plasmids, respectively. Also transfection with wt.gp$160_{BX08}$ plasmid resulted in a significant expression of membrane bound gp160 despite the absence of Rev (FIG. 22*a*, lane 3). Co-transfection with equimolar amounts of Rev encoding plasmid seemed to increase this expression somewhat (FIG. 22*a*, lane 4). This is seen despite the lower transfection effectivity using two plasmids and the use of only half the amount of wt.gp$160_{BX08}$ DNA when combined with pRev. The amounts of secreted HIV-1 glycoproteins from gp120 and gp141 accumulating in the cell supernatants seemed higher than the amounts of cell associated glycoproteins at the time of harvesting of the cells. Interestingly, the amounts of gp160 produced from the "humanized" gene were about equal to the amounts produced by the wt.gp$160_{BX08}$+pRev genes, respectively (FIG. 22*a*, lane 4 and 6). The processing of gp160, gp150 and gp140 into gp120 plus a gp41, or fractions of gp41, produced from wild type or synthetic genes in the 293 cell-line did not function well under these experimental conditions. Same phenomenon was seen in RIPA from 293-CD4 cells and HeLa-CD4 cells infected by HIV-$1_{MN}$ (Vinner et al., 19999). Because of the absence of CCR5 these cell-lines could, however, not be infected by HIV-1 strain BX08.

Example 6b

Radio Immuno Precipitation Assay (RIPA) of Synthetic BX08 Transfected Cells Showing Expression of Glycoproteins From Synthetic BX08 env Plasmids The synthetic envelope plasmid DNA were transfected into the human embryonic kidney cell line 293 (ATCC, Rockville, Md.) using calcium phosphate (CellPhect Transfection kit, Pharmacia). For immune precipitation analysis, transfected 293 cells were treated and analyzed according to the method described in example 6a. To analyze expression from these genes, an SDS-PAGE of the $^{35}$S-labelled HIV-1 envelopes, immune precipitated from the transfected cells is shown in FIG. 22*b*. Both cell-membrane associated and secreted HIV-1 envelope glycoproteins in the cell supernatants were assayed. Transfection of 293 cells with the synthetic BX08 gene encoding gp120 (syn.gp120BX08) in lane 4, and syn.gp140BX08 (lane 5) that did not contain revencoding regions, resulted in abundant amounts of HIV-1 gp120. Thus, the expressions were Rev independent and expressed in roughly same high amounts as the syn.gp120MN and syn.gp160MN genes (lane 3 and 2, respectively) already showed by our group and others to be markedly increased in comparison with HIV MN wild type genes including rev (Vinner et al 1999).

Transfection with syn.gp150 plasmid (lanes 7 and 8) resulted in significant expression of membrane associated gp120 and low detectable amounts of truncated form of gp41 (cell pellet in lane 7) with no detectable HIV-1 glycoprotein in the cell supernatant lane 8. It is concluded that the synthetic BX08 genes expres the envelope glycoproteins of expected size which are recognized by human anti-HIV-1 antiserum.

Example 6C FACS

To quantitate the surface expression of HIV glycoproteins from the wild type and synthetic BX08 envelope genes transfection experiments were done and cell surface expression examined by FACS (flow cytometer).

10 μg of the BX08 envelope plasmid (wild type BX08 gp160 or synBX08 gp160) plus 10 μg of an irrelevant carrier plasmid pBluescript were used to transfect a 80–90% confluent layer of 293 cells in tissue culture wells (25 cm²) using the CellPect kit (Pharmacia). After 48 hours cells were Versene treated, washed and incubated with a mouse monoclonal IgG antibodies to HIV gp120 (NEA-9301, NEN™, Life-Science Products Inc., Boston) for time 30 min. on wet ice followed by washing in PBS, 3% FCS and incubation with Phyto-Erytrin (PE) labelled rat anti-mouse IgG1 (Cat #346270, Becton Dickinson) according to the manufacture. After washing the cells were fixed in PBS, 1% paraformaldehyd, 3% FCS, and analysed on a FACS (FACScan, Becton-Dicknsson). Table 5 show in duplicate expression of BX08 gp160 from 11% of the cells transfected with wild type BX08 (number 1 and 2) compared to the 48% of cells expression BX08 glycoprotein when transfected with the synthetic gene (number 3 and 4). Thus, a several-fold higher expression is obtained using the synthetic BX08 gene.

TABLE 5

FACS analysis of 293 cells transfected with synBX08gp160 (No 1 and 2) and wt.gp16+BX08 (No 3 and 4) and stained with monoclonal antibodies to surface expressed HIV glycoproteins. A higher expression was obtained with the synthetic gene (mean 48%) as compared to the wild type gene (mean 11%).

| 50 ul | 45 ul | A | B | C | C–A | C–B |
|---|---|---|---|---|---|---|
| 1 syn.gp160BX08 + | pBluescript SK+ | 2.57 | 2.85 | 36.91 | 34.34 | 34.06 |
| 2 syn.gp160BX08 + | pBluescript SK+ | 2.83 | 2.14 | 58.42 | 55.59 | 56.28 |
| 3 wt.gp160BX08 + | pBluescript SK+ | 1.95 | 1.52 | 7.51 | 5.56 | 5.99 |
| 4 wt.gp160BX08 + | pBluescript SK+ | 2.97 | 1.42 | 14.41 | 11.44 | 12.99 |

A: No primary antibody added (control for unspecific secondary Ab binding)
B: Neither Primary Ab nor Secondary Ab added (autoflouroscense control)
C: Primary Ab and secondary Ab added.

Example 6D

Analyses of the Surface Expression and Biological Functionality

To analyse the surface expression and biological functionality from the wild type and synthetic BX08 envelope genes transfection experiments were done and cell fusion microscopically studied using HIV envelope receptor expressing cells.

10 μg of the BX08 envelope plasmid (wt.BX08gp160 or syn.BX08gp160 or empty WRG7079 vector plasmid) plus 5 μg of a plasmid (pEGFP, Clonetech) expressing green fluorescent protein (GFP) were transfected into 2×10⁶ adherent U87.CD4.CCR5 cells (NIH AIDS Res. & Reference program, catalog #4035) stably expressing CD4 and CCR5, using the CellPhect transfection kit (Pharmacia). After 48 hours the cells were examined by microscopy and photographed (FIG. 22c). FIG. 22c panel A show the negative control (empty WRG7079 plus pGFP) giving no syncytia. Panel B show cells transfected with the wild type BX08 gp160 plasmid where cell-to-cell fusion (syncytia) is seen. Panel C show cells transfected with the same amounts of synBX08 gp160 plasmid and demonstrating a much higher degree of cell-cell fusion. In fact most or all of the cells in the culture plate were fused at this time. This experiment show surface expression of functional HIV gp160 with tropism to the CCR5 receptor, as well as a much higher expression and biological activity from the synthetic BX08 gene as compared to the wild type equivalent.

Example 7

Gene Inoculation of Mice for Immunization

6–7 weeks old female BALB/c mice were purchased from Bomholdtgaard, Denmak. Microbiological status was conventional and the mice were maintained in groups of 4/5 per cage with food and water ad libitum and artificially lighted 12 hours per day. Acclimatization period was 2 days. Mice were anaesthetized with 0.2 ml i.p. of rohypnol:stesolid (1:3, v/v) and DNA inoculated by either i.m. injection of 50 μl 2 mg/ml of plasmid DNA in each tibia anterior muscle at week 0, 9, and 15 and terminated week 18; or gene gun inoculated on shaved abdominal skin using plasmid coated gold particles (0.95 μm particles, 2 μg DNA/mg gold, 0.5 mg gold/shot, 50–71% coating efficiency) with the hand held Helios® gene gun device (BioRad) employing compressed (400 psi) Helium as the particle motive force. Mice were gene gun vaccinated at week 0, 3, 6, 9, 15, and terminated week 18.

Example 8

Serological Assays

Western blotting. The induction of a humoral response to gp120 and gp41 antigens by in vivo expression of the encoded glycoproteins from the synthetic BX08 genes was examined by western immuno blotting (FIG. 27). Mouse antisera (1:40) were evaluated in western blotting using the commercial HIV BLOT 2.2 strips (Genelabs Diagnostic). The conjugate was a 1:200 dilution of the alkaline phosphatase-conjugated rabbit anti-mouse IgG (Dakopatts, Glostrup, Denmark). Buffers, incubation condition and color development were used according to the manufacturer. In these western blotting strips the gp160 band from HIV-1 IIIB contain of an oligomeric form of gp41 in a higher concentration than the monomeric gp41 band on the strip (Genelabs Diagnostic). HIV-$1_{IIIB}$ lysate is used in these commercial strips where the gp160 band is composed by addition of tetrameric gp41. All preimmune sera tested negative in western blotting. Mice inoculated with syn.$gp120_{BX08}$ showed antibody response to the heterologous gp120 of HIV-1 IIIB. Inclusion of the extracellular part of gp41 in the gene syn.$gp140_{BX08}$ induced antibody reaction to both gp120 and gp41 in all mice. This confirms the in vivo expression of BX08 gp120 and the extracellular part of gp41. DNA vaccination with syn.$gp160_{BX08}$ encoding the membrane bound glycoprotein induced antibodies to gp120 and gp41 in 50% and 64% of the mice, respectively. DNA vaccination with syn.$gp150_{BX08}$ induced detectable antibodies to gp120 and gp41 in 41% and 53%, respectively.

Induction of different levels of antibodies could explain the difference in numbers of positive reactive mice sera in this qualitative western blotting.

ELISA. Mouse anti HIV-1 gp120 antibodies were measured by indirect ELISA. Briefly, wells of polystyrene plates Maxisorb (Nunc) were coated for 2 days at room temperature with HIV-1 IIIB recombinant gp120 (Intracel) at 0.2 µg/100 µl of carbonate buffer, pH 9.6. Before use the plates were blocked 1 hour at room temperature with 150 µl/well of washing buffer (PBS, 0.5 M NaCl, 1% Triton-X-100) plus 2% BSA and 2% skimmilk powder. After 3×1 min. washings, mouse plasma was added at 100 µl/well diluted in blocking buffer and ELISA plates incubated for 90 min. at room temperature using a microtiter plate shaker. As standard curve we used a mouse monoclonal antibody to a conserved part of gp120 between V5-C5 (MRDNWRSELYKY) (SEQ ID NO: 116) (#NEA-9301, NEN™ Life Science Products, Inc., Boston, Mass.). As calibration control included on each plate we used a plasma pool from 10 mice vaccinated with BX08 gp120. Plates were again washed 5×1 min. and incubated 1 hour at room temperature with 100 µl/well of HRP-conjugated rabbit anti-mouse IgG (#$P_{260}$, Dakopatts, Glostrup, Denmark) diluted 1:1000 in blocking buffer. Colour was developed with 100 µl/well of peroxidase enzyme substrate consisting of 4 mg of o-phenylenediamine in 11 ml water plus 4 µl hydrogen peroxide (30%, w/w). The enzyme reaction was terminated after 30 min. by 150 µl/well of 1M $H_2SO_4$. The optical density (OD) of wells was measured at 492 nm using a microplate photometer (Molecular Devices, Biotech-Line, Denmark). Anti-HIV-gp120 IgG titers were expressed as the reciprocal plasma dilution resulting in an $OD_{492nm}$ value of 0.500. Mouse anti-HIV-1 BX08 antibodies were also measured by indirect peptide ELISAs as described above using a BX08 V3 peptide (SIHIGPGRAFYTTGD) (SEQ ID NO: 117) (Schafer, Copenhagen, Denmark).

The IgG antibody response to HIV-1$_{IIIB}$ rgp120 quantitated by ELISA is seen in FIG. 28 and FIG. 29. No background activity was observed in preimmune sera or in sera from 4 mice immunized with empty WRG7079 vector in parallel with the BX08 genes. All mice inoculated with the synthetic BX08 genes either by gene gun or by i.m. injection responded and showed a persistent and high titered (about 100–10,000) IgG response to rgp120 as exemplified in FIG. 4. When comparing the median titers for groups of mice (FIG. 29) a moderate antibody response was observed with the wt.gp160$_{BX08}$. Intramuscular and gene gun immunization with a mixture of wt.gp160$_{BX08}$ plasmid plus Rev encoding plasmid did not increase this antibody response. This was found even when both plasmids were coated onto the same gold particles to ensure co-transfection of single target cells. However, to ensure inoculation of equal amounts of total DNA only half of the amount of wt.BX08 plasmid was used when mixing with pRev which may have contributed to the lower antibody response when pRev was included. A 5-fold improvement of the antibody response was obtained using the syn.gp160$_{BX08}$ gene. This antibody response seemed further improved using the syn.gp150$_{BX08}$ gene where the cytoplasmic internalization signals were eliminated but only using gene gun inoculation. For both the gene gun inoculation of skin and i.m injection the highest antibody titers to rgp120 were induced by genes encoding secreted gp120/gp140 glycoproteins versus membrane bound gp150/gp160 glycoproteins, respectively. In general, equal antibody and ELISA titers to rgp120 were obtained using gene gun and i.m. injection of the BX08 vaccine genes.

Example 9

Neutralization Assay

Mouse plasma was diluted in culture medium (RPMI-1640 medium (Gibco) supplemented with antibiotics (Gibco), Nystatin (Gibco) and 10% FCS (Bodinco)) and heat inactivated at 60° C. for 30 min. Of the HIV-1 strain BX08 (50 TCID$_{50}$ per ml propagated in PBMC) 250 µl was incubated for 1 hour at room temperature with 250 µl dilution of mouse serum (four five-fold dilutions of mouse serum, final dilutions 1:20 to 1:2500). After incubation 1×10$^6$ PBMC in 500 µl culture medium was added to the virus-serum mixture and incubated overnight at 37° C. in 5% $CO_2$. Subsequently, eight replicates of 105 PBMC in 200 µl culture medium were cultured in 96-well culture plates (Nunc) at 37° C. in 5% $CO_2$. After seven days in culture the concentration of HIV antigen in the culture supernatant was quantitated using HIV antigen detection ELISA (Nielsen et al., 1987). This ELISA is performed using human IgG, purified from high titered patient sera, both as capture antibody and biotin-linked as detecting antibody. In brief, anti-HIV-capture IgG diluted 1:4000 in PBS, 100 µl/well, are coated onto Immunoplates (Nunc) overnight at 4° C. After washing five times in washing buffer 100 µl of supernatants are applied and incubated overnight at 4° C. Plates are washed 5 times before incubation with 100 µl HIV-IgG conjugated with biotin diluted 1:1000 in dilution buffer, plus 10% HIV-1 sero-negative human plasma for 3 hours at room temperature. Five times 1 min. washing in washing buffer are followed by 30 min. incubation with 100 µl of 1:1000 avidine-peroxidase (Dako P$_{347}$ diluted in dilution buffer). Six times 1 min. washings, 5 in washing buffer and the last one are done in dH$_2$O before colour is developed with 100 µl of peroxidase enzyme substrate consisting of 4 mg of OPD in 11 ml water plus 4 µl hydrogen peroxide (30%, w/w). The enzyme reaction is terminated after 30 minutes by additional 150 µl of 1M H$_2$SO$_4$. The HIV antigen concentration in cultures, preincubated with mouse serum, was expressed relatively to cultures without mouse serum (culture medium), and the percentage inhibitions of the different dilutions of mouse serum were.calculated. The 50% inhibitory concentration (IC$_{50}$) for each mouse serum was determined by interpolation from the plots of percent inhibition versus the dilution of serum, and the neutralizing titer of the serum was expressed as the reciprocal value of the IC$_{50}$. In each set-up a human serum pool known to neutralise other HIV-1 strains was included in the same dilutions as the mouse serum as a calibratin control. For assay of neutralization of the heterologous SHIV89.6P the MT-2-cell-killing format was used (Crawford et al., 1999). The assay stock of SHIV89.6P was grown in human PBMC.

The neutralizing IC$_{50}$ antibody titers of plasma pools from 10 mice from each group were measured at different time points (week 0, 9, and 18). A positive background in some preimmune sera and thus in all week 0 serum pools was noted even after dilution and heat inactivation that was found earlier to lower this background. In general the neutralizing titers to BX08 virus of such serum pools were transient and low ranging from 1:6–1:150 above background (data not shown). A possible cross-neutralization reaction to a heterologous, primary HIV-1 envelope was tested using the SHIV89.6P which is relevant in macaque models of AIDS and serum pools from mice DNA immunized i.m. with syn.gp140$_{BX08}$ Preimmune serum had a titer of 1:37, which is indicative of a slightly positive background, whereas the 18 week p.i. serum had a positive neutralizing titer of 1:254 above background.

Example 10

CTL Assay

The cellular immune response in mice following gene gun or i.m. genetic immunization with the different vaccine plasmids were examined (FIG. 26). Spleen was removed aseptically and gently homogenized to single cell suspension, washed 3 times in RPMI-1640 supplemented with 10% FCS and resuspended to a final concentration of $5 \times 10^7$ cell/ml. The cells were then incubated 5 days with mitomycin-C treated (50 µg/ml for 1 hour) mouse $P_{815}$ (H-2D$^d$) stimulator cells at a ratio of 10:1 in medium supplemented with $5 \times 10^{-5}$ M β-mercaptoethanol. For assay of CTL response to HIV-1 BX08, $P_{815}$ stimulator cells and target cells were pulsed with 20 µg/ml of the HIV-1 BX08 V3 peptide containing a conserved murine H-2D$^d$ restricted CTL epitope (IGPGRAFYTT) (SEQ ID NO: 118) (Lapham et al., 1996). After stimulation, splenocytes were washed three times with RPMI-1640 supplemented with 10% FCS and resuspended to a final concentration of $5 \times 10^6$ cells/ml. 100 IAI of cell suspension was added in triplicate to U-bottom 96-well microtiter plates and a standard 4 hour $^{51}$Cr-release assay performed (Marker et al., 1973).

All synthetic BX08 plasmids induced a high specific CTL response thus confirming the in vivo expression and in vivo immunogenicity. The highest CTL response was obtained with syn.gp150$_{BX08}$ followed by syn.gp120$_{BX08}$-syn.gp140$_{BX08}$, and syn.gp160$_{BX08}$, respectively. Thus, the CTL response induced did not correlate with the antigen being secreted or not. However, i.m. DNA immunization with syn.gp150$_{BX08}$ containing six putative CpG motifs induced a higher CTL response than gene gun immunization (FIG. 26). This difference could be explained by the high amount of DNA used in the i.m. injections.

The T-lymphocyte cytokine profile of spleen cells after ConA stimulation as well as serum antibody $IgG_{2a}/IgG_1$ at week 18 were investigated. Neither the IFNγ/IL-4 nor the $IgG_{2a}/IgG_1$ ratios, which both reflects a Th1-type of immune response, were significantly higher for the i.m. immunized mice when compared with gene gun immunized mice (student t-test and Mann-Withney U-test). Thus, the CTL response did not correlate with a certain Th-type of response and the DNA immunization technique did not bias the immune response using synthetic BX08 genes.

Example 11

Antibody Responses to DNA Vaccination With synBX08 env Plasmid

A relatively low and variable antibody response (1 of 10 mice) was obtained with gene gun inoculation of the syn.gp140BX08 plasmid vaccine starting at week 9, FIG. 23, right panel. A higher numbers of responders 3/10 with high IgGl antibody responses at an earlier onset (week 3–9) was obtained with the syn.gp140BX08 plasmid using i.m. injection, left panel. Sera from later time points may show more responders and/or higher titers but are not assayed. However, these results show the induction of an antibody response to the BX08 V3 peptide by DNA vaccination using one of the described synthetic BX08 constructs.

References

Webster R G, Robinson H L. DNA vaccines: A review of developments. Biopharmaceuticals 1997, 4:273–292.

Rosenberg E S et al. Vigorous HIV-1 specific CD4+T cell responses associated with control of viremia. Science 1997, 278:1447–1450.

Boyer J et al. Nature Med 1997, 3:526–532.

Choe H et al. The beta-chemokine receptors CCR3 and CCR5 facilitate infection by primary isolates. Cell 1996, 85(7):1135–48.

Dragic T et al. Co-receptors: gateways to the cell. HIV advantaces in Research and Therapy 1997 (9): 2–12.

Karlsson A C et al. Characterization of the viral population during primary HIV-1 infection. AIDS 1998, 12:839–847.

Haas J, Park E C, Seed B. Codon usage limitation in the expression of HIV-1 envelope glycoprotein. Curr. Biol. 1996, 6:315–324.

André S, Seed B, Eberle J et al. Increased immune response elicited by DNA vaccination with a synthetic gp120 sequence with optimized codon usage. J. Virol. 1998, 72: 1497–1503.

Letvin N L et al. Potent protective anti-HIV immue responses generated by bimodal HIV envelope DNA plus protein vaccination. PNAS 1997, 94: 9378–9383.

Bryder K et al. Improved humoral and cellular immune responses against the gp120 V3 loop of HIV-1 following genetic immunization with a chimeric DNA vaccine encoding the V3 inserted into the hepatitis B surface antigen. Scand J Immunol 1998 Apr, 47(4):289–95.

Kwong P D, et al. Structure of an HIV gp120 envelope glycoprotein in complex with the CD4 receptor and a neutralizing human antibody. Nature 1998 393: 648–659.

Wyatt R et al. The antigenic structure of the HIV gp120 envelope glycoprotein. Nature 1998, 393: 705–711.

Sauter M S, et al. An internalization signal in the SIV trasmembrane protein cytoplasmic domain modulates expression of envelope glycoproteins on the cell surfacej. Cell Biol. 1996, 132: 795–811.

Mascola J R, et al. Potent and synergistic neutralization of HIV-1 primary isolates by hyperimmune anti-HIV immunogl obulin combined with monoclonal antibodies 2F5 and 2G12. J. Virol. 1997, 71(10): 7198–7206.

Molecular Cloning: A Laboratory Manual With the Lab Manual Source Book 1996-Sambrook, J./Fritsch, E. F./Maniatis, T.

Nielsen C M; Bygbjerg I C; Vestergaard B F. Detection of HIV antigens in eluates from whole blood collected on filterpaper, Lancet, Mar. 7, 1987 1(8532):566–7.

Harada-S, Koyanagi Y; Yamamoto N, Infection of HTLV-III/LAV in HTLV-I-carrying cells MT-2 and MT-4 and application in a plaque assay. Science, 229(4713):563–6 Aug. 9, 1985.

Verrier F C et al. Antibodies to several conformation-dependent epitopes of gp120/gp41 inhibit CCR-5-dependent cell-to-cell fusion mediated by the native envelope glycoprotein of a primary macrophage-tropic HIV-1 isolate. Proc Natl Acad Sci USA, Aug. 19, 1997, 94(17):9326–31.

Chan D C et al. Core structure of gp41 from the HIV envelope glycoprotein; Cell, Apr. 18, 1997 89(2):263–73.

Weiner, M. P., Costa, G. L., Schoettlin, W., Cline, J., Marthur, E., and Bauer, J. C. Gene 1994, 151:119–123.

Nelson, M., and McClelland, M. Methods Enzymol., 1992, 216: 279–303

Cloning Vectors: A Laboratory manual, P. H. Pouwels et al. 1985, supp. 1987.

Watson, J. D. et al. Molecular Biology of the Gene, Volumes I and II, the Benjamin/Cummings Publishing Company Inc, Menlo Park, Calif., 1987.

Darnell, J. E. et al. *Molecular Cell Biology, Scientific American Books*, New York (1986). Old, R. W. et al, *Principles of Gene Manipulation*: An Introduction to Genetic Engineering, 2nd edition, University of California press, 1981.

Ausubel et al. *Current Protocols in Molecular Biology*, John Wiley & Sons, New York, 1992.

Wilbur, W. J. and Lipman, D. J. Rapid similarity searches of nucleic acid and protein data banks, Proc Natl Acad Sci USA, 1983, 80:726–730.

Vinner L, H. V. Nielsen, K. Bryder, S. L. Corbet, C. Nielsen, and A. Fomsgaard. Gene gun DNA vaccination with Rev-independent synthetic HIV-1 gp160 envelope gene using mammalian codons. Vaccine. Apr. 23, 1999 17(17):2166–75.

Marker, O. and Volkert M. Studies on cell-mediated immunity to lymphocyte choriomeningitis virus in mice. J. Exp. Med. 1973, 137:1511–1525.

Lapham, C., B. Golding, J. Inman, R. Blackburn, J. Manischewitz, P. Highet, and H. Golding. Brucella abortus conjugated with a peptide derived from the V3 loop of human immunodeficiency virus (HIV) type 1 induces HIV-specific cytotoxic T-cell responses in normal and in CD4+ cell-depleted BALB/c mice. J. Virol. 1996, 70(5):3084–3092.

Crawford, J. M., P. L. Earl, B. Moss, K. A. Reimann, M. S. Wyand, K. H. Manson, M. Bilska, J. T. Zhou, C. D. Pauza, P. W. H. I. Parren, D. R. Burton, J. G. Sodroski, N. L. Letvin, and D. C. Montefiori. Characterization of primary isolate-like variants of simian-human immunodeficiency virus. J. Virol. 1999, 73(12):10199–10207.

What is claimed is:

1. A method for producing a nucleotide sequence construct comprising the following steps:
    a) obtaining a first nucleotide sequence of an HIV gene from a patient within the first 12 months of infection;
    b) designing a second nucleotide sequence utilising the most frequent codons from mammalian highly expressed proteins to encode the same amino acid sequence as the first nucleotide sequence of a) encodes
    c) redesigning the second nucleotide sequence of b) so that restriction enzyme sites surrounds the regions of the nucleotide sequence which encode functional regions of the amino acid sequence and so that selected restriction enzyme sites are removed thereby obtaining a third nucleotide sequence encoding the same amino acid sequence as the first and the second nucleotide sequence of a) and b) encode;

d) redesigning the third nucleotide sequence of c) so that the terminal snuts contain convenient restriction enzyme sites for cloning into an expression vehicle;

e) producing the snuts between restriction enzyme sites of c) and terminal snuts of d).

2. A method according to claim 1, wherein the HIV gene is the gene encoding the envelope.

3. A method according to claim 1, wherein the HIV is a group M virus.

4. A method according to claim 1, wherein the HIV is subtype B.

5. A method according to claim 1, wherein the first nucleotide sequence is obtained by direct cloning.

6. A method according to claim 1, wherein the HIV in step a) is isolated with the first 11 months of infection, such a 10, 9, 8, 7, 6, 5, 4, 3, 2, 1, or 0.5 month after infection.

7. A method according to claim 1, wherein the redesigning in step c) is carried out after the second nucleotide sequence of step b) has been divided into pieces, so that each piece comprises only different restriction enzyme sites.

8. A method according to claim 7, wherein the second nucleotide sequence of step b) is divided into 3 pieces.

9. A method according to claim 1, wherein the second nucleotide sequence of step b) is designed utilising the most frequent codons from human highly expressed proteins to encode the same amino acid sequence as the first nucleotide sequence of step a) encodes.

10. A nucleotide sequence construct obtainable by the method of any one of claims 1–9.

11. A nucleotide sequence construct in isolated form which has a nucleotide sequence with the general formula (I), (II), (III), or (IV) or subsequences thereof $$P_1\text{-}S_{495ClaI}\text{-}S_{650\text{-}720EcoRI}\text{-}P_2\text{-}S_{1265gp120} \qquad (I)$$

$$P_1\text{-}S_{495ClaI}\text{-}S_{650\text{-}720EcoRI}\text{-}P_2\text{-}S_{1265XhoI}\text{-}S_{1465PstI}\text{-}P_{4gp140} \qquad (II)$$

$$P_1\text{-}S_{495ClaI}\text{-}S_{650\text{-}720EcoRI}\text{-}P_2\text{-}S_{1265XhoI}\text{-}S_{1465PstI}\text{-}P_{4gp150} \qquad (III)$$

$$P_1\text{-}S_{495ClaI}\text{-}S_{650\text{-}720EcoRI}\text{-}P_2\text{-}S_{1265XhoI}\text{-}S_{1465PstI}\text{-}P_{4gp160}\text{-}S_{2060SacII}\text{-}P_5 \qquad (IV)$$

wherein $P_1$ designates the nucleotide sequence SEQ ID NO:41, a nucleotide sequence complementary thereto, or a nucleotide sequence with a sequence identity of at least 90% thereto;

wherein $S_{495ClaI}$ designates the nucleotide sequence SEQ ID NO: 7, a nucleotide sequence complementary thereto, or a nucleotide sequence with a sequence identity of at least 95% thereto;

wherein $S_{650\text{-}720EcoRI}$ designates the nucleotide sequence SEQ ID NO: 9, a nucleotide sequence complementary thereto, or a nucleotide sequence with a sequence identity of at least 95% thereto;

wherein $P_2$ designates the nucleotide sequence SEQ ID NO: 43, a nucleotide sequence complementary thereto, or a nucleotide sequence with a sequence identity of at least 85% thereto;

wherein $S_{1265gp120}$ designates the nucleotide sequence SEQ ID NO: 19, a nucleotide sequence complementary thereto, or a nucleotide sequence with a sequence identity of at least 70% thereto;

wherein $S_{1265XhoI}$ designates the nucleotide sequence SEQ ID NO: 17, a nucleotide sequence complementary thereto, or a nucleotide sequence with a sequence identity of at least 80% thereto;

wherein $S_{1465}PsiI$ designates the nucleotide sequence SEQ ID NO: 23, a nucleotide sequence complementary thereto, or a nucleotide sequence with a sequence identity of at least 90% thereto;

wherein $P_{4gp140}$ designates the nucleotide sequence SEQ ID NO: 57, a nucleotide sequence complementary thereto, or a nucleotide sequence with a sequence identity of at least 85% thereto;

wherein $P_{4gp150}$ designates the nucleotide sequence SEQ ID NO: 55, a nucleotide sequence complementary thereto, or a nucleotide sequence with a sequence identity of at least 85% thereto;

wherein $P_{4gp160}$ designates the nucleotide sequence SEQ ID NO: 53, a nucleotide sequence complementary thereto, or a nucleotide sequence with a sequence identity of at least 85% thereto;

wherein $S_{2060sacII}$ designates the nucleotide sequence SEQ ID NO: 33, a nucleotide sequence complementary thereto, or a nucleotide sequence with a sequence identity of at least 98% thereto; and wherein $P_5$ designates the nucleotide sequence SEQ ID NO: 59, a nucleotide sequence complementary thereto, or a nucleotide sequence with a sequence identity of at least 85% thereto.

12. A nucleotide sequence construct according to claim 11, with the formula (I)

$$P_1\text{-}S_{495ClaI}\text{-}S_{650\text{-}720EcoRI}\text{-}P_2\text{-}S_{1265gp120} \qquad (I).$$

13. A nucleotide sequence construct according to claim 11, with the formula (II)

$$P_1\text{-}S_{495ClaI}\text{-}S_{650\text{-}720EcoRI}\text{-}P_2\text{-}S_{1265XhoI}\text{-}S_{1465PstI}\text{-}P_{4gp140} \qquad (II).$$

14. A nucleotide sequence construct according to claim 11, with the formula (III)

$$P_1\text{-}S_{495ClaI}\text{-}S_{650\text{-}720EcoRI}\text{-}P_2\text{-}S_{1265XhoI}\text{-}S_{1465PstI}\text{-}P_{4gp150} \qquad (III).$$

15. A nucleotide sequence construct according to claim 11, with the formula (IV)

$$P_1\text{-}S_{495ClaI}\text{-}S_{650\text{-}720EcoRI}\text{-}P_2\text{-}S_{1265XhoI}\text{-}S_{1465PstI}\text{-}P_{4gp160}\text{-}S_{200SacII}\text{-}P_5 \qquad (IV).$$

16. A nucleotide sequence construct according to claim 11 consisting essentially of the subsequence $P_1$.

17. A nucleotide sequence construct according to claim 11 consisting essentially of the subsequence $S_{495ClaI}$.

18. A nucleotide sequence construct according to claim 11 consisting essentially of the subsequence $S_{650\text{-}720EcoRI}$.

19. A nucleotide sequence construct according to claim 11 consisting essentially of the subsequence $P_2$.

20. A nucleotide sequence construct according to claim 11 consisting essentially of the subsequence $S_{1265gp120}$.

21. A nucleotide sequence construct according to claim 11 consisting essentially of the subsequence $S_{1265XhoI}$.

22. A nucleotide sequence construct according to claim 11 consisting essentially of the subsequence $S_{1465PstI}$.

23. A nucleotide sequence construct according to claim 11 consisting essentially of the subsequence $P_{4gp140}$.

24. A nucleotide sequence construct according to claim 11 consisting essentially of the subsequence $P_{4gp150}$.

25. A nucleotide sequence construct according to claim 11 consisting essentially of the subsequence $P_{4gp160}$.

26. A nucleotide sequence construct according to claim 11 consisting essentially of the subsequence $S_{2060SacII}$.

27. A nucleotide sequence construct according to claim 11 consisting essentially of the subsequence $P_5$.

28. A nucleotide sequence construct with a sequence identity of more than 85% to the nucleotide sequence construct in claim 11.

29. A nucleotide sequence construct according to claim 11, wherein the sequence identity is more than 90% such as more than 95%, 98%, or 99%.

30. A nucleotide sequence construct according to claim 11, wherein the sequence identity is 100%.

31. A nucleotide sequence construct according to claim 11, coding for an HIV envelope or parts thereof with an improved immunogenicity obtained by mutating the nucleotide sequence construct of claim 11 such that one or more glycosylation sites in the amino acid sequence have been removed.

32. A nucleotide sequence construct according to claim 11 with a mutation at positions A307C+C309A and/or A325C+C327G and/or A340C+C342A and/or A385C+C387A and/or A469C+C471A or any combination of those.

33. A nucleotide sequence construct according to claim 11, coding for an HIV envelope or parts thereof with a binding site for the CXCR4 co-receptor in the third variable region.

34. A nucleotide sequence construct according to claim 33 with a mutation at positions G865C+A866G.

35. A nucleotide sequence construct according to claim 11, coding for an HIV envelope or parts thereof, wherein an immunodominant epitope has been modified.

36. A nucleotide sequence construct according to claim 35, wherein an immunodominant epitope in the third variable region has been modified.

37. A nucleotide sequence construct according to claim 36 with a deletion of nucleotides 793–897.

38. A nucleotide sequence construct according to claim 11, wherein an immunodominant epitope has been removed from gp41.

39. A nucleotide sequence construct according to claim 11, coding for an HIV envelope or parts thereof, wherein the cleavage site between gp41 and gp120 is removed.

40. A nucleotide sequence construct according to claim 39 with a mutation at position C1423A.

41. A nucleotide sequence construct according to claim 11 consisting essentially of the subsequence $P_1$, $S_{495ClaI}$, $S_{650\text{-}720EcoRI}$, and $P_2$.

42. A nucleotide sequence construct according to claim 11 consisting essentially of the subsequence $S_{1265XhoI}$, $S_{1465PstI}$-, and $P_{4gp140}$.

43. A nucleotide sequence construct according to claim 11 consisting essentially of the subsequence $S_{1265XhoI}$, $S_{1465PstI}$, $P_{4gp160}$, $S_{2060SacII}$, and $P_5$.

44. An expression vehicle selected from a group of viral vectors consisting of simliki forest virus (sfv), adenovirus and Modified Vaccinia Virus Ankara (MVA), further comprising a nucleotide sequence construct according to claim 11.

45. A method of individualised immunotherapy wherein the virus from a newly diagnosed patient is directly cloned, the envelope is produced with highly expressed codons, inserted into any of the nucleotide sequence constructs of claim 11, and administered to the patient.

46. A method for immunising an animal, including a human being, against HIV, comprisirn administering to the animal the nucleotide sequence according to claim 11.

47. A method for treating an animal, including a human being, diagnosed with an HIV infection comprising administering to the animal the nucleotide sequence according to claim 11 within 24 weeks of primary infection.

48. A method for producing a polypeptide comprising inserting a nucleic acid construct according to claim 11 into a vector which is able to replicate in a host cell, introducing the resulting recombinant vector into the host cell, culturing the host cell in a culture medium under conditions sufficient to effect expression of the polypeptide, and recovering the polypeptide from the host cell or culture medium.

* * * * *